US008071309B2

(12) United States Patent
Ecker et al.

(10) Patent No.: US 8,071,309 B2
(45) Date of Patent: *Dec. 6, 2011

(54) METHODS FOR RAPID IDENTIFICATION OF PATHOGENS IN HUMANS AND ANIMALS

(75) Inventors: David J. Ecker, Encinitas, CA (US); Richard H. Griffey, Vista, CA (US); Rangarajan Sampath, San Diego, CA (US); Steven A. Hofstadler, Oceanside, CA (US); John McNeil, La Jolla, CA (US); Stanley T. Crooke, Carlsbad, CA (US); Lawrence Blyn, Mission Viejo, CA (US); Ray Ranken, Encinitas, CA (US); Thomas A. Hall, Oceanside, CA (US)

(73) Assignee: Ibis Biosciences, Inc., Carlsbad, CA (US)

(*) Notice: Subject to any disclaimer, the term of this patent is extended or adjusted under 35 U.S.C. 154(b) by 319 days.

This patent is subject to a terminal disclaimer.

(21) Appl. No.: 11/930,002

(22) Filed: Oct. 30, 2007

(65) Prior Publication Data

US 2009/0148829 A1   Jun. 11, 2009

Related U.S. Application Data

(63) Continuation of application No. 10/728,486, filed on Dec. 5, 2003, now Pat. No. 7,718,354, which is a continuation-in-part of application No. 10/323,233, filed on Dec. 18, 2002, now abandoned, and a continuation-in-part of application No. 10/326,051, filed on Dec. 18, 2002, now abandoned, and a continuation-in-part of application No. 10/325,527, filed on Dec. 18, 2002, now abandoned, and a continuation-in-part of application No. 10/325,526, filed on Dec. 18, 2002, now abandoned.

(60) Provisional application No. 60/431,319, filed on Dec. 6, 2002, provisional application No. 60/443,443, filed on Jan. 29, 2003, provisional application No. 60/443,788, filed on Jan. 30, 2003, provisional application No. 60/447,529, filed on Feb. 14, 2003, provisional application No. 60/501,926, filed on Sep. 11, 2003.

(51) Int. Cl.
*C12Q 1/68* (2006.01)
(52) U.S. Cl. ........................................ 435/6.12
(58) Field of Classification Search .................. None
See application file for complete search history.

(56) References Cited

U.S. PATENT DOCUMENTS

| | | |
|---|---|---|
| 4,075,475 A | 2/1978 | Risby et al. |
| 4,683,195 A | 7/1987 | Mullis et al. |
| 4,683,202 A | 7/1987 | Mullis et al. |
| 4,965,188 A | 10/1990 | Mullis et al. |
| 5,015,845 A | 5/1991 | Allen et al. |
| 5,072,115 A | 12/1991 | Zhou |
| 5,143,905 A | 9/1992 | Sivasubramanian et al. |
| 5,213,961 A | 5/1993 | Bunn et al. |
| 5,219,727 A | 6/1993 | Wang et al. |
| 5,288,611 A | 2/1994 | Kohne |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,808 A | 1/1996 | Grinnell |
| 5,484,908 A | 1/1996 | Froehler et al. |
| 5,502,177 A | 3/1996 | Matteucci et al. |
| 5,503,980 A | 4/1996 | Cantor et al. |
| 5,504,327 A | 4/1996 | Sproch et al. |
| 5,504,329 A | 4/1996 | Mann et al. |
| 5,523,217 A | 6/1996 | Lupski et al. |
| 5,527,669 A | 6/1996 | Resnick et al. |
| 5,527,675 A | 6/1996 | Coull et al. |
| 5,527,875 A | 6/1996 | Yokoyama et al. |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,641,632 A | 6/1997 | Kohne |
| 5,645,985 A | 7/1997 | Froehler et al. |

(Continued)

FOREIGN PATENT DOCUMENTS

AU    2003245488    6/2002

(Continued)

OTHER PUBLICATIONS

Aaserud et al., "Accurate base composition of double-strand DNA by mass spectrometry" *J. Am. Soc. Spec.* (1996) 7:1266-1269.
Aaserud et al., "DNA sequencing with balckbody infrared radioactive dissociation of electrosprayed ions" Int. J. Mass. Spectrom. Ion Processes, (1997) 167-168: 705-712.
Adam et al., Molecular structure of the two-dimensional hexon crystalline array and of adenovirus capsid: *Acta Microbiol. Immuno. Hung.* (1998) 45:305-310.
Adam et al., "Intertype specific epitope structure of adenovirus hexon" *Acta Microbiol. Immuno. Hung.* (1998) 45:311-316.
Adam et al., "Characterization of intertype specific epitopes on adenovirus hexons" *Arch. Virol.* (1998) 143:1669-1682.
Adrian et al., "DNA restriction analysis of adenovirus prototypes 1 to 41" *Arch. Virol.* (1986) 91 :277-290.

(Continued)

*Primary Examiner* — Kenneth R. Horlick
*Assistant Examiner* — David Thomas
(74) *Attorney, Agent, or Firm* — Casimir Jones S.C.; Christopher C. Sappenfield

(57) ABSTRACT

The present invention provides methods of: identifying pathogens in biological samples from humans and animals, resolving a plurality of etiologic agents present in samples obtained from humans and animals, determining detailed genetic information about such pathogens or etiologic agents, and rapid detection and identification of bioagents from environmental, clinical or other samples.

72 Claims, 38 Drawing Sheets

U.S. PATENT DOCUMENTS

| | | | |
|---|---|---|---|
| 5,683,869 A | 11/1997 | Ramsay Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,707,802 A | 1/1998 | Sandhu et al. |
| 5,712,125 A | 1/1998 | Uhlen |
| 5,716,825 A | 2/1998 | Hancock et al. |
| 5,727,202 A | 3/1998 | Kucala |
| 5,745,751 A | 4/1998 | Nelson et al. |
| 5,747,246 A | 5/1998 | Pannetier et al. |
| 5,747,251 A | 5/1998 | Carson et al. |
| 5,753,467 A | 5/1998 | Jensen et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |
| 5,770,367 A | 6/1998 | Southern et al. |
| 5,777,324 A | 7/1998 | Hillenkamp |
| 5,814,442 A | 9/1998 | Natarajan et al. |
| 5,822,824 A | 10/1998 | Dion |
| 5,828,062 A | 10/1998 | Jarrell et al. |
| 5,830,653 A | 11/1998 | Froehler et al. |
| 5,830,655 A | 11/1998 | Monforte et al. |
| 5,830,853 A | 11/1998 | Backstrom et al. |
| 5,832,489 A | 11/1998 | Kucala |
| 5,834,255 A | 11/1998 | vanGemen et al. |
| 5,845,174 A | 12/1998 | Yasui et al. |
| 5,849,492 A | 12/1998 | Rogan |
| 5,849,497 A | 12/1998 | Steinman |
| 5,849,901 A | 12/1998 | Mabilat et al. |
| 5,851,765 A | 12/1998 | Koster |
| 5,856,174 A | 1/1999 | Lipschutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,876,938 A | 3/1999 | Stolowitz et al. |
| 5,885,775 A | 3/1999 | Haff et al. |
| 5,900,481 A | 5/1999 | Lough et al. |
| 5,928,905 A | 7/1999 | Stemmer et al. |
| 5,928,906 A | 7/1999 | Koster |
| 5,965,363 A | 10/1999 | Monforte et al. |
| 5,965,383 A | 10/1999 | Vogel et al. |
| 5,972,693 A | 10/1999 | Rothberg et al. |
| 5,976,798 A | 11/1999 | Parker et al. |
| 5,981,176 A | 11/1999 | Wallace |
| 5,981,178 A | 11/1999 | Tsui et al. |
| 5,981,190 A | 11/1999 | Israel |
| 5,994,066 A | 11/1999 | Bergeron et al. |
| 6,001,564 A | 12/1999 | Bergeron et al. |
| 6,001,584 A | 12/1999 | Karin et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer et al. |
| 6,018,713 A | 1/2000 | Coli et al. |
| 6,024,925 A | 2/2000 | Little et al. |
| 6,028,183 A | 2/2000 | Lin et al. |
| 6,043,031 A | 3/2000 | Koster et al. |
| 6,046,005 A | 4/2000 | Ju |
| 6,051,378 A | 4/2000 | Monforte et al. |
| 6,054,278 A | 4/2000 | Dodge et al. |
| 6,055,487 A | 4/2000 | Margery et al. |
| 6,060,246 A | 5/2000 | Summerton et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,133,436 A | 10/2000 | Koster et al. |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,187,842 B1 | 2/2001 | Kobayashi et al. |
| 6,194,144 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koster et al. |
| 6,261,769 B1 | 7/2001 | Everett et al. |
| 6,265,716 B1 | 7/2001 | Hunter et al. |
| 6,265,718 B1 | 7/2001 | Park et al. |
| 6,266,131 B1 | 7/2001 | Hamada et al. |
| 6,266,144 B1 | 7/2001 | Li |
| 6,268,129 B1 | 7/2001 | Gut et al. |
| 6,268,131 B1 | 7/2001 | Kang et al. |
| 6,268,144 B1 | 7/2001 | Koster |
| 6,268,146 B1 | 7/2001 | Shultz |
| 6,270,973 B1 | 8/2001 | Lewiz et al. |
| 6,270,974 B1 | 8/2001 | Shultz et al. |
| 6,274,726 B1 | 8/2001 | Laugharn, Jr. et al. |
| 6,277,573 B1 | 8/2001 | Koster |
| 6,277,578 B1 | 8/2001 | Shultz et al. |
| 6,277,634 B1 | 8/2001 | McCall et al. |
| 6,286,146 B1 | 9/2001 | Rocker |
| 6,300,076 B1 | 10/2001 | Koster |
| 6,303,297 B1 | 10/2001 | Lincoln et al. |
| 6,312,893 B1 | 11/2001 | Van Ness et al. |
| 6,312,902 B1 | 11/2001 | Shultz et al. |
| 6,322,970 B1 | 11/2001 | Little et al. |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,428,956 B1 | 8/2002 | Crooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 | 9/2002 | Oefner |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton, Jr. |
| 6,475,738 B2 | 11/2002 | Shuber et al. |
| 6,479,239 B1 | 11/2002 | Anderson et al. |
| 6,500,621 B2 | 12/2002 | Koster |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,568,055 B1 | 5/2003 | Tang et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton et al. |
| 6,613,509 B1 | 9/2003 | Chen |
| 6,613,520 B2 | 9/2003 | Ashby |
| 6,623,928 B2 | 9/2003 | Van Ness et al. |
| 6,638,714 B1 | 10/2003 | Linnen et al. |

| | | | | | |
|---|---|---|---|---|---|
| 6,680,476 B1 | 1/2004 | Hidalgo et al. | 2003/0187615 A1 | 10/2003 | Epler et al. |
| 6,682,889 B1 | 1/2004 | Wang et al. | 2003/0190605 A1 | 10/2003 | Ecker et al. |
| 6,705,530 B2 | 3/2004 | Kiekhaefer | 2003/0190635 A1 | 10/2003 | McSwiggen |
| 6,706,530 B2 | 3/2004 | Hillenkamp | 2003/0194699 A1 | 10/2003 | Lewis et al. |
| 6,716,634 B1 | 4/2004 | Myerson | 2003/0203398 A1 | 10/2003 | Bramucci et al. |
| 6,783,939 B2 | 8/2004 | Olmsted et al. | 2003/0220844 A1 | 11/2003 | Marmellos et al. |
| 6,800,289 B2 | 10/2004 | Nagata et al. | 2003/0224377 A1 | 12/2003 | Wengel et al. |
| 6,813,615 B1 | 11/2004 | Colasanti et al. | 2003/0225529 A1 | 12/2003 | Ecker et al. |
| 6,836,742 B2 | 12/2004 | Brekenfeld | 2003/0228571 A1 | 12/2003 | Ecker et al. |
| 6,852,487 B1 | 2/2005 | Baraney et al. | 2003/0228597 A1 | 12/2003 | Cowsert et al. |
| 6,856,914 B1 | 2/2005 | Pelech | 2003/0228613 A1 | 12/2003 | Bornarth et al. |
| 6,875,593 B2 | 4/2005 | Froehler et al. | 2004/0005555 A1 | 1/2004 | Rothman et al. |
| 6,906,316 B2 | 6/2005 | Sugiyama et al. | 2004/0013703 A1 | 1/2004 | Ralph et al. |
| 6,906,319 B2 | 6/2005 | Hoyes | 2004/0014957 A1 | 1/2004 | Eldrup et al. |
| 6,914,137 B2 | 7/2005 | Baker | 2004/0023207 A1 | 2/2004 | Polansky |
| 6,977,148 B2 | 12/2005 | Dean et al. | 2004/0023209 A1 | 2/2004 | Jonasson |
| 6,994,962 B1 | 2/2006 | Thilly | 2004/0029129 A1 | 2/2004 | Wang et al. |
| 7,022,835 B1 | 4/2006 | Rauth et al. | 2004/0038206 A1 | 2/2004 | Zhang et al. |
| 7,024,370 B2 | 4/2006 | Epler et al. | 2004/0038208 A1 | 2/2004 | Fisher et al. |
| 7,108,974 B2 | 9/2006 | Ecker et al. | 2004/0038234 A1 | 2/2004 | Gut et al. |
| 7,198,893 B1 | 4/2007 | Koster et al. | 2004/0038385 A1 | 2/2004 | Langlois et al. |
| 7,217,510 B2 | 5/2007 | Ecker et al. | 2004/0081993 A1 | 4/2004 | Cantor et al. |
| 7,226,739 B2 | 6/2007 | Ecker et al. | 2004/0101809 A1 | 5/2004 | Weiss et al. |
| 7,255,992 B2 | 8/2007 | Ecker et al. | 2004/0110169 A1 | 6/2004 | Ecker et al. |
| 7,285,422 B1 | 10/2007 | Little et al. | 2004/0111221 A1 | 6/2004 | Beattie et al. |
| 7,312,036 B2 | 12/2007 | Sampth et al. | 2004/0117129 A1 | 6/2004 | Ecker et al. |
| 7,321,828 B2 | 1/2008 | Cowsert et al. | 2004/0117354 A1 | 6/2004 | Azzaro et al. |
| 7,349,808 B1 | 3/2008 | Kreiswirth et al. | 2004/0121309 A1 | 6/2004 | Ecker et al. |
| 7,390,458 B2 | 6/2008 | Burow et al. | 2004/0121310 A1 | 6/2004 | Ecker et al. |
| 7,419,787 B2 | 9/2008 | Koster et al. | 2004/0121311 A1 | 6/2004 | Ecker et al. |
| 7,501,251 B2 | 3/2009 | Koster et al. | 2004/0121312 A1 | 6/2004 | Ecker et al. |
| 7,666,588 B2 | 2/2010 | Ecker et al. | 2004/0121313 A1 | 6/2004 | Ecker et al. |
| 7,718,354 B2 | 5/2010 | Ecker et al. | 2004/0121314 A1 | 6/2004 | Ecker et al. |
| 7,741,036 B2 | 6/2010 | Ecker et al. | 2004/0121315 A1 | 6/2004 | Ecker et al. |
| 7,781,162 B2 | 8/2010 | Ecker et al. | 2004/0121329 A1 | 6/2004 | Ecker et al. |
| 2001/0039263 A1 | 11/2001 | Matthes et al. | 2004/0121335 A1 | 6/2004 | Ecker et al. |
| 2002/0006611 A1 | 1/2002 | Portugal et al. | 2004/0121340 A1 | 6/2004 | Ecker et al. |
| 2002/0028923 A1 | 3/2002 | Cowsert et al. | 2004/0122598 A1 | 6/2004 | Ecker et al. |
| 2002/0042112 A1 | 4/2002 | Koster et al. | 2004/0122857 A1 | 6/2004 | Ecker et al. |
| 2002/0042506 A1 | 4/2002 | Kristyanne et al. | 2004/0126764 A1 | 7/2004 | Lasken et al. |
| 2002/0045178 A1 | 4/2002 | Cantor et al. | 2004/0137013 A1 | 7/2004 | Katinger et al. |
| 2002/0055101 A1 | 5/2002 | Bergereon et al. | 2004/0161770 A1 | 8/2004 | Ecker et al. |
| 2002/0090320 A1 | 7/2002 | Burow et al. | 2004/0180328 A1 | 9/2004 | Ecker et al. |
| 2002/0120408 A1 | 8/2002 | Kreiswirth et al. | 2004/0185438 A1 | 9/2004 | Ecker et al. |
| 2002/0137057 A1 | 9/2002 | Wold et al. | 2004/0191769 A1 | 9/2004 | Marino et al. |
| 2002/0138210 A1 | 9/2002 | Wilkes et al. | 2004/0202997 A1 | 10/2004 | Ecker et al. |
| 2002/0150903 A1 | 10/2002 | Koster | 2004/0209260 A1 | 10/2004 | Ecker et al. |
| 2002/0150927 A1 | 10/2002 | Matray et al. | 2004/0219517 A1 | 11/2004 | Ecker et al. |
| 2002/0168630 A1 | 11/2002 | Fleming et al. | 2004/0253583 A1 | 12/2004 | Ecker et al. |
| 2002/0187490 A1* | 12/2002 | Tiedje et al. ............. 435/6 | 2004/0253619 A1 | 12/2004 | Ecker et al. |
| 2003/0017487 A1 | 1/2003 | Xue et al. | 2005/0026147 A1 | 2/2005 | Walker et al. |
| 2003/0027135 A1 | 2/2003 | Ecker et al. | 2005/0026641 A1 | 2/2005 | Hokao |
| 2003/0039976 A1 | 2/2003 | Haff | 2005/0027459 A1 | 2/2005 | Ecker et al. |
| 2003/0050470 A1 | 3/2003 | An et al. | 2005/0065813 A1 | 3/2005 | Michelevich et al. |
| 2003/0064483 A1 | 4/2003 | Shaw et al. | 2005/0130196 A1 | 6/2005 | Hofstadler |
| 2003/0073112 A1 | 4/2003 | Zhang et al. | 2005/0130216 A1 | 6/2005 | Becker et al. |
| 2003/0082539 A1 | 5/2003 | Ecker et al. | 2005/0142584 A1 | 6/2005 | Willson et al. |
| 2003/0084483 A1 | 5/2003 | Simpson et al. | 2005/0250125 A1 | 11/2005 | Novakoff |
| 2003/0101172 A1 | 5/2003 | De La Huerga | 2005/0266397 A1 | 12/2005 | Ecker et al. |
| 2003/0104410 A1 | 6/2003 | Mittmann | 2005/0266411 A1 | 12/2005 | Hofstadler et al. |
| 2003/0104699 A1 | 6/2003 | Minamihaba et al. | 2006/0020391 A1 | 1/2006 | Kreiswirth et al. |
| 2003/0113738 A1* | 6/2003 | Liu et al. ............. 435/6 | 2006/0057605 A1 | 3/2006 | Sampath et al. |
| 2003/0113745 A1 | 6/2003 | Monforte et al. | 2006/0121520 A1 | 6/2006 | Ecker et al. |
| 2003/0119018 A1 | 6/2003 | Omura et al. | 2006/0172330 A1 | 8/2006 | Osborn et al. |
| 2003/0124556 A1 | 7/2003 | Ecker et al. | 2006/0205040 A1 | 9/2006 | Sampath et al. |
| 2003/0125192 A1 | 7/2003 | Moon | 2006/0240412 A1 | 10/2006 | Hall et al. |
| 2003/0129589 A1 | 7/2003 | Koster et al. | 2006/0259249 A1 | 11/2006 | Sampath et al. |
| 2003/0134312 A1 | 7/2003 | Burgyone et al. | 2006/0275788 A1 | 12/2006 | Ecker et al. |
| 2003/0148281 A1 | 8/2003 | Glucksmann | 2007/0048735 A1 | 3/2007 | Ecker et al. |
| 2003/0148284 A1 | 8/2003 | Vision et al. | 2007/0218467 A1 | 9/2007 | Ecker et al. |
| 2003/0167133 A1 | 9/2003 | Ecker et al. | 2008/0160512 A1 | 7/2008 | Ecker et al. |
| 2003/0167134 A1 | 9/2003 | Ecker et al. | 2008/0311558 A1 | 12/2008 | Ecker et al. |
| 2003/0175695 A1 | 9/2003 | Ecker et al. | 2009/0004643 A1 | 1/2009 | Ecker et al. |
| 2003/0175696 A1 | 9/2003 | Ecker et al. | 2009/0023150 A1 | 1/2009 | Koster et al. |
| 2003/0175697 A1 | 9/2003 | Ecker et al. | 2009/0042203 A1 | 2/2009 | Koster et al. |
| 2003/0175729 A1 | 9/2003 | Van Eijk et al. | 2009/0092977 A1 | 4/2009 | Koster et al. |
| 2003/0186247 A1 | 10/2003 | Smarason et al. | 2009/0125245 A1 | 5/2009 | Hofstadler et al. |
| 2003/0187588 A1 | 10/2003 | Ecker et al. | 2009/0148836 A1 | 6/2009 | Ecker et al. |
| 2003/0187593 A1 | 10/2003 | Ecker et al. | 2009/0148837 A1 | 6/2009 | Ecker et al. |

| | | | |
|---|---|---|---|
| 2009/0182511 A1 | 7/2009 | Ecker et al. | |
| 2009/0239224 A1 | 9/2009 | Ecker et al. | |
| 2010/0070194 A1 | 3/2010 | Ecker et al. | |
| 2010/0145626 A1 | 6/2010 | Ecker et al. | |
| 2010/0184035 A1 | 7/2010 | Hall et al. | |

FOREIGN PATENT DOCUMENTS

| | | |
|---|---|---|
| CN | 1202204 | 12/1998 |
| DE | 19732086 | 1/1999 |
| DE | 19802905 | 7/1999 |
| DE | 19824280 | 12/1999 |
| DE | 19852167 | 5/2000 |
| DE | 19943374 | 3/2001 |
| DE | 10132147 | 2/2003 |
| EP | 0281390 | 9/1988 |
| EP | 0620862 | 10/1994 |
| EP | 0633321 | 11/1995 |
| EP | 1035219 | 9/2000 |
| EP | 1138782 | 10/2001 |
| EP | 1234888 | 8/2002 |
| EP | 1308506 | 5/2003 |
| EP | 1310571 | 5/2003 |
| EP | 1333101 | 8/2003 |
| EP | 1365031 | 11/2003 |
| EP | 1234888 A3 | 1/2004 |
| EP | 1748072 | 1/2007 |
| FR | 2811321 | 1/2002 |
| GB | 2325002 | 11/1998 |
| GB | 2339905 | 2/2000 |
| JP | 5-276999 | 10/1993 |
| JP | 11137259 A | 5/1999 |
| JP | 2004-200 | 1/2004 |
| JP | 2004-24206 | 1/2004 |
| JP | 2004-201641 | 7/2004 |
| JP | 2004-201679 | 7/2004 |
| WO | WO 88/03957 | 6/1988 |
| WO | WO 90/15157 | 12/1990 |
| WO | WO 92/08117 | 5/1992 |
| WO | WO 92/09703 | 6/1992 |
| WO | WO 92/05182 | 11/1992 |
| WO | WO 92/19774 | 11/1992 |
| WO | WO 93/03186 | 2/1993 |
| WO | WO9305182 A1 | 3/1993 |
| WO | WO 93/08297 | 4/1993 |
| WO | WO 94/16101 | 7/1994 |
| WO | WO 94/19490 | 9/1994 |
| WO | WO 94/21822 | 9/1994 |
| WO | WO 95/04161 | 2/1995 |
| WO | WO 95/11996 | 5/1995 |
| WO | WO 95/13395 | 5/1995 |
| WO | WO 95/13396 | 5/1995 |
| WO | WO95/31997 | 11/1995 |
| WO | WO9606187 A1 | 2/1996 |
| WO | WO 96/16186 | 5/1996 |
| WO | WO 96/29431 | 9/1996 |
| WO | WO 96/32504 | 10/1996 |
| WO | WO 96/35450 | 11/1996 |
| WO | WO 96/37630 | 11/1996 |
| WO | WO 97/33000 | 9/1997 |
| WO | WO 97/34909 | 9/1997 |
| WO | WO 97/37041 | 10/1997 |
| WO | WO 97/47766 | 12/1997 |
| WO | WO 98/03684 | 1/1998 |
| WO | WO 98/12355 | 3/1998 |
| WO | WO 98/14616 | 4/1998 |
| WO | WO 98/15652 | 4/1998 |
| WO | WO 98/20020 | 5/1998 |
| WO | WO 98/20157 | 5/1998 |
| WO | WO 98/20166 | 5/1998 |
| WO | WO 98/26095 | 6/1998 |
| WO | WO 98/31830 | 7/1998 |
| WO | WO 98/35057 | 8/1998 |
| WO | WO 98/40520 | 9/1998 |
| WO | WO 98/54751 | 12/1998 |
| WO | WO9854571 A1 | 12/1998 |
| WO | WO 99/05319 | 2/1999 |
| WO | WO 99/12040 | 3/1999 |
| WO | WO 99/13104 | 3/1999 |
| WO | WO 99/14375 | 3/1999 |
| WO | WO 99/29898 | 6/1999 |
| WO | WO 99/31278 | 6/1999 |
| WO | WO 99/57318 | 11/1999 |
| WO | WO 99/58713 | 11/1999 |
| WO | WO 99/60183 | 11/1999 |
| WO | WO0032750 A1 | 6/2000 |
| WO | WO0038636 A1 | 7/2000 |
| WO | WO 00/63362 | 10/2000 |
| WO | WO 00/66789 | 11/2000 |
| WO | WO0066762 A2 | 11/2000 |
| WO | WO0077260 A1 | 12/2000 |
| WO | WO0100828 A2 | 1/2001 |
| WO | WO 01/07648 | 2/2001 |
| WO | WO 01/12853 | 2/2001 |
| WO | WO0120018 A2 | 3/2001 |
| WO | WO 01/23604 | 4/2001 |
| WO | WO 01/23608 | 4/2001 |
| WO | WO 01/32930 | 5/2001 |
| WO | WO 01/40497 | 6/2001 |
| WO | WO 01/46404 | 6/2001 |
| WO | WO 01/51661 | 7/2001 |
| WO | WO 01/51662 | 7/2001 |
| WO | WO 01/57263 | 8/2001 |
| WO | WO 01/57518 | 8/2001 |
| WO | WO 01/73119 | 10/2001 |
| WO | WO 01/73199 | 10/2001 |
| WO | WO 01/77392 | 10/2001 |
| WO | WO0196388 A2 | 12/2001 |
| WO | WO 02/02811 | 1/2002 |
| WO | WO 02/10186 | 2/2002 |
| WO | WO 02/10444 | 2/2002 |
| WO | WO 02/18641 | 3/2002 |
| WO | WO 02/21108 | 3/2002 |
| WO | WO 02/22873 | 3/2002 |
| WO | WO 02/24876 | 3/2002 |
| WO | WO 02/50307 | 6/2002 |
| WO | WO 02/057491 | 7/2002 |
| WO | WO 02/070664 | 9/2002 |
| WO | WO 02/070728 | 9/2002 |
| WO | WO02070737 A2 | 9/2002 |
| WO | WO 02/077278 | 10/2002 |
| WO | WO 02/099034 | 12/2002 |
| WO | WO 02/099095 | 12/2002 |
| WO | WO 02/099129 | 12/2002 |
| WO | WO 02/099130 | 12/2002 |
| WO | WO 03/002750 | 1/2003 |
| WO | WO 03/008636 | 1/2003 |
| WO | WO03001976 A2 | 1/2003 |
| WO | WO 03/012058 | 2/2003 |
| WO | WO 03/012074 | 2/2003 |
| WO | WO 03/014382 | 2/2003 |
| WO | WO 03/016546 | 2/2003 |
| WO | WO 03/020890 | 3/2003 |
| WO | WO03018636 A2 | 3/2003 |
| WO | WO 03/033732 | 4/2003 |
| WO | WO 03/054162 | 7/2003 |
| WO | WO 03/054755 | 7/2003 |
| WO | WO 03/060163 | 7/2003 |
| WO | WO 03/075955 | 9/2003 |
| WO | WO 03/088979 | 10/2003 |
| WO | WO 03/093506 | 11/2003 |
| WO | WO 03/097869 | 11/2003 |
| WO | WO 03/100035 | 12/2003 |
| WO | WO 03/100068 | 12/2003 |
| WO | WO 03/102191 | 12/2003 |
| WO | WO 03/104410 | 12/2003 |
| WO | WO 2004/003511 | 1/2004 |
| WO | WO2004009849 A1 | 1/2004 |
| WO | WO 2004/011651 | 2/2004 |
| WO | WO 2004/013357 | 2/2004 |
| WO | WO 2004/040013 | 5/2004 |
| WO | WO 2004/044123 | 5/2004 |
| WO | WO 2004/044247 | 5/2004 |
| WO | WO 2004/052175 | 6/2004 |
| WO | WO 2004/053076 | 6/2004 |
| WO | WO 2004/053141 | 6/2004 |
| WO | WO 2004/053164 | 6/2004 |
| WO | WO 2004/060278 | 7/2004 |
| WO | WO 2004/070001 | 8/2004 |

| | | |
|---|---|---|
| WO | WO 2004/072230 | 8/2004 |
| WO | WO 2004/072231 | 8/2004 |
| WO | WO 2004/101809 | 11/2004 |
| WO | WO 2005/003384 | 1/2005 |
| WO | WO 2005/012572 | 2/2005 |
| WO | WO2005009202 A2 | 2/2005 |
| WO | WO 2005/024046 | 3/2005 |
| WO | WO2005036369 A2 | 4/2005 |
| WO | WO 2005/053141 | 6/2005 |
| WO | WO 2005/054454 | 6/2005 |
| WO | WO2005086634 A2 | 9/2005 |
| WO | WO 2005/075686 | 10/2005 |
| WO | WO 2005/091971 | 10/2005 |
| WO | WO 2005/098047 | 10/2005 |
| WO | WO2005116263 A2 | 12/2005 |
| WO | WO 2006/089762 | 8/2006 |
| WO | WO 2006/094238 | 9/2006 |
| WO | WO 2006/116127 | 11/2006 |
| WO | WO2006135400 A2 | 12/2006 |
| WO | WO2007014045 A2 | 2/2007 |
| WO | WO 2007/086904 | 8/2007 |
| WO | WO2008104002 A2 | 8/2008 |
| WO | WO 2008/118809 | 10/2008 |

OTHER PUBLICATIONS

Adzhar et al., "Universal oligonucleotides for the detection of infectious bronchitis virus by the polymerase chain reaction" Avian Pathology (1996) 25:817-836.

Agostini et al. "Complete genome of a JC virus genotype Type 6 from the brain of an African American with progressive multifocal leukoencephalopathy" (1998) 1:267-272.

Akalu et al., "Rapid identification of subgenera of human adenovirus by serological and PCR assays" *J. Virol Methods* (1998) 71:187-196.

Allaouchiche et al., "Clinical Impact of Rapid Oxacillin Susceptibility Testing Using a PCR Assay in *Staphylococcus aureus* Bactaeremia" J. Infect. (1999) 39(3):198-204.

Allawi, H.T. & Santa Lucia J., Jr. Thermodynamics and NMR of internal G.T. mismatches in DNA, Biochemistry, 36, 10581-94 (1997).

Altschul et al., J. Mol. Biol., 215, 403-410 (1990).

Altschul et al., Nucl. Acid Res., 25:3389-3402 (1997).

Alves-Silva, J. et al., "The Ancestry of Brazilian mtDNA Lineages," *Am. J. Hum. Genet.* (2000) 67:444-461.

Amano et al., "Detection of influenza virus: traditional approaches and development of biosensors" Anal. Bioanal. Chem. (2005) 381:156-164.

Amexis et al., "Quantitiative mutant analysis of viral quasispecies by chip-based matrix-assisted laser desorption/ionization of time-of-flight mass spectrometry" PNAS (2001) 98(21):12097-12102; Correction: 98(24):14186.

Anderson et al., "Sequence and organization of the human mitochondrial genome," *Nature* (1981) 290:457-465.

Anderson and Young, Quantitative Filter Hybridization in Nucleic Acid Hybridization (1985).

Andreasson et al., "Mitochondrial Sequence Analysis for Forensic Identification Using Pyrosequencing Technology" *BioTechniques* (2002) 32:124-133.

Anthony et al., "Use of the Polymerase Chain Reaction for Rapid Detection of High-Level Mupirocin Resistance in Staphylococci" Eur. J. Clin. Microbiol. Infect. Dis. (1999) 18(1):30-34.

Application for Grant by David Mitchell Lubmann dated Oct. 25, 1992 and Oct. 29, 1992.

Application for Continuation Grant by David Mitchell Lubmann dated Jun. 10, 1994 and Jun. 24, 1994.

Application for Grant by David Mitchell Lubmann dated Sep. 1, 1994 and Sep. 27, 1994.

Application for Continuation Grant by David Mitchell Lubmann dated Jun. 4, 1996 and Jun. 14, 1996.

U.S. Appl. No. 09/798,007 Office Communication Mailed Apr. 16, 2002.

U.S. Appl. No. 09/798,007 Office Communication Mailed Jun. 20, 2002.

U.S. Appl. No. 09/798,007 Office Communication Mailed Nov. 6, 2002.

U.S. Appl. No. 09/798,007 Office Communication Mailed Jan. 8, 2003.

U.S. Appl. No. 09/798,007 Office Communication Mailed Jan. 31, 2003.

U.S. Appl. No. 09/798,007 Office Communication Mailed Feb. 27, 2003.

U.S. Appl. No. 09/798,007 Office Communication Mailed May 20, 2003.

U.S. Appl. No. 09/798,007 Office Communication Mailed May 28, 2003.

U.S. Appl. No. 09/798,007 Office Communication Mailed Jul. 11, 2003.

U.S. Appl. No. 09/798,007 Office Communication Mailed Sep. 22, 2003.

U.S. Appl. No. 09/798,007 Office Communication Mailed Nov. 19, 2003.

U.S. Appl. No. 09/798,007 Office Communication Mailed Jun. 30, 2004.

U.S. Appl. No. 09/798,007 Office Communication Mailed Aug. 10, 2004.

U.S. Appl. No. 09/798,007 Office Communication Mailed Feb. 10, 2005.

U.S. Appl. No. 09/891,793 Office Communication Mailed Dec. 18, 2002.

U.S. Appl. No. 09/891,793 Office Communication Mailed May 19, 2003 interview summary report.

U.S. Appl. No. 09/891,793 Office Communication Mailed May 23, 2003.

U.S. Appl. No. 09/891,793 Office Communication Mailed Aug. 26, 2003.

U.S. Appl. No. 09/891,793 Office Communication Mailed Nov. 13, 2003.

U.S. Appl. No. 09/891,793 Office Communication Mailed Mar. 9, 2004.

U.S. Appl. No. 09/891,793 Office Communication Mailed Jun. 14, 2004.

U.S. Appl. No. 09/891,793 Office Communication Mailed Jul. 13, 2004.

U.S. Appl. No. 09/891,793 Office Communication Mailed Aug. 10, 2004.

U.S. Appl. No. 09/891,793 Office Communication Mailed Oct. 20, 2004.

U.S. Appl. No. 09/891,793 Office Communication Mailed Mar. 8, 2005.

U.S. Appl. No. 09/891,793 Office Communication Mailed May 19, 2005.

U.S. Appl. No. 09/891,793 Office Communication Mailed Aug. 11, 2005.

U.S. Appl. No. 09/891,793 Office Communication Mailed Mar. 16, 2006.

U.S. Appl. No. 09/891,793 Office Communication Mailed Jul. 12, 2006.

U.S. Appl. No. 09/891,793 Office Communication Mailed Sep. 13, 2006.

U.S. Appl. No. 09/891,793 Office Communication Mailed Nov. 20, 2006.

U.S. Appl. No. 09/891,793 Office Communication Mailed Jul. 22, 2008.

U.S. Appl. No. 10/156,608 Office Communication Mailed Apr. 1, 2004.

U.S. Appl. No. 10/156,608 Office Communication Mailed Aug. 10, 2004.

U.S. Appl. No. 10/156,608 Office Communication Mailed Oct. 14, 2004.

U.S. Appl. No. 10/156,608 Office Communication Mailed Nov. 19, 2004.

U.S. Appl. No. 10/156,608 Office Communication Mailed Dec. 9, 2004.

U.S. Appl. No. 10/156,608 Office Communication Mailed May 23, 2005.

U.S. Appl. No. 10/156,608 Office Communication Mailed May 26, 2005.

U.S. Appl. No. 10/156,608 Office Communication Mailed Jul. 20, 2005.
U.S. Appl. No. 10/156,608 Office Communication Mailed Sep. 15, 2005.
U.S. Appl. No. 10/156,608 Office Communication Mailed Jun. 2, 2006.
U.S. Appl. No. 10/323,438 Office Communication Mailed Nov. 20, 2003.
U.S. Appl. No. 10/323,438 Office Communication Mailed Jul. 26, 2004.
U.S. Appl. No. 10/325,527 Office Communication Mailed Dec. 3, 2003.
U.S. Appl. No. 10/325,527 Office Communication Mailed Aug. 16, 2004.
U.S. Appl. No. 10/325,527 Office Communication Mailed Mar. 11, 2005.
U.S. Appl. No. 10/326,642 Office Communication Mailed Nov. 21, 2003.
U.S. Appl. No. 10/326,642 Office Communication Mailed Jul. 14, 2004.
U.S. Appl. No. 10/418,514 Office Communication Mailed Sep. 29, 2005.
U.S. Appl. No. 10/418,514 Office Communication Mailed Feb. 27, 2006.
U.S. Appl. No. 10/418,514 Office Communication Mailed Mar. 27, 2007.
U.S. Appl. No. 10/418,514 Office Communication Mailed Dec. 6, 2007.
U.S. Appl. No. 10/418,514 Office Communication Mailed Apr. 15, 2008.
U.S. Appl. No. 10/418,514 Office Communication Mailed Jul. 1, 2008.
U.S. Appl. No. 10/418,514 Office Communication Mailed Mar. 23, 2009.
U.S. Appl. No. 10/418,514 Office Communication Mailed Sep. 29, 2009.
U.S. Appl. No. 10/660,122 Office Communication Mailed Mar. 17, 2006.
U.S. Appl. No. 10/660,122 Office Communication Mailed Jul. 6, 2006.
U.S. Appl. No. 10/660,122 Office Communication Mailed Sep. 19, 2006.
U.S. Appl. No. 10/660,122 Office Communication Mailed Apr. 20, 2007.
U.S. Appl. No. 10/660,122 Office Communication Mailed Sep. 19, 2007.
U.S. Appl. No. 10/660,122 Office Communication Mailed Mar. 21, 2008.
U.S. Appl. No. 10/660,122 Office Communication Mailed Jul. 9, 2008.
U.S. Appl. No. 10/660,122 Office Communication Mailed Sep. 17, 2008.
U.S. Appl. No. 10/660,996 Office Communication Mailed Feb. 28, 2006.
U.S. Appl. No. 10/660,996 Office Communication Mailed May 30, 2006.
U.S. Appl. No. 10/660,996 Office Communication Mailed Jul. 12, 2006.
U.S. Appl. No. 10/660,996 Office Communication Mailed Sep. 5, 2006.
U.S. Appl. No. 10/660,996 Office Communication Mailed Nov. 22, 2006.
U.S. Appl. No. 10/660,996 Office Communication Mailed Jul. 10, 2007 with associated Information Disclosure Statement filed Feb. 21, 2007.
U.S. Appl. No. 10/660,997 Office Communication Mailed Mar. 13, 2006.
U.S. Appl. No. 10/660,997 Office Communication Mailed May 26, 2006.
U.S. Appl. No. 10/660,997 Office Communication Mailed Sep. 18, 2006.
U.S. Appl. No. 10/660,997 Office Communication Mailed Nov. 21, 2006.
U.S. Appl. No. 10/660,997 Office Communication Mailed Apr. 26, 2007 with associated Information Disclosure Statement filed Feb. 20, 2007.
U.S. Appl. No. 10/660,998 Office Communication Mailed May 1, 2006.
U.S. Appl. No. 10/660,998 Office Communication Mailed Aug. 3, 2006.
U.S. Appl. No. 10/660,998 Office Communication Mailed Jan. 24, 2007.
U.S. Appl. No. 10/660,998 Office Communication Mailed Aug. 7, 2007.
U.S. Appl. No. 10/660,998 Office Communication Mailed Dec. 11, 2007.
U.S. Appl. No. 10/660,998 Office Communication Mailed Sep. 19, 2008.
U.S. Appl. No. 10/660,998 Office Communication Mailed Apr. 7, 2009.
U.S. Appl. No. 10/728,486 Office Communication Mailed Apr. 10, 2006.
U.S. Appl. No. 10/728,486 Office Communication Mailed Jul. 27, 2006.
U.S. Appl. No. 10/728,486 Office Communication Mailed Oct. 17, 2007.
U.S. Appl. No. 10/728,486 Office Communication Mailed Dec. 20, 2006.
U.S. Appl. No. 10/728,486 Office Communication Mailed May 11, 2007.
U.S. Appl. No. 10/728,486 Office Communication Mailed Jan. 23, 2008.
U.S. Appl. No. 10/728,486 Office Communication Mailed Nov. 3, 2008.
U.S. Appl. No. 10/754,415 Office Communication Mailed Mar. 13, 2006.
U.S. Appl. No. 10/754,415 Office Communication Mailed Aug. 28, 2006.
U.S. Appl. No. 10/754,415 Office Communication Mailed Nov. 17, 2006.
U.S. Appl. No. 10/754,415 Office Communication Mailed Feb. 27, 2007.
U.S. Appl. No. 10/754,415 Office Communication Mailed Aug. 30, 2007.
U.S. Appl. No. 10/754,415 Office Communication Mailed Oct. 10, 2007.
U.S. Appl. No. 10/754,415 Office Communication Mailed Jun. 12, 2008.
U.S. Appl. No. 10/754,415 Office Communication Mailed Jun. 4, 2009.
U.S. Appl. No. 10/829,826 Office Communication Mailed Jul. 6, 2007.
U.S. Appl. No. 10/829,826 Office Communication Mailed Apr. 4, 2008.
U.S. Appl. No. 10/829,826 Office Communication Mailed Dec. 10, 2008.
U.S. Appl. No. 10/844,938 Office Communication Mailed Feb. 2, 2007.
U.S. Appl. No. 10/844,938 Office Communication Mailed Aug. 7, 2007.
U.S. Appl. No. 10/844,938 Office Communication Mailed May 20, 2008.
U.S. Appl. No. 10/844,938 Office Communication Mailed Jan. 30, 2009.
U.S. Appl. No. 10/891,337 Office Communication Mailed Apr. 20, 2009.
U.S. Appl. No. 10/930,002 Office Communication Mailed Sep. 29, 2009.
U.S. Appl. No. 10/933,928 Office Communication Mailed Jun. 2, 2006.
U.S. Appl. No. 10/943,344 Office Communication Mailed Feb. 27, 2007.
U.S. Appl. No. 10/943,344 Office Communication Mailed May 21, 2008.
U.S. Appl. No. 10/943,344 Office Communication Mailed Feb. 23, 2009.

U.S. Appl. No. 10/943,344 Office Communication Mailed Oct. 14, 2009.
U.S. Appl. No. 11/059,776 Office Communication Mailed Jan. 19, 2007.
U.S. Appl. No. 11/059,776 Office Communication Mailed May 29, 2007.
U.S. Appl. No. 11/059,776 Office Communication Mailed Jan. 23, 2008.
U.S. Appl. No. 11/060,135 Office Communication Mailed Dec. 21, 2006.
U.S. Appl. No. 11/060,135 Office Communication Mailed Mar. 8, 2007.
U.S. Appl. No. 11/060,135 Office Communication Mailed Jul. 24, 2007.
U.S. Appl. No. 11/060,135 Office Communication Mailed Mar. 25, 2008.
U.S. Appl. No. 11/060,135 Office Communication Mailed Jan. 2, 2009.
U.S. Appl. No. 11/060,135 Office Communication Mailed Jul. 15, 2009.
U.S. Appl. No. 11/070,632 Office Communication Mailed Jun. 30, 2008.
U.S. Appl. No. 11/070,632 Office Communication Mailed Oct. 6, 2008.
U.S. Appl. No. 11/070,632 Office Communication Mailed Jul. 23, 2009.
U.S. Appl. No. 11/136,134 Office Communication Mailed Jun. 20, 2007.
U.S. Appl. No. 11/136,134 Office Communication Mailed Mar. 26, 2008.
U.S. Appl. No. 11/136,134 Office Communication Mailed Oct. 31, 2008.
U.S. Appl. No. 11/136,134 Office Communication Mailed Feb. 12, 2009.
U.S. Appl. No. 11/136,134 Office Communication Mailed May 21, 2009.
U.S. Appl. No. 11/210,516 Office Communication Mailed Jun. 8, 2007.
U.S. Appl. No. 11/210,516 Office Communication Mailed Oct. 19, 2007.
U.S. Appl. No. 11/233,630 Office Communication Mailed Jun. 8, 2007.
U.S. Appl. No. 11/233,630 Office Communication Mailed Jul. 13, 2007.
U.S. Appl. No. 11/233,630 Office Communication Mailed Apr. 16, 2008.
U.S. Appl. No. 11/233,630 Office Communication Mailed Oct. 2, 2008.
U.S. Appl. No. 11/331,978 Office Communication Mailed Nov. 15, 2007.
U.S. Appl. No. 11/331,978 Office Communication Mailed Aug. 15, 2008.
U.S. Appl. No. 11/331,978 Office Communication Mailed Oct. 17, 2008.
U.S. Appl. No. 11/331,978 Office Communication Mailed Jun. 2, 2008 (interview summary).
U.S. Appl. No. 11/331,987 Office Communication Mailed Jul. 16, 2007.
U.S. Appl. No. 11/331,987 Office Communication Mailed Oct. 22, 2007.
U.S. Appl. No. 11/331,987 Office Communication Mailed Jul. 9, 2008.
U.S. Appl. No. 11/331,987 Office Communication Mailed Nov. 20, 2009.
U.S. Appl. No. 11/404,561 Office Communication Mailed May 16, 2008.
U.S. Appl. No. 11/404,561 Office Communication Mailed Feb. 4, 2009.
U.S. Appl. No. 11/409,535 Office Communication Mailed Oct. 31, 2007.
U.S. Appl. No. 11/409,535 Office Communication Mailed Apr. 16, 2008.
U.S. Appl. No. 11/491,376 Office Communication Mailed Oct. 31, 2008.
U.S. Appl. No. 11/491,376 Office Communication Mailed Apr. 22, 2009.
U.S. Appl. No. 11/582,859 Office Communication Mailed Oct. 21, 2008.
U.S. Appl. No. 11/582,863 Office Communication Mailed Aug. 20, 2007.
U.S. Appl. No. 11/582,863 Office Communication Mailed Jun. 17, 2008.
U.S. Appl. No. 11/582,863 Office Communication Mailed Feb. 26, 2009.
U.S. Appl. No. 11/582,875 Office Communication Mailed Nov. 17, 2009.
U.S. Appl. No. 11/582,930 Office Communication Mailed Sep. 14, 2007.
U.S. Appl. No. 11/582,930 Office Communication Mailed May 2, 2008.
U.S. Appl. No. 11/582,930 Office Communication Mailed Oct. 24, 2008.
U.S. Appl. No. 11/582,930 Office Communication Mailed Jan. 16, 2009.
U.S. Appl. No. 11/582,930 Office Communication Mailed Jul. 2, 2009.
U.S. Appl. No. 11/685,598 Office Communication Mailed Aug. 18, 2009.
U.S. Appl. No. 11/754,163 Office Communication Mailed Jul. 28, 2009.
U.S. Appl. No. 11/754,169 Office Communication Mailed Aug. 25, 2009.
U.S. Appl. No. 11/754,174 Office Communication Mailed Aug. 3, 2009.
U.S. Appl. No. 11/754,182 Office Communication Mailed Jul. 2, 2009.
U.S. Appl. No. 11/929,707 Office Communication Mailed Jul. 17, 2009.
U.S. Appl. No. 11/929,707 Office Communication Mailed Oct. 2, 2009.
U.S. Appl. No. 12/211,641 Office Communication Mailed Apr. 17, 2009.
U.S. Appl. No. 12/326,800 Office Communication Mailed Oct. 21, 2009.
U.S. Appl. No. 90/010,209 Office Communication Mailed Jun. 27, 2008.
U.S. Appl. No. 90/010,209 Office Communication Mailed Jul. 22, 2008.
U.S. Appl. No. 90/010,210 Office Communication Mailed Jun. 27, 2008.
U.S. Appl. No. 90/010,210 Office Communication Mailed Jul. 22, 2008.
U.S. Appl. No. 90/010,447 Office Communication Mailed Apr. 24, 2009.
U.S. Appl. No. 90/010,447 Office Communication Mailed Mar. 12, 2009.
U.S. Appl. No. 90/010,447 Office Communication Mailed Oct. 29, 2009.
U.S. Appl. No. 90/010,448 Office Communication Mailed Apr. 24, 2009.
U.S. Appl. No. 90/010,448 Office Communication Mailed Mar. 12, 2009.
Arbique et al., "Comparison of the Velogene Rapid MRSA Identification Assay, Denka MRSA-Screen Assay, and BBL Crystal MRSA ID System for rapid identification of methicillin-resistant *Staphylococcus aureus*" Diagn. Microbiol. Infect. Dis. (2001) 40(1-2):5-10.
Archer, G. L. et al., "Detection of Methicillin Resistance in Staphylococci by Using a DNA Probe," *Antimicrob. Agents Chemother.* (1990) 34(9): 1720-1724.
Armstrong, P. et al., "Sensitive and Specific Colorimetric Dot Assay to Detect Eastern Equine Encephalomyelitis Viral RNA in Mosquitoes After PCR Amplification" J. Med, Entomol. (1995) 32(1): 42-52.
Arnal et al., "Quantification of Hepatitis A virus in shellfish by competitive reverse transcription PCR with coextraction of standard RNA" Applied and Environmental Microbiology, American Society for Microbiology (1999) 65(1):322-326.

Aronsson et al., Persistence of the influenza A/WSN/33 virus RNA at midbrain levels of immunodefective mice, Online Publication Date: Apr. 1, 2001, Journal of the NeuroVirology 7:117-124, 2001.

Ausubel et al., Current Protocols in Molecular Biology (Relevant portions of the book).

Avellon et al. "Rapid and sensitive diagnosis of human adenovirus infections by a generic polymerase chain reaction" *J. Virol. Methods* (2001) 92:113-120.

Azevedo et al. "Detection of influenza, parainfluenza, adenovirus and respiratory syncytial virus during asthma attacks in children older than two years old." Allergol. Immunopathol. (2003) 31:311-317.

Baba et al., "Genome and virulence determinants of high virulence community-acquired MRSA" Lancet (2002) 359:1819-1827.

Bahrmand et al., "Polymerase chain reaction of bacterial genomes with single universal primer: application to distinguishing mycobacteria species" *Molecular and Cellular Probes* (1996) 10:117-122.

Bahrmand et al., "Use of restriction enzyme analysis of amplified DNA coding for the hsp65 gene and polymerase chain reaction with universal primer for rapid differentiation of *Mycobacterium* species in the clinical laboratory" *Scandinavian Journal of Infectious Diseases* (1998) 30:477-480.

Bai, J, T.H. Liu and D.M.. Lubman, "Matrix-Assisted Laser Desorption/Ionization Mass Spectrometry of Restriction Enzyme-Digested Plasmid DNA Using an Active Nafion Substrate," 8 Rapid Commun. Mass Spectrom. 687-691 (1994) ('787 reexamination).

Baker et al., "Review and re-analysis of domain-specific 16S primers" *J. Microbiol. Methods* (2003) 55:541-555.

Banik et al. "Multiplex PCR assay for rapid identification of oculopathogenic adenoviruses by amplification of the fiber and hexon genes" *J. Clin. Microbiol* (2005) 43:1064-1068.

Barbour et al. "Identification of an uncultivatable *Borrelia* species in the hard tick *Amblyomma americanum*: Possible agent of a Lyme disease-like illness" The Journal of Infectious Diseases (1996) 173:403-409.

Barns et al., "Detection of diverse new *Francisella*-like bacteria in environmental samples." Applied and Environmental Microbiology (2005) 71:5494-5500.

Baron, E. J., "Genetic Aspects of Methicillin Resistance in *Staphylococcus aureus* and Methods Used for its Detection in Clinical Laboratories in the United States," *J. Chemother*. (1995) 7(Suppl. 3): 87-92.

Barr et al., "An Influenza A(H3) Reassortant Was Epidemic in Australia and New Zealand in 2003" J. Med. Virol. (2005) 76:391-397.

Barski, P. et al., "Rapid assay for detection of methicillin-resistant *Staphylococcus aureus* using multiplex PCR," *Mol. Cell Probes* (1996) 10:471-475.

Bastia et al., "Organelle DNA analysis of *Solanum* and *Brassica* somatic hybrids by PCR with 'universal primers'." *Theoretical and Applied Genetics* (2001) 102:1265-1272.

Batey et al., "Preparation of Isotopically Labeled Ribonucleotides for Multidimensional NMR Spectroscopy of RNA" *Nucleic Acids Research* (1992) 20:4515-4523.

Baumer et al., "Age-related Human mtDNA Deletions: A Heterogeneous Set of Deletions Arising at a Single Pair of Directly Repeated Sequences" *Am. J. Hum. Genet.* (1994) 54:618-630.

Beall, B., et al. "Survey of emm Gene Sequences and T-Antigen Types from Systemic *Streptococcus pyogenes* Infection Isolates Collected in San Francisco, California; Atlanta, Georgia; and Connecticut in 1994 and 1995" (1997), J. Clin. Micro. 35, 1231-1235.

Beall et al., "Sequencing emm-Specific PCR Products for Routine and Accurate Typing of Group A Streptococci" (1996) J. Clin. Micro. 34, 953-958.

Benko, M. et al., "Family Adenoviridae", Virus taxonomy, VIIIth report of the International Committee on Taxonomy of Viruses (2004) Fauquet, C.M. et al. (Eds.) Academic Press, New York, pp. 213-228.

Benson et al., "Advantages of *Thermococcus kodakaraenis* (KOD) DNA polymerase for PCR-mass spectrometry based analyses" *J. Am. Soc. Mass Spectrom.* (2003) 14:601-604.

Berencsi, G. et al., "Molecular Biological Characterization of Adenovirus DNA", Acta Microbiol. Immunol. Hung, 1998, vol. 45, Nos. 3-4; pp. 297-304.

Bisno, A.L. (1995) "*Streptococcus pyogenes*," Infectious Diseases and Their Etiologic Agents in "Principles and Practice of Infectious Diseases", eds., Mandell, G.L., Bennett, J.E. & Dolin, R. (Churchill Livingston, New York), vol. 2, pp. 1786-1799.

Black et al., "Detection of trace levels of tricothecene mycotoxins in human urine by gas chromatography-mass spectrometry" *J. Chromatog* (1986) 367:103-115.

Blaiotta, G. et al., "PCR detection of staphylococcal enterotoxin genes in *Staphyiococcus* spp. strains isolated from meat and dairy products. Evidence for new variants of seG and sel in *S. aureus* AB-8802," *J. Appl. Microbiol.* (2004) 97:719-730.

BLAST Search results (Mar. 2006).

Boivin-Jahns et al., "Bacterial Diversity in a Deep-Subsurface Clay Environment" *Applied and Environmental Microbiology* (1996) 62:3405-3412.

Bolton and McCarthy, Proc. Natl. Acad. Sci. U.S.A., 48, 1390 (1962).

Bont, Thomas et al., "Matrix-assisted laser desorption/ionization time-of-flight mass spectrometry-based detection of microsatellite instabilities in coding DNA sequences: a novel approach to identify DNA-mismatch repair-deficient cancer cells," Clinical Chemistry, 49(4):552-561 Apr. 2003.

Borrow et al., "SiaD PCR Elisa for confirmation and identification of serogroup Y and W135 meningococcal infections" *FEMS Microbiological Letters* (1998) 159:209-214.

Boubaker, K. et al., "Panton-Valentine Leukocidin and Staphylococcal Skin Infections in Schoolchildren," *Emerg.Infct. Dis.* (2004) 10(1):121-124.

Bowen et al., "The native virulence plasmid combination affects the segregational stability of a theta-replicating shuttle vector in *Bacillus anthracis* var, New Hampshire" *J. Appl. Microbiol.* (1999) 87:270-278.

Bowers, K. M. et al., "Screening for methicillin resistance in *Staphylococars aureus* and coagulase-negative staphylococci: evaluation of three selective and Mastalex-MRSA latex agglutination," *Br. J. Biomed. Sci.* (2003) 60(2):71-74.

Brakstad, O. G, et al., "Multiplex polylnerase chain reaction for detection of genes for *Staphylococcus aureus* themonuclease and methicillin resistance and correlation with oxacillin resistance," *APMIS* (1993) 101:681-688.

Brakstad, O. G. et al., "Direct identification of *Staphylococcus aureus* in blood cultures by detection of the gene, encoding the thermostable nuclease or the gene product," *APMIS* (1995) 103:209-218.

Brandt, C.D., et al., "Infections in 18,000 Infants and Children in a Controlled Study of Respiration Tract Disease. I. Adenovirus Pathogenicity in Relation to Serologic Type and Illness Syndrome," Am. J. Epidemio.; 1969, vol. 90, No. 6, pp. 484-500.

Brayshaw, D. P., "Methicillin-resistant *Staphylococcus aureus*: evaluation of detection techniques on laboratory-passaged organisms," *Br. J Biomed. Sci.* (1999) 56:170-176.

Brightwell et al., "Development of internal controls for PCR detection of *Bacillus anthracis*" Molecular and Cellular Probes (1998) 12(6):367-377.

Brightwell, G. et a., "Genetic targets for the detection and identifiaction of Venezuelan equine encephalitis viruses," Arch. Virol (1998) 143(4): 731-742.

Bronzoni, R. V. M. et al., "Multiplex nested PCR for Brazilian *Alphavirus* diagnosis," *Trans. R. Soc. Trop. Med. Hyg.* (2004) 98(8): 456-461.

Bronzoni, R. V. M. et al., "Duplex Reverse Transcription-PCR Followed by Nested PCR Assats for Detection and Identification of Brazilan Alphaviruses and Flaviviruses." *J. Clin. Microbiol.* (2005) 43(2): 696-702.

Brown, "Advances in Molecular Diagnostics for Avian Influenza" Dev. Biol. (2006) 124:93-97.

Brownstein et al., "Modulation of Non-Templated Nucleotide Addition by Taq DNA Polymerase: Primer Modifications that Facilitate Genotyping" BioTechniques (1996) 20:1004-1010.

Brunaud et al., "T-DNA integration into the *Arabidopsis* genome depends on sequences of pre-insertion sites" EMBO Rep. (2002) 3(12):1152-1157.

Buck et al., "Design Strategies and Performance of Custom DNA Sequencing Primers" Biotechniques (1999) 27:528-536.

Butel et al. "Cell and molecular biology of simian virus 40: implications for human infections and diseases" J. Natl. Cancer Institute (1999) 91(2):119-134.

Butler "DNA profiling and quantitation of human DNA" CCQM BAWG 04122005.

Campbell et al., "Detection of California serogroup Bunyaviruses in tissue culture and mosquito pools by PCR" *J. Virol. Methods* (1996) 57:175-179.

Carracedo et al., "DNA commission of the international society for forensic genetics: guidelines for mitochondrial DNA typing" *Forensic Science International* (2000) 110:79-85.

Carroll, K. C. et al., "Rapid Detection of the Staphylococcal *mecA* Gene from BACTEC Blood Culture Bottles by the Polymerase Chain Reaction," *Am. J. Clin. Pathol.* (1996) 106:600-5.

Case et al., "Maternal inheritance of mitochondrial DNA polymorphisms in cultured human fibroblasts," *Somatic Cell Genetics* (1981) 7:103-108.

Cattoli et al., "Comparison of three rapid detection systems for type A influenza virus on tracheal swabs of experimentally and naturally infected birds" Avian Pathology (2004) 33(4):432-437.

Cavassini, M. et al., "Evaluation of MRSA-Screen, a Simple Anti-PBP 2a Slide Latex Agglutination Kit, for Rapid Detection of Methicillin Resistance in *Staphylococcus aureus*," *J. Clin. Microbial.* (1999) 37(5): 1591-1594.

Cespedes et al., "Polymerase chain reaction restriction fragment length polymorphism analysis of a short fragment of the cytochrome b gene for identification of flatfish species" *J. Food Protection* (1998) 61:1684-1685.

Chamberlin et al., "New RNA polymerase from *Escerichia coli* infected with bacteriophage T7" Nature 228:227 (1970).

Chandra, S. et al., "Virus reduction in the preparation and intravenous globulin: in vitro experiments," *Transfusion* (1999) 39(3): 249-257.

Chang, P.-K. et al., "aflT, a MFS transporter-encoding gene located in the aflatoxin gene cluster, does not have a significant role in aflatoxin secretion," Fungal Genet.Biol. (2004) 41:911-920.

Chaves, F. et al., "Molecular Characterization of Resistance to Mupirocin in Methidlin-Susceptible and -Resistant Isolates of *Staphylococcus aureus* from Nasal Samples," *J. Clin. Microbiol.* (2004) 42(2):822-824.

Chelly et al., "Transcription of the dystrophin gene in human muscle and non-muscle tissue" Nature (1988) 333(6176):858-860.

Chen et al., "Universal primers for amplification of mitochondrial small subunit ribosomal RNA-encoding gene in scleractinian corals" *Marine Biotechnology* (2000) 2:146-153.

Chen et al., "A universal PCR primer to detect members of the Potyviridae and its use to examine the taxonomic status of several members of the family" *Archives of Virology* (2001) 146:757-766.

Chen, Y. Z. et al., "A BAC-Based STS-Content Map Spanning a 35-Mb Region of Human Chromosome 1p35-36," Genomics (2001) 74(1):55-70.

Chen, N. et al., "The genomic sequence of ectromelia virus, the causative agent of mousepox," *Virology* (2003) 317:165-186.

Chen et al., "Genetic mapping of the cold-adapted phenotype of B/Ann Arbor/1/66, the master donor virus for live attenuated influenza vaccines (FluMist)" Virology (2006) 345:416-423.

Chen, CH, K. Tang, N. Taranenko and S. Allman, "Laser Desorption Mass Spectrometry for Fast DNA Sequencing," (Nov. 1994), http://www.ornl.gove/sci/techresources/Human_Genome/publicat/94SANTA/sequencing/seqtoc.shtml ('787 reexamination).

Chmielewicz, B. et al., "Development of a PCR-Based Assay for Detection, Quantification, and Genotyping of Human Adenoviruses," Clin. Chem., 2005, vol. 51, No. 8, pp. 1365-1373.

Cho et al., "Application of the ribonuclease P (RNase P) RNA gene sequence for phylogenetic analysis of the gene *Saccharomonospora*" *International Journal of Systematic Bacteriology* (1998) 48:1223-1230.

Choi et al., "Detection and subtying of swine influenza H1N1, H1N2 and H3N2 viruses in clinical samples using two multiplex RT-PCR assays" J. Virol. Methods (2002) 102:53-59.

Choi, S. et al., "Real-Time PCR Quantification of Human Adenoviruses in Urban Rivers Indicates Genome Prevalence but Low Infectivity," Appl. Environ. Microbiol., 2005, vol. 71, No. 11, pp. 7426-7433.

Christel, LA et al., "Rapid, Automated Nucleic Acid Probe Assays Using Silicon Microstructures for Nucleic Acid Concentration" J. Biomech. Eng., 1999, 121, 22-27.

Claas, E.C.J. et al., "Internally Controlled Real-Time PCT Monitoring of Adenovirus DNA Load in Serum or Plasma of Transplant Recipients," J. Clin. Microbiol., 2005, vol. 43, No. 4, pp. 1738-1744.

Cloney, L. et al., "Rapid detection of *mecA* in methicillin resistant *Stuphylococcus aureus* using cycling probe technology," *Mol. Cell Probes* (1999) 13:191-197.

Conrads et al., "16S-23S rDNA internal transcribed spacer sequences for analysis of the phylogenetic relationships among species of the genus *Fusobacterium*" *International Journal of Systematic and Evolutionary Microbiology* (2002) 52:493-499.

Contreras-Salazar et al. "up regulation of the Epstein-Barr virus (EBV)-encoded membrane protein LMP in the Burkitt's lymphoma line Daudi after exposure to n-Butyrate and after EBV superinfection" J. Virol. (1990) 64(11):5441-5447.

Cornel et al., "Polymerase chain reaction species diagnostic assay for *Anopheles quadrimaculatus* cryptic species (Diptera: Culicidae) based on ribosomal DNA ITS2 sequences" *Journal of Medical Entomology* (1996) 33:109-116.

Couto, I. et al., "Devetopment of Methicillin Resistance in Clinical Isolates of *Staphylococcus sciuri* by Transcriptional Activation of the *mecA* Homologue Native to the Species," *J. Bacteriol.* (2003) 185(2):645-653.

Crain et al., "Applications of mass spectrometry of the characterization of oligonucleotides and nucleic acids" *Curr. Opin. Biotechnol.* (1998) 9:25-34.

Crawford-Miksza, L.K. et al., "Analysis of 15 Adenovirus Hexon Proteins Reveals the Location and Structure of Seven Hypervariable Regions Containing Serotype-Specific Residues," J. Virol., 1996, vol. 70, No. 3, pp. 1836-1844.

Crawford-Miksza, L.K. et al., "Adenovirus Serotype Evolution is Driven by Illegitimate Recombination in the Hypervariable Regions of the Hexon Protein," Virol., 1996, vol. 224, pp. 357-367.

Crawfor-Miksza et al., "Strain variation in adenovirus serotypes 4 and 7a causing acute respiratory disease." (1999) 37:1107-1112.

Crespillo et al., "Mitochondrial DNA sequences for 118 individuals from northeastern Spain" *Int. J. Legal Med.* (2000) 114:130-132.

Cui, L. et al., "Contribution of a Thickened Cell Wall and Its Glutamine Nonamidated Component to the Vancomycin Resistance Expressed by *Staphylococcus aureus* Mu50," *Antimicrob. Agents Chemother.* (2000) 44(9):2276-2285.

Dasen et al., "Classification and identification of Propionibacteria based on 16S ribosomal RNA genes and PCR" *Systematic and Applied Microbiology* (1998) 21:251-259.

De Sousa, M. A. et al., "Bridges from hospitals to the laboratory: genetic portraits of methicillin-resistant *Staphylococcus aureus* clones," *FEMS Immunol. Med. Microbiol.* (2004) 40:101-111.

Deforce et al., "Analysis of oligonucleotides by ESI-MS" *Advances in Chromatography* (2000) 40:539-566.

Deforce et al., "Characterization of DNA Oligonucleotides by Coupling of Capillary Zone Electrophoresis to Electrospray Ionization Q-TOF Mass Spectrometry" *Analytical Chemistry* (1998) 70:3060-3068.

De Jong, J.C. et al., "Adenoviruses from Human Immunodeficiency Virus-Infected Individuals, Including Two Strains That Represent New Candidate Serotypes Ad50 and Ad51 of Species B1 and D, Respectively," J. Clin. Microbiol., 1999, vol. 37, No. 12, pp. 3940-3945.

De La Puente-Redondo et al., "Comparison of different PCR approaches for typing of *Francisella tularensis* strains." (2000) 38:1016-1022.

Del Blanco et al., "Genotyping of *Francisella tularensis* strains by pulsed-field gel electrophoresis, amplified fragment length polymorphism fingerprinting, and 16S rRNA gene sequencing." (2002) 40:2964-2972.

Del Vecchio, V. G. et al., "Molecular Genotyping of Methicillin-Resistant *Staphylococcus aureus* via Fluorophore-Enhanced Repetitive-Sequence PCR," *J. Clin. Microbiol.* (1995) 33(8):2141-2144.

Demesure et al., "A set of universal primers for amplification of polymorphic non-coding regions of mitochondrial and chloroplast DNA in plants" *Molecular Ecology* (1995) 4:129-131.

Denis et al., "Development of a semiquantitative PCR assay using internal standard and colorimetric detection on microwell plate for pseudorabies virus" Mol. Cell. Probes (1997) 11(6):439-448.

Deurenberg et al., "Rapid detection of Panton-Valentine leukocidin from clinical isolates of *Staphylococcus aureus* strains by real-time PCR" FEMS Microbiol. Lett. (2004) 240(2):225-228.

Deurenberg et al., "The prevalence of the *Staphylococcus aureus* tst gene among community- and hospital-acquired strains and isolates from Wegener's Granulomatosis patients" FEMS Microbiol. Lett. (2005) 245:185-189.

Dias Neto et al., "Shotgun sequencing of the human transcriptome with ORF expressed sequence tags" *PNAS* (2000) 97:3491-3496.

Di Guilmi, A.M. et al., "Human adenovirus serotype 3 (Ad3) and the Ad3 fiber p[protein bind to a 130-kDa membrane protein on HeLa cells," Virus Res., 1995, vol. 38, pp. 71-81.

Diep, B. A. et al., "Complete genome sequence of USA300, an epidemic clone of community acquired meticillin-resistant *Staphylococcus aureus*," *Lancet* (2006) 367:731-739.

Dinauer et al., "Sequence-based typing of HLA class II DQB1" *Tissue Anigens* (2000) 55:364-368.

Ding et al., "A high-throughput gene expression analysis technique using competitive PCR and matrix-assisted laser desorption ionization time-of-flight MS" PNAS (2003) 100(6):3059-3064.

Donehower, et al., "The use of primers from highly conserved pol regions to identify uncharacterized retroviruses by the polymerase chain reaction," J. Vir. Methods (1990) 28:33-46.

Donofrio et al., "Detection of influenza A and B in respiratory secretions with the polymerase chain reaction" PCR methods and applications, Cold Spring Harbor Lab. Press vol. 1, No. 4, (1992) pp. 263-268.

Doty et al., Proc. Natl. Acad. Sci. USA 46:461 (1960).

Drosten et al., New England Journal of Medicine, 2003, 348.

Dubernet et al., "A PCR-based method for identification of *Lactobacilli* at the genus level" *FEMS Microbiology Letters* (2002) 214:271-275.

EBI Accession No. AEM14131 (Jan. 11, 2007)—Bacterial DNA PCR Primer SEQ ID No. 874.

Ebner, K. et al., "Molecular Detection and Quantitative Analysis of the Entire Spectrum of Human Adenoviruses by a Two-Reaction Real-Time PCR Assay," J. Clin. Microbiol., 2005, vol. 43, No. 7, pp. 3049-3053.

Ebner et al., "Typing of human adenoviruses in specimens of immunosuppressed patients by PCR-fragment length analysis and real-time quantitative PCR" Journal of Clinical Microbiology (2006) 44:2808-2815.

Echavarria, M. et al., "PCR Method for Detection of Adenovirus in Urine of Healthy and Human Immunodeficiency Virus-Infected Individuals," J. Clin. Microbiol., 1998, vol. 36, No. 11, pp. 3323-3326.

Echavarria, M. et al., "Detection of Adenoviruses (AdV) in Culture-Negative Environmental Samples by PCR During an AdV-Associated Respiratory Disease Outbreak," J. Clin. Microbiol., 2000, vol. 38, No. 8, pp. 2982-2984.

Echavarria, M. et al., "Prediction of severe disseminated adenovirus infection by serum PCR," Lancet, 2001, vol. 358, pp. 384-385.

Echavarria, M. et al., "Rapid Detection of Adenovirus in Throat Swab Specimens by PCR During Respiratory Disease Outbreaks among Military Recruits", J. Clin. Microbiol., 2003, vol. 41, No. 2, pp. 810-812.

Echavarria, M. et al., "Use of PCR to demonstrate of Adenovirus Species B, C, of F as Well as Coinfection with Two Adenovirus Species in Children with Flu-Like Symptoms", J. Clin. Microbiol, 2006, vol. 44, No. 2, pp. 625-627.

Ecker et al., "Rapid identification and strain-typing of respiratory pathogens for epidemic surveillance" PNAS (2005) 102(22):8012-8017.

Ecker et al., "The Ibis T5000 Universal Biosensor: An Automated Platform for Pathogen Identification and Strain Typing" JALA (2006) 11 :341-351.

Edwards, K.M. et al., "Adenovirus Infections in Young Children", Pediatrics, 1985, vol. 76, No. 3, pp. 420-424.

Ellis et al., "Molecular diagnosis of influenza" Rev. Med. Virol. (2002) 12(6):375-389.

Elnifro et al., "PCR and Restriction Endonuclease Analysis for Rapid Identification of Adenovirus Subgenera" *Journal of Clinical Microbiology* (2000) 38:2055-2061.

Elsayed, S. et al., "Development and Validation of a Molecular Beacon Probe-Based Real-Time Polymerase Chain Reaction Assay for Rapid Detection of Methicillin Resistance in *Staphylococcus aureus* ," Arch. Pathol. Lab. Med. (2003) 127:845-849.

EMBL Accession No. S90302, Human, Muscle, Mitochondrial Mutant, 22 nt, segment 2 of 2 (XP002436791) Nov. 26, 1993.

EMBL Accession AJ552897 (Mar. 29, 2003).

EMBL Accession AR321656 (Aug. 12, 2003).

EMBL Accession L15697 (Mar. 4, 2000).

EMBL Accession AB068711 (May 21, 2003).

EMBL Accession Z48571 (Jun. 9, 1995).

Enright, M. C, et al., "Multilocus Sequence Typing for Characterization of Methicillin-Resistant and Methicillin-Susceptible Clones of *Staphylococcus aureus*," *J. Clin. Microbial.* (2000) 38(3): 1008-1015.

Enright, M. C. et al., "The evolutionary history of methicillin-resistant *Staphylococcus aureus* (MRSA)," PNAS(2002) 99(11): 7687-7692.

Enright, M. C. et al., "The evolution of a resistant pathogen—the case of MRSA," *Curr. Opin. Pharmacol.* (2003) 3:474-479.

Enright, M.C., et al., "Multilocus Sequence Typing of *Streptococcus pyogenes* and the Relationships between emm Type and Clone" Infection and Immunity, 2001, 69, 2416-2427.

Eremeeva et al., "Evaluation of a PCR Assay for Quantitation of *Rickettsia rickettsii* and Closely Related Spotted Fever Group Rickettsiae" J. Clin. Microbiol. (2003) 41(12):5466-5472.

Erlich (ed.). PCR Technology, Stockton Press (1989).

Esmans et al., "Liquid Chromatography-Mass Spectrometry in Nucleoside, nucleotide and modified nucleotide characterization" *J. of Chromatography A* (1998) 794:109-127.

Evans & Wareham, "Practical Algorithms for Universal DNA Primer Design: An Exercise in Algorithm Engineering".

European Patent Office Communication 96(2) EPC for 02709785.6 dated Nov. 20, 2006.

European Patent Office Communication 94(3) EPC for 02709785.6 dated Nov. 4, 2009.

European Patent Office Communication for 06849755.1 dated Mar. 12, 2008.

European Patent Office Communication for 07760292.8 dated Apr. 7, 2009.

European Search Report for 02709785.6 dated Oct. 10, 2005.

European Supplemental Search Report for 03796752.8 dated Aug. 14, 2007.

European Supplemental Search Report for 03810055.8 dated Jul. 9, 2007.

European Supplemental Search Report for 02709785.6-2405 (PCT/US0206763) dated Oct. 12, 2005.

European Supplemental Search Report for 04752257.8 dated Feb. 15, 2006.

European Supplemental Search Report for 05751872.2 dated Jan. 28, 2008.

European Supplemental Search Report for 05753037 dated Aug. 28, 2009.

European Supplemental Search Report for 05856582.1 dated Nov. 10, 2008.

European Supplemental Search Report for 04775904.8 dated Jul. 25, 2008.

Facklam, R., et al., "emm Typing and Validation of Provisional M Types for Group A Streptococci" (1999) Emerging Infectious Diseases, 5, 247-253.

Fang, H. et al., "Rapid Screening and Identification of Methicillin-Resistant *Staphylococcus aureus* from Clinical Samples by Selective-Broth and Real-Time PCR Assay," *J. Clin. Microbial.* (2003) 41 (7):2894-2899.

Farlow et al., "*Francisella tularensis* Strain Typing Using Multiple-Locus, Variable-Number Tandem Repeat Analysis" Journal of Critical Microbiology, (2001) 39(9):3186-3192.

Farrell, D. J., "The Reliability of Microscan Conventional and Rapid Panels to Identify *Staphylococcus aureus* and Detect Methicillin Resistance: an Evaluation Using the Tube Coagulase Test and *mec* A PCR," *Pathology* ( 1997) 29:406-410.

Fedele C G et al., "Multiplex polymerase chain reaction for the simultaneous detection and typing of polyomavirus JC, BK, and SV40 DNA in clinical samples", Journal of Virological Methods, 82(2), Oct. 1999, pp. 137-144.

Fedele C G et al., "Quantitation of polyomavirus DNA by a competitive nested polymerase chain reaction," Journal of Virological Methods, 88(1):51-61 (Jul. 2000).

Feng, P., "Impact of molecular biology on the detection of food pathogens" Mol. Biotechnol., 1997, 7, 267-278.

Figueiredo et al., "Identification of Brazilian flaviviruses by a simplified reverse transcription-polymerase chain reaction method using *Flavivirus* universal primers" *American Journal of Tropical Medicine and Hygiene* (1998) 59:357-362.

Flora, et al., "Dual-micro-ESI source for precise mass determination on a quadrupole time-of-flight mass spectrometer for genomic and proteomic applications" *Anal. Bioanal. Chem.* (2002) 373:538-546.

Fong, W. K., et al., "Rapid Solid-Phase Immunoassay for Detection of Methicillin-Resistant *Staphylococcus aureus* Using Cycling Probe Technology." *J. Clin. Microbiol.* (2000) 38(7): 2525-2529.

Fox et al., "Identification and Detection of Bacteria: Electrospray MS-MS Versus Derivatization/GC-MS" *Proceedings of the ERDEC Scientific Conference on Chemical and Biological Defense Research* (1994) 39-44.

Fox et al., "Identification of *Brucella* by Ribosomal-spacer-region PCR and differentiation of, *Brucella canis* from other *Brucella* spp. pathogenic for humans by carbohdrate profiles" *Journal of Clinical Microbiology* (1998) 36:3217-3222.

Fox et al., "Report of the 'Bioterrorism Workshop' Duke University Thomas Center on Apr. 24, 2002 organized by US Army Research Office" *Journal of Microbiological Methods* (2002) 51 :247-254.

Fox, J.P. et al., "The Virus Watch Program: A Continuing Surveillance of Viral Infections in Metropolitan New York Families", Am. J. Epidemiol., 1969, vol. 89, No. 1, pp. 25-50.

Francois et al. "Sequence-specific recognition and cleavage of duplex DNA via triple-helix formation by oligonucleotides covalently linked to a phenanthroline-copper chelate" Proc. Natl. Acad. Sci. USA (1989) 86:9702-9706.

Francois, P. et al., "Rapid Detection of Methicillin-Resistant *Staphylococcus aureus* Directly from Sterile or Nonsterile Clinical Samples by a New Molecular Assay," *J. Clin. Microbiol.* (2003) 41(1):254-260.

Fraser et al., "The Minimal Gene Complement of *Mycoplasma genitalium*" *Science* (1995) 270:397-403.

Freiberg et al. Genome-wide mRNA profiling: impact on compound evaluation and target identification in anti-bacterial research. Targets 1(1):20-29 (2002).

Freymuth et al., "Comparison of Multiplex PCR Assays and Conventional Techniques for the Diagnostic of Respiratory Virus Infections in Children Admitted to Hospital with an Acute Respiratory Illness" J. Med. Virol. (2006) 78(11):1498-1504.

Freymuth, F. et al., "Detection of respiratory syncytial virus, parainfluenzavirus 3, adenovirus and rhinovirus sequences in respiratory tract of infants by polymerase chain reaction and hybridization", Clin. Dian. Virol. 1997, vol. 8, pp. 31-40.

Fuerstenau et al., "Molecular Weight Determination of Megadalton DNA Electrospray Ions Using Charge Detection Time-of-flight Mass Spectrometry" *Rapid Comm. Mass Spec.* (1995) 9:1528-1538.

Fujimoto, T. et al., "Single-Tube Multiplex PCR for Rapid and Sensitive Diagnosis of Subgenus B and Other Subgenera Adenoviruses in Clinical Samples", Microbiol. Immunol., 2000, vol. 44, No. 10, pp. 821-826 (abstract only).

Fujimura, S, et al., "Characterization of the *mupA* Gene in Strains of Methicillin-Resistant *Staphylococcus aureus* with a Low Level of Resistance to Mupirocin," *Antimicrob. Agents Chemother.* (2001) 45(2):641-642.

Fujimura, S. et al., "Isoleucyl-tRNA Synthetase Mutations in *Staphylococcus aureus* Clinical Isolates and in Vitro Selection of Low-Level Mupirocin-Resistant Strains," *Antimicrob. Agents Chemother.* (2003) 47(10): 3373-3374.

Fujioka et al., "Analysis of enterovirus genotypes using single-strand conformation polymorphisms of polymerase chain reaction products" *J. Virol. Meth.* (1995) 51 :253-258.

Gabriel et al., "Improved mtDNA sequence analysis of forensic remains using a "mini-primer set" amplification strategy" *Journal of Forensic Sciences* (2001) 46:247-253.

Gall, J.G.D. et al., "Construction and Characterization of Hexon-Chimeric Adenoviruses: Specification of Adenovirus Serotype", J. Virol, 1998, vol. 72, No. 12, pp. 10260-10264.

Gammelin et al., "Two Subtypes of Nucleoproteins (NP) of Influenza A Viruses" Virology (1989) 170:71-80.

Garcia et al., "Quantitative Real-Time PCR Detection of Rift Valley Fever Virus and Its Application to Evaluation of Antiviral Compounds" J. Clin. Microbiol. (2001) 39(12):4456-61.

Garcia-Martinez et al. "Use of the 16s-23s ribosomal genes spacer region in studies of prokaryotic diversity" Journal of Microbiological Methods (1999) 36:55-64.

Gattermann et al., "Heteroplasmic Point Mutations of Mitochondrial DNA Affecting Subunit I of Cytochrome c Oxidase in Two Patients with Acquired Idiopathic Sideroblastic Anemia" Blood (1997) 90:4961-4972.

Gaydos, C.A. et al., "Adenovirus Vaccines in the U.S. Military", Military Med., 1995, vol. 160, No. 6, pp. 300-304.

Geha et al., "Multiplex PCR for Identification of Methicillin-Resistant Staphylococci in the Clinical Laboratory" J. Clin. Microbiol. (1994) 32:1768-1772.

GenBank Accession No. NC_000913.
GenBank accession No. AE009948.1 (gi:22535226; Aug. 8, 2002).
GenBank accession No. AE009949.1 (gi:19913450; Apr. 3, 2002).
GenBank accession No. AE015927.1 (gi:28204652; Feb. 4, 2003).
GenBank accession No. AE015929.1 (gi:27316888; Jan. 2, 2003).
GenBank accession No. AF274728 (gi:11612419; Dec. 11, 2000).
GenBank accession No. AF276257.1 (gi:1457889; Jul. 1, 2001).
GenBank Accession AF304460 (Jul. 11, 2001).
GenBank Accession No. M21150 Apr. 26, 1993.
GenBank Accession No. AF375051.1 (Jun. 26, 2001).
GenBank Accession No. BX571857.1 (gi:49243355; Jun. 25, 2004).
GenBank Accession No. Z48571 (Jun. 9, 1995).
GenBank Accession No. X84646 (Jul. 2, 1995).
GenBank GI:147581 [online] Sep. 14, 1992 [retrieved on Jul. 20, 20091 from http://www.ncbi.nlm.nih.gov/sviewer/viewer.fqi?l47581:OLDID:114614.
GenBank GI:15922990 [online] Oct. 4, 2001 [retrieved on Jun. 22, 2008] retrieved from: http://www.ncbi.nlm.nih.gov/entrez/viewer.fcgi?l5922990:OLD08:50885 (pp. 1, 12, 15, 148, 216, 476, 722, 723, 725, 881, 1251).
GenBank GI:18542231 [online] Sep. 16, 2003 [retrieved on Jun. 23, 20081 retrieved from http://www.ncbi.nlm.nih.gov/entrez/viewer.fcgi?db=nuccore&id=l8542231 (2 pages).
GenBank GI:174375 [online] Aug. 11, 1995 [retrieved on Jul. 20, 20091 retrieved from http://www.ncbi.nlm.nih.gov/nuccore/l74375.
Genbank GI:21281729 [online], publicly available at least as of May 31, 2002 [retrieved on Apr. 11, 20081, retrieved from: http://www.ncbi.nlm.nih.gov/entrez/viewer.fcgi?21281729:OLD11 :599579 (pp. 1, 723 and 1137).
GenBank GI:42813 [online] Feb. 28, 1992 [retrieved on Jul. 20, 2009] retrieved from the Internet at http://www.ncbi.nlm.nih.gov/sviewer/viewer.fqi?42813:OLDID :25896.
GenBank GI:49243355 [online] Jun. 24, 2004 [retrieved on Jul. 27, 2009] retrieved from http://www.ncbi.nlm.nih.govlsviewer/viewer.fi?49243355:OLDO4:1481434.
GenBank GI:73916349 [online] Sep. 30, 2005 [retrieved on Jul. 25, 2009] retrieved from http://www.ncbi.nlm.nih.gov/nuccore/73916349.

GenBank GI:78099429 [online] Mar. 11, 2006 [retrieved on Jul. 22, 2009] retrieved from http://www.ncbi.nlm.nih.gov/sviewer/viewer.fi?78099429:NCBI:12971731.

Gendel et al., "Computational analysis of the specificity of 16S rRNA-derived signature sequences for identifying food-related microbes" Food Microbiology (1996) 13:1-15.

Gibb et al., "Development and evaluation of a 5' fluorogenic nuclease assay to detect and differentiate between Ebola Virus subtypes Zaire and Sudan", Journal of Clinical Microbiology, 39(11):4125-4130 (Nov. 2001).

Gilbert et al., "Comparison of commercial assays for the quantitation of HBV DNA load in health care workers: calibration differences" J. Virol. Methods (2002) 100(1-2):37-47.

Giles et al., "Maternal inheritance of human mitochondrial DNA," PNAS (1980) 77:6715-6719.

Gill, S. R. et al., "Insights on Evolution of Virulence and Resistance from the Complete Genome Analysis of an Early Methicillin-Resistant Staphylococcus aureus Strain and a Biofilm-Producing Methicillin-Resistant Staphylococcus epidemidis Strain," J. Bacteriol. (2005) 187(7): 2426-2438.

Gilliland et al., "Analysis of cytokine mRNA and DNA: detectionf and quantitation by competitive polymerase chain reaction" PNAS (1990) 87(7):2725-2729.

Ginther et al., "Identifying individuals by sequencing mitochondrial DNA from teeth," Nature Genetics (1992) 2:135-138.

Gjoen et al., "Specific detection of coxsackie viruses A by the polymerase chain reaction" Clinical and Diagnostic Virology (1997) 8:183-188.

Golden et al., Pilot Study of COBAS PCR and Ligase Chain Reaction for Detection of Rectal Infections Due to Chlamydia trachomatis, J. Clin. Microbiol., 41(5):2174-2175 (May 2003).

Goto et al., "Applications of the partial 16S rDNA sequence as an index for rapid identification of species in the genus Bacillus" J. Gen. Appl. Microbiol. (2000) 46:1-8.

Gravet et al., "Characterization of a novel structural member, LukE-LukD, of the bi-component staphylococcal leucotoxins family" FEBS Lett. (1998) 436(2):202-208.

Gray, G.C. et al., "Adult Adenovirus Infections: Loss of Orphaned Vaccines Precipitates Military Respiratory Disease Epidemics", Clin. Infect. Diseases, 2000, vol. 31, pp. 663-670.

Greenberg et al., "Intraspecific nucleotide sequence variability surrounding the origin of replication in human mitochondrial DNA," Gene (1983) 21 :33-49.

Griffey et al., "Detection of base pair mismatches in duplex DNA and RNA oligonucleotides using electrospray mass spectrometry" Proceedings of SPIE—The International Society for Optical Engineering (1997) 2985:82-86.

Griffin et al., "Direct genetic analysis by matrix-assisted laser desorption/ionization mass spectrometry" PNAS (1999) 96:6301-6306.

Griffin et al., "Single-nucleotide polymorphism analysis by MALDI-TOF mass spectrometry" Trends in Biotechnology (2000) 18:77-84.

Grondahl, B. et al., "Rapid Identification of Nine Microorganisms Causing Acute Respiratory Tract Infections by Single-Tube Multiplex Reverse Transcription-PCR: Feasibility Study", J. Clin. Microbiol., 1999, vol. 37, No. 1, pp. 1-7.

Grundmann, H. et al., "Emergence and resurgence of meticillin-resistant Staphylococcus aureus as a public-health threat," Lancet (2006) 368: 874-885.

Grzybowski "Extremely high levels of human mitochondrial DNA heteroplasmy in single hair roots" Electrophoresis (2000) 21 :548-553.

Gu, Z et al., "Multiplexed, Real-Time PCR for Quantitative Detection of Human Adenovirus", J. Clin. Microbiol., 2003, vol. 41, No. 10, pp. 4636-4641.

Guatelli et al., "Nucleic Acid Amplification in Vitro: Detection of Sequences with Low Copy Numbers and Application to Diagnosis of Human Immunodeficiency Virus Type 1 Infection" Clin. Microbiol. Rev. (1989) 2(2):217-226.

Haff et al., "Multiplex Genotyping of PCR Products with Mass Tag-Labeled Primers" Nucleic Acids Research (1997) 25(18):3749-3750.

Hahner et al., "Analysis of short tandem repeat polymorphisms by electrospray ion trap mass spectrometry" Nucleic Acids Research (2000) 28:E82.

Heim, A. et al., "Rapid and Quantitative Detection of Human Adenovirus DNA by Real-Time PCR", J. Med. Virol., 2003, vol. 70, pp. 228-239.

Haines, J.D., et al., "Medical response to bioterrorism: Are we prepared?" J. Okla. State Med. Assoc. 2000, 93, 187-196.

Hall et al., "Base composition analysis of human mitochondrial DNA using electrospray ionization mass spectrometry: a novel tool for the identification and differentiation of humans" Analytical Biochemistry (2005) 344:53-69.

Hamdad, F. et al., "Detection of Methicillin/Oxacillin Resistance and Typing in Aminoglycoside-Susceptible Methicillin-Resistant and Kanamycin-Tobramycin-Resistant Methicillin-Susceptible" Microbial Drug Resistance (2006) 12(3): 177-185.

Hamels et al., "Consensus PCR and Microarray for Diagnosis of the Genus Staphylococcus, Species, and Methicillin Resistance" BioTechniques (2001) 31(6):1364-1366.

Hammerle et al., "A sensitive PCR assay system for the quantitation of viral genome equivalents: hepatitis C virus (HCV)" Arch. Virol. (1996) 141 :2103-2114.

Hannis et al., "Accurate characterization of the tyrosine hydroxylase forensic allele 9.3 through development of electrospray ionization Fourier transform ion cyclotron resonance mass spectrometry" Rapid Communications in Mass Spectrometry (1999) 13:954-962.

Hannis et al., "Detection of double-stranded PCR amplicons at the attomole level electrosprayed from low nanomolar solutions using FT-ICR mass spectrometry" Fresenius Journal of Analytical Chemistry (2001) 369: 246-251.

Hannis et al., "Genotyping short tandem repeats using flow injection and electrospray ionization Fourier transform ion cyclotron resonance mass spectrometry" Rapid Communications in Mass Spectrometry (2001) 15:348-350.

Hannis et al., "Genotyping complex short tandem repeats using electrospray ionization Fourier transform ion cyclotron resonance multistage mass spectrometry" Proceedings of SPIE—The International Society for Optical Engineering (2000) 3926:36-47.

Hanssen, A.M. et al., "SCCmec in staphylococci: genes on the move," FEMS Immuol. Med. Microbiol. (2006) 46:8-20.

Hasebe, F. et al. "Combined Detection and Genotyping of Chikungunya Virus by a Specific Reverse Transcription-Polymerase Chain Reaction," J. Med. Virol. (2002) 67(3): 370-374.

Hassan et al., "Inter- and Intraspecies Variations of the 16S-23S rDNA Intergenic Spacer Region of Various Streptococcal Species" Systematic and Applied Microbiology (2003) 26(1):97-103.

Haugland et al., "Identification of putative sequence specific PCR primers for detection of the toxigenic fungal species Stachybotrys chartarum" Mol. Cell. Probes (1998) 12:387-396.

Hayashi et al., "Phylogenetic analysis of the human gut microbiota using 16S rDNA clone libraries and strictly anaerobic culture-based methods" Microbiology and Immunology (2002) 46:535-548.

Henchal et al., "Sensitivity and specificity of a universal primer set for the rapid diagnosis of dengue virus infections by polymerase chain reaction and nucleic acid hybridization" American Journal of Tropical Medicine and Hygiene (1991) 45:418-428.

Herrmann et al., "Differentiation of Chlamydia spp. By Sequence Determination and Restriction Endonuclease Cleavage of RNase P RNA Genes" J. Clin. Microbiol. (1996) 34:1897-1902.

Higgins et al., "Competitive oligonucleotide single-base extension combined with mass spectrometric detection for mutation screening" BioTechniques (1997) 23:710-714.

Higgins, J.A., et al., Sensitive and Rapid Identification of Biological Threat AgentsHiggins et al., "Competitive oligonucleotide single-base extension combined with mass spectrometric detection for mutation screening" BioTechniques (1997) 23:710-714. Ann. NY Acad. Sci. , 1999, 894, 130-148.

Hill, F., et al., "Polymerase recognition of synthetic oligodeoxyribonucleotides incorporating degenerate pyrimidine and purine bases," Proc. Natl. Acad. Sci. USA 95:4258-4263 (1998).

Hiramatsu, K. et al., "The emergence and evolution of methicillin-resistant Staphylococcus aureus ," Trends Microbiol. (2001) 9(10):486-493.

Hoffmann et al., "Rescue of influenza B virus from eight plasmids" *PNAS* (2002) 99:11411-11416.

Hoffmann et al., "Universal primer set for the full-length amplification of all influenza A viruses" *Archives of Virology* (2001) 146:2275-2289.

Hofstadler et al., "TIGER: the universal biosensor" Inter. J. Mass Spectrom. (2005) 242:23-41.

Hodgson et al. Molecular Characterization of the Gene Encoding High-Level Mupirocin Resistance in *Staphylococcus aureus* J2870. Antimicrobial Agents and Chemotherapy 38(5):1205-1208, May 1994.

Holden, M. T. G. et al., "Complete genomes of two clinical *Staphylocuccus aureus* strain: Evidence for the rapid evolution of virulence and drug resistance," *PNAS* (2004) 101(26):9786-9791.

Holland et al., "Mitochondrial DNA Sequence Analysis of Human Skeletal Remains: Identification of Remains from the Vietnam War," *Journal of Forensic Sciences* (1993) 38:542-553.

Holland, M.M. and T.J. Parsons "Mitochondrial DNA analsysis_ Validation and use for forensic casework" (1999) Forensic Science Review, vol. 11, pp. 25-51.

Holm et al., "Removing near-neighbour redundancy from large protein sequence collections" *Bioinformatics* (1998) 14:423-429.

Holmes et al., "Whole-Genome Analysis of Human Influenza A Virus Reveals Multiple Persistent Lineages and Reassortment among Recent H3N2 Viruses" PLoS Biol. (2005) 3(9):1579-1589.

Honda et al., "Universal method of hypersensitive nested PCR toward forensic DNA typing" *International Congress Series* (1998) 7:28-30.

Hongoh et al., "Evaluation of primers and PCR conditions for the analysis of 16s rRNA genes from a natural environment" FEMS Microbiol. Lett. (2003) 221 :299-304.

Hood, E., "Chemical and biological weapons: New questions, new answers" Environ. Health Perspect., 1999, 107:931-932.

Houng, H.-S. H. et al., "Rapid type-specific diagnosis of adenovirus type 4 infection using a hexon-based quantitative fluorogenic PCR", Diagn. Microbiol. Infect. Dis., 2002, vol. 42, pp. 227-236.

Howell et al., "Persistent Heteroplasmy of a Mutation in the Human mtDNA Control Region: Hypermutation as an Apparent Consequence of Simple-Repeat Expansion/Contraction" *Am. J. Hum. Genet.* (2000) 66:1589-1598.

Huber et al., On-line cation exchange for suppression of adduct formation in negative-ion electrospray mass spectrometry of nucleic acids. Anal. Chem. (1998) 70:5288-5295.

Huletsky, A. et al., New real-time PCR assay for rapid detection of methicillin-resistant *Staphylococcus aureus* directly from specimens containing a mixture of staphylococci. J. Clin. Microbial. (2004) 42(5): 1875-84.

Hung, "Detection of SARS coronavirus RNA in the cerebrospinal fluid of a patient with severe acute respiratory syndrome" Clin. Chem. (2003) 49:2108.

Hunag, C. et al., "Detection of arboviral RNA directly from mosquito homogenates by reverse transcription-polymerase chain reaction," *J. Virol. Methods* (2001) 94(1-2): 121-128.

Hurdle, J. G. et al., "Analysis of Mupirocin Resistance and Fitness in *Staphylococcus aureus* by Molecular Genetic and Structural Modeling Techniques," *Antimicrob. Agents Chemother.* (2004) 48(11):4366-4376.

Hurst et al., "Detection of bacterial DNA polymerase chain reaction products by matrix-assisted laser desorption/ionization mass spectrometry" *Rapid Commun. Mass. Spec.* (1996) 10:377-382.

Hurst et al., "MALDI-TOF Analysis of Polymerase Chain Reaction Products from Methanotrophic Bacteria" *Anal. Chem.* (1998) 70:2693-2698.

Hutchison et al., "Maternal inheritance of mammalian mitochondrial DNA," *Nature* (1974) 251 :536-538.

Hyde-Deruyscher, R. et al., "Polyomavirus early-late switch is not regulated at the level of transcription initiation and is associated with changes in RNA processing" Proc. Natl. Acad. Sci. USA (1988) 85:8993-8997.

Ieven, M. et al., "Rapid Detection of Methicillin Resistance in Coagulase-Negative Staphylococci by Commercially Available Fluorescence Test," *J. Clin. Microbiol.* (1995) 33(8):2183-2185.

Ihle et al., "Efficient purification of DNA fragments using a protein binding membrane" *Nucleic Acids Research* (2000) 28:e76.

Inglis, T. J. et al., "Rapid Genotypic Confirmation of Methicillin Resistance," *Pathology* (1996) 28(3):259-261.

Ingman et al., "Mitochondrial genome variation and the origin of modern humans" *Nature* (2000) 408:708-713.

Australian Search Report for AU 2003297687 dated Sep. 4, 2008.
Australian Search Report for AU 2003302236 dated Sep. 10, 2008.
Australian Search Report for AU 2004248107 dated Jul. 30, 2008.
Canadian patent office communication for Application No. 2,567,839 dated Apr. 7, 2009.
Canadian patent office communication for Application No. 2,525,498 dated Feb. 5, 2009.
Chinese Office Communication for CN2004800161.9 dated Jun. 12, 2009.
International Prelim. Exam. Report for PCT/US02/20336 dated May 12, 2004.
International Prelim. Exam. Report for PCT/US2005/033707 dated Mar. 20, 2007.
International Search Report for PCT/US02/20336 dated Feb. 3, 2003.
International Search Report for PCT/US02/20336 dated May 12, 2004.
International Search Report for PCT/US02/06763 dated Oct. 23, 2002.
International Search Report for PCT/US03/009802 dated Aug. 20, 2004.
International Search Report for PCT/US03/22835 dated Dec. 12, 2003.
International Search Report for PCT/US03/38757 dated Jun. 24, 2004.
International Search Report for PCT/US03/38795 dated Apr. 19, 2004.
International Search Report for PCT/US03/38830 dated Aug. 25, 2004.
International Search Report for PCT/US03/38505 dated Apr. 12, 2005.
International Search Report for PCT/US03/38761 dated Dec. 30, 2005.
International Search Report for PCT/US04/007236 dated Feb. 24, 2006.
International Search Report for PCT/US2004/011877 dated Apr. 20, 2006.
International Search Report for PCT/US04/012671 dated Sep. 28, 2007.
International Search Report for PCT/US04/015123 dated Oct. 3, 2005.
International Search Report for PCT/US04/015196 dated Jul. 1, 2005.
International Search Report for PCT/US2004/028869 dated Jul. 17, 2006.
International Search Report for PCT/US04/033742 dated May 15, 2006.
International Search Report for PCT/US2005/000386 dated May 9, 2006.
International Search Report for PCT/US05/005356 dated Aug. 7, 2007.
International Search Report for PCT/US05/007022 dated Oct. 20, 2006.
International Search Report for PCT/US2005/018031 dated Jun. 28, 2006.
International Search Report for PCT/US05/018337 dated Oct. 10, 2006.
International Search Report for PCT/US05/024799 dated Dec. 28, 2006.
International Search Report for PCT/US05/030058 dated Aug. 20, 2007.
International Search Report for PCT/US05/033707 dated Feb. 6, 2006.
International Search Report for PCT/US05/06133 dated Jul. 26, 2007.
International Search Report for PCT/US05/09557 dated Sep. 19, 2005.
International Search Report for PCT/US06/007747 dated Sep. 5, 2006.

International Search Report for PCT/US2006/040747 dated Mar. 17, 2009.
International Search Report for PCT/US06/015160 dated Oct. 10, 2006.
International Search Report for PCT/US2006/061307 dated Jan. 9, 2008.
International Search Report for PCT/US2007/020045 dated Jan. 8, 2009.
International Search Report for PCT/US2007/066194 dated Jan. 15, 2008.
International Search Report for PCT/US2008/054926 dated Jan. 26, 2009.
International Search Report for PCT/US2008/057717 dated Jan. 13, 2009.
International Search Report for PCT/US2008/064891 dated Aug. 28, 2008.
International Search Report for PCT/US2008/057901 dated Jun. 29, 2009.
International Search Report for PCT/US2008/065332 dated Nov. 28, 2008.
International Search Report for PCT/US2009/045635 dated Oct. 7, 2009.
Inyaku, K. et al., "Rapid Detection and Identification of Mycobacteria in Sputum Samples by Nested Polymerase Chain Reaction and Restriction Fragment Length Polymorphisms of dnaJ Heat Shock Protein Gene," 42 J. Med. Sci. 21-31 (1993) ('787 reexamination).
Isola et al., "MALDI-TOF mass spectrometric method for detection of hybridized DNA oligomers" Analytical Chemistry (2001) 73:2126-2131.
Iqbal et al., "A review of molecular recognition technologies for detection of biological threat agents" Biosensors & Bioelectronics, 15:549-578 (2000).
Ito, T. et al., "Structural Comparison of Three Types of Staphylococcal Cassette Chromosome mec Integrated in the Chromosome in Methicillin-Resistant Staphylococcus aureus," Antimicrob. Agents Chemother. (2001) 45(5): 1323-1336.
Ito, T. et al., "Insights on antibiotic resistance of Staphylococcus aureus from its whole genome: genomic island SCC," Drug Resist. Updat. (2003) 6(1):41-52.
Jackson et al., "Mass spectrometry for genotyping: an emerging tool for molecular medicine" Molecular Medicine Today (2000) 6:271-276.
Jambrina et al., GenBank: AF005737.1 influenza B virus B/Panama/45/90 polymerase (PB2) mRNA, complete cds, (1997), pp. 1-3.
James et al., "Borelia lonestari infection after a bite by an Amblyomma americanum tick" The Journal of Infectious Diseases (2001) 183:1810-1814.
Jankowski et al., "Mass spectrometry of DNA. Part 2. Quantitative estimation of base composition" European Journal of Mass Spectrometry in Biochemistry, Medicine, and Environmental Research (1980) 1:45-52.
Jansen et al., "Genotype-by-environment Interaction in Genetic Mapping of Multiple Quantitative Trait Loci" Theor. Appl. Genet. (1995) 91:33-37.
Jaulhac, B. et al., "Specific detection of the toxic shock syndrome toxin-1 gene using the polymerase chain reaction" Mol. Cel. Probes (1991) 5:281-284.
Jaulhac, B. et al., "Synthetic DNA probes for detection of genes for enterotoxins A, B, C, D, E and for TSST-1 in staphylococcal strains," J. Appl. Bacterial. (1992) 72(5):386-392.
Jensen et al., "Rapid Identification of Bacteria on the Basis of Polymerase C+A409hain Reaction-Amplified Ribosomal DNA Spacer Polymorphisms" Appl. Environ. Microbiol. (1993) 59:945-952.
Jeong, J, et al., "Early Screening of Oxacillin-Resistant Staphylococcus aureus and Staphylcoccus epidermidis from Blood Culture," J. Korean Med. Sci. (2002) 17: 168-172.
Jiang et al., "Multiple Trait Analysis of Genetic Mapping for Quantitative Trait Loci Genetics" Genetics (1995) 140:1111-1127.
Jiang et al., "A highly efficient and automated method of purifying and desalting PCR products for analysis by electrospray ionization mass spectrometry." Anal. Biochem. (2003) 316:50-57.

Johansson et al., "Evaluation of PCR-based methods for discrimination of Francisella species and subspecies and development of a specific PCR that distinguishes the two major subspecies of Francisella tularensis." Journal of Clinical Microbiology (2000) 38:4180-4185.
Johnson et al. "Detection of genes for enterotoxins, exfoliative toxins, and toxic shock Syndrome toxin 1 in Staphylococcus aureus by the polymerase chain reaction" J. Clin. Microbiol. (1991) 29:426-430.
Johnson et al., "Precise molecular weight determination of PCR products of the rRNA intergenic spacer region using electrospray quadrupole mass spectroemtry for differentiation of B. subtilis and B. atrophaeus, closely related species of bacilli" Journal of Microbiological Methods (2000) 40:241-254.
Jonas, D. et al., "Rapid PCR-Based Identification of Methicillin-Resistant Staphylococcus aureus from Screening Swabs," J. Clin. Microbiol. (2002) 40(5): 1821-1823.
Jurinke C et al., "Application of nested PCR and mass specctrometry for DNA based virus detection: HBV-DNA detected in the majority of isolated anti-Hbc positive sera", Genetic Analysis: Biomolecular Engineering, Elsevier Science Publishing, US, 14(3):97-102 (Jan. 3, 1998)+A627+A661.
Jurinke et al., "Detection of hepatitis B virus DNA in serum samples via nested PCR and MALDI-TOF mass spectrometry" Genetic Analysis: Biomolecular Engineering (1996) 13:67-71.
Jurinke et al., "MALDI-TOF Mass Spectrometry. A Versatile Tool for High-Performance DNA Analysis" Molecular Biotechnology (2004) 26(2):147-163.
Kacian et al., "A Replicating RNA Molecule Suitable for a Detailed Analysis of Extracellular Evolution and Replication" Proc. Natl. Acad. Sci. USA 69:3038 (1972).
Kageyama et al., "Rapid detection of human fecal Eubacterium species and related genera by nested PCR method" Microbiology and Immunology (2001) 45:315-318.
Kajon, A.E. et al., "Genome Type Analysis of Brazilian Adenovirus Strains of Serotypes 1, 2, 3, 5, and 7 Collected Between 1976 and 1995", J. Med. Virol., 1999, vol. 58, pp. 408-412.
Katano, H., et al., "Identification of Adeno-associated virus contamination in cell and virus stocks by PCR", Biotechniques, Informa Life Sciences Publishing, Westborough, MA, US, 36(4):676-680 (Apr. 2004).
Katayama, Y. et al., "Genetic Organization of the Chromosome Region Surrounding mecA in Clinical Staphylococcal Strains: Role of IS431-Mediated mecI Deletion in Expression of Resistance in med-Canying, Low-Level Methicillin-Resistant Staphylococcus haemolyticus," Antimicrob. Agents Chemother. (2001) 45(7): 1955-1963.
Ke et al., "Development of a PCR Assay for Rapid Detection of Enterococci" Journal of Clinical Microbiology (1999) 37:3497-3503.
Kearns, A. M. et al., "Rapid detection of methicillin-resistant staphylococci by multiplex PCR," J. Hosp. Infect. (1999) 43:33-37.
Keller et al., "Empirical Statistical Model to Estimate the Accuracy of Peptide Identifications Made by MS/MS and Database Search" Anal. Chem (2002) 74:5383-5392.
Khan, A.S., et al., "An outbreak of Crimean-Congo haemorrhagic fever in the United Arab Emirates, 1994-1995" Am. J. Trop. Med. Hyg., 1997, 57, 519-525.
Khan, S. A. et al., "Simultaneous detection of erythromycin-resistant methylase genes ermA and ermC from Staphylococcus spp. By multiplex-PCR," Mol. Cell Probes (1999) 13:381-387.
Kidd, A.H. et al., "Rapid Subgenus Identification of Human Adenovirus Isolates by a General PPCR", J. Clin. Microbiol., 1996, vol. 34, No. 3, pp. 622-627.
Kilbourne, "Influenza Pandemics: Can We Prepare for the Unpredictable?" Viral Immunol. (2004) 17(3):350-357.
Kilbourne, "Influenza Pandemics of the 20th Century" Emerg. Infect. Dis. (2006) 12(1):9-14.
Kilpatrick et al., "Group-Specific Identification of Polioviruses by PCR Using Primer Containing Mixed-Base or Deoxyinosine Residues at Positions of Codon Degeneracy" J. Clin. Microbiol. (1996) 34:2990-2996.

Kim et al. "Identification of Mycobacterial species by comparative sequence analysis of the RNA polymerase gene (rpoB)" Journal of Clinical Microbiology 37(6):1714-1720, Jun. 1999.

Kinney et al., American J. Trop. Med. Hyg., (1998), vol. 59, No. 6, p. 952-954.

Kitagawa et al. "Rapid diagnosis of methicillin-resistant *Staphylococcus aureus* bacteremia by nested polymerase chain reaction" Ann. Surgery (1996) 224:665-671.

Kolbert et al., "Branched-DNA Assay for Detection of the mecA Gene in Oxacillin-Resistant and Oxacillin-Sensitive Staphylococci" J. Clin. Microbiol. (1998) 36:2640-2644.

Krafft, A.E. et al., "Evaluation of PCR Testing of Ethanol-Fixed Nasal Swab Specimens as an Augmented Surveillance Strategy for Influenza Virus and Adenovirus Identification", J. Clin. Microbiol., 2005, vol. 43, No. 4, pp. 1768-1775.

Kramer, L. D. et al., "Dection of St. Louis Encephalitis and Western Equine Encephalomyelitis RNA in Mosquitoes Tested Without Maintainance of a Cold Chain," J. Am. Mosq. Control Assoc. (2001) 17(4): 213-215.

Kramer, L. D. et al., "Dection of Encephalitis Viruses in Mosquitoes (Diptera: Culicidea) and Avian Tissues," *J. Med. Entomol.* (2002) 39(2): 312-323.

Krahmer et al., "Electrospray quadrupole mass spectrometry analysis of model oligonucleotides and polymerase chain reaction products: determination of base substitutions, nucleotide additions/deletions, and chemical modifications" *Anal. Chem.* (1999) 71 :2893-2900.

Krahmer et al., "MS for identification of single nucleotide polymorphisms and MS/MS for discrimination of isomeric PCR products" *Anal. Chem.* (2000) 72:4033-4040.

Kroes et al., "Bacterial diversity within the human subgingival crevice," Proc. Natl. Acad. Sci. USA (1999) 96:14547-14552.

Kresken, M. et al., "Prevalence of mupirocin resistance in clinical isolates of *Staphylococcus aureus* and *Staphylococcus epidermidis* : results of the Antimicrobial Resistance Surveillance Study of the Paul-Ehrlich-Society for Chemotherapy, 2001," Int. J. Antimicrob. Agents (2004) 23:577-581.

Krishnan, P.U. et al., "Detection of methicillin and mupirocin resistance in *Staphylococcus aureus* isolates using conventional and molecular methods: a descriptive study from a burns unit with high prevalence of MRSA," J. Clin. Pathol. (2002) 55:745-748.

Krossoy et al., "The putative polymerase sequence of infectious anemia virus suggests a new geneus within the Orthomyxoviridae" Journal of Virology (1999) 73:2136-2142.

Ksiaxek, Thomas G., et al., "A novel coronavirus associated with severe acute respiratory syndrome," New England Journal of Medicine, 348(20):1953-1966 (Apr. 10, 2003).

Kupke et al., "Molecular Characterization of Lantibiotic-synthesizing Enzyme EpiD Reveals a Function for Bacterial Dfp Proteins i Coenzyme A Biosynthesis" *Journal of Biological Chemistry* (2000) 275:31838-31846.

Kuroda, M., et al., "Whole genome Sequencing of meticillin-resistant *Staphylococcus aureus*", The Lancet, 357(9264):1225-1240 (Apr. 21, 2001).

Kwok, S. and R. Hguchi, "Avoiding false positives with PCR" Nature, 1989, 339,237-238.

Labandeira-Rey, M. et al., "*Staphylococcus aureus* Panton Valentine Leukocidin Causes Necrotizing Pneumonia" Sciencexpress (Jan. 18, 2007).

Lacroix et al., "PCR-Based Technique for the Detection of Bacteria in Semen and Urine" *J. Microbiol. Meth.* (1996) 26:61-71.

Lacroix, L. et al., "Triplex Formation by Oligonucleotides Containing 5-(1-Propynyl)-2'-deoxyuridine: Decreased Magnesium Dependence and Improved Intracellular Gene Targeting" Biochem. (1999) 38(6):1893-1901.

Lamb et al., "Sequence of Interrupted and Uninterrupted mRNAs and Cloned DNA Coding for the Two Overlapping Nonstructural Proteins of Influenza Virus" Cell (1980) 21 :475-485.

Lambert, A.J. et al., "Detection of North American Eastern and Western Equine Encephalitis Viruses by Nucleic Acid Amplification Assays," *J. Clin. Microbiol.* (2003) 41(1): 379-385.

Lau et al., "Nucleic acid sequence-based amplification methods to detect avian influenza virus" Biochem. Biophys. Res. Commun. (2004) 313:336-342.

Lau et al., "A real-time PCR for SARS-coronavirus incorporating target gene pre-amplification" Biochem. Biophys. Res. Comm. (2003) 312:1290-1296.

Lebedev, Y. et al "Oligonucleotides containing 2-aminoadenine and 5-methycytosine are more effective as primers for PCR amplification than their nonmodified counterparts" Genetic Analysis: Biomolecular Engineering (1996) 13:15-21.

Lednicky, J. A. et al., "Polyomaviruses and Human Tumors: A Brief Review of Current Concenpts and Interpretations," Front. Biosci. (1999) 4:d153-164.

Lee, J.A. et al., "Rapid Identification of Human Adenovirus Types 3 and 7 from Respiratory Specimens via Multiplex Type-Specific PCR", J. Clin. Microbiol., 2005, vol. 43, No. 11, pp. 5509-5514.

Lee, J.H. et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," *J. Am. Mosq. Control Assoc.* (2002) 18(1): 26-31.

Leif et al., "Isolation and characterization of the proton-translocating NADH: ubiquinone oxidoreductase from *Escherichia coli*" *Eur. J. Biochem.* (1995) 230:538-548.

Lengyel, A. et al., "Characterization of the Main Protein Components of Adenovirus Virion and its Possible Use in Laboratory Diagnostics", Acta Microbiol. Immunol. Hung., 1998, vol. 45, Nos. 3-4; pp. 281-283.

Leroy et al., "Diagnosis of Ebola haemorrhagic fever by RT-PCR in an epidemic setting", Journal of Medical Virology, 60:463-467 (2000).

Levi, K. et al., "Evaluation of an Isothermal Signal Amplification Method for Rapid Detection of Methicillin-Resistant *Staphylococcus aureus* from Patient-Screening Swabs," J. Clin. Microbiol. (2003) 41(7):3 187-3191.

Levine et al., "PCR-based detection of *Bacillus anthracis* in formalin-fixed tissue from a patient receiving ciprofloxacin" Journal of Clinical Microbiology (2002) 40(11):4360-4362.

Levison et al., "Recent developments of magnetic beads for use in nucleic acid purification" Journal of Chromatography (1998) A 816:107-111.

Lewers et al., "Detection of Linked QTL for Soybean Brown Stem Rot Resistance in 'BSR 101' as Expressed in a Growth Chamber Environment" *Molecular Breeding* (1999) 5:33-42.

Le Cann et al., "Quantification of human astroviruses in sewage using real-time RT-PCR" Res. Microbiol. (2004) 155(1):11-15.

Li, Q.-G. et al., "Analysis of 15 Different Genome Types of Adenovirus Type 7 Isolated on Five Continents", J. Virol., 1986, vol. 60, No. 1, pp. 331-335.

Li, Q.-G. et al., "Comparison of 17 Genome Types of Adenovirus Type 3 Identified among Strains Recovered from Six Continents", J. Clin. Microbiol, 1988. vol. 26, No. 5, pp. 1009-1015.

Li, Q.-G. et al., "Genetic variability of hexon loops 1 and 2 between seven genome types of adenovirus serotype 7", Arch. Virol., 1999, vol. 144, No. 9, pp. 1739-1749.

Li et al., "Screening of the high yield influenza B virus on MDCK cell and cloning of its whole genome" International Congress Series 1263 (2004) 610-614.

Li et al., "Single nucleotide polymorphism determination using primer extension and time of flight mass spectrometry" *Electrophoresis* (1999) 20:1258-1265.

Li et al., "Evolution of H9N2 influenza viruses from domestic poultry in Mainland China" Virology (2005) 340:70-83.

Liebermann, H. et al., "Mapping of linear epitopes on fibre knob of human adenovirus serotype 5", Virus Res., 2001, vol. 73, No. 2, pp. 145-151.

Liebermann, H. et al., "Mapping of Epitopes on the Fiber Knobs of Human Adenovirus Serotypes 8 and 15", Intervirology, 2002, vol. 45, pp. 59-66.

Lim et al., "The microRNAs of *Caenorhabditis elegans*" Genes and Development 17:991-1008 (2003).

Limbach, P.A., et al., "Enzymatic Sequencing of Oligonucleotides with Electrospray Mass Spectrometry" 42nd ASMS Conference on Mass Spectrometry (Jun. 1994) ('787 reexamination).

Limoncu, M. H. et al., "Emergence of phenotypic resistance to ciprofloxacin and levofloxacin in methicillin-resistant and methicillin-sensitive *Staphylococcus aureus* strains," Int. J. Antimicrob. Agents (2003) 21:420-424.

Lin et al., "Oxidative Damage to Mitochondrial DNA in Atrial Muscle of Patients with Atrial Fibrillation," Free Radical Biology and Medicine, 35(10):1310-1318 (2003).

Lin, B. et al., "Use of Oligonucleotide Microarrays for Rapid Detection and Serotyping of Acute Respiratory Disease-Associated Adenoviruses", J. Clin. Microbiol., 2004, vol. 42, No. 7, pp. 3232-3239.

Lina, G. et al., "Involvement of Panton-Valentine Leukocidin-Producing *Staphylococcus auraes* in Primary Skin Infections and Pneumonia," Clin. Infect. Dis. (1999) 29(5):1128-1132.

Lina, G. et al., "Bacterial Competition for Human Nasal Cavity Colonization: Role of Staphylococcal agr Alleles," Appl. Environ. Microbiol. (2003) 69(1):18-23.

Linssen, B. et al., "Development of Reverse Transcription-PCR Assays Specific for Detection of Equine Encephalitis Viruses," *J. Clin. Microbiol.* (2000) 38(4): 1527-1535.

Little, et al., "Rapid Sequencing of Oligonucleotides by High-Resolution Mass Spectrometry" *J. Am. Chem. Soc.* (1994) 116:4893-4897.

Little, et al., "MALDI on a Chip: Analysis of Arrays of Low-Femtomole to Subfemtomole Quantities of Synthetic Oligonucleotides and DNA Diagnostic Products Dispensed by a Piezoelectric Pipet" *Analytical Chemistry* (1997) 69:4540-4546.

Liu et al., "An unusual gene arrangement for the putative chromosome replication origin and circadian expression of dnaN in *Synechococcus* sp. Strain PCC 7942" *Gene* (1996) 172:105-109.

Liu et al., "Improving the microdialysis procedure for electrospray ionization mass spectrometry of biological samples" *Journal of Mass Spectrometry* (1997) 32:425-431.

Liu et al., "Interregional Transmission of the Internal Protein Genes of H2 Influenza Virus in Migratory Ducks from North America to Eurasia" Virus Genes (2004) 29(1):81-86.

Livermore, D. M., "The threat from the pink corner," Ann. Med. (2003) 35(4):226-234.

Loakes et al., "Nitroindoles as universal bases" *Nucleosides and Nucleotides* (1995) 14:1001-1003.

Loo, J. A et al., "Applying Charge Discrimination with Electrospray Ionization-Mass Spectrometry to Protein Analysis," J. Am. Soc. Mass. Spectrom. (1995) 6:1098-1104.

Lott, "Nucleotide Sequence Analysis of the 5-8s rDNA and Adjacent ITS2 Region of *Candida albicans* and Related Species" Yeast, 9:1199-1206 (1999).

Louie, L. et al., "Evaluation of Three Rapid Methods for Detection of Methicillin Resistance in *Staphylococcus aureus*," J. Clin. Microbiol. (2000) 38(6):2170-2173.

Love et al., "Cloning and sequence of the groESL heat-shock operon of *Pasteurella multocida*" Gene (1995) 166:179-180.

Lovseth, A. et al., "Modified Multiplex PCR Method for Detection of Pyrogenic Exotoxin Genes in Staphylococcal Isolates," J. Clin. Microbiol. (2004) 42(8):3869-3872.

Lowe et al., "A computer program for selection of oligonucleotide primers for polymerase chain reactions" Nucleic Acids Research, (1990) vol. 18(7):1757-1761.

Lu, X. et al., "Molecular typing of human adenoviruses by PCR and sequencing of a partial region of the hexon gene", Arch. Virol.,., 2006, vol. 15, No. 8, pp. 1587-1602.

Ludwig W. "Bacterial phylogeny based on 16s and 23s rRNA sequence analysis" FEMS Microbiol Rev 15(2-3):155-73, Oct. 1994.

Ludwig, S.L. et al., "Prevalence of Antibodies to Adenovirus Serotypes 4 and 7 among Unimmunized US Army Trainees: Results of Retrospective Nationwide Seroprevalence Survey", J. Infect. Dis., (1998) 178, pp. 1776-1778.

Lukashov, V. V. et al., "Evolutionary Relationships among Parvoviruses: Virus-Host Coevolution among Autonomous Primate Parvoviruses and Links between Adeno-Associated and Avian Parvoviruses," J. Virol. (2001) 75(6):2729-2740.

Ma, X. X. et al., "Novel Type of Staphylococcal Cassette Chromosome mec Identified in Community-Acquired Methicillin-Resistant *Staphylococcus aureus* Strains," Antimicrob. Agents Chemother. (2002) 46(4):1147-1152.

Mack and Sninsky, "A sensitive method for the identification of uncharacterized viruses related to known virus groups: Hepadnavirus model system," Proc. Natl. Acad. Sci. USA (1988) 85:6977-6981.

Magnuson, VL, "Substrate nucleotide-determined non-templated addition of adenine by Taq DNA polymerase: Implications for PCR-based genotyping and cloning" Biotechniques, 21 :700-709 (Oct. 1996).

Maiwald et al., "Characterization of contaminating DNA in Taq polymerase which occurs during amplification with a primer set for Legionella 5S ribosomal RNA" *Molecular and Cellular Probes* (1994) 8:11-14.

Malasig, M.D. et al., "Simplified Microneutralization Test for Serotyping Adenovirus Isolates", J. Clin. Microbiol., 2001, vol. 39, No. 8, pp. 2984-2986.

Mangrum et al., "Solution composition and thermal denaturation for the production of single-stranded PCR amplicons: piperdine-induced destabilization of the DNA duplex?" *Journal of the American Society for Mass Spectrometry* (2002) 13:232-240.

Manian, F. A,, "Asymptomatic Nasal Carriage of Mupirocin-Resistant, Methicillin-Resistant *Staphylococcus aureus* (MRSA) in a Pet Dog Associated with MRSA Infection in Household Contacts," Clin. Infect. Dis. (2003) 36:e26-e28.

Marmur et al., "Strand Separation and Specific Recombination in Deoxyribonucleic Acids: Biological Studies" Proc. Natl. Acad. Sci. USA 46:453 (1960).

Martemyanov et al., "Extremely Thermostable Elongation Factor G from *Aquifex aeolicus*: Cloning, Expression, Purification, and Characterization in a Heterologous Translation System" *Protein Expr. Purif.* (2000) 18:257-261.

Martineau, F. et al., "Species-Specific and Ubiquitous-DNA-Based Assays for Rapid Identification of *Staphylococcus aureus*," J. Clin. Microbial. (1998) 36(3):618-623.

Martineau, F. et al., "Development of a PCR Assay for Identification of Staphylococci at Genus and Species Levels," J. Clin. Microbial. (2001) 39(7):2541-2547.

Martin-Lopez, J. V. et al., "Simultaneous PCR detection of ica cluster and methicillin and mupirocin resistance genes in catheter-isolated *Staphylococcus*," Int. Microbial. (2004) 7:63-66.

Mason et al., "Diversity and linkage of replication and mobilisation genes in *Bacillus* rolling circle-replicating plasmids from diverse geographical origins" FEMS Microbiol. Ecol. 2002, 42:235-241.

Matray et al., "Synthesis and properties of RNA analogs—oligoribonucleotide N3'->P5' phosphoramidates" *Nucleic Acids Res* (1999) 3976-3985.

Matsuoka, M. et al., "Characteristic expression of three genes, msr(A), mph(C) and erm(Y), that confer resistance to macrolide antibiotics on *Staphylococcus aureus*," FEMS Microbiol. Lett. (2003) 220:287-293.

May, "Percent sequence identity: The need to be explicit" Structure (2004) 12(5):737-738.

McCabe et al., "Bacterial Species Identification after DNA Amplification with a Universal Primer Pair" *Molecular Genetics and Metabolism* (1999) 66:205-211.

McLafferty et al., "Comparison of Algorithms and Databases for Matching Unknown Mass Spectra" *J. Am. Soc. Mass Spectrom.* (1998).

McLuckey, S.A., et al., "Ion Trap Tandem Mass Spectrometry Applied to Small Multiply Charged Oligonucleotides with a Modified Base," 5 J. Am. Soc. Mass. Spectrom. 1994 5:740-747.

Mehrotra et al., "Multiplex PCR for detection of genes for *Staphylococcus aureus* enterotoxins, exfoliative toxins, toxic shock syndrome toxin 1, and methicillin resistance", Journal of Clinical Microbiology, Washington, DC US 38(3):1032-1035 (Mar. 1, 2000)+A256.

Meiyu et al., "Detection of flaviviruses by reverse transcriptase-polymerase chain reaction with the universal primer set" *Microbiology and Immunology* (1997) 41 :209-213.

Mellor et al., "Genotype Dependence of Hepatitis C Virus Load Measurement in Commercially Available Quantitative Assays" J. Clin. Microbiol. (1999) 37(8):2525-2532.

Merlino, J. et at., "New Chromogenic Identification and Detection of *Staphylococcus aureus* and Methicillin-Resistant *S. aureus.*" J. Clin. Microbiol (2000) 38(6): 2378-2380.

Merlino, J. et al., "Rapid Detection of Non-Multidrug-Resistant and Multidrug-Resistant Methicillin-Resistant *Staphylococcus aureus* Using Cycling Probe Technology for the mecA Gene," Eur. J. Clin. Microbiol. Infect. Dis. (2003) 22: 322.323.

Messmer et al., "Discrimination of *Streptococcus pneumoniae* from other upper respiratory tract streptococci by arbitrarily primed PCR" *Clinical Biochemistry* (1995) 28:567-572.

Metzgar, D. et al., "PCR Analysis of Egyptian Respiratory Adenovirus Isolates, Including Identification of Species, Serotypes and Coinfections", J. Clin. Microbiol., 2005, vol. 43, No. 11, p. 5743-5752.

Miller et al., "A compendium of human mitochondrial DNA control region: development of an international standard forensic database," Croat Med. J. (2001) 42:315-327.

Miragaia, M. et al., "Genetic Diversity among Methicillin-Resistant *Staphylococcus epidemidis* (MRSE)," Microbial Drug Resistance (2005) 11(2):83-93.

Miura-Ochiai, R. et al., "Quantitative detection and rapid identification of human adenoviruses", J. Clin. Microbiol., 2007, vol. 45, No. 3, pp. 958-967.

Mollet et al. "rpoB sequence analysis as a novel basis for bacterial identification" Molecular Microbiology 26(5):1005-1011 (1997).

Monroy, A.M. et al., "Exvaluation of Reverse Transcriptase Polymerase Chain Reaction for the Detection of Eastern Equine Encephalumyelitis Virus during Vector Surveillance," *J. Med. Entomol.* (1996) 33(3): 449-457.

Moore et al., "Development and Evaluation of a Real-Time Nucleic Acid Sequence Based Amplification Assay for Rapid Detection of Influenza A" J. Med. Virol. (2004) 74(4):619-628.

Moricca et al., "Detection of *Fusarium oxysporum* f.sp. Vasinfectum in cotton tissue by polymerase chain reaction" *Plant Pathology* (1998) 47:486-494.

Morinaga, N. er al., "Purification, Cloning and Charactarizarion of Variant LukE-LukD with Strong Leukocidal Activity of Staphylococcal Bi-Component Leukotoxin Family," Microbiol. Immunol. (2003) 47(1):81-90.

Morse et al., "Nucleotide Sequence of Part of the ropC Gene Encoding the B Subunit of DNA-Dependent RNA Polymerase from some Gram-Positive Bacteria and Comparative Amino Acid Sequence Analysis" *System Appl. Microbiol.* (1996) 19:150-157.

Muddiman et al., "Application of secondary ion and matrix-assisted laser desorption-ionization time-of-flight mass spectrometry for the quantitative analysis of biological molecules" *Mass Spectrometry Reviews* (1995) 14:383-429.

Muddiman et al., "Important aspects concerning the quantification of biomolecules by time-of-flight secondary-ion mass spectrometry" *Applied Spectroscopy* (1996) 50:161-166.

Muddiman et al., "Characterization of PCR Products from Bacilli Using Electrospray Ionization FTICR Mass Spectrometry" *Anal. Chem.* (1996) 68:3705-3712.

Muddiman et al., "Length and base composition of PCR-amplified nucleic acids using mass measurements from electrospray ionization mass spectrometry" *Anal. Chem.* (1997) 69:1543-1549.

Muddiman et al., "Sequencing and Characterization of Larger Oligonucleotides by Electrospray Ionization Fourier Transform Ion Cyclotron Resonance Mass Spectrometry" *Reviews in Analytical Chemistry* (1998) 17:1-68.

Muddiman et al., "Precise mass measurement of a double-stranded 500 base-pair (309 kDa) polymerase chain reaction product by negative ion electrospray ionization fourier transform ion cyclotron resonance mass spectrometry" *Rapid Commun. Mass Spec.* (1999) 13:1201-1204.

Muhammad et al., "Electrospray ionization quadrupole time-of-flight mass spectrometry and quadrupole mass spectrometry for genotyping single nucleotide substitutions in intact polymerase chain reaction products in K-ras and p53" *Rapid Commun. Mass Spectrom* . (2002) 16:2278-2285.

Murakami, K. et al., "Identification of Methicillin-Resistant Strains of Staphylococci by Polymerase Chain Reaction," J. Clin. Microbiol. (1991) 29(10):2240-2244.

Mushegian et al., "A minimal gene set for ceullular life derived by comparison of complete bacterial genomes" Proc. Natl. Acad. Sci. USA (1996) 93:10268-10273.

Na et al., "Detection and typing of respiratory adenoviruses in a single-tube multiplex polymerase chain reaction" Journal of Medical Virology (2002) 66:512-517.

Nagpal et al., "Utility of 16S-23S RNA spacer region methodology: how similar are interspace regions within a genome and between strains for closely related organisms?" *Journal of Microbiological Methods* (1998) 33:211-219.

Nagy, M. et al., "Sequence Analysis of Porcine Adenovirus Serotype 5 Fibre Gene: Evidence for Recombination", Virus Genes, 2002, vol. 24, No. 2, pp. 181-185.

Nakagawa et al., "Gene sequences and specific detection for Panton-Valentine leukocidin" Biochem. Biophys. Res. Commun. (2005) 328(4):995-1002.

Nakao et al., "Development of a Direct PCR Assay for Detection of the Diphtheria Toxin Gene" *J. Clin. Microbiol.* (1997) 35:1651-1655.

Narita et al., "Phage conversion of Panton-Valentine leukocidin in *Staphylococcus aureus*: molecular analysis of a PVL-converting phage, phiSLT" Gene (2001) 268(1-2):195-206.

Naumov et al., "Discrimination of the Soil Yest Species *Williopsis saturnus* and *Williopsis suaveolens* by the Polymerase Chain Reaction with the Universal Primer N21" *Microbiology* (Moscow)(Translation of Mikrobiologiya) (2000) 69:229-233.

Neumann et al., "Host Range Restriction and Pathogenicity in the Context of Influenza Pandemic" Emerg. Infect. Dis. (2006) 12(6):881-886.

New England Biolabs (NEB) Catalog (1998-1999) pp. 1, 79, 121, 284.

Newcombe et al. "PCR of peripheral blood for diagnosis of meningococcal disease" (1996) 34:1637-1640.

Ng et al., "Serial analysis of the plasma concentration of SARS coronavirus RNA in pediatric patients with severe acute respiratory syndrome" Clin. Chem. (2003) 49:2085.

Ng et al., "Quantitative analysis and prognostic implication of SARS coronavirus RNA in the plasma and serum of patients with severe acute respiratory syndrome" Clin. Chem. (2003) 49:1976-1980.

Nilsson et al., "Evaluation of mitochondrial DNA coding region assays for increased discrimination in forensic analysis" *Forensic Science International: Genetics* (2008) 2:1-8.

Nishikawa et al., "Reconstitution of active recombinant Shiga toxin (Stx)1 from recombinant StxI-A and StxI-B subunits independently produced by *E. coli* clones" *FEMS* (1999) 178:13-18.

Norder et al., "Typing of Hepatitis B Virus Genomes by a Simplified Polymerase Chain Reaction" *J. Med. Virol.* (1990) 31 :215-221.

Nordhoff, E., et al., "Matrix Assisted Laser Desorption/Ionization Mass Spectrometry of Nucleic Acids with Wavelengths in the Ultraviolet and Infrared" 6 Rapid Commun. Mass Spectrom. 771-776 (1992) ('787 reexamination).

Nubel et al., "PCR primers to amplify 16S rRNA genes from Cyanobacteria," Applied and Environmental Microbiology, 63(8):3327-3332 (Aug. 1997).

Null et al., "Preparation of single-stranded PCR products for electrospray ionization mass spectrometry using the DNA repair enzyme lambda exonuclease" *Analyst* (2000) 125:619-626.

Null et al., "Genotyping of Simple and Compound Short Tandem Repeat Loci Using Electrospray Ionization Fourier Transform Ion Cyclotron Resonance Mass Spectrometry" Analytical Chemistry (2001) 73:4514-4521.

Null et al., "Perspectives on the use of electrospray ionization Fourier transform ion cyclotron resonance mass spectrometry for short tandem repeat genotyping in the post-genome era" *Journal of Mass Spectrometry* (2001) 36:589-606.

Null et al., "Evaluation of sample preparation techniques for mass measurements of PCR products using ESI-FT-ICR mass spectrometry" *Journal of the American Society for Mass Spectrometry* (2002) 13:338-344.

Null et al., "Determination of a correction to improve mass measurement accuracy of isotopically unresolved polymerase chain reaction amplicons by electrospray ionization Fourier transform ion cyclotron resonance mass spectrometry" *Rapid Comm. Mass Spectrom.* (2003) 17:1714-1722.

Null et al., "Implications of hydrophobicity and free energy of solvation for characterization of nucleic acids by electrospray ionization mass spectrometry" *Anal. Chem.* (2003) 75:1331-1339.

Nunes, E. L. et al., "Detection of ileS-2 Gene Encoding Mupirocin Resistance in Methicillin-Resistant *Staphylococcus aureus* by Multiplex PCR" Diagn. Microbiol. Infect. Dis. (1999) 34(2): 77-81.

Nygren et al., "Quantification of HIV-1 Using Multiple Quantitative Polymerase Chain Reaction Standards and Bioluminometric Detection" Anal. Biochem. (2001) 288(1):28-38.

Oberacher H et al., "Increased foresnic efficiency of DNA fingerprints through simultaneous resolution of length and nucleotide variability by high-performance mass spectrometry," Human Mutation 29(3):427-432 (Mar. 2008)+A613+A714.

Oberacher et al., "Analysis of polymerase chain reaction products by on-line liquid chromatography-mass spectrometry for genotyping of polymeric short tandem repeat loci" (2001) 73:5109-5115.

Oberste, et al., "Molecular phylogeny and proposed classification of the Simian picornaviruses," J. Virol. (2002) 76:1244-1251.

Oberste, et al., "Improved molecular identification of enteroviruses by RT-PCR and amplicon sequencing," J. Clin. Virol. (2003) 26:375-377.

Oberste, et al., "Molecular epidemiology and type-specific detection of echovirus 11 isolates from the Americas, Europe, Africa, Australia, southern Asia and the Middle East," Virus Res. (2003) 91 :241-248.

O'Guinn, M.L. et al., "Field Detection of Eastern Equine Encephalitis Virus in the Amazon Basin Region of Peru Using Reverse Transcription-Polymerase Chain Reaction Adapted for Field Identification of Arthropod-Borne Pathogens," *Am. J. Trop. Med. Hyg*. (2004) 70(2): 164-171.

Oizumi, N, et al., "Relationship between mutations in the DNA gyrase and topoisomerase IV genes and nadifloxacin resistance in clinically isolated quinolone-resistant *Staphylococcus aureus*," Journal of Infection and Chemotherapy: Official Journal of the Japan Society of Chemotherapy, 7(3):191-194 (Sep. 2001).

Okada, M. et al., "Detection and sequence-based typing of human adenoviruses using sensitive universal primer sets for the hexon gene", Arch. Virol., 2007, vol. 152, No. 1, pp. 1-9.

Okuma, K. et al., "Dissemination of New Methicillin-Resistant *Staphylococcus aureus* Clones in the Community," J. Clin. Mcrobiol. (2002) 40(11):4289-4294.

Oliveira, D. C. et al., "Genetic Organization of the Downstream Region of the mecA Element in Methicillin-Resistant *Staphylococcus aureus* Isolates Carrying Different Polymorphisms of This Region," Antimicrob. dients Chemother. (2000) 44(7): 1906-1910.

Oliveira, D. C. et al., "Multiplex PCR Strategy for Rapid Identification of Structural Types and Variants of the mec Element in Methicillin-Resistant *Staphylococcus aureus*," Antimicrob. Agents Chemother. (2002) 46(7):2155-2161.

Olsen et al. "Transhemispheric exchange of Lyme disease spyrochetes by seabirds" Journal of Clinical Microbiology (1995) 33:3270-3274.

Osiowy, C. et al., "Direct Detection of Respiratory Syncytial Virus, Parainfluenze Virus, and Adenovirus in Clinical Respiratory Specimens by a Multiplex Reverse Transcription-PCR Assay", J. Clin. Microbiol., 1998, vol. 36, No. 11, pp. 3149-3154.

Ostrander, E. A. et al., "Identification and Characterization of Dinucleotide Repeat (CA)n Markers for Genetic Mapping in Dog," Genomics (1993) 16(1):207-213.

Ounissi, H. et al., "Gene Homogeneity for Aminoglycoside-Modifying Enzymes in Gram-Positive Cocci," Antimicrob. Agents Chemother. (1990) 34(11):2164-2168.

Pan, Z.-Q et al., "Oligonucleotide-targeted degradation of U1 and U2 snRNAs reveals differential interactions of simian virus 40 pre-mRNAs with snRNPs," Nucleic Acids Res. (1989) 17(16):6553-6568.

Pannetier et al., "Quantitative titration of nucleic acids by enzymatic amplification reactions run to saturation" (1993) 21 :577-583.

Parson et al., "Population data for 101 Austrian Caucasian mitochondrial DNA d-loop sequences: Application of mtDNA sequence analysis to a forensic case" *Int. J. Legal Med.* (1998) 111:124-132.

Pastorino, B. et al., "Development of a TaqMan PCR assay without RNA extraction step for the detection and quantification of African Chikungunya viruses," *J. Virol. Methods* (2005) 124(1-2): 65-71.

Paterson et al., "Fine Mapping of Quantitative Trait Loci Using Selected Overlapping Recombinant Chromosomes, in an Interspecies Cross of Tomato" *Genetics* (1990) 124:735-742.

Pawa, A. et al., "Co-transfer of plasmids in association with conjugative transfer of mupirocin or mupirocin and penicillin resistance in methicillin-resistant *Staphylococcus aureus*;" J. Med. Microbiol. (2000) 49: 1103-1107.

Payne et al. Antimicrobials: The challenge of antibiotic resistant bacterial pathogens: the medical need, the market and prospects for new antimicrobial agents. Current Opinion in Microbiology 7:435-438 (2004).

Peng et al., "Rapid detection of *Shigella* species in environmental sewage by an immunocapture PCR with universal primers" *Applied and Environmental Microbiology* (2002) 68:2580-2583.

Perez-Roth, E. et al., "Multiplex PCR for Simultaneous Identification of *Staphylococcus aureus* and Detection of Methicillin and Mupirocin Resistance," J. Clin. Microbial. (2001) 39(11):4037-4041.

Peters et al., "Quantification of the detection of Pneumocystis carinii by DNA amplification" Mol. Cell. Probes (1992) 6:115-117.

Pfeffer, M. et al., "Genus-Specific Detection of Alphaviruses by a Semi-Nested Reverse Transcription-Polymerase Chain Reaction," *Am. J. Trop. Med Hyg.* (1 997) 57(6): 709-718.

Pfeffer, M. et al., "Specific Detection of Chikungunya Virus Using a RT-PCR/Nested PCR Combination," *J. Vet. Med. B* (2002) 49(1): 49-54.

Pieles, U, et al., Matrix-Assisted Laser Desorption Ionization Time-of-Flight Spectrometry: A Powerful Tool for the Mass and Sequence Analysis of Natural and Modified Oligonucleotides 21 Nucleic Acids Res. 3191-3196 (1993) ('787 reexamination).

Pillai, S.D., :Rapid molecular detection of microbial pathogens: breakthroughs and challenges Arch Virol., 1997, 13 Suppl., 67-82.

Piper, J. et al., "Commercially Available Technique for Rapid Laboratory Detection of Methicillin Resistance Among *Staphylococcus aureus*," Diagn. Microbial. Infect. Dis. (1988) 11(3): 177-180.

Poddar, S.K., "Detection of adenovirus using PCR and molecular beacon", J. Virol. Methods., 1999, vol. 82, No. 1, pp. 19-26.

Pomerantz et al., "Determination of oligonucleotide composition from mass spectrometrically measured molecular weight" *Journal of the American Society for Mass Spectrometry* (1993) 4:204-209.

Pring-Akerblom, P., et al., "PCR-based detection and typing of human adenoviruses in clinical samples", Res. Virol., 1997, vol. 148, No. 3, pp. 225-231.

Pring-Akerblom, P., et al., "Multiplex Polymerase Chain Reaction for Subgenus-Specific Detection of Human Adenoviruses in Clinical Samples", J. Med. Virol., 1999, vol. 58, No. 1, pp. 87-92.

Promega T4 Polynucleotide Kinase, Promega Technical Bulletin No. 519, Jul. 2002.

Puthavathana et al., "Molecular characterization of the complete genome of human influenza H5N1 virus isolates from Thailand" J. Gen. Virol. (2005) 86:423-433.

Qadri, S. M. et al., "Rapid Detection of Methicillin-Resistant *Staphylococcus aureus* by Crystal MRSA ID System," J. Clin. Microbiol. (1994) 32(7):1830-1832.

Raaum, R. L. et al., "Catarrhine primate divergence dates estimated from complete mitochondrial genomes: concordance with fossil and nuclear DNA evidence," *J. Hum. Evol.* (2005) 48:237-257.

Ramisse et al., "Identification and characterization of *Bacillus anthracis* by multiplex PCR analysis of sequences on plasmids pX01 and pX02 and chromosomal DNA" FEMS Microbiology Letters (1996) 145(1):9-16.

Rangarajan, Sampath, et al., "Rapid identification of emerging infectious agents using PCR and electrospray ionization mass spectrometry" Ann. N.Y. Acad. of Sci (2007) 1102:109-120.

Reid et al., "Primary diagnosis of foot-and-mouth disease by reverse transcription polymerase chain reaction" *Journal of Virological Methods* (2000) 89:167-176.

Reilly et al., "Design and use of 16S ribosomal DNA-directed primers in competitive PCRs to enumerate proteolytic bacteria in the rumen" *Microb. Ecol.* (2002) 43:259-270.

Reischl, Frontiers Biosci., 1996, 1, Application of Molecular Biology-Based Methods to the Diagnosis of Infectious Diseases 1, e72-e77.

Reischl, U. et al., "Rapid Identification of Methicillin-Resistant *Staphylococcuss aureus* and Simultaneous Species Confirmation Using Real-Time Fluorescence PCR," J. Clin. Microbiol. (2000) 38(6):2429-2433.

Roberts, M.M. et al., "Three-Dimensional Structure of the Adenovirus Major Coat Protein Hexon", Science, 1986, vol. 232, No. 4754, pp. 1148-1151.

Robinson, D. A. et al., "Multilocus sequence typing and the evolution of methicillin-resistant *Staphylococcus aureus*," Clin. Microbiol. Infect. (2004) 10:92-97.

Rong et al., "Design and Application of 60mer oligonucleotide microarray in SARS coronavirus detection", Chinese Sci. Bull., 2003, 48, 1165-1169.

Ross et al., "Discrimination of Single-Nucleotide Polymorphisms in Human DNA Using Peptide Nucleic Acid Probes Detected by MALDI-TOF Mass Spectrometry" *Anal. Chem.* (1997) 69:4197-4202.

Ross et al., "Analysis of DNA fragments from conventional and microfabricated PCR devices using delayed extraction MALDI-TOF mass spectrometry" *Anal. Chem.* (1998) 70:2067-2073.

Ruan et al., Comparative full-length genome sequence analysis of 14 SARS coronavirus isolates and common mutations associated with the putative origins of infection, Lancet (2003) 361:1832.

Rota et al., "Sequencing of a cDNA clone of the nucleoprotein gene of influenza B/Ann Arbor/1/86" Nucleic Acids Research (1989) 17:3595.

Ruest et al., "Comparison of the Directigen Flu A+B test, the QuickVue Influenza Test, and Clinical Case Definition to Viral Culture and Reverse Transcription-PCR for Rapid Diagnosis of Influenza Virus Infection" J. Clin. Microbiol. (2003) 41(8):3487-3493.

Rupf et al., "Quantitative determination of *Streptococcus mutans* by using competitive polymerase chain reaction" Eur. J. Oral. Sci. (1999) 107(2):75-81.

Russell, K.L. et al., "Transmission Dynamics and Prospective Environmental Sampling of Adenovirus in a Military Recruit Setting", J. Infect. Dis., 2006, vol. 194, No. 7, pp. 877-885.

Sabat, A. et al., "Comparison of PCR-Based Methods for Typing *Staphylococcus aureus* Isolates," J. Clin. Microbiol. (2006) 44(10):3804-3807.

Sackesen, C. et al., "Use of polymerase chain reaction for detection of adenovirus in children with or without wheezing", Turk. J. Pediatr., 2005, vol. 47, No. 3, pp. 227-231.

Sakai, H. et al., "Simultaneous Detection of *Staphylococcus aureus* and Coagulase-Negative Staphylococci in Positive Blood Cultures by Real-Time PCR with Two Fluorescence Resonance Energy Transfer Probe Sets," J. Clin. Microbiol. (2004) 42(12):5739-5744.

Sala et al., "Ambiguous base pairing of the purine analogue 1-(2'deoxy-B-D-ribofuranosyl)-imidazole-4-carboxamide during PCR" *Nucl. Acids Res.* (1996) 24:3302-3306.

Sambrook et al., Molecular Cloning: A Laboratory Manual, 2nd Edition, Cold Spring Harbor Press, Cold Spring Harbor, NY 1989.

Sampath et al., "Rapid Identification of Emerging Pathogens: Coronavirus" Emerg. Infect. Dis. (2005) 11(3):373-379.

Sampath et al "Global surveillance of emerging influenza virus genotypes by mass spectrometry" Plos One (2007) 5:e489.

Sampath et al "Rapid Identification of Emerging Infectious Agents Using PCR and Electrospray Ionization Mass Spectrometry" Ann. N.y. Acad. Sci. (2007) 1102:109-120.

Sanchez et al., "Detection and Molecular Characterizatio of Ebola viruses causing disease in human and nonhuman primates" The Journal of Infectious Diseases, 179(1):S164-S169 (1999).

Sanchez, J.L. et al., "Epidemic of Adenovirus-Induced Respiratory Illness Among US Military Recruits: Epidemiologic and Immunologic Risk Factors in Healthy, Young adults", J. Med. Virol., 2001, vol. 65, No. 4, pp. 710-718.

Sanchez-Seco, M. P. et al., "A generic nested-RT-PCR followed by sequencing for detection and identification of members of the alphavirus genus," *J. Virol. Methods* (2001) 95(1-2): 153-161.

Santos et al. "Identification and phylogenetic sorting of bacterial lineages with universally conserved genes and proteins" Environmental Microbiology 6(7):754-759, Jul. 2004.

Sarantis, H. et al., "Comprehensive Detection and Serotyping of Human Adenoviruses by PCR and Sequencing", J. Clin. Microbial., 2004, vol. 42, No. 9, pp. 3963-3969.

Sauer et al., "A novel procedure for efficient genotyping of single nucleotide polymorphisms" *Nucleic Acids Research* (2000) 28:E13.1.

Scaramozzino et al., "Comparison of *Flavivirus* universal primer pairs and development of a rapid, highly sensitive heminested reverse transcription-PCR assay for detection of flaviviruses targeted to a conserved region of the NS5 gene sequences" *J. Clin. Microbiol.* (2001) 39:1922-1927.

Schabereiter-Gurtner et al "Application of broad-range 16s rRNA PCR amplification and DGGE fingerprinting for detection of tick-infecting bacteria" The Journal of Microbiological Methods (2003 52:251-260.

Scheffner, M. et al., "The E6 Oncoprotein Encoded by Human Papillomavirus Types 16 and 18 Promotes the Degradation of p53," Cell (1990) 63:1129-1136.

Schena M. "Genome analysis with gene expression microarrays" Bioessays (1996) 18:427-431.

Scheuermann et al. "Polymerase chain-reaction-based mRNA quantification Using an internal standard: analysis of oncogene expression" (1993) 218:446-473.

Schlecht, N. F. et al., "Viral Load as a Predictor of the Risk of Cervical Intraepithelial Neoplasia," Int. J. Cancer (2003) 103:519-524.

Schmidt et al., "Analysis of a marine pikoplankton community by 16s rRNA gene cloning and sequencing," J. Bacteriol. (1991) 173:4371-4378.

Schmitz, F. J. et al., "Specific information concerning taxonomy, pathogenicity and methicillin resistance of staphylococci obtained by a multiplex PCR." J. Med. Microbiol. (1997) 46:773-778.

Schmitz, F. J. et al., "Development of a multiplex-PCR for direct detection of the genes for enterotoxin B and C, and toxic shock syndrome toxin-1 in *Staphylococcus aureus* isolates," J. Med. Microbiol. (1998) 47(4):335-340.

Schmitz, F. J. et al., "Development of Resistance to Ciprofloxacin, Rifampin, and Mupirocin in Methicillin-Susceptible and -Resistant *Staphylococcus aureus* Isolates," Antimicrob. Agents Chemother. (2000) 44(11): 3229-3231.

Schram et al., "Mass Spectrometry of Nucleic Acid Components" *Biomedical Applications of Mass Spectrometry* (1990) 34:203-280.

Schultz et al., "Polymerase chain reaction products analyzed by charge detection mass spectrometry" *Rapid Communications in Mass Spectrometry* (1999) 13:15-20.

Schwartz, M, et al., "Prenatal diagnosis of alpha-1-antitrypsin deficiency using polymerase chain reaction (PCR). Comparison of conventional RFLP methods with PCR used in combination with allele specific oligonucleotides or RFLP analysis," 36 Clin. Genet. 419-426 (1989) ('787 reexamination).

Schweiger et al., "Application of a Fluorogenic PCR Assay for Typing and Subtyping of Influenza Viruses in Respiratory Samples" J. Clin. Microbiol. (2000) 38(4):1552-1558.

Sciacchitano et al., "Analysis of polymerase chain reaction-amplified DNA fragments of *Clostridium botulinum* type E neurotoxin gene by high performance capillary electrophoresis." *J. Liq. Chromatogr. Relat. Technol.* (1996) 19:2165-2178.

Scott-Taylor, T.H. et al., "Conserved Sequences of the Adenovirus Genome for Detection of all Human Adenovirus Types by Hybridization", J. Clin. Microbiol., 1992, vol. 30, No. 7, pp. 1703-1710.

Seifarth, et al., "Rapid identification of all known retroviral reverse transcriptase sequences with a novel versatile detection assay," AIDS Res. Human Retrovir. (2000) 16:721-729.

Sellner, L. N. et al., "Sensitive detection of Ross River virus—a one-tube nested RT-PCR," *J. Virol. Methods* (1994) 49(1): 47-58.

Sellner, L., "A Single-Tube Nested RT-PCR for the Detection of Ross River Virus," *Methods Mol. Biol.* (1998) 92: 145-152.

Senko et al., "Determination of Monoisotopic Masses and Ion Populations for Large Biomolecules from Resolved Isotopic Distributions," *J. Am. Soc. Mass Spectrom.* (1995) 6:229.

Seshadri et al., "Differential Expression of Translational Elements by Life Cycle Variants of *Coxiella burnetii*" *Infect. Immun.* (1999) 67:6026-6033.

Shadan, F. F. et al., "n-Butyrate, a Cell Cycle Blocker, Inhibits the Replication of Polyomaviruses and Papillomaviruses but Not That of Adenoviruses and Herpesviruses," *J. Virol.* (1994) 68(8):4785-4796.

Shaver et al., "Variation in 16S-23S rRNA intergenic spacer regions among *Bacillus subtilis* 168 isolates" *Molecular Microbiology* (2001) 42:101-109.

Shaver et al., "Restriction fragment length polymorphism of rRNA operons for discrimination and intergenic spacer sequences for cataloging *Bacillus subtilis* sub-groups" *J. Microbiol Methods* (2002) 50:215-223.

Shi et al., "Design and application of 60mer oligonucleotide microarray in SARS coronavirus detection" Chinese Sci. Bull. (2003) 48:1165-1169.

Shimaoka, M. et al., "Development of Enzyme-Labeled Oligonucleotide Probe for Detection of mecA gene in Methicillin-Resistant *Staphylococcus aureus*," J. Clin. Microbiol (1994) 32(8): 1866-1869.

Shimaoka, M. et al., "Detection of the gene for toxic shock syndrome toxin 1 in Siaphylococcus aureus by enzyme-labelled oligonucleotideprobes," J. Med. Microbiol. (1996) 44:215-218.

Shrestha, N. K. et al., "Rapid Identification of *Staphylococcus aureus* and the mecA Gene from BacT/ALERT Blood Culture Bottles by Using the Lightcycler System," J. Clin. Microbiol. (2002) 40(1):2659-2661.

Simonsen et al., "The Impact of Influenza Epidemics on Hospitalizations" J. Infect. Dis. (2000) 181:831-837.

Skov, R L. et al., "Evaluation of a new 3-h hybridization method for detecting the mecA gene in *Staphylococcus aureus* and comparison with existing genotypic and phenotypic susceptibility testing methods," J. Antimicrob. Chemother. (1999) 43: 467-475.

Smirnov et al. "Application of DNA-binding polymers for preparation of DNA for analysis by matrix-assisted laser desorption/ionization mass spectrometry." Rapid Comm in Mass Spectrometry (2001) 15:1427-1432.

Smith and Waterman, Adv. Appl. Math., 1981, 2, 482-489.

Song et al., "Identification of cry11-type genes from *Bacilus thuringiensis* strains and characterization of a novel cry11-type gene" App. Environ. Microbiol. (2003) 69:5207-5211.

Spackman et al., "Development of a real-time reverse transcriptase PCR assay for type A influenza virus and the avian H5 and H7 hemagglutinin subtypes" Journal of Clinical Microbiology (2002) 40:3256-3260.

Spiess, et al., Trehalose is a potent PCR enhancer: Lowering of DNA melting temperature and thermal stabilization of Taq polymerase by the disaccharide trehalose, In: Clinical Chemistry, 2004, 50(7):1256-1259.

Srinivasan et al., "Matrix-assisted laser desorption/ionization time-of-flight mass spectrometry as a rapid screening method to detect mutations causing Tay-Sachs disease" *Rapid Communications in Mass Spectrometry* (1997) 11:1144-1150.

Steffens et al., "Sequence analysis of mitochondrial DNA hybervariable regions using infrared fluorescence detection" *BioTechniques* (1998) 24:1044-1046.

Stephensen CB et al., "Phylogenetic analysis of a highly conserved region of the polymerase gene from 11 coronaviruses and development of a consensus polymerase chain reaction assay" Virus Research Amsterdam NL, 60(2):181-189 (Apr. 1, 1999).

Stone et al., "Rapid detection and simultaneous subtype differentiation of influenza A viruses by real time PCR" (2004) *Journal of Virological Methods* (2004) 117:103-112.

Stoneking et al., "Population variation of human mDNA control region sequences detected by enzymatic amplification and sequence-specific oligonucleotide probes," American Journal of Human Genetics (1991) 48:370-382.

Stratagene, 1988 Catalog, p. 39.

Strommenger, B. et al., "Multiplex PCR Assay for Simultaneous Detection of Nine Clinically Relevant Antibiotic Resistance Genes in *Staphylococcus aureus*," J. Clin. Microbial. (2003) 41(9):4089-4094.

Studdert, M. J. et al., "Polymerase chain reaction tests for the identification of Ross River, Kunjin and Murray Valley encephalitis virus infections in horses," *Aust. Vet. J.* (2003) 81(1-2): 76-80.

Stuhlmeier, R et al., "Fast, simultaneous, and sensitive detection of staphylococci," J. Clin. Pathol. (2003) 56:782-785.

Sumner et al. "PCR Amplification and Comparison of Nucleotide Sequences from the groESL Heat Shock Operon of *Ehrlichia* Species" Journal of Critical Microbiology (1997) 35:2087-2092.

Sundsfjord, A. et al., "Genetic methods for detection of antimicrobial resistance," APMIS (2004) 112:815-837.

Swanborg, R.H., "Human herpesvirus 6 and *Chlamydia pneumoniae* as etiologic agents in multiple sclerosis—a critical review" Microbes and Infection, 4:1327-1333 (2002).

Swaminathan, B., et al., Emerging Infectious Diseases, 2001, 7, 382-389.

Swenson, J. M. et al., "Perfomance of Eight Methods, Including Two New Rapid Methods, for Detection of Oxacillin Resistance in a Challenge Set of *Staphylococcus aureus* Organisms," J. Clin. Microbial. (2001) 39(10):3785-3788.

Takagaki, Y. et at., "Four factors are required for 3'-end cleavage of pre-mRNAs," Genes Dev. (1989) 3:1711-1724.

Takahashi et al., "Characterization of gryA, gryB, grlA and grlB mutations in fluoroquinolone-resistant clinical isolates of *Staphylococcus aureus*" *J. Antimicrob. Chemother* (1998) 41 :49-57.

Takahata M, et al., "Mutations in the gyrA and grlA genes of quinolone-resistant clinical isolates of methicillin-resistant *Staphylococcus aureus*," The Journal of Antimicrobial Chemotherapy, 38(3):543-546 (Sep. 1996).

Takayama, R. et al., "Quantification of Adenovirus Species B and C Viremia by Real-Time PCR in Adults and Children Undergoing Stem Cell Transplantation", J. Med. Virol., 2007, vol. 79, No. 3, pp. 278-284.

Takeuchi et al., "Serotyping of Adenoviruses on Conjunctival Scrapings by PCR and Sequence Analysis" *Journal of Clinical Microbiology* (1999) 37:1839-1845.

Talaat et al., "Genome-directed primers for selective labeling of bacterial transcripts for DNA microarray analysis" *Nature Biotechnology* (2000) 18:676-682.

Tan, T. Y., "Use of molecular techniques for the detection of antibiotic resistance in bacteria," Expert. Rev. Mol. Diagn. (2003) 3(1):93-103.

Tanabe, F. et al., "The Properties and mec A Gene of the Methicillin-Resistant *Staphylccoccus aureus* Isolated in Fukushima Medical College Hospital," Fukushima J. Med. Sci (1993) 39(1):35-42.

Tang, K., "Matrix-Assisted Laser Desorption/Ionization Mass Spectrometry of Oligonucleotides," Dissertation submitted to the Faculty of Vanderbilt University (Aug. 1994).

Tang, K, N.I. Taranenko, S.L. Allman, L.Y. Chang and C.H. Chen, "Double-Stranded DNA Analysis by Matrix Assisted Laser Desorption/Ionization," 42nd ASMS Conference on Mass Spectrometry (Jun. 1994).

Tang, K, N.I. Taranenko, S.L. Allman, L.Y. Chang and C.H. Chen, "Detection of 500-Nucleotide DNA by Laser Desorption Mass Spectrometry," Rapid Commun. Mass Spectrom. (Sep. 1994) 8: 727-730.

Tatuch et al., "Heteroplasmic mtDNA mutation (T-G) at 8993 can cause Leigh disease when the percentage of abnormal mtDNA is high" *Am. J. Hum. Genet.* (1992) 50:852-858.

Tarassishin, L. et al., "Adenovirus core protein VII displays a linear epitope conserved in a range of human adenoviruses", J. Gen. Virol., 1999, vol. 80, pp. 47-50.

Tarassishin, L. et al., "An epitope on the adenovirus fibre tail is common to all human subgroups", Ach. Virol., 2000, vol. 145, pp. 805-811.

Taubenberger et al., "Characterization of the 1918 influenza virus polymerase genes" Nature (2005) 437:889-893.

Taylor, L.H., et al., Philos. Trans. R. Soc. Lond B. Biol. Sci. 2001, 356, 983-989.
Tenover, F. C. et al., "Characterization of a Strain of Community-Associated Methicillin-Resistant Slaphylococcus aureus Widely Disseminated in the United States," J. Clin.Microbiol. (2006) 44(1):108-118.
Teramura, T. et al., "Quantitative detection of serum adenovirus in a transplant recipient", Lancet, 2002, vol. 359, pp. 1945.
Thiel, et al., "Infectious RNA transcribed in vitro from a cDNA copy of the human coronavirus genome cloned in vaccinia virus" J. Gen. Virology 2001 82:1273-1281.
Thompson et al., "Influenza-Associated Hospitalizations in the United States" JAMA (2004) 292:1333-1340.
Thompson et al., "Clustal W: Improving the sensitivity of progressive multiple sequence alignment through sequence weighting, position-specific gap penalties and weight matrix choice" Nucleic Acid Res. (1994) 22:4673-80.
Tokue, Y. et al., "Comparison of a Polymerase Chain Reaction Assay and a Conventional Microbiologic Method for Detection of Methicillin-Resistant Slaphylococcus aureus," Antimicrob. Agents Chemother. (1992) 36(1):6-9.
Tong et al., "Ligation reaction specificities of an NAD+-dependent DNA ligase from the hyperthermophile *Aquifex aeolicus*" *Nucleic Acids Res* (2000) 28:1447-1454.
Top, F., JR., "Control of Adenovirus Acute Respiratory Disease in U.S. Army Trainees", Yale J. Biol. Med., 1975, vol. 48, pp. 185-195.
Torroni et al., "Classification of European mtDNAs from an Analysis of Three European Populations" *Genetics* (1996) 144:1835-1850.
Towner, K. J. et al., "Development and evaluation of a PCR-based immunoassay for the rapid detection of methicillin-resistant *Staphylococcus aureus*," J. Med. Microbial. (1998) 47:607-613.
Tsuneyoshi et al., "Mass spectrometric gene diagnosis of one-base substitution from polymerase chain reaction amplified human DNA" (1997) 11:719-722.
Tsunoda et al., Time and Memory Efficient Algorithm for Extracting Palindromic and Repetitive Subsequences in Nucleic Acid Sequences Pacific Symposium on Biocomputing (1999) 4:202-213.
Udo, E. E. et al., "Rapid detection of methicillin resistance in staphylococci using a slide latex agglutination kit," Int. J Antimicrob. Agents. (2000) 15(1):19-24.
Udo, E. E. et al., "Genetic analysis of methicillin-resistant *Staphylococcus aureus* expressing high- and low-level mupirocin resistance." J. Med. Microbiol. (2001) 50:909-515.
Udo, E. E. et al., "A chromosomal location of the mupA gene in *Staphylococcus aureus* expressing high-level mupirocin resistance," J. Antimicrob. Chemother. (2003) 51:1283-1286.
Unal et al., "Detection of Methicillin-Resistant Staphylococci by Using the Polymerase Chain Reaction" J. Clin. Microbiol. (1992) 30:1685-1691.
Unpublished U.S. Appl. No. 10/318,463, filed Dec. 13, 2002.
Unpublished U.S. Appl. No. 10/323,186, filed Dec. 18, 2002.
Unpublished U.S. Appl. No. 10/323,187, filed Dec. 18, 2002.
Unpublished U.S. Appl. No. 10/324,721, filed Dec. 18, 2002.
Unpublished U.S. Appl. No. 10/728,486, filed Dec. 5, 2003.
Unpublished U.S. Appl. No. 11/209,439, filed Aug. 23, 2005.
Unpublished U.S. Appl. No. 11/233,630, filed Sep. 2, 2005.
Unpublished U.S. Appl. No. 11/682,259, filed Mar. 5, 2007.
Unpublished U.S. Appl. No. 60/604,329, filed Aug. 24, 2004.
Unpublished U.S. Appl. No. 60/632,862, filed Dec. 3, 2004.
Unpublished U.S. Appl. No. 60/639,068, filed Dec. 22, 2004.
Unpublished U.S. Appl. No. 60/648,188, filed Jan. 28, 2005.
Unpublished U.S. Appl. No. 60/658,248, filed Mar. 3, 2005.
Unpublished U.S. Appl. No. 90/010,209, filed Jun. 27, 2008.
Unpublished U.S. Appl. No. 90/010,210, filed Jun. 27, 2008.
Upton, A. et al., "Mupirocin and *Staphylococcus aureus*: a recent paradigm of emerging antibiotic resistance," J. Antimicrob. Chemother. (2003) 51: 613-617.
Vabret, A., et al., "Development of a PCR- and hybridization-based assay (PCR Adenovirus Consensusâ) for the detection and the species identification of adenoviruses in respiratory specimens", J. Clin. Virol., 2004, vol. 31, No. 2, pp. 116-122.

Van Aerschot et al., "In search of acyclic analogues as universal nucleosides in degenerate probes" *Nucleosides and Nucleotides* (1995) 14:1053-1056.
Van Baar et al., "Characterization of Bacteria by Matrix Assisted Laser Desorption/Ionization and Electrospray Mass Spectrometry" *FEMS Microbiol. Review* (2000) 24:195-219.
Van Camp et al., "Amplification and sequencing of variable regions in bacteria 23S ribosomal RNA genes with conserved primer sequences" *Current Microbiology* (1993) 27:147-151.
Vanchiere et al. "Detection of BK virus and Simian virus 40 in the urine of healthy children" Journal of Medical Virology (2005) 75:447-454.
Van Der Vossen et al., "DNA based typing, identification and detection systems for food spoilage microorganisms: development and implementation" *Int. J. Food Microbiol.* (1996) 33:35-49.
Van Der Zee, et al., "Rapid and alternative screening methods for microbiological analysis" J. AOAC Int., 1997, 80, 934-940.
Van Dinten et al., "Proteolytic Processing of the Open Reading Frame 1b-Encoded Part of Arterivirus Replicase Is Mediated by nsp4 Serine Protease and Is Essential for Virus Replication" J. Virology, 1999, vol. 73, pp. 2027-2037.
Van Elden et al., "Simultaneous Detection of Influenza Viruses A and B Using Real-Time Quantitative PCR" J. Clin. Microbiol. (2001) 39(1):196-200.
Van Elden et al., "Clinical diagnosis of influenza virus infection: evaluation of diagnostic tools in general practice" Br. J. Gen. Pract. (2001) 51:630-634.
Van Ert et al., "Mass spectrometry provides accurate characterization of two genetic marker types in *Bacillus anthracis*" *Biotechniques* (2004) 37:642-644, 646, 648.
Van Leeuwen, W. B. et al., "Rapid Detection of Methicillin-Resistance in *Staphylococus aureus* Isolates by the MRSA-Screen Latex Agglutination Test," J. Clin. Microbiol. (1999) 37(9):3029-3030.
Van Leeuwen, W. B. et al., "Multilocus Sequence Typing of *Staphylococcus aureus* with DNA Array Technology," J. Clin. Microbiol. (2003) 41(7):3323-3326.
Vanderhallen et al., "Identification of Encephalomyocarditis Virus in Clinical Samples by Reverse Transcription-PCR Followed by Genetic Typing Using Sequence Analysis" *J. Clin. Microbiol.* (1998) 36:3463-3467.
Vannuffel, P. et al.. "Specific Detection of Methicillin-Resistant *Staphylococcus* Species by Multiplex PCR," J. Clin Microbiol. (1995) 33(11):2864-2867.
Vannuffel, P. et al., "Rapid and Specific Molecular Identification of Methicillin-Resistant *Staphylococcus aureus* in Endotracheal Aspirates from Mechanically Ventilated Patients," J Clin. Microbiol. (1998) 36(8):2366-2368.
Videla, C. et al., "Genomic analysis of adenovirus isolated from Argentinean children with acute lower respiratory infections", J. Clin. Virol., 1999, vol. 14, pp. 67-71.
Vilchez, Regis A et al., "Detection of polyomavirus simian virus 40 tumor antigen DNA in AIDS related systemic non-Hodgkin lymphoma," J. AIDS Journal of Acquired Immune Deficiency Syndromes, 29(2):109-116 (Feb. 1, 2002).
Voelter C et al., "Screening human tumor samples with a broad-spectrum polymerase chain reaction method for the detection of polyomaviruses", Virology, Academic Press, Orlando, US 237(2):389-396 (Oct. 1997).
Volokhov et al. Microarray analysis of erythromycin resistance determinants. Journal of Applied Microbiology 95:787-798 (2003).
Von Eiff, C. et al., "Pathogenesis of infections due to coagulase-negative staphylococci," Lancet Infect. Dis. (2002) 2:677-685.
Walker, E. S. et al., "A Decline in Mupimcin Resistance in Methicillin-Resistant *Staphylococcus aureus* Accompanied Administrative Control of Prescriptions," J. Clin. Microbiol. (2004) 42(6):2792-2795.
Wallace, et al., "The Enigma of Endonuclease VII. DNA Repair," 2:441-453 (2003).
Wallet, F. et al., "Choice of a routine method for detecting methicillin-resistance in staphylococci," I Antimicrob. Chemother. (1996) 37:901-909.
Walters et al., "Genotyping single nucleotide polymorphisms using intact polymerase chain reaction products by electrospray quadrupole mass spectrometry" *Rapid Communications in Mass Spectrometry* (2001) 15:1752-1759.

Wang, G. et al., "Targeted Mutagenesis in Mammalian Cells Mediated by Intracellular Triple Helix Formation," Mol. Cell. Biol. (1995) 15(3):1759-1768.

Ward et al., "Design and performance testing of quantitative real time PCR assays for influenza A and B viral load measurement" *Journal of Clinical Virology* (2004) 29:179-188.

Weissenbacher, M. et al., "Etiologic and Clinical Evaluation of Acute Lower Respiratory Tract Infections in Young Argentinean Children: An Overview", Rev. Infect. Dis., 1990, vol. 12, Suppl. 8; pp. S889-S898.

Welham et al., "The Characterization of Micro-organisms by Matrix-assisted Laser Desorption/Ionization Time-of-flight Mass Spectrometry" *Rapid Communications in Mass Spectrometry* (1998) 12:176-180.

Wertheim, H. F. et al., "Effect of Mupirocin Treatment on Nasal, Pharyngeal, and Perineal Carriage of *Staphylococcus aureus* in Healthy Adults," Antimicrob. Agents Chemother. (2005) 49(4):1465-1467.

Westermann, P. et al., "Inhibition of expression of SV40 virus large T-antigen by antisense oligodeoxyribonucleotides," Biomed. Biochim. Acta (1989) 1:85-93.

Whiley, David M et al., "Simultaneous detection and differentiation of human polyomaviruses JC and BK by a rapid and sensitive PCR-ELAHA assay and a survey of the JCV subtypes within an Australian population," Journal of Medical Virology, 72(3):467-472 (Mar. 2004).

Wichelhaus, T. A. et al., "Rapid Detection of Epidemic Strains of Methicillin-Resistant *Staphylococcus aureus*," J. Clin. Microbiol. (1999) 37(3):690-693.

Wickham, T.J., "Targeting adenovirus", Gene Therapy, 2000, vol. 7, pp. 110-114.

Widjojoatmodjo et al. "The magnetic Immuno polymerase chain reaction assay for direct detection of *Salmonellae* in fecal samples" J. Clin. Microbiol. (1992) 30(12):3195-3199.

Widjojoatmodjo et al., "Rapid Identification of Bacteria by PCR-Single-Strand Conformation Polymorphism" *Journal of Clinical Microbiology* (Dec. 1994) 32:3002-3007.

Winger et al., "High resolution accurate mass measurements of biomolecules using a new electrospray ionization ion cyclotron resonance mass spectrometer" J. Am. Soc. Mass Spectrom. 4, 566, 1993.

Wintzingerode et al. "Base-specific fragmentation of amplified 16s rRNA genes analyzed by mass spectrometry: A tool for rapid bacterial identification" PNAS 99(10):7039-7044, 2002.

Wolter et al., "Negative Ion FAB Mass Spectrometric Analysis of Non-Charged Key Intermediates in Oligonucleotide Synthesis: Rapid Identification of Partially Protected Dinucleoside Monophosphates" *Biomed. Environ. Mass Spectrom.* (1987) 14:111-116.

Woo et al., "Identification of *Leptospira inadai* by continuous monitoring of fluorescence during rapid cycle PCR" *Systematic and Applied Microbiology* (1998) 21:89-96.

Wood, S.R. et al., "Rapid Detection and Serotyping of Adenovirus by Direct Immunofluorescence", J. Med. Virol., 1997, vol. 51, No. 3, pp. 198-201.

Wright et al., "Typing and Subtyping of Influenza Viruses in Clinical Samples by PCR" J. Clin. Microbiol. (1995) 33(5):1180-1184.

Wu et al., "Genetic Organization of the mecA Region in Methicillin-Susceptible and Methicillin-Resistant Strains of *Staphylococcus sciuri*" J. Bacteriol. (1998) 180(2):236-242.

Wu et al., "Establishment of a fluorescent polymerase chain reaction method for the detection of SARS-associated coronavirus and its clinical application" Chin. Med. J. (2003) 116:988-990.

Wunschel et al., "Discrimination Among the *B. cereus* Group, in Comparison to *B. subtilis*, by Structural Carbohydrate Profiles and Ribosomal RNA Spacer Region PCR" *System. Appl. Microbiol.* (1994) 17:625-635.

Wunschel et al., "Analysis of double-stranded polymerase chain reaction products from the *Bacillus cereus* group by electrospray ionization Fourier transform ion cyclotron resonance mass spectrometry" Rapid Communications in Mass Spectrometry (1996) 10:29-35.

Wunschel et al., "Mass spectrometric characterization of DNA for molecular biological applications: Advances using MALDI and ESI" Advances in Mass Spectrometry (1998) 14:Chapter 15/377-Chapter 15/406.

Wunschel et al., "Heterogeneity in *Baciullus cereus* PCR products detected by ESI-FTICR mass spectrometry" Anal. Chem. (1998) 70:1203-1207.

Xu et al. "Electrospray mass tag dideoxy DNA sequencing" Anal. Chem. (1997) 69:3595-3602.

Xu et al., "Intercontinental Circulation of Human Influenza A(H1N2) Reassortant Viruses During the 2001-2002 Influenza Season" J. Infect. Dis. (2002):186:1490-1493.

Xu, W. et al., "Species-Specific Identification of Human Adenoviruses by a Multiplex PCR Assay", J. Clin. Microbiol., 2000, vol. 38, No. 11, pp. 4114-4120.

Xu, W. et al., "Type-Specific Identification of Human Adenovirus, 3, 7, and 21 by a Multiplex PCR Assay", J. Med. Virol., 2001, vol. 64, No. 4, pp. 537-542.

Yao et al., "Mass Spectrometry Based Proteolytic Mapping for Rapid Virus Detection" *Anal. Chem.* (2002) 74:2529-2534.

Yasui et al., "A specific oligonucleotide primer for the rapid detection of *Lactobacillus lindneri* by polymerase chain reaction" *Can. J. Microbiol.* (1997) 43:157-163.

Ye, K. et al., "Three Distinct Promoters Direct Transcription of Different 5' Untranslated Regions of the Human Interleukin 1 Type I Receptor: A Possible Mechanism for Control of Translation," Cytokine (1996) 8(6):421-429.

Yun, H J et al., "Increased antibacterial activity of OW286, a novel fluoronaphthyridone antibiotic, against *Staphylococcus aureus* strains with defined mutations in DNA gyrase and toposiomerase IV", International Journal of Antimicrobial Agents, Amsterdam, NL, 25(4):334-337 (Apr. 1, 2005).

Zeng et al., "Precision Mapping of Quantitative Trait Loci" *Genetics* (1994) 136:1457-1468.

Zhang et al., "Detection and identification of human influenza viruses by the polymerase chain reaction" J. Virol. Methods (1991) 33(1-2):165-189.

Zhang, K. et al., "New Quadriplex PCR Assay for Detection of Methicillin and Mupirocin Resistance and Simultaneous Discrimination of *Staphylococcus aureus* from Coagulase-Negative Staphylococci," J. Clin. Microbiol. (2004) 42(11):4947-4955.

Zhang, Y.-Q. et al., "Genome-based analysis of virulence genes in a non-biofilm-forming *Staphylococcus epidemidis* strain (ATCC 12228):" Mol. Microbiol. (2003) 49(6):1577-1593.

Butler J.M., et al., High Throughput Genotyping of Forensic STRs and SNPs using Time-of-Flight Mass Spectrometry, 9th International Symposium on Human Identification, 1998, Orlando FL.

Deyde V.M., et al., "Genomic Signature-Based Identification of Influenza A Viruses Using RT-PCR/Electro-Spray Ionization Mass Spectrometry (ESI-MS) Technology," PLoS One, 2010, vol. 5 (10), pp. e13293.

European Search Report for Application No. EP10175659.1, mailed on Feb. 9, 2011, 4 pages.

Examiner Interview Summary mailed Jun. 7, 2011 for U.S. Appl. No. 11/930,108, filed Oct. 31, 2007.

Extended European Search Opinion for Application No. EP10175659.1, mailed on Feb. 21, 2011, 5 pages.

Extended European Search Report for Application No. EP10179789.2, mailed on Mar. 22, 2011, 9 pages.

Extended European Search Report for Application No. EP10179791.8, mailed on Mar. 17, 2011, 7 pages.

Extended European Search Report for Application No. EP10179795.9, mailed on Mar. 22, 2011, 9 pages.

Final Office Action mailed Apr. 14, 2011 for U.S. Appl. No. 12/049,949, filed Mar. 17, 2008.

Final Office Action mailed Jun. 14, 2011 for U.S. Appl. No. 12/616,422, filed Nov. 11, 2009.

"International Preliminary Report on Patentability and Written Opinion for Application No. PCT/US04/007236, mailed on Mar. 16, 2006, 7 pages."

International Preliminary Report on Patentability for Application No. PCT/US2005/018031, mailed on Nov. 29, 2006, 1 page.

Notice of Allowance mailed Apr. 1, 2011 for U.S. Appl. No. 11/233,630, filed Sep. 21, 2005.
Notice of Allowance mailed Jun. 9, 2011 for U.S. Appl. No. 11/331,987, filed Jan. 13, 2006.
Notice of Allowance mailed Jun. 9, 2011 for U.S. Appl. No. 11/491,376, filed Jul. 21, 2006.
Notice of Allowance mailed May 25, 2011 for U.S. Appl. No. 11/929,707, filed Oct. 30, 2007.
Office Action mailed Mar. 24, 2011 for U.S. Appl. No. 11/929,930, filed Oct. 30, 2007.
Ross P., et al., "High Level Multiplex Genotyping by MALDI-TOF Mass Spectrometry," Nature Biotechnology, 1998, vol. 16 (13), pp. 1347-1351.
Alba M.M., et al., "VIDA: a Virus Database System for the Organization of Animal Virus Genome Open Reading Frames," Nucleic Acids Research, vol. 29 (1), pp. 133-136, 2001.
Ausubel F.M., et al., eds., Current Protocols in Molecular Biology, vol. 1, John Wiley & Sons Inc., 2004, Table of Contents.
Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.
Benson D.A., et al., "GenBank," Nucleic Acids Research, 1999, vol. 27 (1), pp. 12-17.
Bishop M.J., et al., "Molecular Sequence Databases" in: Nucleic Acid and Protein Sequence Analysis, 4th Chapter, Bishop M.J., et al., eds, IRL Press, 1987, pp. 83-113.
Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.
Certificate of Correction mailed Jan. 6, 2009 for U.S. Appl. No. 10/660,996, filed Sep. 12, 2003.
Certificate of Correction mailed Aug. 7, 2007 for U.S. Appl. No. 10/660,997, filed Sep. 12, 2003.
Certificate of Correction mailed Dec. 12, 2006 for U.S. Appl. No. 10/156,608, filed May 24, 2002.
Certificate of Correction mailed Jul. 17, 2007 for U.S. Appl. No. 09/891,793, filed Jun. 26, 2001.
Certificate of Correction mailed Mar. 31, 2008 for U.S. Appl. No. 09/891,793, filed Jun. 26, 2001.
Certificate of Correction mailed Mar. 31, 2008 for U.S. Appl. No. 10/156,608, filed May 24, 2002.
Certificate of Correction mailed Mar. 31, 2008 for U.S. Appl. No. 10/660,997, filed Sep. 12, 2003.
Chen R., et al., "Trapping, Detection, and Charge and Mass Measurement of Large Individual Ions (up to $1.1 \times 10^8$ Daltons) by Electrospray Ionization FTICR MS," 42nd ASMS Conference on Mass Spectrometry, 1994.
Chiu N.H., et al., "Mass Spectrometry of Single-Stranded Restriction Fragments Captured by an Undigested Complementary Sequence," Nucleic Acids Research, 2000, vol. 28 (8), pp. E31.
Collins D.W., et al., "Numerical Classification of Coding Sequences," Nucleic Acids Research, 1992, vol. 20 (6), pp. 1405-1410.
Co-pending U.S. Appl. No. 10/318,681, filed Dec. 16, 2002.
Co-pending U.S. Appl. No. 10/521,662, filed Jan. 18, 2005.
Co-pending U.S. Appl. No. 10/754,415, filed Jan. 9, 2004.
Co-pending U.S. Appl. No. 10/807,019, filed Mar. 23, 2004.
Co-pending U.S. Appl. No. 10/845,052, filed May 12, 2004.
Co-pending U.S. Appl. No. 10/964,571, filed Oct. 12, 2004.
Co-pending U.S. Appl. No. 11/674,538, filed Feb. 13, 2007.
Co-pending U.S. Appl. No. 11/929,910, filed Oct. 30, 2007.
Co-pending U.S. Appl. No. 11/930,108, filed Oct. 31, 2007.
Co-pending U.S. Appl. No. 11/930,741, filed Oct. 31, 2007.
Ecker D.J., et al., "Ibis T5000: a universal biosensor approach for microbiology," Nature Reviews Microbiology, 2008, vol. 6 (7), pp. 553-558.
Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.
Enright M.C., et al., "A multilocus sequence typing scheme for *Streptococcus pneumoniae*: identification of clones associated with serious invasive disease," Microbiology, 1998, vol. 144 (Pt 11), pp. 3049-3060.
Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.
Ex Parte Re-Examination Certificate for U.S. Appl. No. 90/010,209 mailed Jul. 7, 2009.
Ex Parte Re-Examination Certificate for U.S. Appl. No. 90/010,210, mailed Dec. 28, 2010.
Ex Parte Re-Examination Certificate for U.S. Appl. No. 90/010,447 mailed Feb. 15, 2011.
Examiner Interview Summary mailed Oct. 3, 2005 for U.S. Appl. No. 10/326,046, filed Dec. 18, 2002.
Examiner Interview Summary mailed Nov. 6, 2008 for U.S. Appl. No. 10/728,486, filed Dec. 5, 2003.
Examiner Interview Summary mailed Feb. 27, 2006 for U.S. Appl. No. 10/326,644, filed Dec. 18, 2002.
Examiner Interview Summary mailed Jan. 27, 2006 for U.S. Appl. No. 10/323,211, filed Dec. 18, 2002.
Examiner Interview Summary mailed May 28, 2008 for U.S. Appl. No. 10/660,998, filed Sep. 12, 2003.
Examiner Interview Summary mailed Oct. 28, 2008 for U.S. Appl. No. 11/331,987, filed Jan. 13, 2006.
Examiner Interview Summary mailed Oct. 29, 2008 for U.S. Appl. No. 11/331,978, filed Jan. 13, 2006.
Examiner Interview Summary mailed Jul. 31, 2006 for U.S. Appl. No. 10/326,643, filed Dec. 18, 2002.
Examiner Interview Summary Record mailed Oct. 29, 2009 for U.S. Appl. No. 10/660,122, filed Sep. 11, 2003.
Final Office Action mailed Aug. 6, 2010 for U.S. Appl. No. 11/929,910, filed Oct. 30, 2007.
Final Office Action mailed Jul. 8, 2010 for U.S. Appl. No. 12/326,800, filed Dec. 2, 2008.
Final Office Action mailed May 12, 2010 for U.S. Appl. No. 11/674,538, filed Feb. 13, 2007.
Final Office Action mailed Feb. 18, 2010 for U.S. Appl. No. 10/754,415, filed Jan. 9, 2004.
Final Office Action mailed Jun. 23, 2010 for U.S. Appl. No. 11/930,017, filed Oct. 30, 2007.
GenBank, "{Deletion 6} [Human, Muscle, Mitochondrial Mutant, 22 nt, Segment 2 of 2]," Accession No. S90302.1, Jun. 10, 1992.
GenBank, "Bovine parainfluenza virus 3 strain Shipping Fever, complete genome," Accesion No. AF178655, Sep. 19, 2000.
GenBank, "*Homo sapiens* Haplotype V Mitochondrion, Complete Genome", Accession No. AF381990.1, Dec. 28, 2001.
GenBank, "Human Isolate L34 Mitochondrion D-loop Region", Accession No. U08081.1, Aug. 16, 1994.
GenBank, "il11b08.y1 Human insulinoma *Homo sapiens* cDNA clone Image:6029534 5—similar to SW:COX3_Human P00414 Cytochrome C Oxidase Polypeptide III ;, mRNA sequence", Accession No. BQ581956.1, Jun. 20, 2002.
GenBank, "or72a01.s1 NCI_CGAP_Lu5 *Homo sapiens* cDNA Clone Image:1601352 3—similar to SW:COX1_Human P00395 Cytochrome C Oxidase Polypeptide I ;, mRNA sequence", Accession No. AI002209.1, Jun. 10, 1998.
Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.
He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.
International Preliminary Examination Report for Application No. PCT/US2002/06763, mailed on Jun. 11, 2003, 6 pages.
International Preliminary Examination Report for Application No. PCT/US2003/09802, mailed on Apr. 8, 2005, 7 pages.

International Preliminary Examination Report for Application No. PCT/US2003/22835, mailed on Mar. 5, 2005, 4 pages.
International Preliminary Examination Report for Application No. PCT/US2003/38505, mailed on Mar. 3, 2006, 5 pages.
International Preliminary Examination Report for Application No. PCT/US2003/38757, mailed on Feb. 2, 2007, 5 pages.
International Preliminary Examination Report for Application No. PCT/US2003/38761, mailed on Jun. 27, 2006, 6 pages.
International Preliminary Report on Patentability and Written Opinion for Application No. PCT/US2005/00386, mailed on Jul. 10, 2006, 6 pages.
International Preliminary Report on Patentability and Written Opinion for Application No. PCT/US2005/030058, mailed on Aug. 10, 2007, 6 pages.
International Preliminary Report on Patentability for Application No. PCT/US2004/033742, mailed on Jun. 20, 2006, 1 page.
International Preliminary Report on Patentability for Application No. PCT/US2006/028397, mailed on Jan. 22, 2008, 1 page.
International Preliminary Report on Patentability for Application No. PCT/US2008/054926, mailed on Aug. 26, 2009, 1 page.
International Preliminary Report on Patentability, Written Opinion and International Search Report for Application No. PCT/US2004/015123, mailed on Oct. 3, 2005, 8 pages.
International Search Report and Written Opinion for Application No. PCT/US2006/028397, mailed on Mar. 5, 2007, 14 pages.
International Search Report and Written Opinion for Application No. PCT/US2008/057717, mailed on Jan. 13, 2009, 18 pages.
International Search Report and Written Opinion for Application No. PCT/US2008/057901, mailed on Aug. 28, 2008, 14 pages.
International Search Report for Application No. PCT/US2003/038505 mailed on Apr. 12, 2005.
Iteman I., et al., "Comparison of Conserved Structural and Regulatory Domains within Divergent 16S rRNA-23S rRNA Spacer Sequences of Cyanobacteria," Microbiology, vol. 146 (Pt 6), pp. 1275-1286, (2000).
Kasai H., et al., "Construction of the gyrB Database for the Identification and Classification of Bacteria," Genome Informatics. Workshop on Genome Informatics, 1998, pp. 13-21.
Kidd-Ljunggren K., et al., "The hepatitis B virus X gene: analysis of functional domain variation and gene phylogeny using multiple sequences," Journal of General Virology, 1995, vol. 76 (pt 9), pp. 2119-2130.
Kikuchi K., et al., "Restriction Fragment Length Polymorphism Analysis of Clinical Isolates of *Mycobacterium haemophilum*," Journal of Clinical Microbiology, vol. 32 (7), pp. 1763-1767, (1994).
Kirpekar F., et al., "Matrix Assisted Laser Desorption/Ionization Mass Spectrometry of Enzymatically Synthesized RNA up to 150 kDa," Nucleic Acids Research, vol. 22 (19), pp. 3866-3870, (1994).
Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.
Kowalak J.A., et al., "A Novel Method for the Determination of Post-Transcriptional Modification in RNA by Mass Spectrometry," Nucleic Acids Research, 1993, vol. 21 (19), pp. 4577-4585.
Laken S.J., et al., "Genotyping by Mass Spectrometric Analysis of Short DNA Fragments," Nature Biotechnology, 1998, vol. 16 (13), pp. 1352-1356.
Marks F., et al., "Genotyping of *Plasmodium falciparum* Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.
Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.
Ni J., et al., "Interpretation of Oligonucleotide Mass Spectra for Determination of Sequence Using Electrospray Ionization and Tandem Mass Spectrometry," Analytical Chemistry, 1996, vol. 68 (13), pp. 1989-1999.
Non-Final Office Action mailed Aug. 4, 2010 for U.S. Appl. No. 12/049,949, filed Mar. 17, 2008.
Non-Final Office Action mailed Apr. 6, 2009 for U.S. Appl. No. 11/331,987, filed Jan. 13, 2006.
Non-Final Office Action mailed Apr. 7, 2006 for U.S. Appl. No. 10/964,571, filed Oct. 12, 2004.
Non-Final Office Action mailed Aug. 7, 2007 for U.S. Appl. No. 10/844,938, filed May 12, 2004.
Non-Final Office Action mailed Jun. 10, 2009 for U.S. Appl. No. 10/844,938, filed May 12, 2004.
Non-Final Office Action mailed Jan. 12, 2010 for U.S. Appl. No. 11/491,376, filed Jul. 21, 2006.
Non-Final Office Action mailed Oct. 13, 2010 for U.S. Appl. No. 10/754,415, filed Jan. 9, 2004.
Non-Final Office Action mailed Sep. 16, 2009 for U.S. Appl. No. 11/233,630, filed Sep. 21, 2005.
Non-Final Office Action mailed Feb. 23, 2009 for U.S. Appl. No. 10/660,122, filed Sep. 11, 2003.
Non-Final Office Action mailed May 26, 2010 for U.S. Appl. No. 11/869,449, filed Oct. 9, 2007.
Non-Final Office Action mailed Jul. 27, 2006 for U.S. Appl. No. 11/209,439, filed Aug. 8, 2005.
Non-Final Office Action mailed Sep. 28, 2009 for U.S. Appl. No. 11/930,017, filed Oct. 30, 2007.
Non-Final Office Action mailed Dec. 29, 2010 for U.S. Appl. No. 12/616,422, filed Nov. 11, 2009.
Non-Final Office Action mailed Apr. 30, 2010 for U.S. Appl. No. 11/930,108, filed Oct. 31, 2007.
Notice of Allowance mailed Jun. 3, 2009 for U.S. Appl. No. 11/331,978, filed Jan. 13, 2006.
Notice of Allowance mailed Aug. 5, 2010 for U.S. Appl. No. 11/233,630, filed Sep. 21, 2005.
Notice of Allowance mailed Aug. 6, 2009 for U.S. Appl. No. 10/728,486, filed Dec. 5, 2003.
Notice of Allowance mailed Dec. 10, 2010 for U.S. Appl. No. 11/233,630, filed Sep. 21, 2005.
Notice of Allowance mailed Dec. 10, 2010 for U.S. Appl. No. 11/491,376, filed Jul. 21, 2006.
Notice of Allowance mailed Nov. 12, 2009 for U.S. Appl. No. 10/728,486, filed Dec. 5, 2003.
Notice of Allowance mailed Dec. 15, 2008 for U.S. Appl. No. 11/331,978, filed Jan. 13, 2006.
Notice of Allowance mailed Sep. 18, 2009 for U.S. Appl. No. 10/660,998, filed Sep. 12, 2003.
Notice of Allowance mailed Nov. 24, 2009 for U.S. Appl. No. 11/331,978, filed Jan. 13, 2006.
Notice of Allowance mailed Oct. 29, 2009 for U.S. Appl. No. 10/660,122, filed Sep. 11, 2003.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Office Action mailed Feb. 2, 2011 for U.S. Appl. No. 11/869,449, filed Oct. 9, 2007.
Office Action mailed Feb. 3, 2011 for U.S. Appl. No. 12/326,800, filed Dec. 2, 2008.
Office Action mailed Dec. 4, 2006 for Indian Application No. 1136KOLNP2003 filed Mar. 4, 2002.
Office Action mailed May 4, 2010 for U.S. Appl. No. 90/010,447, filed Apr. 9, 2009.
Office Action mailed May 4, 2010 for U.S. Appl. No. 90/010,448, filed Apr. 9, 2009.
Office Action mailed Aug. 5, 2010 for European Application No. 02709785.6 filed Mar. 4, 2002.
Office Action mailed Jan. 6, 2011 for Israel Application No. 157661 filed Mar. 4, 2002.
Office Action mailed Mar. 6, 2009 for U.S. Appl. No. 11/233,630, filed Sep. 21, 2005.
Office Action mailed Feb. 7, 2008 for European Application No. 03796752.8 filed Dec. 5, 2003.
Office Action mailed Jun. 7, 2010 for European Application No. 06800205.4 filed Jul. 27, 2006.
Office Action mailed Jan. 8, 2007 for U.S. Appl. No. 09/891,793, filed Jun. 26, 2001.
Office Action mailed Sep. 8, 2006 for Chinese Application No. 02809122.1 filed Mar. 4, 2002.

Office Action mailed Dec. 9, 2009 for U.S. Appl. No. 90/010,210, filed Jun. 27, 2008.
Office Action mailed Dec. 9, 2009 for U.S. Appl. No. 90/010,447, filed Apr. 9, 2009.
Office Action mailed Dec. 9, 2009 for U.S. Appl. No. 90/010,448, filed Apr. 9, 2009.
Office Action mailed Feb. 9, 2007 for Chinese Application No. 02809122.1 filed Mar. 4, 2002.
Office Action mailed Jan. 9, 2008 for Japanese Application No. 2002570692 filed Mar. 4, 2002.
Office Action mailed Nov. 9, 2010 for U.S. Appl. No. 11/331,987, filed Jan. 13, 2006.
Office Action mailed Aug. 10, 2004 for U.S. Appl. No. 10/326,642, filed Dec. 18, 2002.
Office Action mailed Dec. 10, 2009 for U.S. Appl. No. 11/929,910, filed Oct. 30, 2007.
Office Action mailed Feb. 10, 2006 for Australian Application No. 2002244250 filed Mar. 4, 2002.
Office Action mailed Jun. 10, 2009 for U.S. Appl. No. 90/010,210, filed Jun. 27, 2008.
Office Action mailed Jun. 10, 2010 for U.S. Appl. No. 90/010,447, filed Apr. 9, 2009.
Office Action mailed Jun. 10, 2010 for U.S. Appl. No. 90/010,448, filed Apr. 9, 2009.
Office Action mailed Aug. 11, 2010 for U.S. Appl. No. 90/010,447, filed Apr. 9, 2009.
Office Action mailed Aug. 11, 2010 for U.S. Appl. No. 90/010,448, filed Apr. 9, 2009.
Office Action mailed Jun. 11, 2010 for U.S. Appl. No. 90/010,210, filed Jun. 27, 2008.
Office Action mailed May 12, 2002 for U.S. Appl. No. 09/798,007, filed Mar. 2, 2001.
Office Action mailed Aug. 13, 2009 for U.S. Appl. No. 11/674,538, filed Feb. 13, 2007.
Office Action mailed Jul. 13, 2010 for U.S. Appl. No. 11/929,930, filed Oct. 30, 2007.
Office Action mailed Dec. 15, 2008 for Israel Application No. 157661 filed Mar. 4, 2002.
Office action mailed Dec. 15, 2010 for Canadian Application No. 2508726 filed Dec. 5, 2003.
Office Action mailed Jan. 15, 2008 for Israel Application No. 157661 filed Mar. 4, 2002.
Office Action mailed Mar. 15, 2010 for European Application No. 08730682.5 filed Feb. 25, 2008.
Office Action mailed Apr. 16, 2009 for U.S. Appl. No. 90/010,210, filed Jun. 27, 2008.
Office Action mailed Aug. 16, 2010 for U.S. Appl. No. 11/929,707, filed Oct. 30, 2007.
Office Action mailed Feb. 16, 2011 for U.S. Appl. No. 11/929,910, filed Oct. 30, 2007.
Office Action mailed Mar. 16, 2010 for Canadian Application No. 2616281 filed Jul. 21, 2006.
Office Action mailed Nov. 16, 2009 for Japanese Application No. 2005508488 filed Dec. 5, 2003.
Office Action mailed Nov. 16, 2009 for Japanese Application No. 2005508560 filed Dec. 5, 2003.
Office Action mailed Sep. 17, 2008 for European Application No. 03796752.8 filed Dec. 5, 2003.
Office Action mailed Feb. 18, 2010 for European Application No. 03814656.9 filed Dec. 5, 2003.
Office Action mailed Jan. 18, 2011 for U.S. Appl. No. 11/930,108, filed Oct. 31, 2007.
Office Action mailed May 18, 2005 for New Zealand Application No. 527857 filed Mar. 4, 2002.
Office Action mailed Sep. 18, 2008 for Australian Application No. 2003298030 filed Dec. 5, 2003.
Office Action mailed Sep. 19, 2006 for U.S. Appl. No. 10/660,122, filed Sep. 11, 2003.
Office Action mailed Sep. 20, 2010 for U.S. Appl. No. 90/010,447, filed Apr. 9, 2009.
Office Action mailed Sep. 20, 2010 for U.S. Appl. No. 90/010,448, filed Apr. 9, 2009.
Office Action mailed Apr. 21, 2009 for U.S. Appl. No. 90/010,209, filed Jun. 27, 2008.
Office Action mailed Oct. 21, 2005 for U.S. Appl. No. 10/326,641, filed Dec. 18, 2002.
Office Action mailed Sep. 22, 2010 for Canadian Application No. 2510007 filed Dec. 5, 2003.
Office Action mailed Apr. 23, 2010 for U.S. Appl. No. 90/010,210, filed Jun. 27, 2008.
Office Action mailed Oct. 23, 2003 for New Zealand Application No. 527857 filed Mar. 4, 2002.
Office Action mailed Aug. 24, 2010 for U.S. Appl. No. 90/010,210, filed Jun. 27, 2008.
Office Action mailed Dec. 24, 2004 for New Zealand Application No. 527857 filed Mar. 4, 2002.
Office Action mailed Feb. 24, 2004 for U.S. Appl. No. 10/326,642, filed Dec. 18, 2002.
Office Action mailed Jan. 24, 2005 for U.S. Appl. No. 10/326,642, filed Dec. 18, 2002.
Office Action mailed Jul. 24, 2007 for Mexican Application No. PAA2003007927 filed Sep. 2, 2003.
Office Action mailed Jun. 24, 2008 for European Application No. 06800205.4 filed Jul. 27, 2006.
Office Action mailed Nov. 24, 2009 for U.S. Appl. No. 90/010,210, filed Jun. 27, 2008.
Office Action mailed Sep. 24, 2009 for U.S. Appl. No. 90/010,210, filed Jun. 27, 2008.
Office Action mailed Jun. 25, 2009 for U.S. Appl. No. 11/869,449, filed Oct. 9, 2007.
Office Action mailed Jun. 25, 2009 for U.S. Appl. No. 90/010,210, filed Jun. 27, 2008.
Office Action mailed Aug. 26, 2010 for Canadian Application No. 2508584 filed Dec. 5, 2003.
Office Action mailed Jul. 27, 2009 for Canadian Application No. 2439655 filed Mar. 4, 2002.
Office Action mailed Jul. 28, 2010 for U.S. Application No. 90/010,210, filed Jun. 27, 2008.
Office Action mailed Mar. 29, 2010 for Australian Application No. 2006272776 filed Jul. 21, 2006.
Office Action mailed Oct. 29, 2009 for U.S. Appl. No. 90/010,448, filed Apr. 9, 2009.
Office Action mailed Jul. 30, 2009 for Japanese Application No. 2002570692 filed Mar. 4, 2002.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Office Action mailed Nov. 30, 2009 for U.S. Appl. No. 10/660,122, filed Sep. 11, 2003.
Office Action mailed Sep. 30, 2005 for Chinese Application No. 02809122.1 filed Mar. 4, 2002.
Office Action mailed Jan. 31, 2007 for Philippines Application No. PH12003500824 filed Mar. 4, 2002.
Palys T., et al., "Discovery and Classification of Ecological Diversity in the Bacterial World: the Role of DNA Sequence Data," International Journal of Systematic Bacteriology, 1997, vol. 47 (4), pp. 1145-1156.
Partial European Search Report for Application No. EP01106974, mailed on Dec. 16, 2002, 2 pages.
Roberts M.S., et al., "Recombination and Migration Rates in Natural Populations of Bacillus subtilis and Bacillus mojavensis," Evolution, 1995, vol. 49 (6), pp. 1081-1094.
Supplementary European Search Report for Application No. EP03814656, mailed on Oct. 16, 2007, 2 pages.
Tang K., et al., "Matrix-Assisted Laser Desorption/Ionization of Restriction Enzyme-Digested DNA," Rapid Communications in Mass Spectrometry, 1994, vol. 8 (2), pp. 183-186.
U.S. Appl. No. 60/369,405, filed Apr. 1, 2002.
U.S. Appl. No. 60/397,365, filed Jul. 19, 2002.
U.S. Appl. No. 60/431,319, filed Dec. 6, 2002.
U.S. Appl. No. 60/443,443, filed Jan. 29, 2003.
U.S. Appl. No. 60/443,788, filed Jan. 30, 2003.

U.S. Appl. No. 60/447,529, filed Feb. 14, 2003.
U.S. Appl. No. 60/453,607, filed Mar. 10, 2003.
U.S. Appl. No. 60/461,494, filed Apr. 9, 2003.
U.S. Appl. No. 60/470,175, filed May 12, 2003.
U.S. Appl. No. 60/501,926, filed Sep. 11, 2003.
U.S. Appl. No. 60/509,911, filed Oct. 9, 2003.
U.S. Appl. No. 60/615,387, filed Sep. 30, 2004.
U.S. Appl. No. 60/701,404, filed Jul. 21, 2005.
U.S. Appl. No. 60/705,631, filed Aug. 3, 2005.
U.S. Appl. No. 60/720,843, filed Sep. 27, 2005.
U.S. Appl. No. 60/747,607, filed May 18, 2006.
U.S. Appl. No. 60/771,101, filed Feb. 6, 2006.
U.S. Appl. No. 60/773,124, filed Feb. 13, 2006.
U.S. Appl. No. 60/891,479, filed Feb. 23, 2007.
U.S. Appl. No. 60/941,641, filed Jun. 1, 2007.
Verma S., et al., "Modified Oligonucleotides: Synthesis and Strategy for Users," Annual Review of Biochemistry, 1998, pp. 99-134.
Watanabe K., et al., "ICB Database: the gyrB Database for Identification and Classification of Bacteria," Nucleic Acids Research, 2001, vol. 29 (1), pp. 344-345.
Written Opinion for Application No. PCT/US2004/33742, mailed on May 15, 2006, 5 pages.
Zhang J., et al., "PowerBLAST: A New Network BLAST Application for Interactive or Automated Sequence Analysis and Annotation," Genome Research, 1997, vol. 7 (6), pp. 649-656.

* cited by examiner

B. anthracis ($A_{14}G_9C_{14}T_9$) $MW_{meas}$ = 14072.2)

B. anthracis* ($A_1A^*_{13}G_9C_{14}T_9$) $MW_{meas}$ = 14280.9)

METHODS FOR RAPID IDENTIFICATION OF PATHOGENS IN HUMANS AND ANIMALS

CROSS-REFERENCE TO RELATED APPLICATIONS

This application is a continuation of U.S. application Ser. No. 10/728,486 filed Dec. 5, 2003 now U.S. Pat. No. 7,718,354; which is a continuation-in-part of U.S. application Ser. No. 10/323,233 filed Dec. 18, 2002 now abandoned. U.S. application Ser. No. 10/728,786 is also a continuation-in-part of U.S. application Ser. No. 10/326,051 filed Dec. 18, 2002 now abandoned; and is a continuation-in-part of U.S. application Ser. No. 10/325,527 filed Dec. 18, 2002 now abandoned; and is a continuation-in-part of U.S. application Ser. No. 10/325,526 filed Dec. 18, 2002 now abandoned. U.S. application Ser. No. 10/728,486 also claims the benefit of U.S. provisional application Ser. No. 60/431,319 filed Dec. 6, 2002; and claims the benefit of U.S. provisional application Ser. No. 60/443,443 filed Jan. 29, 2003; and claims the benefit of U.S. provisional application Ser. No. 60/443,788 filed Jan. 30, 2003; and claims the benefit of U.S. provisional application Ser. No. 60/447,529 filed Feb. 14, 2003; and claims the benefit of U.S. provisional application Ser. No. 60/501,926 filed Sep. 11, 2003, each of which is incorporated herein by reference in its entirety.

STATEMENT OF GOVERNMENT SUPPORT

This invention was made with United States Government support under DARPA contract MDA972-00-C-0053. The United States Government has certain rights in the invention.

FIELD OF THE INVENTION

The present invention relates generally to clinical applications of directed to the identification of pathogens in biological samples from humans and animals. The present invention is also directed to the resolution of a plurality of etiologic agents present in samples obtained from humans and animals. The invention is further directed to the determination of detailed genetic information about such pathogens or etiologic agents.

The identification of the bioagent is important for determining a proper course of treatment and/or eradication of the bioagent in such cases as biological warfare and natural infections. Furthermore, the determination of the geographic origin of a selected bioagent will facilitate the identification of potential criminal identity. The present invention also relates to methods for rapid detection and identification of bioagents from environmental, clinical or other samples. The methods provide for detection and characterization of a unique base composition signature (BCS) from any bioagent, including bacteria and viruses. The unique BCS is used to rapidly identify the bioagent.

BACKGROUND OF THE INVENTION

In the United States, hospitals report well over 5 million cases of recognized infectious disease-related illnesses annually. Significantly greater numbers remain undetected, both in the inpatient and community setting, resulting in substantial morbidity and mortality. Critical intervention for infectious disease relies on rapid, sensitive and specific detection of the offending pathogen, and is central to the mission of microbiology laboratories at medical centers. Unfortunately, despite the recognition that outcomes from infectious illnesses are directly associated with time to pathogen recognition, as well as accurate identification of the class and species of microbe, and ability to identify the presence of drug resistance isolates, conventional hospital laboratories often remain encumbered by traditional slow multi-step culture based assays. Other limitations of the conventional laboratory which have become increasingly apparent include: extremely prolonged wait-times for pathogens with long generation time (up to several weeks); requirements for additional testing and wait times for speciation and identification of antimicrobial resistance; diminished test sensitivity for patients who have received antibiotics; and absolute inability to culture certain pathogens in disease states associated with microbial infection.

For more than a decade, molecular testing has been heralded as the diagnostic tool for the new millennium, whose ultimate potential could include forced obsolescence of traditional hospital laboratories. However, despite the fact that significant advances in clinical application of PCR techniques have occurred, the practicing physician still relies principally on standard techniques. A brief discussion of several existing applications of PCR in the hospital-based setting follows.

Generally speaking molecular diagnostics have been championed for identifying organisms that cannot be grown in vitro, or in instances where existing culture techniques are insensitive and/or require prolonged incubation times. PCR-based diagnostics have been successfully developed for a wide variety of microbes. Application to the clinical arena has met with variable success, with only a few assays achieving acceptance and utility.

One of the earliest, and perhaps most widely recognized applications of PCR for clinical practice is in detection of *Mycobacterium tuberculosis*. Clinical characteristics favoring development of a nonculture-based test for tuberculosis include week to month long delays associated with standard testing, occurrence of drug-resistant isolates and public health imperatives associated with recognition, isolation and treatment. Although frequently used as a diagnostic adjunctive, practical and routine clinical application of PCR remains problematic due to significant inter-laboratory variation in sensitivity, and inadequate specificity for use in low prevalence populations, requiring further development at the technical level. Recent advances in the laboratory suggest that identification of drug resistant isolates by amplification of mutations associated with specific antibiotic resistance (e.g., rpoB gene in rifampin resistant strains) may be forthcoming for clinical use, although widespread application will require extensive clinical validation.

One diagnostic assay, which has gained widespread acceptance, is for *C. trachomatis*. Conventional detection systems are limiting due to inadequate sensitivity and specificity (direct immunofluorescence or enzyme immunoassay) or the requirement for specialized culture facilities, due to the fastidious characteristics of this microbe. Laboratory development, followed by widespread clinical validation testing in a variety of acute and nonacute care settings have demonstrated excellent sensitivity (90-100%) and specificity (97%) of the PCR assay leading to its commercial development. Proven efficacy of the PCR assay from both genital and urine sampling, have resulted in its application to a variety of clinical setting, most recently including routine screening of patients considered at risk.

While the full potential for PCR diagnostics to provide rapid and critical information to physicians faced with difficult clinical-decisions has yet to be realized, one recently developed assay provides an example of the promise of this evolving technology. Distinguishing life-threatening causes of fever from more benign causes in children is a fundamental clinical dilemma faced by clinicians, particularly when infections of the central nervous system are being considered. Bacterial causes of meningitis can be highly aggressive, but generally cannot be differentiated on a clinical basis from aseptic meningitis, which is a relatively benign condition that can be managed on an outpatient basis. Existing blood culture methods often take several days to turn positive, and are often confounded by poor sensitivity or false-negative findings in patients receiving empiric antimicrobials. Testing and application of a PCR assay for enteroviral meningitis has been found to be highly sensitive. With reporting of results within 1 day, preliminary clinical trials have shown significant reductions in hospital costs, due to decreased duration of hospital stays and reduction in antibiotic therapy. Other viral PCR assays, now routinely available include those for herpes simplex virus, cytomegalovirus, hepatitis and HIV. Each has a demonstrated cost savings role in clinical practice, including detection of otherwise difficult to diagnose infections and newly realized capacity to monitor progression of disease and response to therapy, vital in the management of chronic infectious diseases.

The concept of a universal detection system has been forwarded for identification of bacterial pathogens, and speaks most directly to the possible clinical implications of a broad-based screening tool for clinical use. Exploiting the existence of highly conserved regions of DNA common to all bacterial species in a PCR assay would empower physicians to rapidly identify the presence of bacteremia, which would profoundly impact patient care. Previous empiric decision making could be abandoned in favor of educated practice, allowing appropriate and expeditious decision-making regarding need for antibiotic therapy and hospitalization.

Experimental work using the conserved features of the 16S rRNA common to almost all bacterial species, is an area of active investigation. Hospital test sites have focused on "high yield" clinical settings where expeditious identification of the presence of systemic bacterial infection has immediate high morbidity and mortality consequences. Notable clinical infections have included evaluation of febrile infants at risk for sepsis, detection of bacteremia in febrile neutropenic cancer patients, and examination of critically ill patients in the intensive care unit. While several of these studies have reported promising results (with sensitivity and specificity well over 90%), significant technical difficulties (described below) remain, and have prevented general acceptance of this assay in clinics and hospitals (which remain dependent on standard blood culture methodologies). Even the revolutionary advances of real-time PCR technique, which offers a quantitative more reproducible and technically simpler system, remains encumbered by inherent technical limitations of the PCR assay.

The principle shortcomings of applying PCR assays to the clinical setting include: inability to eliminate background DNA contamination; interference with the PCR amplification by substrates present in the reaction; and limited capacity to provide rapid reliable speciation, antibiotic resistance and subtype identification. Some laboratories have recently made progress in identifying and removing inhibitors; however background contamination remains problematic, and methods directed towards eliminating exogenous sources of DNA report significant diminution in assay sensitivity. Finally, while product identification and detailed characterization has been achieved using sequencing techniques, these approaches are laborious and time-intensive thus detracting from its clinical applicability.

Rapid and definitive microbial identification is desirable for a variety of industrial, medical, environmental, quality, and research reasons. Traditionally, the microbiology laboratory has functioned to identify the etiologic agents of infectious diseases through direct examination and culture of specimens. Since the mid-1980s, researchers have repeatedly demonstrated the practical utility of molecular biology techniques, many of which form the basis of clinical diagnostic assays. Some of these techniques include nucleic acid hybridization analysis, restriction enzyme analysis, genetic sequence analysis, and separation and purification of nucleic acids (See, e.g., J. Sambrook, E. F. Fritsch, and T. Maniatis, Molecular Cloning: A Laboratory Manual, 2nd Ed., Cold Spring Harbor Laboratory Press, Cold Spring Harbor, N.Y., 1989). These procedures, in general, are time-consuming and tedious. Another option is the polymerase chain reaction (PCR) or other amplification procedure that amplifies a specific target DNA sequence based on the flanking primers used. Finally, detection and data analysis convert the hybridization event into an analytical result.

Other not yet fully realized applications of PCR for clinical medicine is the identification of infectious causes of disease previously described as idiopathic (e.g. *Bartonella henselae* in bacillary angiomatosis, and *Tropheryma whippellii* as the uncultured *bacillus* associated with Whipple's disease). Further, recent epidemiological studies which suggest a strong association between Chlamydia pneumonia and coronary artery disease, serve as example of the possible widespread, yet undiscovered links between pathogen and host which may ultimately allow for new insights into pathogenesis and novel life sustaining or saving therapeutics.

For the practicing clinician, PCR technology offers a yet unrealized potential for diagnostic omnipotence in the arena of infectious disease. A universal reliable infectious disease detection system would certainly become a fundamental tool in the evolving diagnostic armamentarium of the $21^{st}$ century clinician. For front line emergency physicians, or physicians working in disaster settings, a quick universal detection system, would allow for molecular triage and early aggressive targeted therapy. Preliminary clinical studies using species specific probes suggest that implementing rapid testing in acute care setting is feasible. Resources could thus be appropriately applied, and patients with suspected infections could rapidly be risk stratified to the different treatment settings, depending on the pathogen and virulence. Furthermore, links with data management systems, locally regionally and nationally, would allow for effective epidemiological surveillance, with obvious benefits for antibiotic selection and control of disease outbreaks.

For the hospitalists, the ability to speculate and subtype would allow for more precise decision-making regarding antimicrobial agents. Patients who are colonized with highly contagious pathogens could be appropriately isolated on entry into the medical setting without delay. Targeted therapy will diminish development of antibiotic resistance. Furthermore, identification of the genetic basis of antibiotic resistant strains would permit precise pharmacologic intervention. Both physician and patient would benefit with less need for repetitive testing and elimination of wait times for test results.

It is certain that the individual patient will benefit directly from this approach. Patients with unrecognized or difficult to diagnose infections would be identified and treated promptly. There will be reduced need for prolonged inpatient stays, with resultant decreases in introgenic events.

Mass spectrometry provides detailed information about the molecules being analyzed, including high mass accuracy. It is also a process that can be easily automated. Low-resolution MS may be unreliable when used to detect some known agents, if their spectral lines are sufficiently weak or sufficiently close to those from other living organisms in the sample. DNA chips with specific probes can only determine the presence or absence of specifically anticipated organisms. Because there are hundreds of thousands of species of benign bacteria, some very similar in sequence to threat organisms, even arrays with 10,000 probes lack the breadth needed to detect a particular organism.

Antibodies face more severe diversity limitations than arrays. If antibodies are designed against highly conserved targets to increase diversity, the false alarm problem will dominate, again because threat organisms are very similar to benign ones. Antibodies are only capable of detecting known agents in relatively uncluttered environments.

Several groups have reported detection of PCR products using high resolution electrospray ionization-Fourier transform-ion cyclotron resonance mass spectrometry (ESI-FT-ICR MS). Accurate measurement of exact mass combined with knowledge of the number of at least one nucleotide allowed calculation of the total base composition for PCR duplex products of approximately 100 base pairs. (Aaserud et al., J. Am. Soc. Mass Spec., 1996, 7, 1266-1269; Muddiman et al., Anal. Chem., 1997, 69, 1543-1549; Wunschel et al., Anal. Chem., 1998, 70, 1203-1207; Muddiman et al., Rev. Anal. Chem., 1998, 17, 1-68). Electrospray ionization-Fourier transform-ion cyclotron resistance (ESI-FT-ICR) MS may be used to determine the mass of double-stranded, 500 base-pair PCR products via the average molecular mass (Hurst et al., Rapid Commun. Mass Spec. 1996, 10, 377-382). Use of matrix-assisted laser desorption ionization-time of flight (MALDI-TOF) mass spectrometry for characterization of PCR products has been described. (Muddiman et al., Rapid Commun. Mass Spec., 1999, 13, 1201-1204). However, the degradation of DNAs over about 75 nucleotides observed with MALDI limited the utility of this method.

U.S. Pat. No. 5,849,492 reports a method for retrieval of phylogenetically informative DNA sequences which comprise searching for a highly divergent segment of genomic DNA surrounded by two highly conserved segments, designing the universal primers for PCR amplification of the highly divergent region, amplifying the genomic DNA by PCR technique using universal primers, and then sequencing the gene to determine the identity of the organism.

U.S. Pat. No. 5,965,363 reports methods for screening nucleic acids for polymorphisms by analyzing amplified target nucleic acids using mass spectrometric techniques and to procedures for improving mass resolution and mass accuracy of these methods.

WO 99/14375 reports methods, PCR primers and kits for use in analyzing preselected DNA tandem nucleotide repeat alleles by mass spectrometry.

WO 98/12355 reports methods of determining the mass of a target nucleic acid by mass spectrometric analysis, by cleaving the target nucleic acid to reduce its length, making the target single-stranded and using MS to determine the mass of the single-stranded shortened target. Also reported are methods of preparing a double-stranded target nucleic acid for MS analysis comprising amplification of the target nucleic acid, binding one of the strands to a solid support, releasing the second strand and then releasing the first strand which is then analyzed by MS. Kits for target nucleic acid preparation are also provided.

PCT WO97/33000 reports methods for detecting mutations in a target nucleic acid by nonrandomly fragmenting the target into a set of single-stranded nonrandom length fragments and determining their masses by MS.

U.S. Pat. No. 5,605,798 reports a fast and highly accurate mass spectrometer-based process for detecting the presence of a particular nucleic acid in a biological sample for diagnostic purposes.

WO 98/21066 reports processes for determining the sequence of a particular target nucleic acid by mass spectrometry. Processes for detecting a target nucleic acid present in a biological sample by PCR amplification and mass spectrometry detection are reported, as are methods for detecting a target nucleic acid in a sample by amplifying the target with primers that contain restriction sites and tags, extending and cleaving the amplified nucleic acid, and detecting the presence of extended product, wherein the presence of a DNA fragment of a mass different from wild-type is indicative of a mutation. Methods of sequencing a nucleic acid via mass spectrometry methods are also reported.

WO 97/37041, WO 99/31278 and U.S. Pat. No. 5,547,835 report methods of sequencing nucleic acids using mass spectrometry. U.S. Pat. Nos. 5,622,824, 5,872,003 and 5,691,141 report methods, systems and kits for exonuclease-mediated mass spectrometric sequencing.

Thus, there is a need for a method for bioagent detection and identification which is both specific and rapid, and in which no nucleic acid sequencing is required. The present invention addresses this need.

SUMMARY OF THE INVENTION

The present invention is directed towards methods of identifying a pathogen in a biological sample by obtaining nucleic acid from a biological sample, selecting at least one pair of intelligent primers with the capability of amplification of nucleic acid of the pathogen, amplifying the nucleic acid with the primers to obtain at least one amplification product, determining the molecular mass of at least one amplification product from which the pathogen is identified. Further, this invention is directed to methods of epidemic surveillance. By identifying a pathogen from samples acquired from a plurality of geographic locations, the spread of the pathogen to a given geographic location can be determined.

The present invention is also directed to methods of diagnosis of a plurality of etiologic agents of disease in an individual by obtaining a biological sample from an individual, isolating nucleic acid from the biological sample, selecting a plurality of amplification primers with the capability of amplification of nucleic acid of a plurality of etiologic agents of disease, amplifying the nucleic acid with a plurality of primers to obtain a plurality of amplification products corresponding to a plurality of etiologic agents, determining the molecular masses of the plurality of unique amplification products which identify the members of the plurality of etiologic agents.

The present invention is also directed to methods of in silico screening of primer sets to be used in identification of a plurality of bioagents by preparing a base composition probability cloud plot from a plurality of base composition signatures of the plurality of bioagents generated in silico, inspecting the base composition probability cloud plot for overlap of clouds from different bioagents, and choosing primer sets based on minimal overlap of the clouds.

The present invention is also directed to methods of predicting the identity of a bioagent with a heretofore unknown base composition signature by preparing a base composition probability cloud plot from a plurality of base composition signatures of the plurality of bioagents which includes the heretofore unknown base composition, inspecting the base composition probability cloud for overlap of the heretofore unknown base composition with the cloud of a known bioagent such that overlap predicts that the identity of the bioagent with a heretofore unknown base composition signature equals the identity of the known bioagent.

The present invention is also directed to methods for determining a subspecies characteristic for a given pathogen in a biological sample by identifying the pathogen in a biological sample using broad range survey primers or division-wide primers, selecting at least one pair of drill-down primers to amplify nucleic acid segments which provide a subspecies characteristic about the pathogen, amplifying the nucleic acid segments to produce at least one drill-down amplification product and determining the base composition signature of the drill-down amplification product wherein the base composition signature provides a subspecies characteristic about the pathogen.

The present invention is also directed to methods of pharmacogenetic analysis by obtaining a sample of genomic DNA from an individual, selecting a segment of the genomic DNA which provides pharmacogenetic information, using at least one pair of intelligent primers to produce an amplification product which comprises the segment of genomic DNA and determining the base composition signature of the amplification product, wherein the base composition signature provides pharmacogenetic information about said individual.

BRIEF DESCRIPTION OF THE DRAWINGS

FIGS. 1A-1H and FIG. 2 are consensus diagrams that show examples of conserved regions from 16S rRNA (FIGS. 1A-1, 1A-2, 1A-3, 1A-4, and 1A-5), 23S rRNA (3'-half, FIGS. 1B, 1C, and 1D; 5'-half, FIGS. 1E-F), 23S rRNA Domain I (FIG. 1G), 23S rRNA Domain IV (FIG. 1H) and 16S rRNA Domain III (FIG. 2) which are suitable for use in the present invention. Lines with arrows are examples of regions to which intelligent primer pairs for PCR are designed. The label for each primer pair represents the starting and ending base number of the amplified region on the consensus diagram. Bases in capital letters are greater than 95% conserved; bases in lower case letters are 90-95% conserved, filled circles are 80-90% conserved; and open circles are less than 80% conserved. The label for each primer pair represents the starting and ending base number of the amplified region on the consensus diagram. The nucleotide sequence of the 16S rRNA consensus sequence is SEQ ID NO:3 and the nucleotide sequence of the 23S rRNA consensus sequence is SEQ ID NO:4.

FIG. 2 shows a typical primer amplified region from the 16S rRNA Domain III shown in FIG. 1A-1.

FIG. 5 shows the deconvoluted mass spectra of a *Bacillus anthracis* region with and without the mass tag phosphorothioate A (A*). The two spectra differ in that the measured molecular weight of the mass tag-containing sequence is greater than the unmodified sequence.

FIG. 25 shows representative results of the base composition analysis on throat swab samples using the six primer pairs, 5'-emm gene sequencing and the MLST gene sequencing method of the present invention for an outbreak of *Streptococcus pyogenes* (group A *streptococcus*; GAS) at a military training camp.

DESCRIPTION OF EMBODIMENTS

Figures 1, 1A:
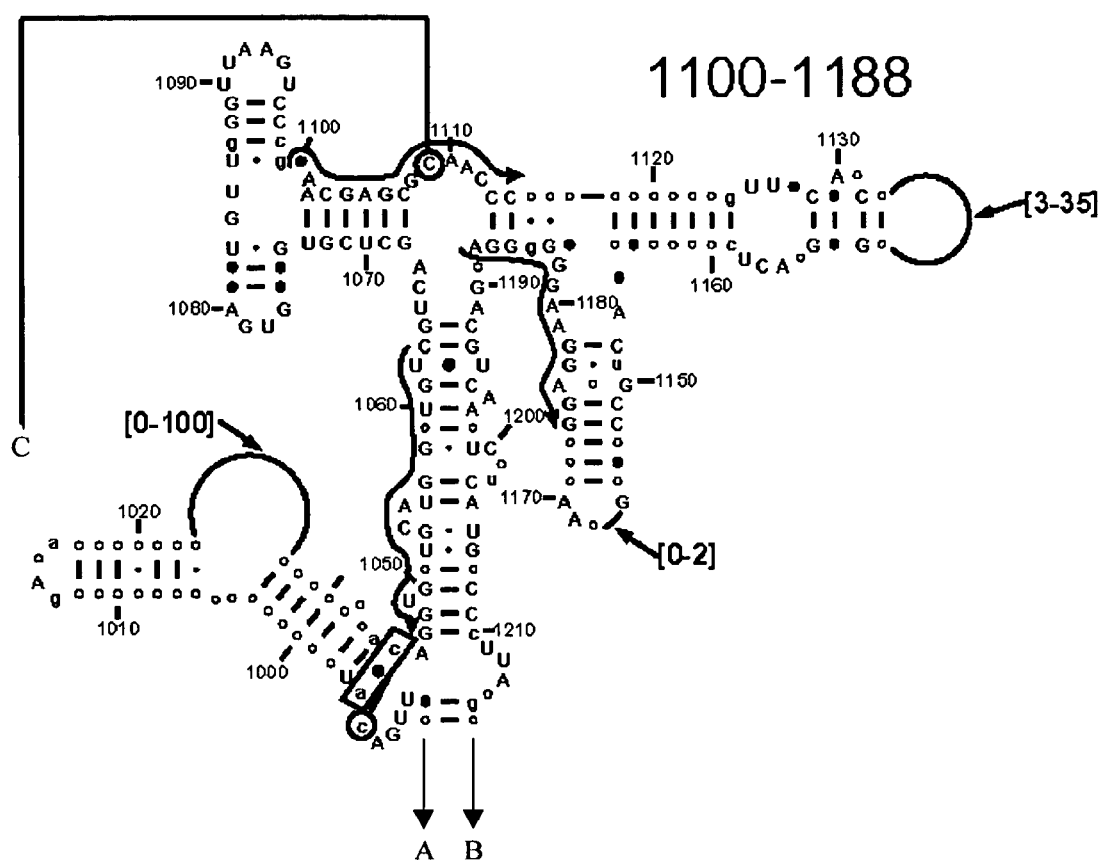
Figures 1, 1A, 2:
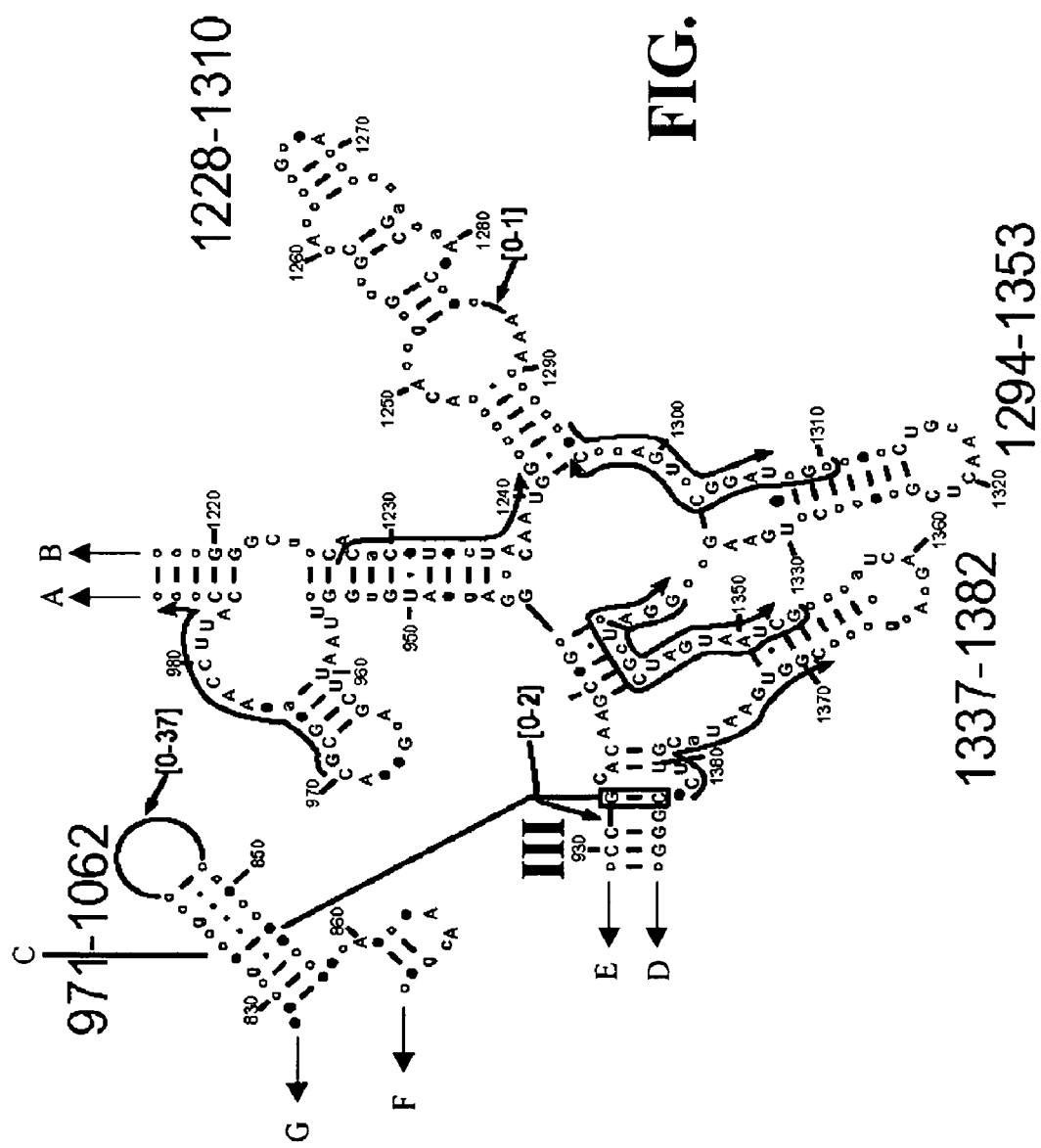

The present invention provides, inter alia, methods for detection and identification of bioagents in an unbiased manner using "bioagent identifying amplicons." "Intelligent primers" are selected to hybridize to conserved sequence regions of nucleic acids derived from a bioagent and which bracket variable sequence regions to yield a bioagent identifying amplicon which can be amplified and which is amenable to molecular mass determination. The molecular mass then provides a means to uniquely identify the bioagent without a requirement for prior knowledge of the possible identity of the bioagent. The molecular mass or corresponding "base composition signature" (BCS) of the amplification product is then matched against a database of molecular masses or base composition signatures. Furthermore, the method can be applied to rapid parallel "multiplex" analyses, the results of which can be employed in a triangulation identification strategy. The present method provides rapid throughput and does not require nucleic acid sequencing of the amplified target sequence for bioagent detection and identification.

In the context of this invention, a "bioagent" is any organism, cell, or virus, living or dead, or a nucleic acid derived from such an organism, cell or virus. Examples of bioagents include, but are not limited, to cells (including, but not limited to, human clinical samples, bacterial cells and other pathogens) viruses, fungi, and protists, parasites, and pathogenicity markers (including, but not limited to, pathogenicity islands, antibiotic resistance genes, virulence factors, toxin genes and other bioregulating compounds). Samples may be alive or dead or in a vegetative state (for example, vegetative bacteria or spores) and may be encapsulated or bioengineered. In the context of this invention, a "pathogen" is a bioagent that causes a disease or disorder.

Despite enormous biological diversity, all forms of life on earth share sets of essential, common features in their genomes. Bacteria, for example have highly conserved sequences in a variety of locations on their genomes. Most notable is the universally conserved region of the ribosome, but there are also conserved elements in other non-coding RNAs, including RNAse P and the signal recognition particle (SRP) among others. Bacteria have a common set of absolutely required genes. About 250 genes are present in all bacterial species (Mushegian et al., Proc. Natl. Acad. Sci. U.S.A., 1996, 93, 10268; and Fraser et al., Science, 1995, 270, 397), including tiny genomes like *Mycoplasma, Ureaplasma* and *Rickettsia*. These genes encode proteins involved in translation, replication, recombination and repair, transcription, nucleotide metabolism, amino acid metabolism, lipid metabolism, energy generation, uptake, secretion and the like. Examples of these proteins are DNA polymerase III beta, elongation factor TU, heat shock protein groEL, RNA polymerase beta, phosphoglycerate kinase, NADH dehydrogenase, DNA ligase, DNA topoisomerase and elongation factor G. Operons can also be targeted using the present method. One example of an operon is the bfp operon from enteropathogenic *E. coli*. Multiple core chromosomal genes can be used to classify bacteria at a genus or genus species level to determine if an organism has threat potential. The methods can also be used to detect pathogenicity markers (plasmid or chromosomal) and antibiotic resistance genes to confirm the threat potential of an organism and to direct countermeasures.

Since genetic data provide the underlying basis for identification of bioagents by the methods of the present invention, it is prudent to select segments of nucleic acids which ideally provide enough variability to distinguish each individual bioagent and whose molecular mass is amenable to molecular mass determination. In one embodiment of the present invention, at least one polynucleotide segment is amplified to facilitate detection and analysis in the process of identifying the bioagent. Thus, the nucleic acid segments that provide enough variability to distinguish each individual bioagent and whose molecular masses are amenable to molecular mass determination are herein described as "bioagent identifying amplicons." The term "amplicon" as used herein, refers to a segment of a polynucleotide which is amplified in an amplification reaction. In some embodiments of the present invention, bioagent identifying amplicons comprise from about 45 to about 150 nucleobases (i.e. from about 45 to about 150 linked nucleosides). One of ordinary skill in the art will appreciate that the invention embodies compounds of 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 nucleobases in length.

As used herein, "intelligent primers" are primers that are designed to bind to highly conserved sequence regions that flank an intervening variable region and yield amplification products which ideally provide enough variability to distinguish each individual bioagent, and which are amenable to molecular mass analysis. By the term "highly conserved," it is meant that the sequence regions exhibit between about 80-100%, or between about 90-100%, or between about 95-100% identity. The molecular mass of a given amplification product provides a means of identifying the bioagent from which it was obtained, due to the variability of the variable region. Thus, design of intelligent primers involves selection of a variable region with appropriate variability to resolve the identity of a particular bioagent. It is the combination of the portion of the bioagent nucleic acid molecule sequence to which the intelligent primers hybridize and the intervening variable region that makes up the bioagent identifying amplicon. Alternately, it is the intervening variable region by itself that makes up the bioagent identifying amplicon.

It is understood in the art that the sequence of a primer need not be 100% complementary to that of its target nucleic acid to be specifically hybridizable. Moreover, a primer may hybridize over one or more segments such that intervening or adjacent segments are not involved in the hybridization event (e.g., a loop structure or hairpin structure). The primers of the present invention can comprise at least 70%, at least 75%, at least 80%, at least 85%, at least 90%, at least 95%, or at least 99% sequence complementarity to the target region within the highly conserved region to which they are targeted. For example, an intelligent primer wherein 18 of 20 nucleobases are complementary to a highly conserved region would represent 90 percent complementarity to the highly conserved region. In this example, the remaining noncomplementary nucleobases may be clustered or interspersed with complementary nucleobases and need not be contiguous to each other or to complementary nucleobases. As such, a primer which is 18 nucleobases in length having 4 (four) noncomplementary nucleobases which are flanked by two regions of complete complementarity with the highly conserved region would have 77.8% overall complementarity with the highly conserved region and would thus fall within the scope of the present invention. Percent complementarity of a primer with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, complementarity of intelligent primers, is between about 70% and about 80%. In other embodiments, homology, sequence identity or complementarity, is between about 80% and about 90%. In yet other embodiments, homology, sequence identity or complementarity, is about 90%, about 92%, about 94%, about 95%, about 96%, about 97%, about 98%, about 99% or about 100%.

The intelligent primers of this invention comprise from about 12 to about 35 nucleobases (i.e. from about 12 to about 35 linked nucleosides). One of ordinary skill in the art will appreciate that the invention embodies compounds of 12, 13, 14, 15, 16, 17, 18, 19, 20, 21, 22, 23, 24, 25, 26, 27, 28, 29, 30, 31, 32, 33, 34, or 35 nucleobases in length.

One having skill in the art armed with the preferred bioagent identifying amplicons defined by the primers illustrated herein will be able, without undue experimentation, to identify additional intelligent primers.

In one embodiment, the bioagent identifying amplicon is a portion of a ribosomal RNA (rRNA) gene sequence. With the complete sequences of many of the smallest microbial genomes now available, it is possible to identify a set of genes that defines "minimal life" and identify composition signatures that uniquely identify each gene and organism. Genes that encode core life functions such as DNA replication, transcription, ribosome structure, translation, and transport are distributed broadly in the bacterial genome and are suitable regions for selection of bioagent identifying amplicons. Ribosomal RNA (rRNA) genes comprise regions that provide useful base composition signatures. Like many genes involved in core life functions, rRNA genes contain sequences that are extraordinarily conserved across bacterial domains interspersed with regions of high variability that are more specific to each species. The variable regions can be utilized to build a database of base composition signatures. The strategy involves creating a structure-based alignment of sequences of the small (16S) and the large (23S) subunits of the rRNA genes. For example, there are currently over 13,000 sequences in the ribosomal RNA database that has been created and maintained by Robin Gutell, University of Texas at Austin, and is publicly available on the Institute for Cellular and Molecular Biology web page on the world wide web of the Internet at, for example, "rna.icmb.utexas.edu/." There is also a publicly available rRNA database created and maintained by the University of Antwerp, Belgium on the world wide web of the Internet at, for example, "rrna.uia.ac.be."

These databases have been analyzed to determine regions that are useful as bioagent identifying amplicons. The characteristics of such regions include: a) between about 80 and 100%, or greater than about 95% identity among species of the particular bioagent of interest, of upstream and downstream nucleotide sequences which serve as sequence amplification primer sites; b) an intervening variable region which exhibits no greater than about 5% identity among species; and c) a separation of between about 30 and 1000 nucleotides, or no more than about 50-250 nucleotides, or no more than about 60-100 nucleotides, between the conserved regions.

As a non-limiting example, for identification of *Bacillus* species, the conserved sequence regions of the chosen bioagent identifying amplicon must be highly conserved among all *Bacillus* species while the variable region of the bioagent identifying amplicon is sufficiently variable such that the molecular masses of the amplification products of all species of *Bacillus* are distinguishable.

Bioagent identifying amplicons amenable to molecular mass determination are either of a length, size or mass compatible with the particular mode of molecular mass determination or compatible with a means of providing a predictable fragmentation pattern in order to obtain predictable fragments of a length compatible with the particular mode of molecular mass determination. Such means of providing a predictable fragmentation pattern of an amplification product include, but are not limited to, cleavage with restriction enzymes or cleavage primers, for example.

Identification of bioagents can be accomplished at different levels using intelligent primers suited to resolution of each individual level of identification. "Broad range survey" intelligent primers are designed with the objective of identifying a bioagent as a member of a particular division of bioagents. A "bioagent division" is defined as group of bioagents above the species level and includes but is not limited to: orders, families, classes, clades, genera or other such groupings of bioagents above the species level. As a non-limiting example, members of the *Bacillus/Clostridia* group or gamma-proteobacteria group may be identified as such by employing broad range survey intelligent primers such as primers that target 16S or 23S ribosomal RNA.

In some embodiments, broad range survey intelligent primers are capable of identification of bioagents at the species level. One main advantage of the detection methods of the present invention is that the broad range survey intelligent primers need not be specific for a particular bacterial species, or even genus, such as *Bacillus* or *Streptomyces*. Instead, the primers recognize highly conserved regions across hundreds of bacterial species including, but not limited to, the species described herein. Thus, the same broad range survey intelligent primer pair can be used to identify any desired bacterium because it will bind to the conserved regions that flank a variable region specific to a single species, or common to several bacterial species, allowing unbiased nucleic acid amplification of the intervening sequence and determination of its molecular weight and base composition. For example, the 16S_971-1062, 16S_1228-1310 and 16S_1100-1188 regions are 98-99% conserved in about 900 species of bacteria (16S=16S rRNA, numbers indicate nucleotide position). In one embodiment of the present invention, primers used in the present method bind to one or more of these regions or portions thereof.

Due to their overall conservation, the flanking rRNA primer sequences serve as good intelligent primer binding sites to amplify the nucleic acid region of interest for most, if not all, bacterial species. The intervening region between the sets of primers varies in length and/or composition, and thus provides a unique base composition signature. Examples of intelligent primers that amplify regions of the 16S and 23S rRNA are shown in FIGS. 1A-11H. A typical primer amplified region in 16S rRNA is shown in FIG. 2. The arrows represent primers that bind to highly conserved regions that flank a variable region in 16S rRNA domain III. The amplified region is the stem-loop structure under "1100-1188." It is advantageous to design the broad range survey intelligent primers to minimize the number of primers required for the analysis, and to allow detection of multiple members of a bioagent division using a single pair of primers. The advantage of using broad range survey intelligent primers is that once a bioagent is broadly identified, the process of further identification at species and sub-species levels is facilitated by directing the choice of additional intelligent primers.

"Division-wide" intelligent primers are designed with an objective of identifying a bioagent at the species level. As a non-limiting example, a *Bacillus anthracis, Bacillus cereus* and *Bacillus thuringiensis* can be distinguished from each other using division-wide intelligent primers. Division-wide intelligent primers are not always required for identification at the species level because broad range survey intelligent primers may provide sufficient identification resolution to accomplishing this identification objective.

"Drill-down" intelligent primers are designed with an objective of identifying a sub-species characteristic of a bioagent. A "sub-species characteristic" is defined as a property imparted to a bioagent at the sub-species level of identification as a result of the presence or absence of a particular segment of nucleic acid. Such sub-species characteristics include, but are not limited to, strains, sub-types, pathogenicity markers such as antibiotic resistance genes, pathogenicity islands, toxin genes and virulence factors. Identification of such sub-species characteristics is often critical for determining proper clinical treatment of pathogen infections.

Chemical Modifications of Intelligent Primers

Ideally, intelligent primer hybridization sites are highly conserved in order to facilitate the hybridization of the primer. In cases where primer hybridization is less efficient due to lower levels of conservation of sequence, intelligent primers can be chemically modified to improve the efficiency of hybridization.

For example, because any variation (due to codon wobble in the $3^{rd}$ position) in these conserved regions among species is likely to occur in the third position of a DNA triplet, oligonucleotide primers can be designed such that the nucleotide corresponding to this position is a base which can bind to more than one nucleotide, referred to herein as a "universal base." For example, under this "wobble" pairing, inosine (I) binds to U, C or A; guanine (G) binds to U or C, and uridine (U) binds to U or C. Other examples of universal bases include nitroindoles such as 5-nitroindole or 3-nitropyrrole (Loakes et al., Nucleosides and Nucleotides, 1995, 14, 1001-1003), the degenerate nucleotides dP or dK (Hill et al.), an acyclic nucleoside analog containing 5-nitroindazole (Van Aerschot et al., Nucleosides and Nucleotides, 1995, 14, 1053-1056) or the purine analog 1-(2-deoxy-β-D-ribofuranosyl)-imidazole-4-carboxamide (Sala et al., Nucl. Acids Res., 1996, 24, 3302-3306).

In another embodiment of the invention, to compensate for the somewhat weaker binding by the "wobble" base, the oligonucleotide primers are designed such that the first and second positions of each triplet are occupied by nucleotide analogs which bind with greater affinity than the unmodified nucleotide. Examples of these analogs include, but are not limited to, 2,6-diaminopurine which binds to thymine, propyne T which binds to adenine and propyne C and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are claimed in U.S. Ser. No. 10/294,203 which is also commonly owned and incorporated herein by reference in entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

A theoretically ideal bioagent detector would identify, quantify, and report the complete nucleic acid sequence of every bioagent that reached the sensor. The complete sequence of the nucleic acid component of a pathogen would provide all relevant information about the threat, including its identity and the presence of drug-resistance or pathogenicity markers. This ideal has not yet been achieved. However, the present invention provides a straightforward strategy for obtaining information with the same practical value based on analysis of bioagent identifying amplicons by molecular mass determination.

In some cases, a molecular mass of a given bioagent identifying amplicon alone does not provide enough resolution to unambiguously identify a given bioagent. For example, the molecular mass of the bioagent identifying amplicon obtained using the intelligent primer pair "16S_971" would be 55622 Da for both *E. coli* and *Salmonella typhimurium*. However, if additional intelligent primers are employed to analyze additional bioagent identifying amplicons, a "triangulation identification" process is enabled. For example, the "16S_1100" intelligent primer pair yields molecular masses of 55009 and 55005 Da for *E. coli* and *Salmonella typhimurium*, respectively. Furthermore, the "23S_855" intelligent primer pair yields molecular masses of 42656 and 42698 Da for *E. coli* and *Salmonella typhimurium*, respectively. In this basic example, the second and third intelligent primer pairs provided the additional "fingerprinting" capability or resolution to distinguish between the two bioagents.

In another embodiment, the triangulation identification process is pursued by measuring signals from a plurality of bioagent identifying amplicons selected within multiple core genes. This process is used to reduce false negative and false positive signals, and enable reconstruction of the origin of hybrid or otherwise engineered bioagents. In this process, after identification of multiple core genes, alignments are created from nucleic acid sequence databases. The alignments are then analyzed for regions of conservation and variation, and bioagent identifying amplicons are selected to distinguish bioagents based on specific genomic differences. For example, identification of the three part toxin genes typical of *B. anthracis* (Bowen et al., J. Appl. Microbiol., 1999, 87, 270-278) in the absence of the expected signatures from the *B. anthracis* genome would suggest a genetic engineering event.

The triangulation identification process can be pursued by characterization of bioagent identifying amplicons in a massively parallel fashion using the polymerase chain reaction (PCR), such as multiplex PCR, and mass spectrometric (MS) methods. Sufficient quantities of nucleic acids should be present for detection of bioagents by MS. A wide variety of techniques for preparing large amounts of purified nucleic acids or fragments thereof are well known to those of skill in the art. PCR requires one or more pairs of oligonucleotide primers that bind to regions which flank the target sequence (s) to be amplified. These primers prime synthesis of a different strand of DNA with synthesis occurring in the direction of one primer towards the other primer. The primers, DNA to be amplified, a thermostable DNA polymerase (e.g. Taq polymerase), the four deoxynucleotide triphosphates, and a buffer are combined to initiate DNA synthesis. The solution is denatured by heating, then cooled to allow annealing of newly added primer, followed by another round of DNA synthesis. This process is typically repeated for about 30 cycles, resulting in amplification of the target sequence.

Although the use of PCR is suitable, other nucleic acid amplification techniques may also be used, including ligase chain reaction (LCR) and strand displacement amplification (SDA). The high-resolution MS technique allows separation of bioagent spectral lines from background spectral lines in highly cluttered environments.

In another embodiment, the detection scheme for the PCR products generated from the bioagent(s) incorporates at least three features. First, the technique simultaneously detects and differentiates multiple (generally about 6-10) PCR products. Second, the technique provides a molecular mass that uniquely identifies the bioagent from the possible primer sites. Finally, the detection technique is rapid, allowing multiple PCR reactions to be run in parallel.

Mass spectrometry (MS)-based detection of PCR products provides a means for determination of BCS that has several advantages. MS is intrinsically a parallel detection scheme without the need for radioactive or fluorescent labels, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons. Intact molecular ions can be generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). For example, MALDI of nucleic acids, along with examples of matrices for use in MALDI of nucleic acids, are described in WO 98/54751 (Genetrace, Inc.).

In some embodiments, large DNAs and RNAs, or large amplification products therefrom, can be digested with restriction endonucleases prior to ionization. Thus, for example, an amplification product that was 10 kDa could be digested with a series of restriction endonucleases to produce a panel of, for example, 100 Da fragments. Restriction endonucleases and their sites of action are well known to the skilled artisan. In this manner, mass spectrometry can be performed for the purposes of restriction mapping.

Upon ionization, several peaks are observed from one sample due to the formation of ions with different charges. Averaging the multiple readings of molecular mass obtained from a single mass spectrum affords an estimate of molecular mass of the bioagent. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), ion trap, quadrupole, magnetic sector, time of flight (TOF), Q-TOF, and triple quadrupole.

In general, the mass spectrometric techniques which can be used in the present invention include, but are not limited to, tandem mass spectrometry, infrared multiphoton dissociation and pyrolytic gas chromatography mass spectrometry (PGC-MS). In one embodiment of the invention, the bioagent detection system operates continually in bioagent detection mode using pyrolytic GC-MS without PCR for rapid detection of increases in biomass (for example, increases in fecal contamination of drinking water or of germ warfare agents). To achieve minimal latency, a continuous sample stream flows directly into the PGC-MS combustion chamber. When an increase in biomass is detected, a PCR process is automatically initiated. Bioagent presence produces elevated levels of large molecular fragments from, for example, about 100-7,000 Da which are observed in the PGC-MS spectrum. The observed mass spectrum is compared to a threshold level and when levels of biomass are determined to exceed a predetermined threshold, the bioagent classification process described hereinabove (combining PCR and MS, such as FT-ICR MS) is initiated. Optionally, alarms or other processes (halting ventilation flow, physical isolation) are also initiated by this detected biomass level.

The accurate measurement of molecular mass for large DNAs is limited by the adduction of cations from the PCR reaction to each strand, resolution of the isotopic peaks from natural abundance $^{13}C$ and $^{15}N$ isotopes, and assignment of the charge state for any ion. The cations are removed by in-line dialysis using a flow-through chip that brings the solution containing the PCR products into contact with a solution containing ammonium acetate in the presence of an electric field gradient orthogonal to the flow. The latter two problems are addressed by operating with a resolving power of >100,000 and by incorporating isotopically depleted nucleotide triphosphates into the DNA. The resolving power of the instrument is also a consideration. At a resolving power of 10,000, the modeled signal from the $[M-14H+]^{14-}$ charge state of an 84 mer PCR product is poorly characterized and assignment of the charge state or exact mass is impossible. At a resolving power of 33,000, the peaks from the individual isotopic components are visible. At a resolving power of 100,000, the isotopic peaks are resolved to the baseline and assignment of the charge state for the ion is straightforward. The $[^{13}C,^{15}N]$-depleted triphosphates are obtained, for example, by growing microorganisms on depleted media and harvesting the nucleotides (Batey et al., Nucl. Acids Res., 1992, 20, 4515-4523).

While mass measurements of intact nucleic acid regions are believed to be adequate to determine most bioagents, tandem mass spectrometry (MS$^n$) techniques may provide more definitive information pertaining to molecular identity or sequence. Tandem MS involves the coupled use of two or more stages of mass analysis where both the separation and detection steps are based on mass spectrometry. The first stage is used to select an ion or component of a sample from which further structural information is to be obtained. The selected ion is then fragmented using, e.g., blackbody irradiation, infrared multiphoton dissociation, or collisional activation. For example, ions generated by electrospray ionization (ESI) can be fragmented using IR multiphoton dissociation. This activation leads to dissociation of glycosidic bonds and the phosphate backbone, producing two series of fragment ions, called the w-series (having an intact 3' terminus and a 5' phosphate following internal cleavage) and the a-Base series (having an intact 5' terminus and a 3' furan).

The second stage of mass analysis is then used to detect and measure the mass of these resulting fragments of product ions. Such ion selection followed by fragmentation routines can be performed multiple times so as to essentially completely dissect the molecular sequence of a sample.

If there are two or more targets of similar molecular mass, or if a single amplification reaction results in a product that has the same mass as two or more bioagent reference standards, they can be distinguished by using mass-modifying "tags." In this embodiment of the invention, a nucleotide analog or "tag" is incorporated during amplification (e.g., a 5-(trifluoromethyl) deoxythymidine triphosphate) which has a different molecular weight than the unmodified base so as to improve distinction of masses. Such tags are described in, for example, PCT WO97/33000, which is incorporated herein by reference in its entirety. This further limits the number of possible base compositions consistent with any mass. For example, 5-(trifluoromethyl)deoxythymidine triphosphate can be used in place of dTTP in a separate nucleic acid amplification reaction. Measurement of the mass shift between a conventional amplification product and the tagged product is used to quantitate the number of thymidine nucleotides in each of the single strands. Because the strands are complementary, the number of adenosine nucleotides in each strand is also determined.

In another amplification reaction, the number of G and C residues in each strand is determined using, for example, the cytidine analog 5-methylcytosine (5-meC) or propyne C. The combination of the A/T reaction and G/C reaction, followed by molecular weight determination, provides a unique base composition. This method is summarized in FIG. 4 and Table 1.

TABLE 1

| Mass tag | Double strand sequence | Single strand Sequence | Total mass this strand | Base info this strand | Base info other strand | Total base comp. Top strand | Total base comp. Bottom strand |
|---|---|---|---|---|---|---|---|
| T*mass (T* − T) = x | T*ACGT*ACGT* AT*GCAT*GCA | T*ACGT*ACGT* | 3x | 3T | 3A | 3T 2A 2C 2G | 3A 2T 2G 2C |
| | | AT*GCAT*GCA | 2x | 2T | 2A | | |
| C*mass (C* − C) = y | TAC*GTAC*GT ATGC*ATGC*A | TAC*GTAC*GT | 2x | 2C | 2G | | |
| | | ATGC*ATGC*A | 2x | 2C | 2G | | |

The mass tag phosphorothioate A (A*) was used to distinguish a *Bacillus anthracis* cluster. The *B. anthracis* ($A_{14}G_9C_{14}T_9$) had an average MW of 14072.26, and the *B. anthracis* ($A_1A^*_{13}G_9C_{14}T_9$) had an average molecular weight of 14281.11 and the phosphorothioate A had an average molecular weight of +16.06 as determined by ESI-TOF MS. The deconvoluted spectra are shown in FIG. 5.

In another example, assume the measured molecular masses of each strand are 30,000.115Da and 31,000.115 Da respectively, and the measured number of dT and dA residues are (30,28) and (28,30). If the molecular mass is accurate to 100 ppm, there are 7 possible combinations of dG+dC possible for each strand. However, if the measured molecular mass is accurate to 10 ppm, there are only 2 combinations of dG+dC, and at 1 ppm accuracy there is only one possible base composition for each strand.

Signals from the mass spectrometer may be input to a maximum-likelihood detection and classification algorithm such as is widely used in radar signal processing. The detection processing uses matched filtering of BCS observed in mass-basecount space and allows for detection and subtraction of signatures from known, harmless organisms, and for detection of unknown bioagent threats. Comparison of newly observed bioagents to known bioagents is also possible, for estimation of threat level, by comparing their BCS to those of known organisms and to known forms of pathogenicity enhancement, such as insertion of antibiotic resistance genes or toxin genes.

Processing may end with a Bayesian classifier using log likelihood ratios developed from the observed signals and average background levels. The program emphasizes performance predictions culminating in probability-of-detection versus probability-of-false-alarm plots for conditions involving complex backgrounds of naturally occurring organisms and environmental contaminants. Matched filters consist of a priori expectations of signal values given the set of primers used for each of the bioagents. A genomic sequence database (e.g. GenBank) is used to define the mass basecount matched filters. The database contains known threat agents and benign background organisms. The latter is used to estimate and subtract the signature produced by the background organisms. A maximum likelihood detection of known background organisms is implemented using matched filters and a running-sum estimate of the noise covariance. Background signal strengths are estimated and used along with the matched filters to form signatures that are then subtracted. The maximum likelihood process is applied to this "cleaned up" data in a similar manner employing matched filters for the organisms and a running-sum estimate of the noise-covariance for the cleaned up data.

Although the molecular mass of amplification products obtained using intelligent primers provides a means for identification of bioagents, conversion of molecular mass data to a base composition signature is useful for certain analyses. As used herein, a "base composition signature" (BCS) is the exact base composition determined from the molecular mass of a bioagent identifying amplicon. In one embodiment, a BCS provides an index of a specific gene in a specific organism.

Figure 18:
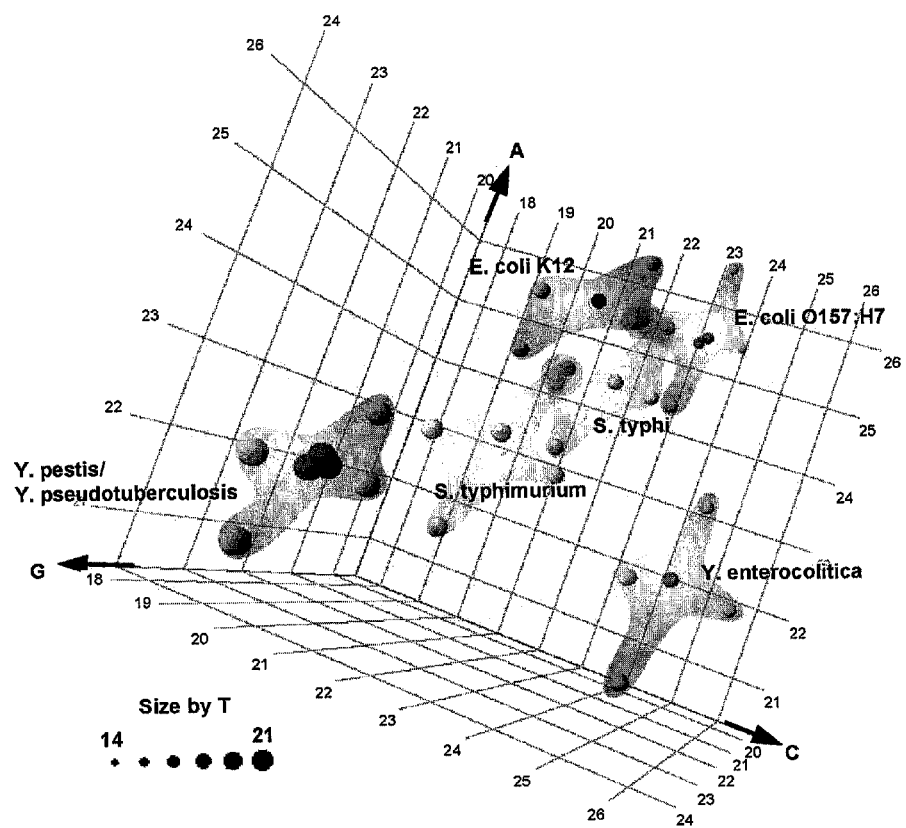
FIG. 18 shows a representative base composition probability cloud for a region of the RNA polymerase B gene from a cluster of enterobacteria. The dark spheres represent the actual base composition of the organisms. The lighter spheres represent the transitions among base compositions observed in different isolates of the same species of organism.

Base compositions, like sequences, vary slightly from isolate to isolate within species. It is possible to manage this diversity by building "base composition probability clouds" around the composition constraints for each species. This permits identification of organisms in a fashion similar to sequence analysis. A "pseudo four-dimensional plot" can be used to visualize the concept of base composition probability clouds (FIG. 18). Optimal primer design requires optimal choice of bioagent identifying amplicons and maximizes the separation between the base composition signatures of individual bioagents. Areas where clouds overlap indicate regions that may result in a misclassification, a problem which is overcome by selecting primers that provide information from different bioagent identifying amplicons, ideally maximizing the separation of base compositions. Thus, one aspect of the utility of an analysis of base composition probability clouds is that it provides a means for screening primer sets in order to avoid potential misclassifications of BCS and bioagent identity. Another aspect of the utility of base composition probability clouds is that they provide a means for predicting the identity of a bioagent whose exact measured BCS was not previously observed and/or indexed in a BCS database due to evolutionary transitions in its nucleic acid sequence.

It is important to note that, in contrast to probe-based techniques, mass spectrometry determination of base composition does not require prior knowledge of the composition in order to make the measurement, only to interpret the results. In this regard, the present invention provides bioagent classifying information similar to DNA sequencing and phylogenetic analysis at a level sufficient to detect and identify a given bioagent. Furthermore, the process of determination of a previously unknown BCS for a given bioagent (for example, in a case where sequence information is unavailable) has downstream utility by providing additional bioagent indexing information with which to populate BCS databases. The process of future bioagent identification is thus greatly improved as more BCS indexes become available in the BCS databases.

Another embodiment of the present invention is a method of surveying bioagent samples that enables detection and identification of all bacteria for which sequence information is available using a set of twelve broad-range intelligent PCR primers. Six of the twelve primers are "broad range survey primers" herein defined as primers targeted to broad divisions of bacteria (for example, the *Bacillus/Clostridia* group or gamma-proteobacteria). The other six primers of the group of twelve primers are "division-wide" primers herein defined as primers that provide more focused coverage and higher resolution. This method enables identification of nearly 100% of known bacteria at the species level. A further example of this embodiment of the present invention is a method herein designated "survey/drill-down" wherein a subspecies characteristic for detected bioagents is obtained using additional primers. Examples of such a subspecies characteristic include but are not limited to: antibiotic resistance, pathogenicity island, virulence factor, strain type, sub-species type, and clade group. Using the survey/drill-down method, bioagent detection, confirmation and a subspecies characteristic can be provided within hours. Moreover, the survey/drill-down method can be focused to identify bioengineering events such as the insertion of a toxin gene into a bacterial species that does not normally make the toxin.

The present methods allow extremely rapid and accurate detection and identification of bioagents compared to existing methods. Furthermore, this rapid detection and identification is possible even when sample material is impure. The methods leverage ongoing biomedical research in virulence, pathogenicity, drug resistance and genome sequencing into a method which provides greatly improved sensitivity, specificity and reliability compared to existing methods, with lower rates of false positives. Thus, the methods are useful in a wide variety of fields, including, but not limited to, those fields discussed below.

In other embodiments of the invention, the methods disclosed herein can identify infectious agents in biological samples. At least a first biological sample containing at least a first unidentified infectious agent is obtained. An identification analysis is carried out on the sample, whereby the first infectious agent in the first biological sample is identified. More particularly, a method of identifying an infectious agent in a biological entity is provided. An identification analysis is carried out on a first biological sample obtained from the biological entity, whereby at least one infectious agent in the biological sample from the biological entity is identified. The obtaining and the performing steps are, optionally, repeated on at least one additional biological sample from the biological entity.

The present invention also provides methods of identifying an infectious agent that is potentially the cause of a health condition in a biological entity. An identification analysis is carried out on a first test sample from a first infectious agent differentiating area of the biological entity, whereby at least one infectious agent is identified. The obtaining and the performing steps are, optionally, repeated on an additional infectious agent differentiating area of the biological entity.

Biological samples include, but are not limited to, hair, mucosa, skin, nail, blood, saliva, rectal, lung, stool, urine, breath, nasal, ocular sample, or the like. In some embodiments, one or more biological samples are analyzed by the methods described herein. The biological sample(s) contain at least a first unidentified infectious agent and may contain more than one infectious agent. The biological sample(s) are obtained from a biological entity. The biological sample can be obtained by a variety of manners such as by biopsy, swabbing, and the like. The biological samples may be obtained by a physician in a hospital or other health care environment. The physician may then perform the identification analysis or send the biological sample to a laboratory to carry out the analysis.

Biological entities include, but are not limited to, a mammal, a bird, or a reptile. The biological entity may be a cow, horse, dog, cat, or a primate. The biological entity can also be a human. The biological entity may be living or dead.

An infectious agent differentiating area is any area or location within a biological entity that can distinguish between a harmful versus normal health condition. An infectious agent differentiating area can be a region or area of the biological entity whereby an infectious agent is more likely to predominate from another region or area of the biological entity. For example, infectious agent differentiating areas may include the blood vessels of the heart (heart disease, coronary artery disease, etc.), particular portions of the digestive system (ulcers, Crohn's disease, etc.), liver (hepatitis infections), and the like. In some embodiments, one or more biological samples from a plurality of infectious agent differentiating areas is analyzed the methods described herein.

Infectious agents of the invention may potentially cause a health condition in a biological entity. Health conditions include any condition, syndrome, illness, disease, or the like, identified currently or in the future by medical personnel. Infectious agents include, but are not limited to, bacteria, viruses, parasites, fungi, and the like.

In other embodiments of the invention, the methods disclosed herein can be used to screen blood and other bodily fluids and tissues for pathogenic and non-pathogenic bacteria, viruses, parasites, fungi and the like. Animal samples, including but not limited to, blood and other bodily fluid and tissue samples, can be obtained from living animals, who are either known or not known to or suspected of having a disease, infection, or condition. Alternately, animal samples such as blood and other bodily fluid and tissue samples can be obtained from deceased animals. Blood samples can be further separated into plasma or cellular fractions and further screened as desired. Bodily fluids and tissues can be obtained from any part of the animal or human body. Animal samples can be obtained from, for example, mammals and humans.

Clinical samples are analyzed for disease causing bioagents and biowarfare pathogens simultaneously with detection of bioagents at levels as low as 100-1000 genomic copies in complex backgrounds with throughput of approximately 100-300 samples with simultaneous detection of bacteria and viruses. Such analyses provide additional value in probing bioagent genomes for unanticipated modifications. These analyses are carried out in reference labs, hospitals and the LRN laboratories of the public health system in a coordinated fashion, with the ability to report the results via a computer network to a common data-monitoring center in real time. Clonal propagation of specific infectious agents, as occurs in the epidemic outbreak of infectious disease, can be tracked with base composition signatures, analogous to the pulse field gel electrophoresis fingerprinting patterns used in tracking the spread of specific food pathogens in the Pulse Net system of the CDC (Swaminathan et al., Emerging Infectious Diseases, 2001, 7, 382-389). The present invention provides a digital barcode in the form of a series of base composition signatures, the combination of which is unique for each known organism. This capability enables real-time infectious disease monitoring across broad geographic locations, which may be essential in a simultaneous outbreak or attack in different cities.

In other embodiments of the invention, the methods disclosed herein can be used for detecting the presence of pathogenic and non-pathogenic bacteria, viruses, parasites, fungi and the like in organ donors and/or in organs from donors. Such examination can result in the prevention of the transfer of, for example, viruses such as West Nile virus, hepatitis viruses, human immunodeficiency virus, and the like from a donor to a recipient via a transplanted organ. The methods disclosed herein can also be used for detection of host versus graft or graft versus host rejection issues related to organ donors by detecting the presence of particular antigens in either the graft or host known or suspected of causing such rejection. In particular, the bioagents in this regard are the antigens of the major histocompatibility complex, such as the HLA antigens. The present methods can also be used to detect and track emerging infectious diseases, such as West Nile virus infection, HIV-related diseases.

In other embodiments of the invention, the methods disclosed herein can be used for pharmacogenetic analysis and medical diagnosis including, but not limited to, cancer diagnosis based on mutations and polymorphisms, drug resistance and susceptibility testing, screening for and/or diagnosis of genetic diseases and conditions, and diagnosis of infectious diseases and conditions. In context of the present invention, pharmacogenetics is defined as the study of variability in drug response due to genetic factors. Pharmacogenetic investigations are often based on correlating patient outcome with variations in genes involved in the mode of action of a given drug. For example, receptor genes, or genes involved in metabolic pathways. The methods of the present invention provide a means to analyze the DNA of a patient to provide the basis for pharmacogenetic analysis.

The present method can also be used to detect single nucleotide polymorphisms (SNPs), or multiple nucleotide polymorphisms, rapidly and accurately. A SNP is defined as a single base pair site in the genome that is different from one individual to another. The difference can be expressed either as a deletion, an insertion or a substitution, and is frequently linked to a disease state. Because they occur every 100-1000 base pairs, SNPs are the most frequently bound type of genetic marker in the human genome.

For example, sickle cell anemia results from an A-T transition, which encodes a valine rather than a glutamic acid residue. Oligonucleotide primers may be designed such that they bind to sequences that flank a SNP site, followed by nucleotide amplification and mass determination of the amplified product. Because the molecular masses of the resulting product from an individual who does not have sickle cell anemia is different from that of the product from an individual who has the disease, the method can be used to distinguish the two individuals. Thus, the method can be used to detect any known SNP in an individual and thus diagnose or determine increased susceptibility to a disease or condition.

In one embodiment, blood is drawn from an individual and peripheral blood mononuclear cells (PBMC) are isolated and simultaneously tested, such as in a high-throughput screening method, for one or more SNPs using appropriate primers based on the known sequences which flank the SNP region. The National Center for Biotechnology Information maintains a publicly available database of SNPs on the world wide web of the Internet at, for example, "ncbi.nlm.nih.gov/SNP/."

The method of the present invention can also be used for blood typing. The gene encoding A, B or U blood type can differ by four single nucleotide polymorphisms. If the gene contains the sequence CGTGGTGACCCTT (SEQ ID NO:5), antigen A results. If the gene contains the sequence CGTCGTCACCGCTA (SEQ ID NO:6) antigen B results. If the gene contains the sequence CGTGGT-ACCCCTT (SEQ ID NO:7), blood group 0 results ("–" indicates a deletion). These sequences can be distinguished by designing a single primer pair which flanks these regions, followed by amplification and mass determination.

The method of the present invention can also be used for detection and identification of blood-borne pathogens such as *Staphylococcus aureus* for example. The method of the present invention can also be used for strain typing of respiratory pathogens in epidemic surveillance. Group A streptococci (GAS), or *Streptococcus pyogenes*, is one of the most consequential causes of respiratory infections because of prevalence and ability to cause disease with complications such as acute rheumatic fever and acute glomerulonephritis. GAS also causes infections of the skin (impetigo) and, in rare cases, invasive disease such as necrotizing fasciitis and toxic shock syndrome. Despite many decades of study, the underlying microbial ecology and natural selection that favors enhanced virulence and explosive GAS outbreaks is still poorly understood. The ability to detect GAS and multiple other pathogenic and non-pathogenic bacteria and viruses in patient samples would greatly facilitate our understanding of GAS epidemics. It is also essential to be able to follow the spread of virulent strains of GAS in populations and to distinguish virulent strains from less virulent or avirulent streptococci that colonize the nose and throat of asymptomatic individuals at a frequency ranging from 5-20% of the population (Bisno, A. L. (1995) in Principles and Practice of Infectious Diseases, eds. Mandell, G. L., Bennett, J. E. & Dolin, R. (Churchill Livingston, N.Y.), Vol. 2, pp. 1786-1799). Molecular methods have been developed to type GAS based upon the sequence of the emm gene that encodes the M-protein virulence factor (Beall et al., J. Clin. Micro., 1996, 34, 953-958; Beall et al., J. Clin. Micro., 1997, 35, 1231-1235; and Facklam et al., Emerging Infectious Diseases, 1999, 5, 247-253). Using this molecular classification, over 150 different emm-types are defined and correlated with phenotypic properties of thousands of GAS isolates (www.cdc.gov/ncidod/biotech/strep/strepindex.html) (Facklam et al., Clinical Infectious Diseases, 2002, 34, 28-38). Recently, a strategy known as Multi Locus Sequence Typing (MLST) was developed to follow the molecular Epidemiology of GAS. In MLST, internal fragments of seven housekeeping genes are amplified, sequenced, and compared to a database of previously studied isolates (www.test.mlst.net/).

The present invention enables an emm-typing process to be carried out directly from throat swabs for a large number of samples within 12 hours, allowing strain tracking of an ongoing epidemic, even if geographically dispersed, on a larger scale than ever before achievable.

In another embodiment, the present invention can be employed in the serotyping of viruses including, but not limited to, adenoviruses. Adenoviruses are DNA viruses that cause over 50% of febrile respiratory illnesses in military recruits. Human adenoviruses are divided into six major serogroups (A through F), each containing multiple strain types. Despite the prevalence of adenoviruses, there are no rapid methods for detecting and serotyping adenoviruses.

In another embodiment, the present invention can be employed in distinguishing between members of the *Orthopoxvirus* genus. Smallpox is caused by the Variola virus. Other members of the genus include *Vaccinia, Monkeypox, Camelpox*, and *Cowpox*. All are capable of infecting humans, thus, a method capable of identifying and distinguishing among members of the *Orthopox* genus is a worthwhile objective.

In another embodiment, the present invention can be employed in distinguishing between viral agents of viral hemorrhagic fevers (VHF). VHF agents include, but are not limited to, Filoviridae (Marburg virus and Ebola virus), Arenaviridae (Lassa, Junin, Machupo, Sabia, and Guanarito viruses), Bunyaviridae (Crimean-Congo hemorrhagic fever virus (CCHFV), Rift Valley fever virus, and Hanta viruses), and Flaviviridae (yellow fever virus and dengue virus). Infections by VHF viruses are associated with a wide spectrum of clinical manifestations such as diarrhea, myalgia, cough, headache, pneumonia, encephalopathy, and hepatitis. Filoviruses, arenaviruses, and CCHFV are of particular relevance because they can be transmitted from human to human, thus causing epidemics with high mortality rates (Khan et al., Am. J. Trop. Med. Hyg., 1997, 57, 519-525). In the absence of bleeding or organ manifestation, VHF is clinically difficult to diagnose, and the various etiologic agents can hardly be distinguished by clinical tests. Current approaches to PCR detection of these agents are time-consuming, as they include a separate cDNA synthesis step prior to PCR, agarose gel analysis of PCR products, and in some instances a second round of nested amplification or Southern hybridization. PCRs for different pathogens have to be run assay by assay due to differences in cycling conditions, which complicate broad-range testing in a short period. Moreover, post-PCR processing or nested PCR steps included in currently used assays increase the risk of false positive results due to carry-over contamination (Kwok et al., Nature, 1989, 339, 237-238).

In another embodiment, the present invention, can be employed in the diagnosis of a plurality of etiologic agents of a disease. An "etiologic agent" is herein defined as a pathogen acting as the causative agent of a disease. Diseases may be caused by a plurality of etiologic agents. For example, recent studies have implicated both human herpesvirus 6 (HHV-6) and the obligate intracellular bacterium *Chlamydia pneumoniae* in the etiology of multiple sclerosis (Swanborg, Microbes and Infection, 2002, 4, 1327-1333). The present invention can be applied to the identification of multiple etiologic agents of a disease by, for example, the use of broad range bacterial intelligent primers and division-wide primers (if necessary) for the identification of bacteria such as *Chlamydia pneumoniae* followed by primers directed to viral housekeeping genes for the identification of viruses such as HHV-6, for example.

In other embodiments of the invention, the methods disclosed herein can be used for detection and identification of pathogens in livestock. Livestock includes, but is not limited to, cows, pigs, sheep, chickens, turkeys, goats, horses and other farm animals. For example, conditions classified by the California Department of Food and Agriculture as emergency conditions in livestock (www.cdfa.ca.gov/ahfss/ah/pdfs/CA_reportable_disease_list_05292002.pdf) include, but are not limited to: Anthrax (*Bacillus anthracis*), Screwworm myiasis (*Cochliomyia hominivorax* or *Chrysomya bezziana*), African trypanosomiasis (Tsetse fly diseases), Bovine babesiosis (*piroplasmosis*), Bovine spongiform encephalopathy (Mad Cow), Contagious bovine pleuropneumonia (*Mycoplasma mycoides mycoides* small colony), Foot-and-mouth disease (Hoof-and-mouth), Heartwater (*Cowdria ruminantium*), Hemorrhagic septicemia (*Pasteurella multocida* serotypes B:2 or E:2), Lumpy skin disease, Malignant catarrhal fever (African type), Rift Valley fever, Rinderpest (Cattle plague), Theileriosis (Corridor disease, East Coast fever), Vesicular stomatitis, Contagious agalactia (*Mycoplasma* species), Contagious caprine pleuropneumonia (*Mycoplasma capricolum capripneumoniae*), Nairobi sheep disease, Peste desi petits ruminants (Goat plague), Pulmonary adenomatosis (Viral neoplastic pneumonia), *Salmonella abortus ovis*, Sheep and goat pox, African swine fever, Classical swine fever (Hog cholera), Japanese encephalitis, Nipah virus, Swine vesicular disease, Teschen disease (*Enterovirus encephalomyelitis*), Vesicular exanthema, Exotic Newcastle disease (Viscerotropic velogenic Newcastle disease), Highly pathogenic avian influenza (Fowl plague), African horse sickness, Dourine (*Trypanosoma equiperdum*), Epizootic lymphangitis (equine blastomycosis, equine histoplasmosis), Equine piroplasmosis (*Babesia equi, B. caballi*), Glanders (Farcy) (*Pseudomonas mallei*), Hendra virus (Equine *morbillivirus*), Horse pox, Surra (*Trypanosoma evansi*), Venezuelan equine encephalomyelitis, West Nile Virus, Chronic wasting disease in cervids, and Viral hemorrhagic disease of rabbits (calicivirus)

Conditions classified by the California Department of Food and Agriculture as regulated conditions in livestock include, but are not limited to: rabies, Bovine brucellosis (*Brucella abortus*), Bovine tuberculosis (*Mycobacterium bovis*), Cattle scabies (multiple types), Trichomonosis (*Tritrichomonas fetus*), Caprine and ovine brucellosis (excluding *Brucella ovis*), Scrapie, Sheep scabies (Body mange) (*Psoroptes ovis*), Porcine brucellosis (*Brucella suis*), Pseudorabies (Aujeszky's disease), Ornithosis (*Psittacosis* or avian *chlamydiosis*) (*Chlamydia psittaci*), Pullorum disease (Fowl typhoid) (*Salmonella gallinarum* and *pullorum*), Contagious equine metritis (*Taylorella equigenitalis*), Equine encephalomyelitis (Eastern and Western equine encephalitis), Equine infectious anemia (Swamp fever), Duck viral enteritis (Duck plague), and Tuberculosis in cervids.

Additional conditions monitored by the California Department of Food and Agriculture include, but are not limited to: Avian tuberculosis (*Mycobacterium avium*), Echinococcosis/Hydatidosis (*Echinococcus* species), Leptospirosis, Anaplasmosis (*Anaplasma marginale* or *A. centrale*), Bluetongue, Bovine cysticercosis (*Taenia saginata* in humans), Bovine genital campylobacteriosis (*Campylobacter fetus venerealis*), Dermatophilosis (Streptothricosis, mycotic dermatitis) (*Dermatophilus congolensis*), Enzootic bovine leukosis (Bovine leukemia virus), Infectious bovine rhinotracheitis (Bovine herpesvirus-1), Johne's disease (Paratuberculosis) (*Mycobacterium avium paratuberculosis*), Malignant catarrhal fever (North American), Q Fever (*Coxiella burnetii*), Caprine (contagious) arthritis/encephalitis, Enzootic abortion of ewes (Ovine chlamydiosis) (*Chlamydia psittaci*), Maedi-Visna (Ovine progressive pneumonia), Atrophic rhinitis (*Bordetella bronchiseptica, Pasteurella multocida*), Porcine cysticercosis (*Taenia solium* in humans), Porcine reproductive and respiratory syndrome, Transmissible gastroenteritis (coronavirus), Trichinellosis (*Trichinella spiralis*), Avian infectious bronchitis, Avian infectious laryngotracheitis, Duck viral hepatitis, Fowl cholera (*Pasteurella multocida*), Fowl pox, Infectious bursal disease (Gumboro disease), Low pathogenic avian influenza, Marek's disease, Mycoplasmosis (*Mycoplasma gallisepticum*), Equine influenza Equine rhinopneumonitis (Equine herpesvirus-1), Equine viral arteritis, and Horse mange (multiple types).

A key problem in determining that an infectious outbreak is the result of a bioterrorist attack is the sheer variety of organisms that might be used by terrorists. According to a recent review (Taylor et al., Philos. Trans. R. Soc. Lond. B. Biol. Sci., 2001, 356, 983-989), there are over 1400 organisms infectious to humans; most of these have the potential to be used in a deliberate, malicious attack. These numbers do not include numerous strain variants of each organism, bioengineered versions, or pathogens that infect plants or animals.

Paradoxically, most of the new technology being developed for detection of biological weapons incorporates a version of quantitative PCR, which is based upon the use of highly specific primers and probes designed to selectively identify specific pathogenic organisms. This approach requires assumptions about the type and strain of bacteria or virus which is expected to be detected. Although this approach will work for the most obvious organisms, like smallpox and anthrax, experience has shown that it is very difficult to anticipate what a terrorist will do.

The present invention can be used to detect and identify any biological agent, including bacteria, viruses, fingi and toxins without prior knowledge of the organism being detected and identified. As one example, where the agent is a biological threat, the information obtained such as the presence of toxin genes, pathogenicity islands and antibiotic resistance genes for example, is used to determine practical information needed for countermeasures. In addition, the methods can be used to identify natural or deliberate engineering events including chromosome fragment swapping, molecular breeding (gene shuffling) and emerging infectious diseases. The present invention provides broad-function technology that may be the only practical means for rapid diagnosis of disease caused by a biowarfare or bioterrorist attack, especially an attack that might otherwise be missed or mistaken for a more common infection.

Bacterial biological warfare agents capable of being detected by the present methods include, but are not limited to, *Bacillus anthracis* (anthrax), *Yersinia pestis* (pneumonic plague), *Franciscella tularensis* (tularemia), *Brucella suis, Brucella abortus, Brucella melitensis* (undulant fever), *Burkholderia mallei* (glanders), *Burkholderia pseudomalleii* (melioidosis), *Salmonella typhi* (typhoid fever), *Rickettsia typhii* (epidemic typhus), *Rickettsia prowasekii* (endemic typhus) and *Coxiella burnetii* (Q fever), *Rhodobacter capsulatus, Chlamydia pneumoniae, Escherichia coli, Shigella dysenteriae, Shigella flexneri, Bacillus cereus, Clostridium botulinum, Coxiella burnetti, Pseudomonas aeruginosa, Legionella pneumophila*, and *Vibrio cholerae*.

Figures 1, 1A, 2, 3:
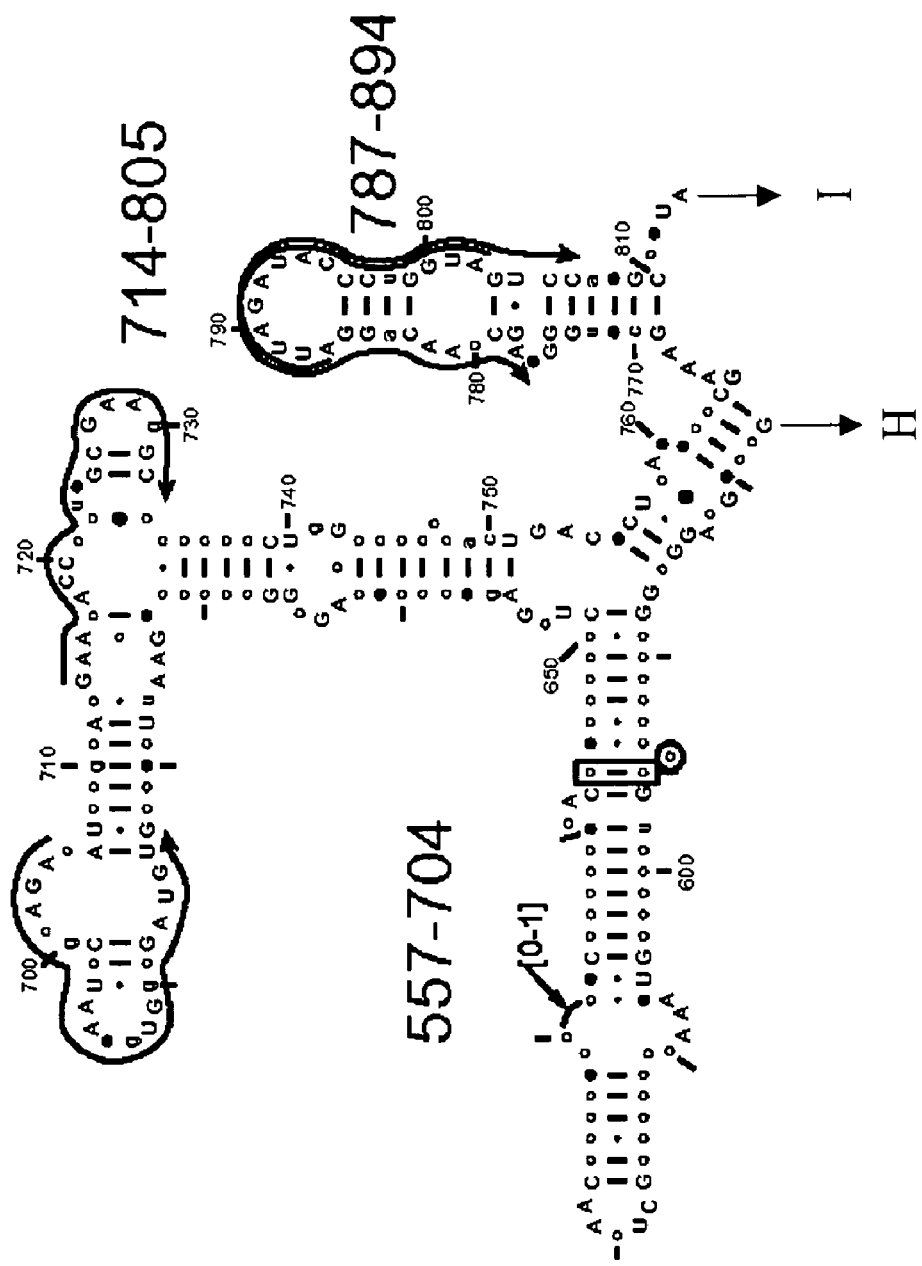
Figures 1, 1A, 2, 3, 4:
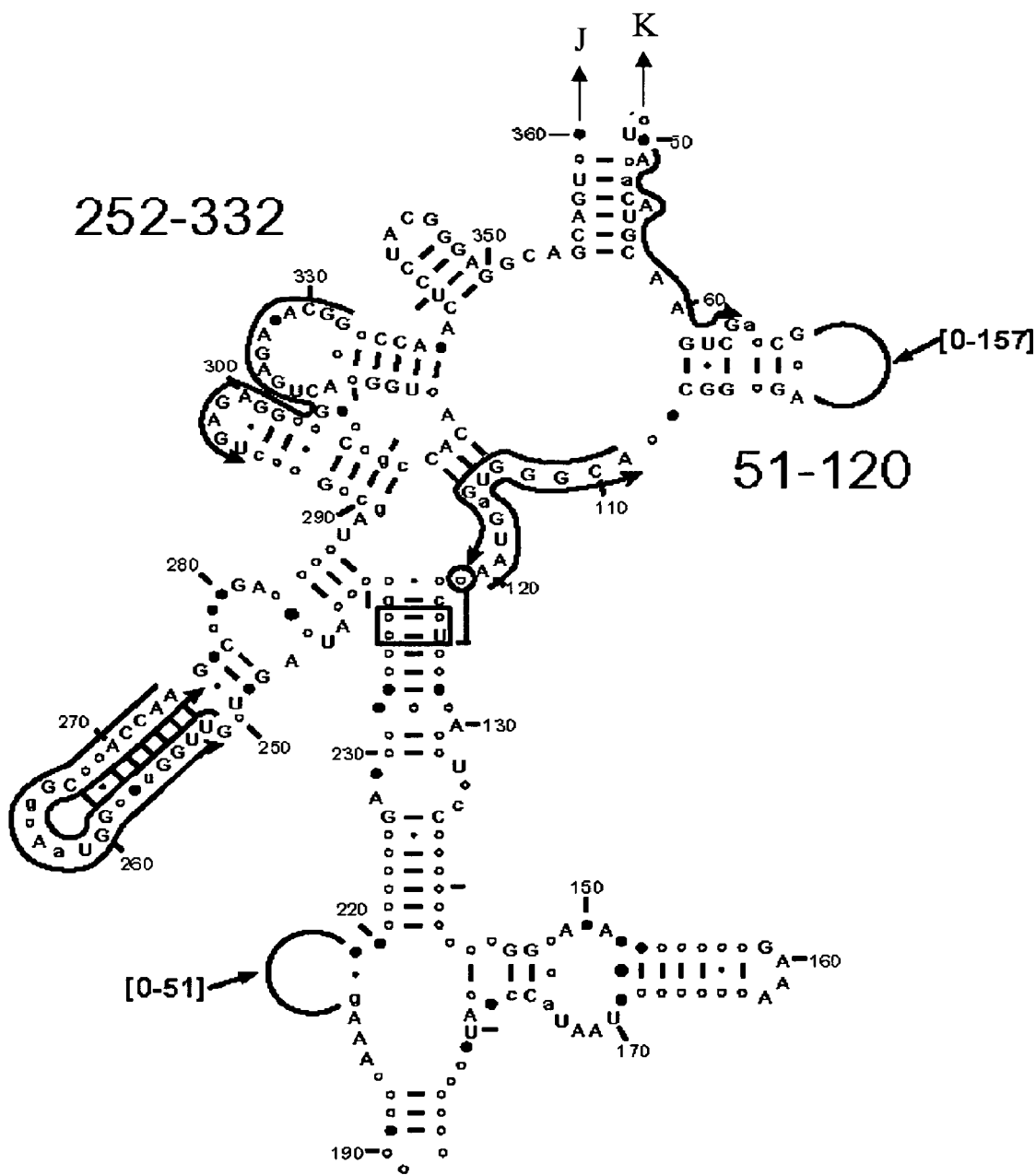
Figures 1, 1A, 2, 3, 4, 5:
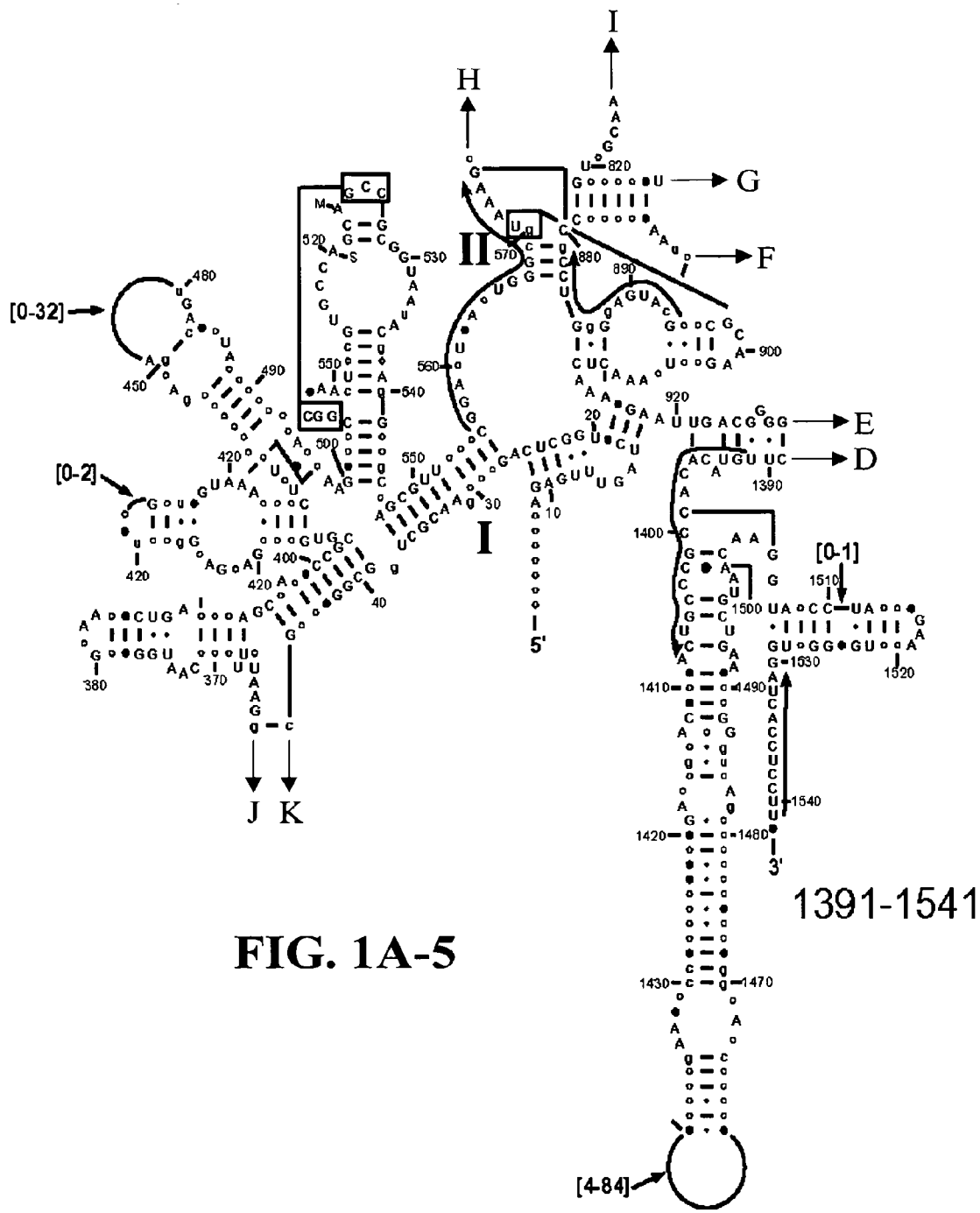

Besides 16S and 23S rRNA, other target regions suitable for use in the present invention for detection of bacteria include, but are not limited to, 5S rRNA and RNase P (FIG. 3).

Fungal biowarfare agents include, but are not limited to, *Coccidioides immitis* (Coccidioidomycosis), and *Magnaporthe grisea*.

Biological warfare toxin genes capable of being detected by the methods of the present invention include, but are not limited to, botulinum toxin, T-2 mycotoxins, ricin, staph enterotoxin B, shigatoxin, abrin, aflatoxin, *Clostridium perfringens* epsilon toxin, conotoxins, diacetoxyscirpenol, tetrodotoxin and saxitoxin.

Parasites that could be used in biological warfare include, but are not limited to: *Ascaris suum, Giardia lamblia, Cryptosporidium,* and *Schistosoma*.

Biological warfare viral threat agents are mostly RNA viruses (positive-strand and negative-strand), with the exception of smallpox. Every RNA virus is a family of related viruses (quasispecies). These viruses mutate rapidly and the potential for engineered strains (natural or deliberate) is very high. RNA viruses cluster into families that have conserved RNA structural domains on the viral genome (e.g., virion components, accessory proteins) and conserved housekeeping genes that encode core viral proteins including, for single strand positive strand RNA viruses, RNA-dependent RNA polymerase, double stranded RNA helicase, chymotrypsin-like and papain-like proteases and methyltransferases.

"Housekeeping genes" refers to genes that are generally always expressed and thought to be involved in routine cellular metabolism.

Examples of (−)-strand RNA viruses include, but are not limited to, arenaviruses (e.g., sabia virus, lassa fever, Machupo, Argentine hemorrhagic fever, flexal virus), bunyaviruses (e.g., hantavirus, nairovirus, phlebovirus, hantaan virus, Congo-crimean hemorrhagic fever, rift valley fever), and mononegavirales (e.g., filovirus, paramyxovirus, ebola virus, Marburg, equine morbillivirus).

Examples of (+)-strand RNA viruses include, but are not limited to, picornaviruses (e.g., coxsackievirus, echovirus, human coxsackievirus A, human echovirus, human enterovirus, human poliovirus, hepatitis A virus, human parechovirus, human rhinovirus), astroviruses (e.g., human astrovirus), calciviruses (e.g., chiba virus, chitta virus, human calcivirus, norwalk virus), nidovirales (e.g., human coronavirus, human torovirus), flaviviruses (e.g., dengue virus 1-4, Japanese encephalitis virus, Kyanasur forest disease virus, Murray Valley encephalitis virus, Rocio virus, St. Louis encephalitis virus, West Nile virus, yellow fever virus, hepatitis c virus) and togaviruses (e.g., Chikugunya virus, Eastern equine encephalitis virus, Mayaro virus, O'nyong-nyong virus, Ross River virus, Venezuelan equine encephalitis virus, Rubella virus, hepatitis E virus). The hepatitis C virus has a 5'-untranslated region of 340 nucleotides, an open reading frame encoding 9 proteins having 3010 amino acids and a 3'-untranslated region of 240 nucleotides. The 5'-UTR and 3'-UTR are 99% conserved in hepatitis C viruses.

In one embodiment, the target gene is an RNA-dependent RNA polymerase or a helicase encoded by (+)-strand RNA viruses, or RNA polymerase from a (−)-strand RNA virus. (+)-strand RNA viruses are double stranded RNA and replicate by RNA-directed RNA synthesis using RNA-dependent RNA polymerase and the positive strand as a template. Helicase unwinds the RNA duplex to allow replication of the single stranded RNA. These viruses include viruses from the family picornaviridae (e.g., poliovirus, coxsackievirus, echovirus), togaviridae (e.g., alphavirus, flavivirus, rubivirus), arenaviridae (e.g., lymphocytic choriomeningitis virus, lassa fever virus), cononaviridae (e.g., human respiratory virus) and Hepatitis A virus. The genes encoding these proteins comprise variable and highly conserved regions that flank the variable regions.

In one embodiment, the method can be used to detect the presence of antibiotic resistance and/or toxin genes in a bacterial species. For example, *Bacillus anthracis* comprising a tetracycline resistance plasmid and plasmids encoding one or both anthracis toxins (px01 and/or px02) can be detected by using antibiotic resistance primer sets and toxin gene primer sets. If the *B. anthracis* is positive for tetracycline resistance, then a different antibiotic, for example quinalone, is used.

While the present invention has been described with specificity in accordance with certain of its embodiments, the following examples serve only to illustrate the invention and are not intended to limit the same.

EXAMPLES

Example 1

Nucleic Acid Isolation and PCR

In one embodiment, nucleic acid is isolated from the organisms and amplified by PCR using standard methods prior to BCS determination by mass spectrometry. Nucleic acid is isolated, for example, by detergent lysis of bacterial cells, centrifugation and ethanol precipitation. Nucleic acid isolation methods are described in, for example, *Current Protocols in Molecular Biology* (Ausubel et al.) and *Molecular Cloning; A Laboratory Manual* (Sambrook et al.). The nucleic acid is then amplified using standard methodology, such as PCR, with primers which bind to conserved regions of the nucleic acid which contain an intervening variable sequence as described below.

General Genomic DNA Sample Prep Protocol: Raw samples are filtered using Supor-200 0.2 μm membrane syringe filters (VWR International). Samples are transferred to 1.5 ml eppendorf tubes pre-filled with 0.45 g of 0.7 mm Zirconia beads followed by the addition of 350 μl of ATL buffer (Qiagen, Valencia, Calif.). The samples are subjected to bead beating for 10 minutes at a frequency of 19 1/s in a Retsch Vibration Mill (Retsch). After centrifugation, samples are transferred to an S-block plate (Qiagen) and DNA isolation is completed with a BioRobot 8000 nucleic acid isolation robot (Qiagen).

Swab Sample Protocol: Allegiance S/P brand culture swabs and collection/transport system are used to collect samples. After drying, swabs are placed in 17×100 mm culture tubes (VWR International) and the genomic nucleic acid isolation is carried out automatically with a Qiagen Mdx robot and the Qiagen QIAamp DNA Blood BioRobot Mdx genomic preparation kit (Qiagen, Valencia, Calif.).

Example 2

Mass Spectrometry

FTICR Instrumentation: The FTICR instrument is based on a 7 tesla actively shielded superconducting magnet and modified Bruker Daltonics Apex II 70e ion optics and vacuum chamber. The spectrometer is interfaced to a LEAP PAL autosampler and a custom fluidics control system for high throughput screening applications. Samples are analyzed directly from 96-well or 384-well microtiter plates at a rate of about 1 sample/minute. The Bruker data-acquisition platform is supplemented with a lab-built ancillary NT datastation which controls the autosampler and contains an arbitrary waveform generator capable of generating complex rf-excite waveforms (frequency sweeps, filtered noise, stored waveform inverse Fourier transform (SWIFT), etc.) for sophisticated tandem MS experiments. For oligonucleotides in the 20-30-mer regime typical performance characteristics include mass resolving power in excess of 100,000 (FWHM), low ppm mass measurement errors, and an operable m/z range between 50 and 5000 m/z.

Modified ESI Source: In sample-limited analyses, analyte solutions are delivered at 150 nL/minute to a 30 mm i.d. fused-silica ESI emitter mounted on a 3-D micromanipulator. The ESI ion optics consists of a heated metal capillary, an rf-only hexapole, a skimmer cone, and an auxiliary gate electrode. The 6.2 cm rf-only hexapole is comprised of 1 mm diameter rods and is operated at a voltage of 380 Vpp at a frequency of 5 MHz. A lab-built electro-mechanical shutter can be employed to prevent the electrospray plume from entering the inlet capillary unless triggered to the "open" position via a TTL pulse from the data station. When in the "closed" position, a stable electrospray plume is maintained between the ESI emitter and the face of the shutter. The back face of the shutter arm contains an elastomeric seal that can be positioned to form a vacuum seal with the inlet capillary. When the seal is removed, a 1 mm gap between the shutter blade and the capillary inlet allows constant pressure in the external ion reservoir regardless of whether the shutter is in the open or closed position. When the shutter is triggered, a "time slice" of ions is allowed to enter the inlet capillary and is subsequently accumulated in the external ion reservoir. The rapid response time of the ion shutter (<25 ms) provides reproducible, user defined intervals during which ions can be injected into and accumulated in the external ion reservoir.

Apparatus for Infrared Multiphoton Dissociation: A 25 watt CW $CO_2$ laser operating at 10.6 μm has been interfaced to the spectrometer to enable infrared multiphoton dissociation (IRMPD) for oligonucleotide sequencing and other tandem MS applications. An aluminum optical bench is positioned approximately 1.5 m from the actively shielded superconducting magnet such that the laser beam is aligned with the central axis of the magnet. Using standard IR-compatible mirrors and kinematic mirror mounts, the unfocused 3 mm laser beam is aligned to traverse directly through the 3.5 mm holes in the trapping electrodes of the FTICR trapped ion cell and longitudinally traverse the hexapole region of the external ion guide finally impinging on the skimmer cone. This scheme allows IRMPD to be conducted in an m/z selective manner in the trapped ion cell (e.g. following a SWIFT isolation of the species of interest), or in a broadband mode in the high pressure region of the external ion reservoir where collisions with neutral molecules stabilize IRMPD-generated metastable fragment ions resulting in increased fragment ion yield and sequence coverage.

Example 3

Identification of Bioagents

Figure 1B:
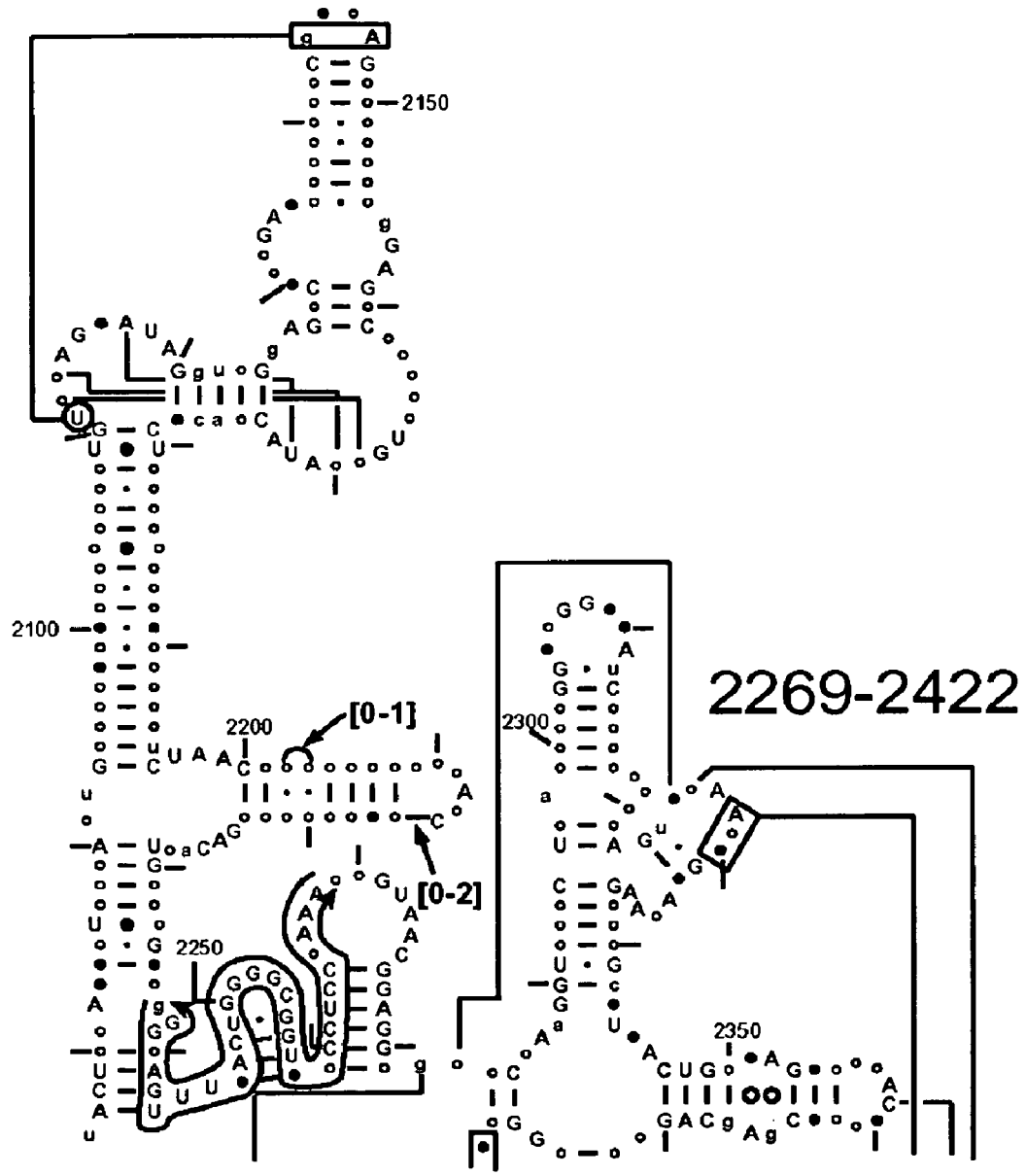
Figure 1C:
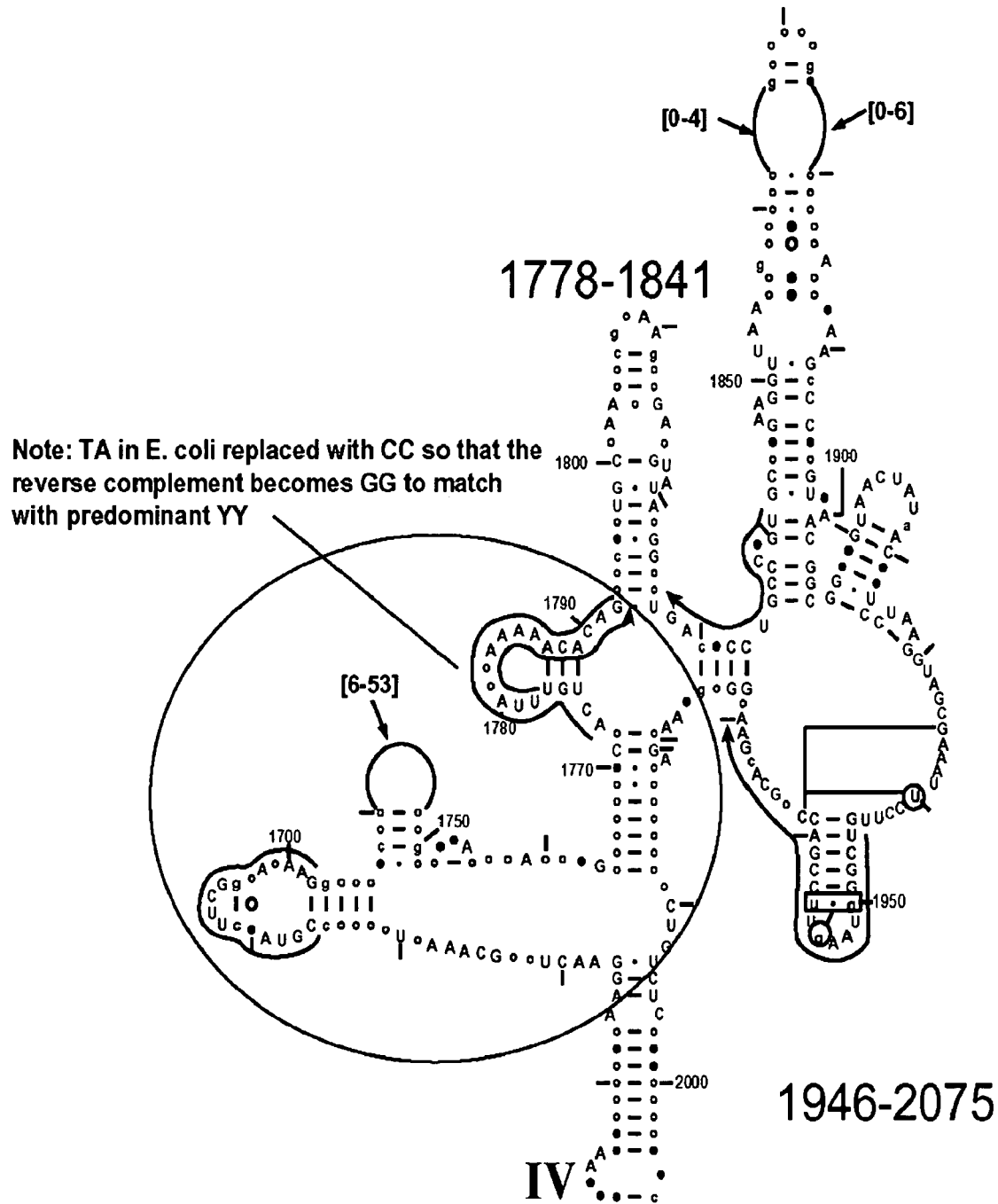
Figure 1D:
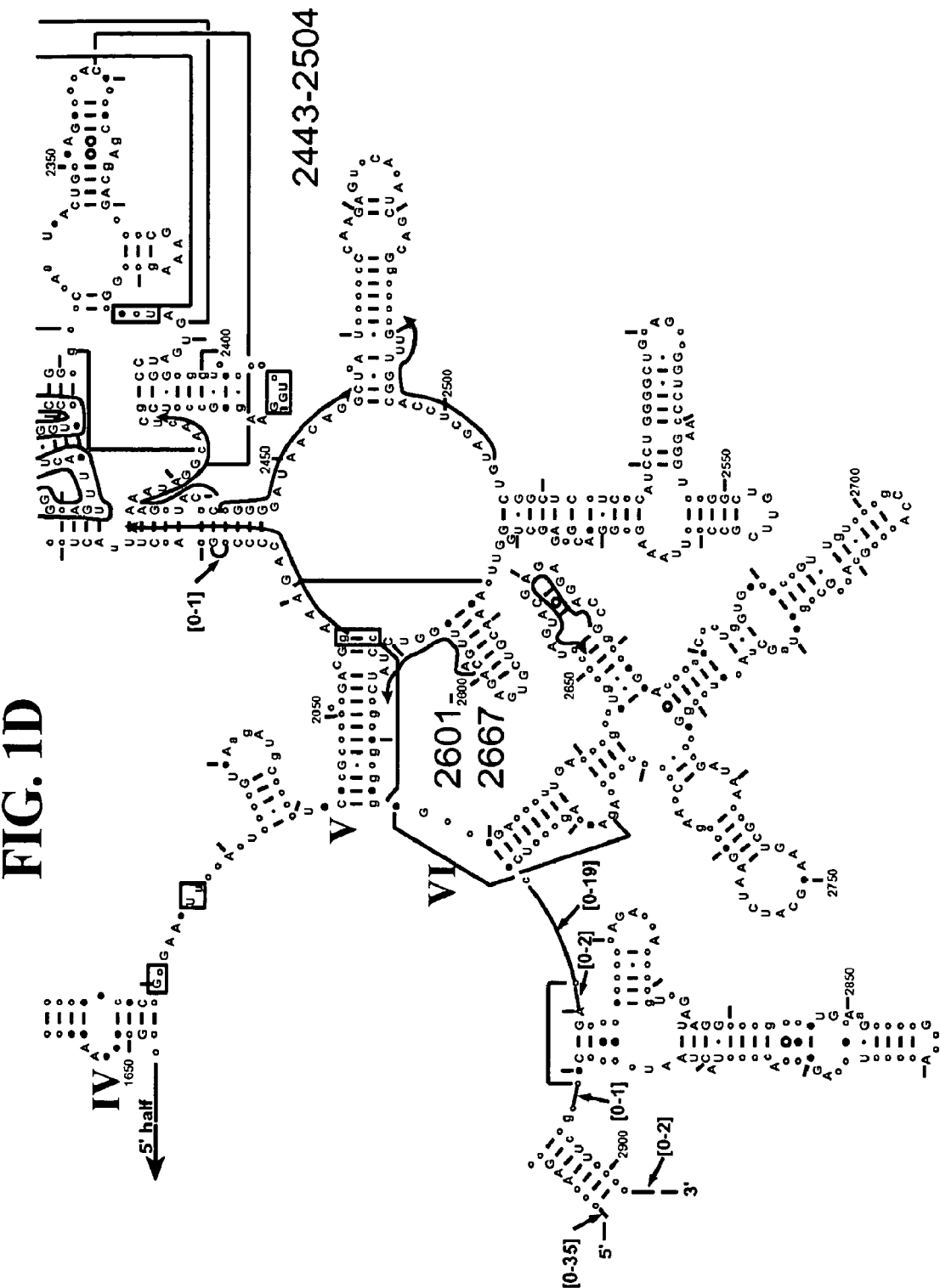
Figure 1E:
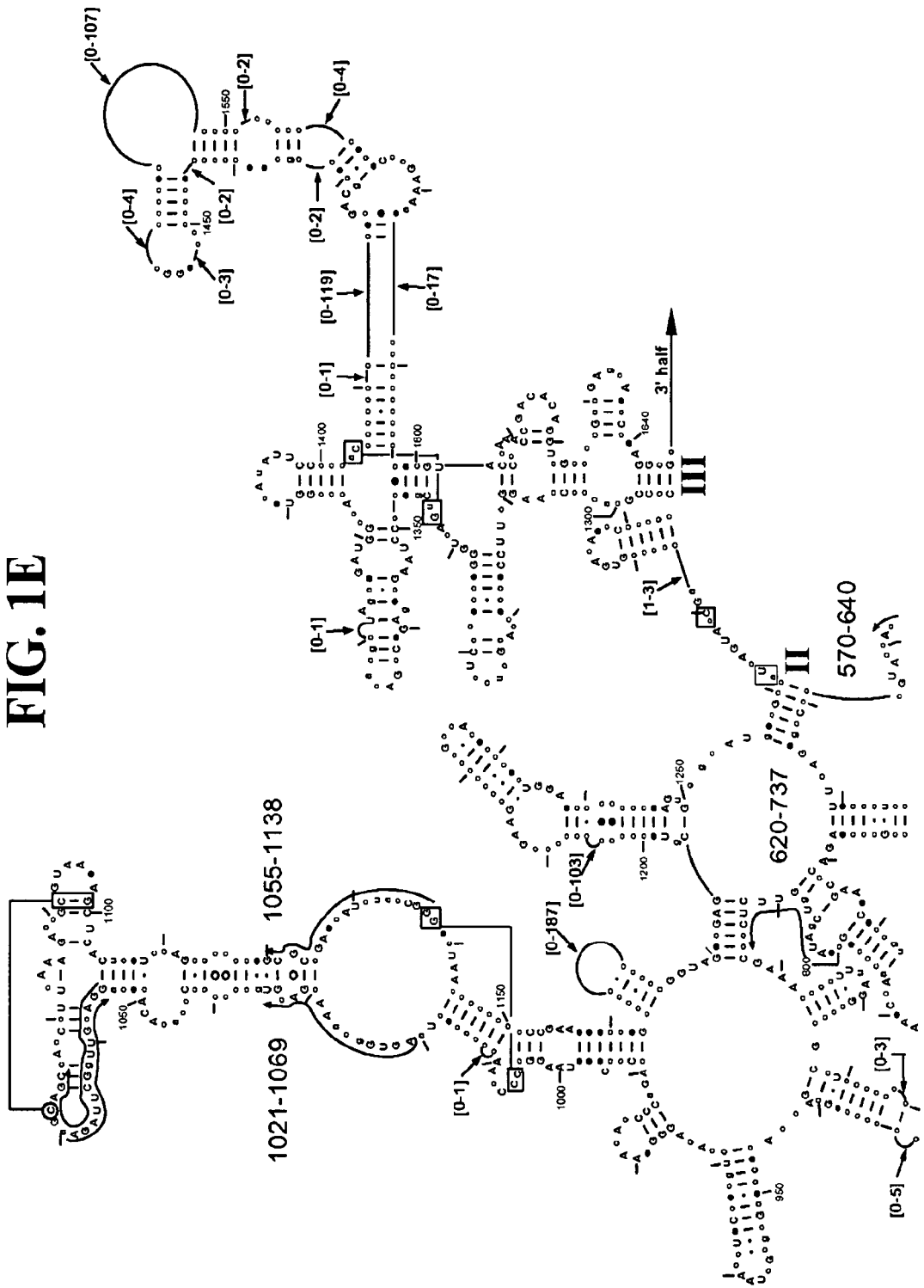
Figure 1F:
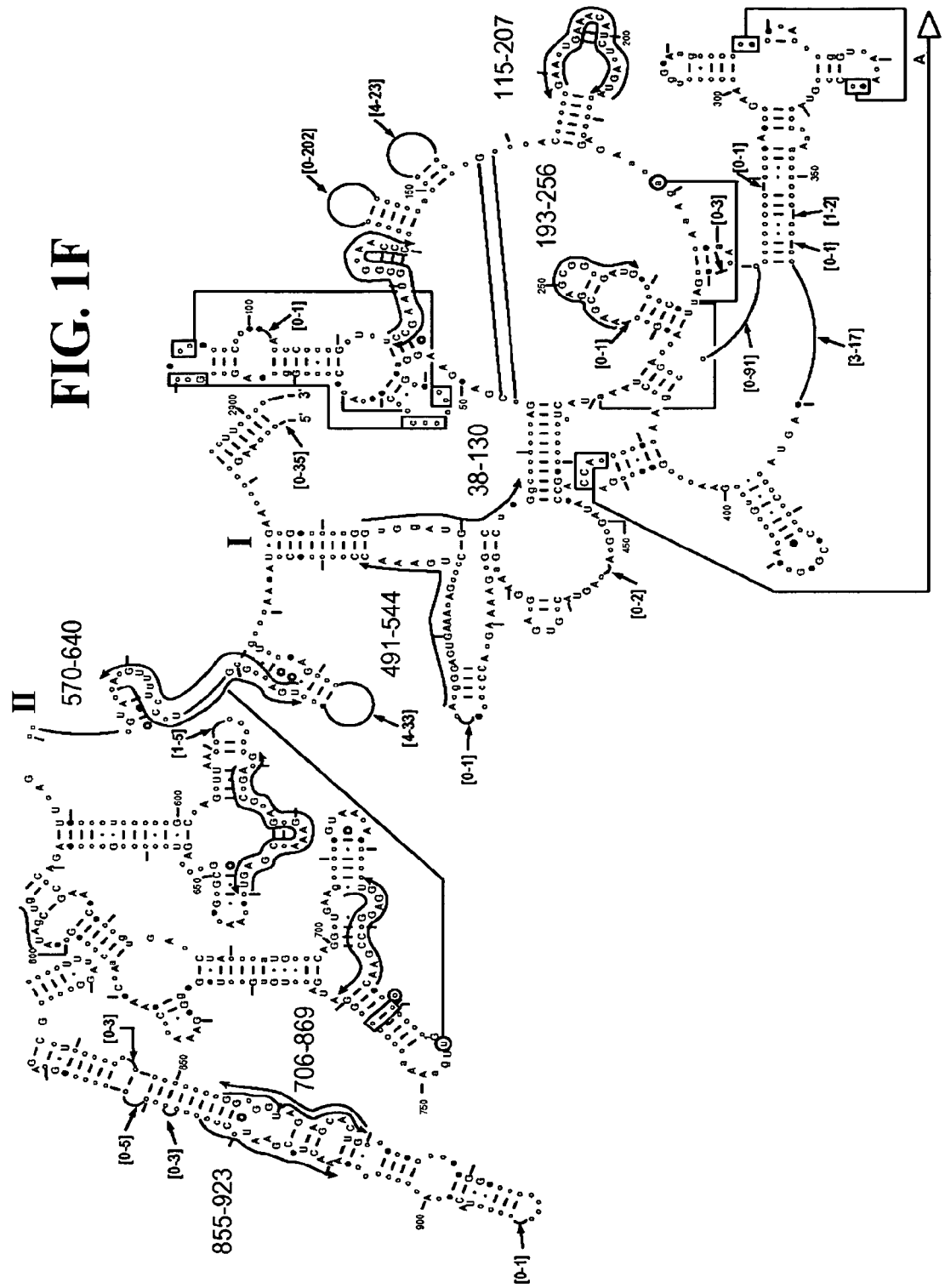
Figure 1G:
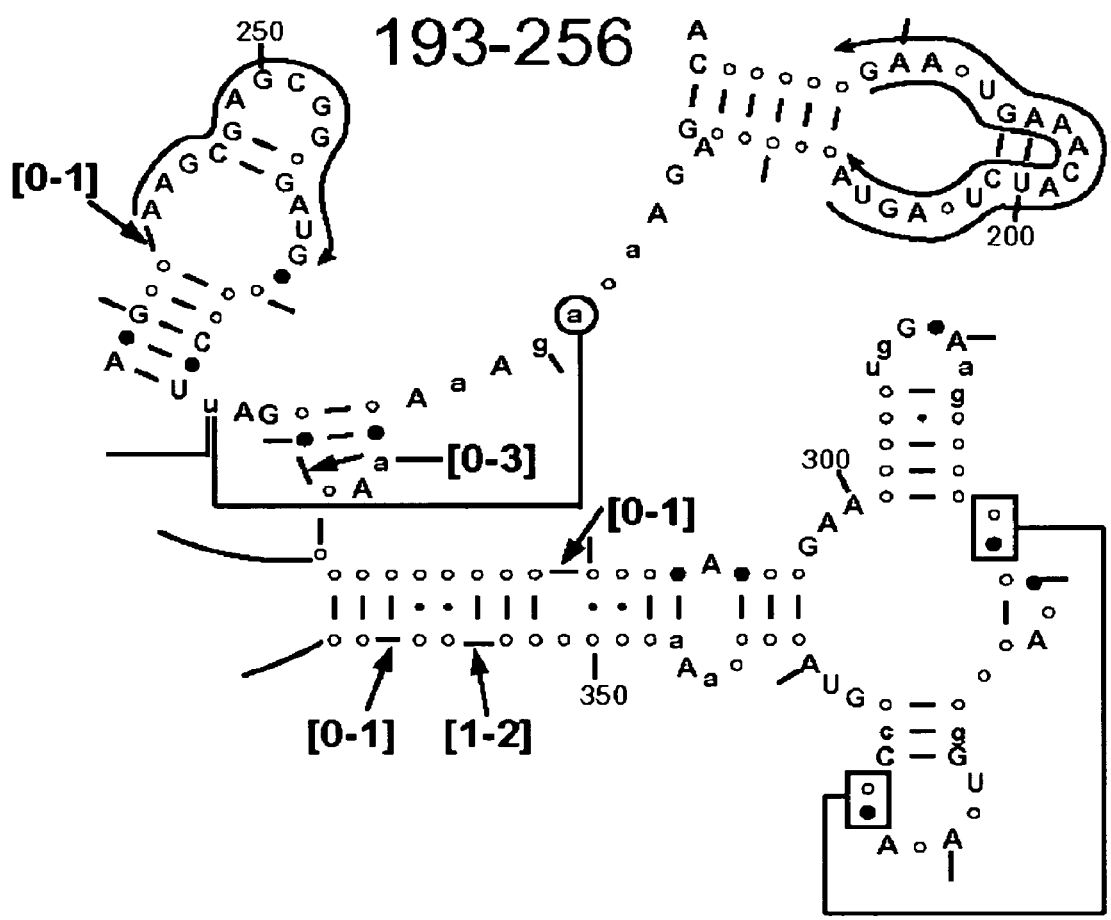
Figure 1H:
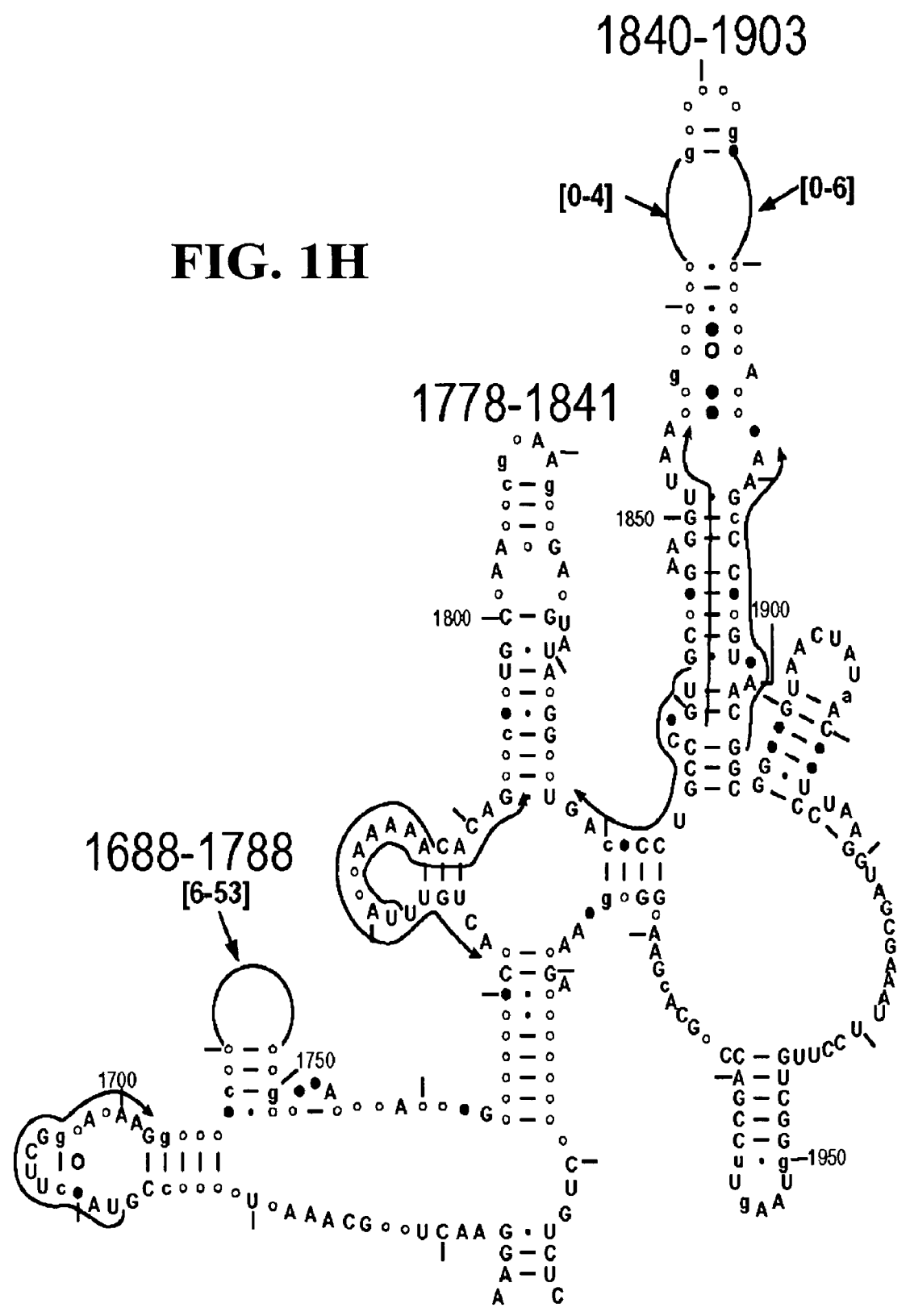
Figure 2:
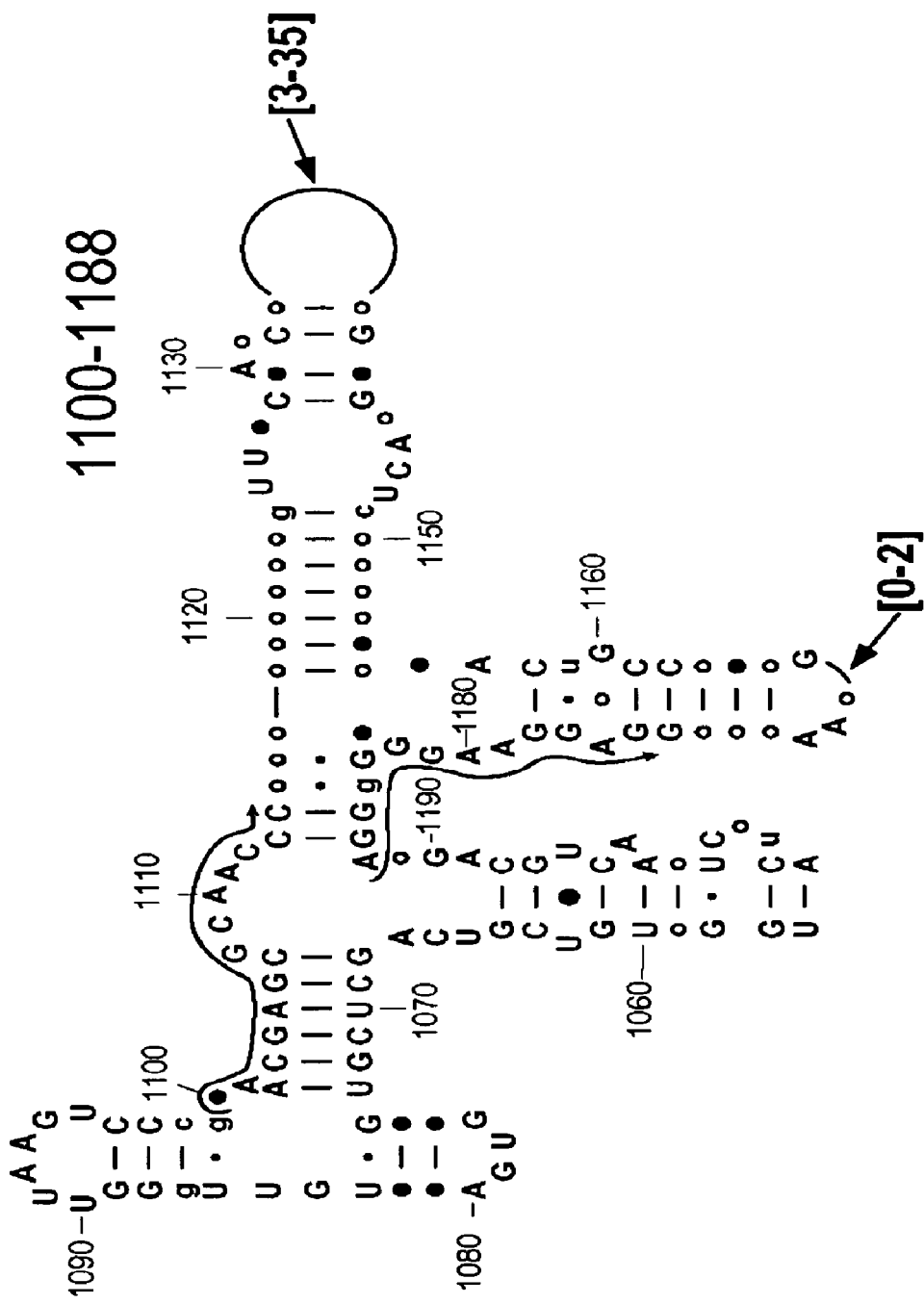
Figure 3:
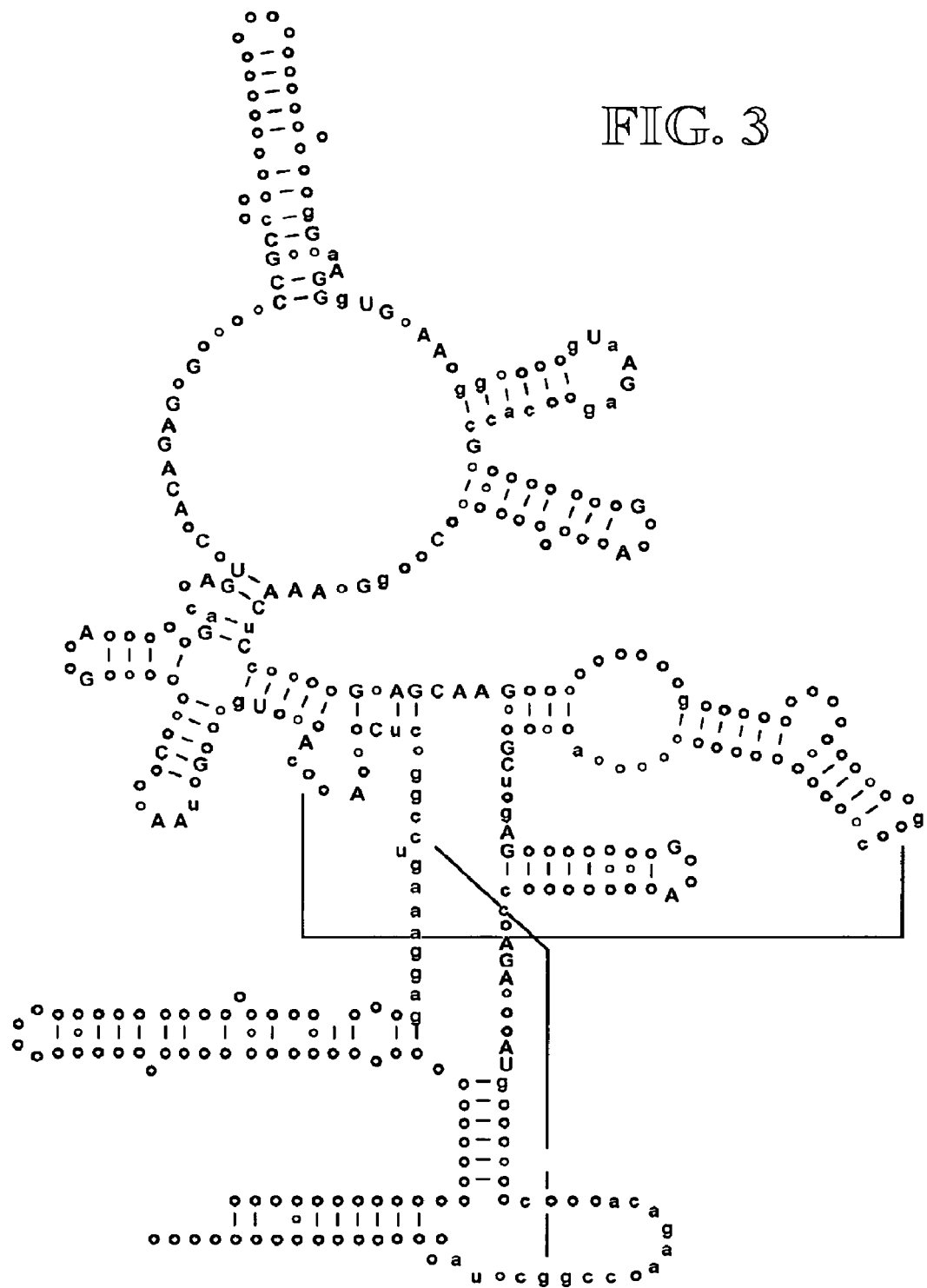
FIG. 3 is a schematic diagram showing conserved regions in RNase P. Bases in capital letters are greater than 90% conserved; bases in lower case letters are 80-90% conserved; filled circles designate bases which are 70-80% conserved; and open circles designate bases that are less than 70% conserved.
Figure 4:
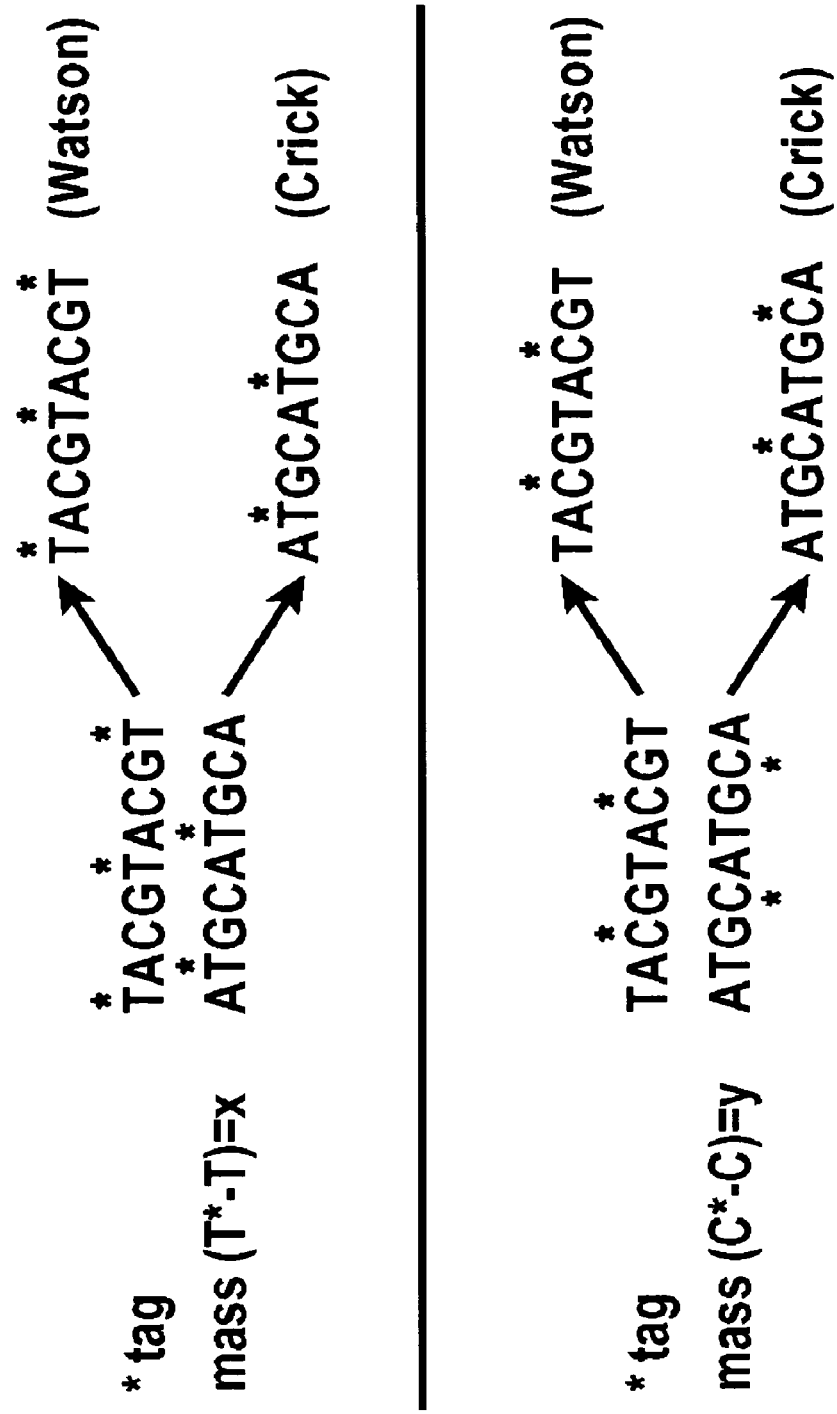
FIG. 4 is a schematic diagram of base composition signature determination using nucleotide analog "tags" to determine base composition signatures.
Figure 6:
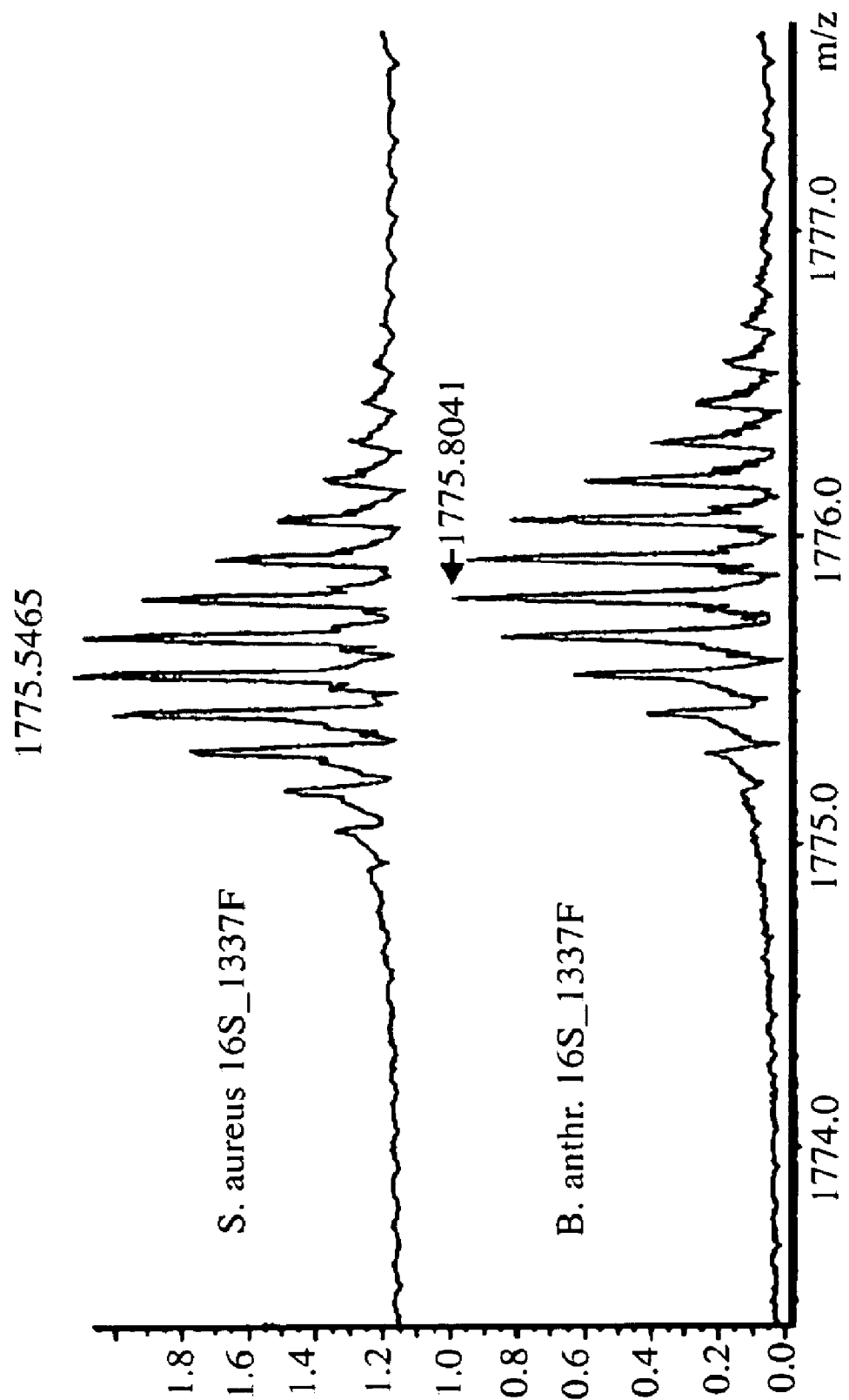
FIG. 6 shows base composition signature (BCS) spectra from PCR products from *Staphylococcus aureus* (*S. aureus* 16S_1337F) and *Bacillus anthracis* (*B. anthr.* 16S_1337F), amplified using the same primers. The two strands differ by only two (AT-->CG) substitutions and are clearly distinguished on the basis of their BCS.
Figure 7:
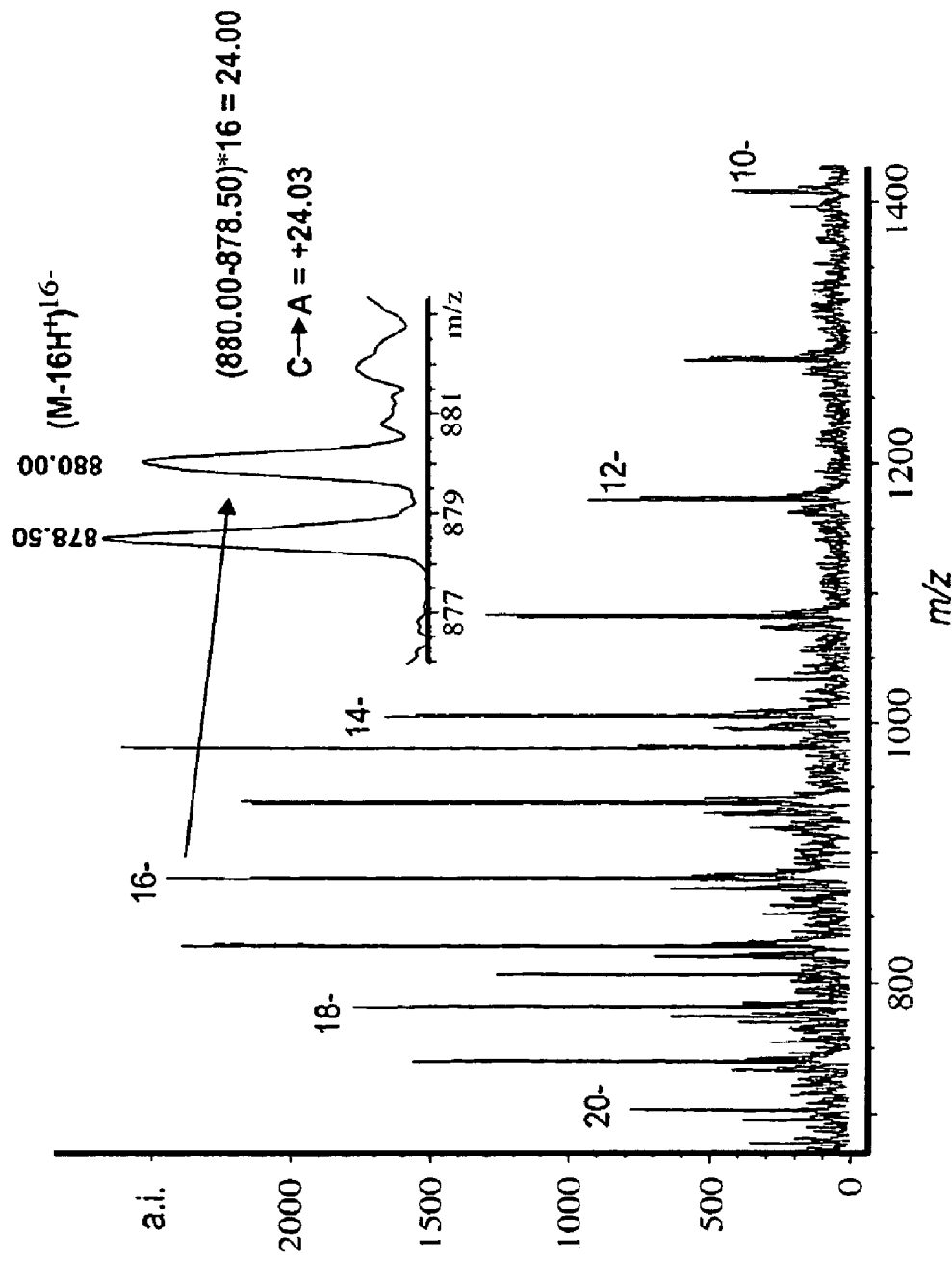
FIG. 7 shows that a single difference between two sequences (A 14 in *B. anthracis* vs. A15 in *B. cereus*) can be easily detected using ESI-TOF mass spectrometry.

Table 2 shows a small cross section of a database of calculated molecular masses for over 9 primer sets and approximately 30 organisms. The primer sets were derived from rRNA alignment. Examples of regions from rRNA consensus alignments are shown in FIGS. 1A-1C. Lines with arrows are examples of regions to which intelligent primer pairs for PCR are designed. The primer pairs are >95% conserved in the bacterial sequence database (currently over 10,000 organisms). The intervening regions are variable in length and/or composition, thus providing the base composition "signature" (BCS) for each organism. Primer pairs were chosen so the total length of the amplified region is less than about 80-90 nucleotides. The label for each primer pair represents the starting and ending base number of the amplified region on the consensus diagram.

Included in the short bacterial database cross-section in Table 2 are many well known pathogens/biowarfare agents (shown in bold/red typeface) such as *Bacillus anthracis* or *Yersinia pestis* as well as some of the bacterial organisms found commonly in the natural environment such as *Streptomyces*. Even closely related organisms can be distinguished from each other by the appropriate choice of primers. For instance, two low G+C organisms, *Bacillus anthracis* and *Staph aureus*, can be distinguished from each other by using the primer pair defined by 16S_1337 or 23S_855 (ΔM of 4 Da).

TABLE 2

Cross Section Of A Database Of Calculated Molecular Masses[1]

| | Primer Regions | | | | | | | | |
|---|---|---|---|---|---|---|---|---|---|
| Bug Name | 16S_971 | 16S_1100 | 16S_1337 | 16S_1294 | 16S_1228 | 23S_1021 | 23S_855 | 23S_193 | 23S_115 |
| *Acinetobacter calcoaceticus* | 55619.1 | 55004 | 28446.7 | 35854.9 | 51295.4 | 30299 | 42654 | 39557.5 | 54999 |
| *Bacillus anthracis* | 55005 | 54388 | 28448 | 35238 | 51296 | 30295 | 42651 | 39560 | 56850 |
| *Bacillus cereus* | 55622.1 | 54387.9 | 28447.6 | 35854.9 | 51296.4 | 30295 | 42651 | 39560.5 | 56850.3 |
| *Bordetella bronchiseptica* | 56857.3 | 51300.4 | 28446.7 | 35857.9 | 51307.4 | 30299 | 42653 | 39559.5 | 51920.5 |
| *Borrelia burgdorferi* | 56231.2 | 55621.1 | 28440.7 | 35852.9 | 51295.4 | 30297 | 42029.9 | 38941.4 | 52524.6 |
| *Brucella abortus* | 58098 | 55011 | 28448 | 35854 | 50683 | | | | |
| *Campylobacter jejuni* | 58088.5 | 54386.9 | 29061.8 | 35856.9 | 50674.3 | 30294 | 42032.9 | 39558.5 | 45732.5 |
| *Chlamydia pnuemoniae* | 55000 | 55007 | 29063 | 35855 | 50676 | 30295 | 42036 | 38941 | 56230 |
| *Clostriduim botulinum* | 55006 | 53767 | 28445 | 35855 | 51291 | 30300 | 42656 | 39562 | 54999 |
| *Clostridium difficile* | 56855.3 | 54386.9 | 28444.7 | 35853.9 | 51296.4 | 30294 | 41417.8 | 39556.5 | 55612.2 |
| *Enterococcus faecalis* | 55620.1 | 54387.9 | 28447.6 | 35858.9 | 51296.4 | 30297 | 42652 | 39559.5 | 56849.3 |
| *Escherichia coli* | 55622 | 55009 | 28445 | 35857 | 51301 | 30301 | 42656 | 39562 | 54999 |
| *Francisella tularensis* | 53769 | 54385 | 28445 | 35856 | 51298 | | | | |
| *Haemophilus influenzae* | 55620.1 | 55006 | 28444.7 | 35855.9 | 51298.4 | 30298 | 42656 | 39560.5 | 55613.1 |
| *Klebsiella pneumoniae* | 55622.1 | 55008 | 28442.7 | 35856.9 | 51297.4 | 30300 | 42655 | 39562.5 | 55000 |
| *Legionella pneumophila* | 55618 | 55626 | 28446 | 35857 | 51303 | | | | |
| *Mycobacterium avium* | 54390.9 | 55631.1 | 29064.8 | 35858.9 | 51915.5 | 30298 | 42656 | 38942.4 | 56241.2 |
| *Mycobacterium leprae* | 54389.9 | 55629.1 | 29064.8 | 35860.9 | 51917.5 | 30298 | 42656 | 39559.5 | 56240.2 |
| *Mycobacterium tuberculosis* | 54390.9 | 55629.1 | 29064.8 | 35860.9 | 51301.4 | 30299 | 42656 | 39560.5 | 56243.2 |
| *Mycoplasma genitalium* | 53143.7 | 45115.4 | 29061.8 | 35854.9 | 50671.3 | 30294 | 43264.1 | 39558.5 | 56842.4 |
| *Mycoplasma pneumoniae* | 53143.7 | 45118.4 | 29061.8 | 35854.9 | 50673.3 | 30294 | 43264.1 | 39559.5 | 56843.4 |
| *Neisseria gonorrhoeae* | 55627.1 | 54389.9 | 28445.7 | 35855.9 | 51302.4 | 30300 | 42649 | 39561.5 | 55000 |
| *Pseudomonas aeruginosa* | 55623 | 55010 | 28443 | 35858 | 51301 | 30298 | 43272 | 39558 | 55619 |
| *Rickettsia prowazekii* | 58093 | 55621 | 28448 | 35853 | 50677 | 30293 | 42650 | 39559 | 53139 |
| *Rickettsia rickettsii* | 58094 | 55623 | 28448 | 35853 | 50679 | 30293 | 42648 | 39559 | 53755 |
| *Salmonella typhimurium* | 55622 | 55005 | 28445 | 35857 | 51301 | 30301 | 42658 | | |
| *Shigella dysenteriae* | 55623 | 55009 | 28444 | 35857 | 51301 | | | | |
| *Staphylococcus aureus* | 56854.3 | 54386.9 | 28443.7 | 35852.9 | 51294.4 | 30298 | 42655 | 39559.5 | 57466.4 |
| *Streptomyces* | 54389.9 | 59341.6 | 29063.8 | 35858.9 | 51300.4 | | | 39563.5 | 56864.3 |
| *Treponema pallidum* | 56245.2 | 55631.1 | 28445.7 | 35851.9 | 51297.4 | 30299 | 42034.9 | 38939.4 | 57473.4 |
| *Vibrio cholerae* | 55625 | 55626 | 28443 | 35857 | 52536 | 29063 | 30303 | 35241 | 50675 |
| *Vibrio parahaemolyticus* | 54384.9 | 55626.1 | 28444.7 | 34620.7 | 50064.2 | | | | |
| *Yersinia pestis* | 55620 | 55626 | 28443 | 35857 | 51299 | | | | |

[1]Molecular mass distribution of PCR amplified regions for a selection of organisms (rows) across various primer pairs (columns). Pathogens are shown in bold. Empty cells indicate presently incomplete or missing data.

FIG. 6 shows the use of ESI-FT-ICR MS for measurement of exact mass. The spectra from 46 mer PCR products originating at position 1337 of the 16S rRNA from *S. aureus* (upper) and *B. anthracis* (lower) are shown. These data are from the region of the spectrum containing signals from the $[M-8H+]^{8-}$ charge states of the respective 5'-3' strands. The two strands differ by two (AT→CG) substitutions, and have measured masses of 14206.396 and 14208.373+0.010 Da, respectively. The possible base compositions derived from the masses of the forward and reverse strands for the *B. anthracis* products are listed in Table 3.

TABLE 3

Possible base composition for *B. anthracis* products

| Calc. Mass | Error | Base Comp. |
|---|---|---|
| 14208.2935 | 0.079520 | A1 G17 C10 T18 |
| 14208.3160 | 0.056980 | A1 G20 C15 T10 |
| 14208.3386 | 0.034440 | A1 G23 C20 T2 |
| 14208.3074 | 0.065560 | A6 G11 C3 T26 |
| 14208.3300 | 0.043020 | A6 G14 C8 T18 |
| 14208.3525 | 0.020480 | A6 G17 C13 T10 |
| 14208.3751 | 0.002060 | A6 G20 C18 T2 |
| 14208.3439 | 0.029060 | A11 G8 C1 T26 |
| 14208.3665 | 0.006520 | A11 G11 C6 T18 |
| 14208.3890 | 0.016020 | A11 G14 C11 T10 |
| 14208.4116 | 0.038560 | A11 G17 C16 T2 |
| 14208.4030 | 0.029980 | A16 G8 C4 T18 |
| 14208.4255 | 0.052520 | A16 G11 C9 T10 |
| 14208.4481 | 0.075060 | A16 G14 C14 T2 |
| 14208.4395 | 0.066480 | A21 G5 C2 T18 |
| 14208.4620 | 0.089020 | A21 G8 C7 T10 |
| 14079.2624 | 0.080600 | A0 G14 C13 T19 |
| 14079.2849 | 0.058060 | A0 G17 C18 T11 |
| 14079.3075 | 0.035520 | A0 G20 C23 T3 |
| 14079.2538 | 0.089180 | A5 G5 C1 T35 |
| 14079.2764 | 0.066640 | A5 G8 C6 T27 |
| 14079.2989 | 0.044100 | A5 G11 C11 T19 |
| 14079.3214 | 0.021560 | A5 G14 C16 T11 |
| 14079.3440 | 0.000980 | A5 G17 C21 T3 |
| 14079.3129 | 0.030140 | A10 G5 C4 T27 |
| 14079.3354 | 0.007600 | A10 G8 C9 T19 |
| 14079.3579 | 0.014940 | A10 G11 C14 T11 |
| 14079.3805 | 0.037480 | A10 G14 C19 T3 |
| 14079.3494 | 0.006360 | A15 G2 C2 T27 |
| 14079.3719 | 0.028900 | A15 G5 C7 T19 |
| 14079.3944 | 0.051440 | A15 G8 C12 T11 |
| 14079.4170 | 0.073980 | A15 G11 C17 T3 |
| 14079.4084 | 0.065400 | A20 G2 C5 T19 |
| 14079.4309 | 0.087940 | A20 G5 C10 T13 |

Among the 16 compositions for the forward strand and the 18 compositions for the reverse strand that were calculated, only one pair (shown in bold) are complementary, corresponding to the actual base compositions of the *B. anthracis* PCR products.

Example 4

BCS of Region from *Bacillus anthracis* and *Bacillus cereus*

A conserved *Bacillus* region from *B. anthracis* ($A_{14}G_9C_{14}T_9$) and *B. cereus* ($A_{15}G_9C_{13}T_9$) having a C to A base change was synthesized and subjected to ESI-TOF MS. The results are shown in FIG. 7 in which the two regions are clearly distinguished using the method of the present invention (MW=14072.26 vs. 14096.29).

Example 5

Identification of Additional Bioagents

In other examples of the present invention, the pathogen *Vibrio cholera* can be distinguished from *Vibrio parahemolyticus* with ΔM>600 Da using one of three 16S primer sets shown in Table 2 (16S_971, 16S_1228 or 16S_1294) as shown in Table 4. The two mycoplasma species in the list (*M. genitalium* and *M. pneumoniae*) can also be distinguished from each other, as can the three mycobacteriae. While the direct mass measurements of amplified products can identify and distinguish a large number of organisms, measurement of the base composition signature provides dramatically enhanced resolving power for closely related organisms. In cases such as *Bacillus anthracis* and *Bacillus cereus* that are virtually indistinguishable from each other based solely on mass differences, compositional analysis or fragmentation patterns are used to resolve the differences. The single base difference between the two organisms yields different fragmentation patterns, and despite the presence of the ambiguous/unidentified base N at position 20 in *B. anthracis*, the two organisms can be identified.

Tables 4a-b show examples of primer pairs from Table 1 which distinguish pathogens from background.

TABLE 4a

| Organism name | 23S_855 | 16S_1337 | 23S_1021 |
|---|---|---|---|
| *Bacillus anthracis* | 42650.98 | 28447.65 | 30294.98 |
| *Staphylococcus aureus* | 42654.97 | 28443.67 | 30297.96 |

TABLE 4b

| Organism name | 16S_971 | 16S_1294 | 16S_1228 |
|---|---|---|---|
| *Vibrio cholerae* | 55625.09 | 35856.87 | 52535.59 |
| *Vibrio parahaemolyticus* | 54384.91 | 34620.67 | 50064.19 |

Table 5 shows the expected molecular weight and base composition of region 16S_1100-1188 in *Mycobacterium avium* and *Streptomyces* sp.

TABLE 5

| Region | Organism name | Length | Molecular weight | Base comp. |
|---|---|---|---|---|
| 16S_1100-1188 | *Mycobacterium avium* | 82 | 25624.1728 | $A_{16}G_{32}C_{18}T_{16}$ |
| 16S_1100-1188 | *Streptomyces* sp. | 96 | 29904.871 | $A_{17}G_{38}C_{27}T_{14}$ |

Table 6 shows base composition (single strand) results for 16S_1100-1188 primer amplification reactions different species of bacteria. Species which are repeated in the table (e.g., *Clostridium botulinum*) are different strains which have different base compositions in the 16S_1100-1188 region.

TABLE 6

| Organism name | Base comp. |
|---|---|
| *Mycobacterium avium* | $A_{16}G_{32}C_{18}T_{16}$ |
| *Streptomyces* sp. | $A_{17}G_{38}C_{27}T_{14}$ |
| *Ureaplasma urealyticum* | $A_{18}G_{30}C_{17}T_{17}$ |
| *Streptomyces* sp. | $A_{19}G_{36}C_{24}T_{18}$ |
| *Mycobacterium leprae* | $A_{20}G_{32}C_{22}T_{16}$ |
| *M. Tuberculosis* | $\mathbf{A_{20}G_{33}C_{21}T_{16}}$ |
| *Nocardia asteroides* | $\mathbf{A_{20}G_{33}C_{21}T_{16}}$ |
| *Fusobacterium necroforum* | $A_{21}G_{26}C_{22}T_{18}$ |
| *Listeria monocytogenes* | $A_{21}G_{27}C_{19}T_{19}$ |
| *Clostridium botulinum* | $A_{21}G_{27}C_{19}T_{21}$ |
| *Neisseria gonorrhoeae* | $A_{21}G_{28}C_{21}T_{18}$ |
| *Bartonella quintana* | $A_{21}G_{30}C_{22}T_{16}$ |

TABLE 6-continued

| Organism name | Base comp. |
|---|---|
| *Enterococcus faecalis* | $A_{22}G_{27}C_{20}T_{19}$ |
| *Bacillus megaterium* | $A_{22}G_{28}C_{20}T_{18}$ |
| *Bacillus subtilis* | $A_{22}G_{28}C_{21}T_{17}$ |
| *Pseudomonas aeruginosa* | $A_{22}G_{29}C_{23}T_{15}$ |
| *Legionella pneumophila* | $A_{22}G_{32}C_{20}T_{16}$ |
| *Mycoplasma pneumoniae* | $A_{23}G_{20}C_{14}T_{16}$ |
| *Clostridium botulinum* | $A_{23}G_{26}C_{20}T_{19}$ |
| *Enterococcus faecium* | $A_{23}G_{26}C_{21}T_{18}$ |
| *Acinetobacter calcoaceti* | $A_{23}G_{26}C_{21}T_{19}$ |
| *Leptospira borgpeterseni* | $A_{23}G_{26}C_{24}T_{15}$ |
| *Leptospira interrogans* | $A_{23}G_{26}C_{24}T_{15}$ |
| *Clostridium perfringens* | $A_{23}G_{27}C_{19}T_{19}$ |
| *Bacillus anthracis* | $A_{23}G_{27}C_{20}T_{18}$ |
| *Bacillus cereus* | $A_{23}G_{27}C_{20}T_{18}$ |
| *Bacillus thuringiensis* | $A_{23}G_{27}C_{20}T_{18}$ |
| *Aeromonas hydrophila* | $A_{23}G_{29}C_{21}T_{16}$ |
| *Escherichia coli* | $A_{23}G_{29}C_{21}T_{16}$ |
| *Pseudomonas putida* | $A_{23}G_{29}C_{21}T_{17}$ |
| *Escherichia coli* | $A_{23}G_{29}C_{22}T_{15}$ |
| *Shigella dysenteriae* | $A_{23}G_{29}C_{22}T_{15}$ |
| *Vibrio cholerae* | $A_{23}G_{30}C_{21}T_{16}$ |
| *Aeromonas hydrophila* | $A_{23}G_{31}C_{21}T_{15}$ |
| *Aeromonas salmonicida* | $A_{23}G_{31}C_{21}T_{15}$ |

TABLE 6-continued

| Organism name | Base comp. |
|---|---|
| *Mycoplasma genitalium* | $A_{24}G_{19}C_{12}T_{18}$ |
| *Clostridium botulinum* | $A_{24}G_{25}C_{18}T_{20}$ |
| *Bordetella bronchiseptica* | $A_{24}G_{26}C_{19}T_{14}$ |
| *Francisella tularensis* | $A_{24}G_{26}C_{19}T_{19}$ |
| *Bacillus anthracis* | $A_{24}G_{26}C_{20}T_{18}$ |
| *Campylobacter jejuni* | $A_{24}G_{26}C_{20}T_{18}$ |
| *Staphylococcus aureus* | $A_{24}G_{26}C_{20}T_{18}$ |
| *Helicobacter pylori* | $A_{24}G_{26}C_{20}T_{19}$ |
| *Helicobacter pylori* | $A_{24}G_{26}C_{21}T_{18}$ |
| *Moraxella catarrhalis* | $A_{24}G_{26}C_{23}T_{16}$ |
| *Haemophilus influenzae* Rd | $A_{24}G_{28}C_{20}T_{17}$ |
| *Chlamydia trachomatis* | $A_{24}G_{28}C_{21}T_{16}$ |
| *Chlamydophila pneumoniae* | $A_{24}G_{28}C_{21}T_{16}$ |
| *C. pneumonia* AR39 | $A_{24}G_{28}C_{21}T_{16}$ |
| *Pseudomonas putida* | $A_{24}G_{29}C_{21}T_{16}$ |
| *Proteus vulgaris* | $A_{24}G_{30}C_{21}T_{15}$ |
| *Yersinia pestis* | $A_{24}G_{30}C_{21}T_{15}$ |
| *Yersinia pseudotuberculos* | $A_{24}G_{30}C_{21}T_{15}$ |
| *Clostridium botulinum* | $A_{25}G_{24}C_{18}T_{21}$ |
| *Clostridium tetani* | $A_{25}G_{25}C_{18}T_{20}$ |
| *Francisella tularensis* | $A_{25}G_{25}C_{19}T_{19}$ |
| *Acinetobacter calcoacetic* | $A_{25}G_{26}C_{20}T_{19}$ |

TABLE 6-continued

| Organism name | Base comp. |
|---|---|
| *Bacteriodes fragilis* | $A_{25}G_{27}C_{16}T_{22}$ |
| *Chlamydophila psittaci* | $A_{25}G_{27}C_{21}T_{16}$ |
| *Borrelia burgdorferi* | $A_{25}G_{29}C_{17}T_{19}$ |
| *Streptobacillus monilifor* | $A_{26}G_{26}C_{20}T_{16}$ |
| *Rickettsia prowazekii* | $A_{26}G_{28}C_{18}T_{18}$ |
| *Rickettsia rickettsii* | $A_{26}G_{28}C_{20}T_{16}$ |
| *Mycoplasma mycoides* | $A_{28}G_{23}C_{16}T_{20}$ |

Figure 8:
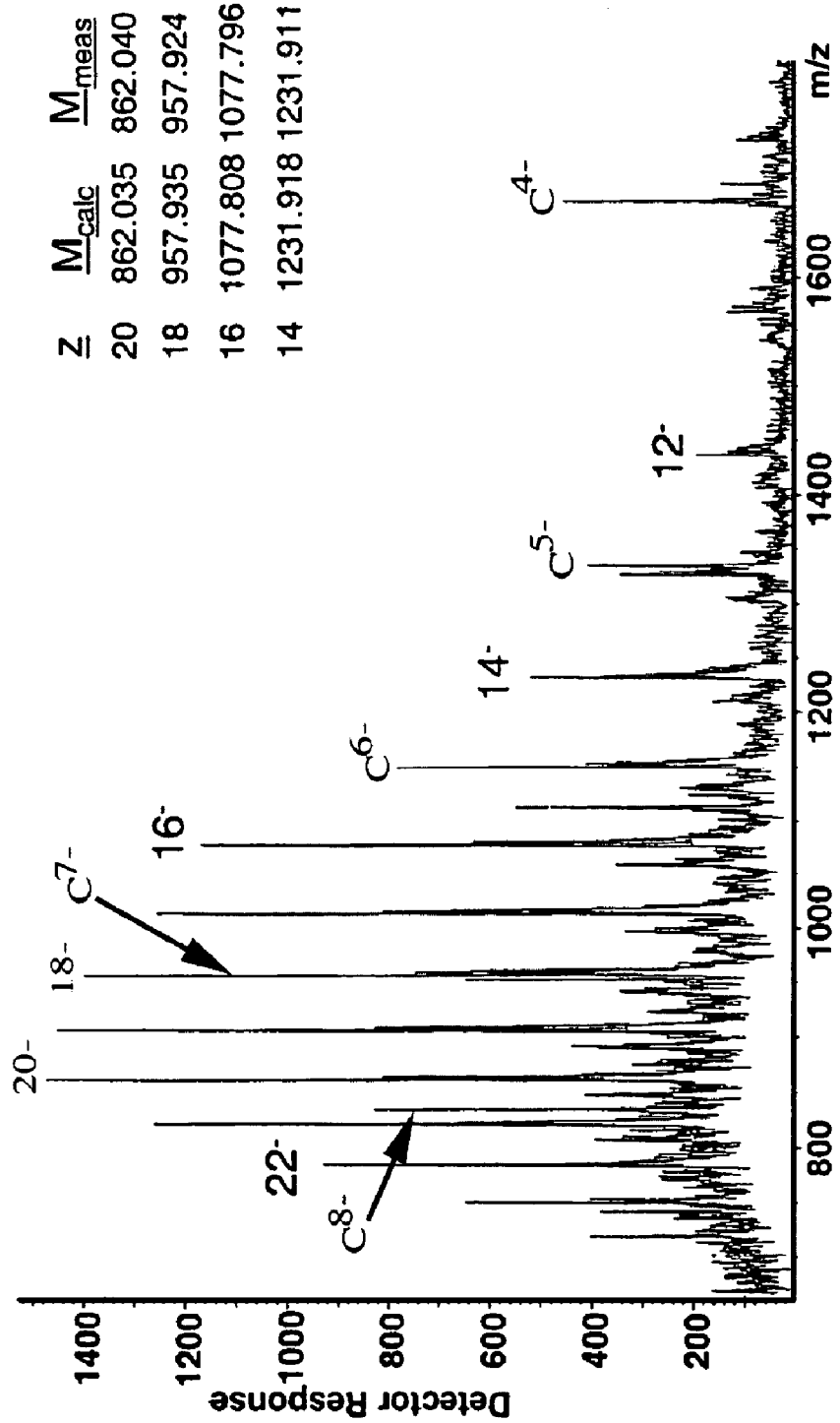
FIG. 8 is an ESI-TOF of *Bacillus anthracis* spore coat protein sspE 56 mer plus calibrant. The signals unambiguously identify *B. anthracis* versus other *Bacillus* species.

The same organism having different base compositions are different strains. Groups of organisms which are highlighted or in italics have the same base compositions in the amplified region. Some of these organisms can be distinguished using multiple primers. For example, *Bacillus anthracis* can be distinguished from *Bacillus cereus* and *Bacillus thuringiensis* using the primer 16S_971-1062 (Table 7). Other primer pairs which produce unique base composition signatures are shown in Table 6 (bold). Clusters containing very similar threat and ubiquitous non-threat organisms (e.g. anthracis cluster) are distinguished at high resolution with focused sets of primer pairs. The known biowarfare agents in Table 6 are *Bacillus anthracis, Yersinia pestis, Francisella tularensis* and *Rickettsia prowazekii*.

TABLE 7

| Organism | 16S_971-1062 | 16S_1228-1310 | 16S_1100-1188 |
|---|---|---|---|
| *Aeromonas hydrophila* | $A_{21}G_{29}C_{22}T_{20}$ | $A_{22}G_{27}C_{21}T_{13}$ | $A_{23}G_{31}C_{21}T_{15}$ |
| *Aeromonas salmonicida* | $A_{21}G_{29}C_{22}T_{20}$ | $A_{22}G_{27}C_{21}T_{13}$ | $A_{23}G_{31}C_{21}T_{15}$ |
| *Bacillus anthracis* | $A_{21}G_{27}C_{22}T_{22}$ | $A_{24}G_{22}C_{19}T_{18}$ | $A_{23}G_{27}C_{20}T_{18}$ |
| *Bacillus cereus* | $A_{22}G_{27}C_{22}T_{22}$ | $A_{24}G_{22}C_{19}T_{18}$ | $A_{23}G_{27}C_{20}T_{18}$ |
| *Bacillus thuringiensis* | $A_{22}G_{27}C_{21}T_{22}$ | $A_{24}G_{22}C_{19}T_{18}$ | $A_{23}G_{27}C_{20}T_{18}$ |
| *Chlamydia trachomatis* | $A_{22}G_{26}C_{20}T_{23}$ | $A_{24}G_{23}C_{19}T_{16}$ | $A_{24}G_{28}C_{21}T_{16}$ |
| *Chlamydia pneumoniae* AR39 | $A_{26}G_{23}C_{20}T_{22}$ | $A_{26}G_{22}C_{16}T_{18}$ | $A_{24}G_{28}C_{21}T_{16}$ |
| *Leptospira borgpetersenii* | $A_{22}G_{26}C_{20}T_{21}$ | $A_{22}G_{25}C_{21}T_{15}$ | $A_{23}G_{26}C_{24}T_{15}$ |
| *Leptospira interrogans* | $A_{22}G_{26}C_{20}T_{21}$ | $A_{22}G_{25}C_{21}T_{15}$ | $A_{23}G_{26}C_{24}T_{15}$ |
| *Mycoplasma genitalium* | $A_{28}G_{23}C_{15}T_{22}$ | $A_{30}G_{18}C_{15}T_{19}$ | $A_{24}G_{19}C_{12}T_{18}$ |
| *Mycoplasma pneumoniae* | $A_{28}G_{23}C_{15}T_{22}$ | $A_{27}G_{19}C_{16}T_{20}$ | $A_{23}G_{20}C_{14}T_{16}$ |
| *Escherichia coli* | $A_{22}G_{28}C_{20}T_{22}$ | $A_{24}G_{25}C_{21}T_{13}$ | $A_{23}G_{29}C_{22}T_{15}$ |
| *Shigella dysenteriae* | $A_{22}G_{28}C_{21}T_{21}$ | $A_{24}G_{25}C_{21}T_{13}$ | $A_{23}G_{29}C_{22}T_{15}$ |
| *Proteus vulgaris* | $A_{23}G_{26}C_{22}T_{21}$ | $A_{26}G_{24}C_{19}T_{14}$ | $A_{24}G_{30}C_{21}T_{15}$ |
| *Yersinia pestis* | $A_{24}G_{25}C_{21}T_{22}$ | $A_{25}G_{24}C_{20}T_{14}$ | $A_{24}G_{30}C_{21}T_{15}$ |
| *Yersinia pseudotuberculosis* | $A_{24}G_{25}C_{21}T_{22}$ | $A_{25}G_{24}C_{20}T_{14}$ | $A_{24}G_{30}C_{21}T_{15}$ |
| *Francisella tularensis* | $A_{20}G_{25}C_{21}T_{23}$ | $A_{23}G_{26}C_{17}T_{17}$ | $A_{24}G_{26}C_{19}T_{19}$ |
| *Rickettsia prowazekii* | $A_{21}G_{26}C_{24}T_{25}$ | $A_{24}G_{23}C_{16}T_{19}$ | $A_{26}G_{28}C_{18}T_{18}$ |
| *Rickettsia rickettsii* | $A_{21}G_{26}C_{25}T_{24}$ | $A_{24}G_{24}C_{17}T_{17}$ | $A_{26}G_{28}C_{20}T_{16}$ |

The sequence of *B. anthracis* and *B. cereus* in region 16S_971 is shown below. Shown in bold is the single base difference between the two species that can be detected using the methods of the present invention. *B. anthracis* has an ambiguous base at position 20.

```
B.anthracis_16S_971
                                              (SEQ ID NO: 1)
GCGAAGAACCUUACCAGGUNUUGACAUCCUCUGACAACCCUAGAGAUAGG

GCUUCUCCUUCGGGAGCAGAGUGACAGGUGGUGCAUGGUU

B.cereus_16S_971
                                              (SEQ ID NO: 2)
GCGAAGAACCUUACCAGGUCUUGACAUCCUCUGAAAACCCUAGAGAUAGG

GCUUCUCCUUCGGGAGCAGAGUGACAGGUGGUGCAUGGUU
```

Example 6

ESI-TOF MS of sspE 56-mer Plus Calibrant

The mass measurement accuracy that can be obtained using an internal mass standard in the ESI-MS study of PCR products is shown in FIG. 8. The mass standard was a 20-mer phosphorothioate oligonucleotide added to a solution containing a 56-mer PCR product from the *B. anthracis* spore coat protein sspE. The mass of the expected PCR product distinguishes *B. anthracis* from other species of *Bacillus* such as *B. thuringiensis* and *B. cereus*.

Example 7

*B. anthracis* ESI-TOF Synthetic 16S_1228 Duplex

Figure 9:
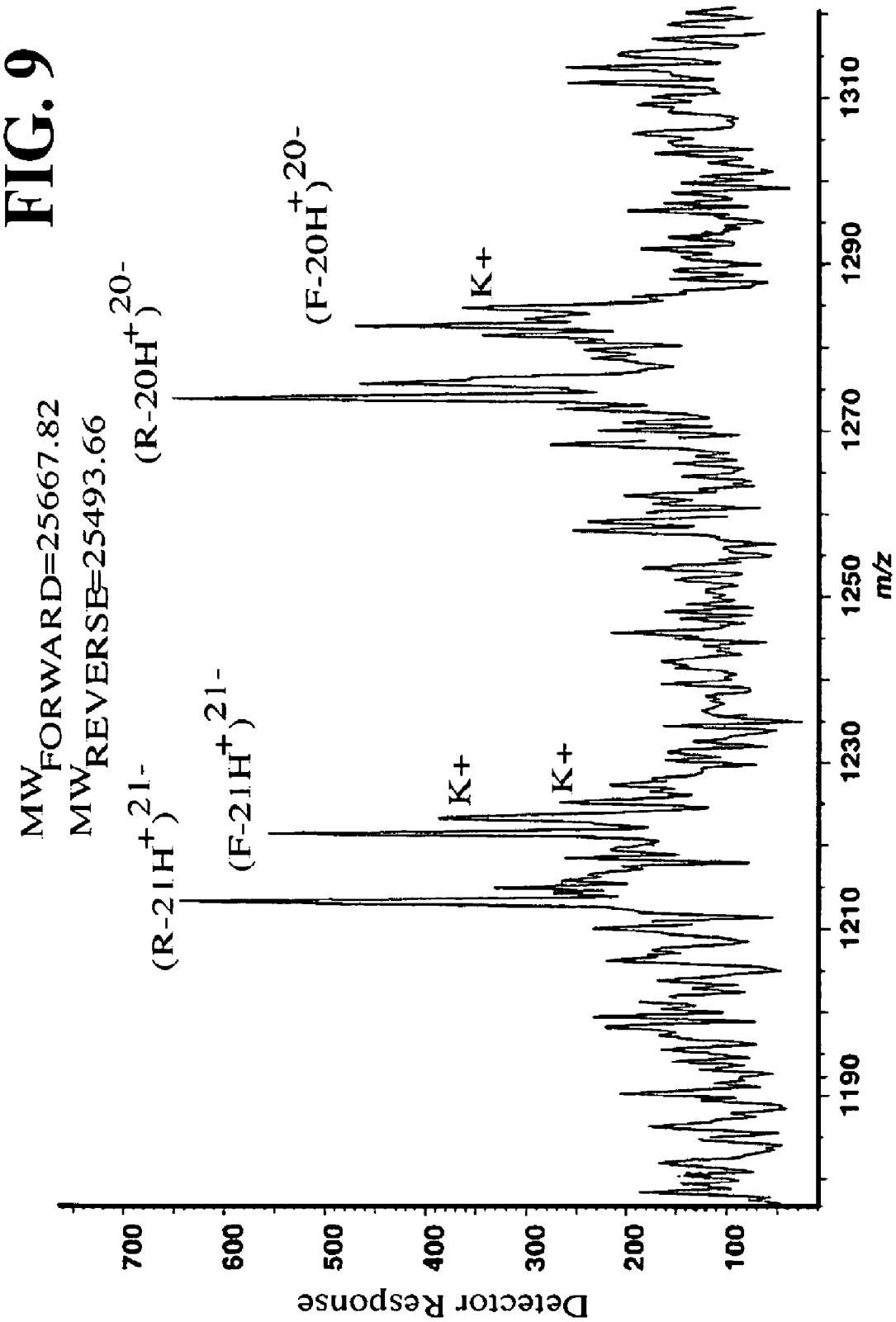
FIG. 9 is an ESI-TOF of a *B. anthracis* synthetic 16S_1228 duplex (reverse and forward strands). The technique easily distinguishes between the forward and reverse strands.

An ESI-TOF MS spectrum was obtained from an aqueous solution containing 5 μM each of synthetic analogs of the expected forward and reverse PCR products from the nucleotide 1228 region of the *B. anthracis* 16S rRNA gene. The results (FIG. 9) show that the molecular weights of the forward and reverse strands can be accurately determined and easily distinguish the two strands. The $[M-21H^+]^{21-}$ and $[M-20H^+]^{20-}$ charge states are shown.

Example 8

ESI-FTICR-MS of Synthetic *B. anthracis* 16S_1337 46 Base Pair Duplex

Figure 10:
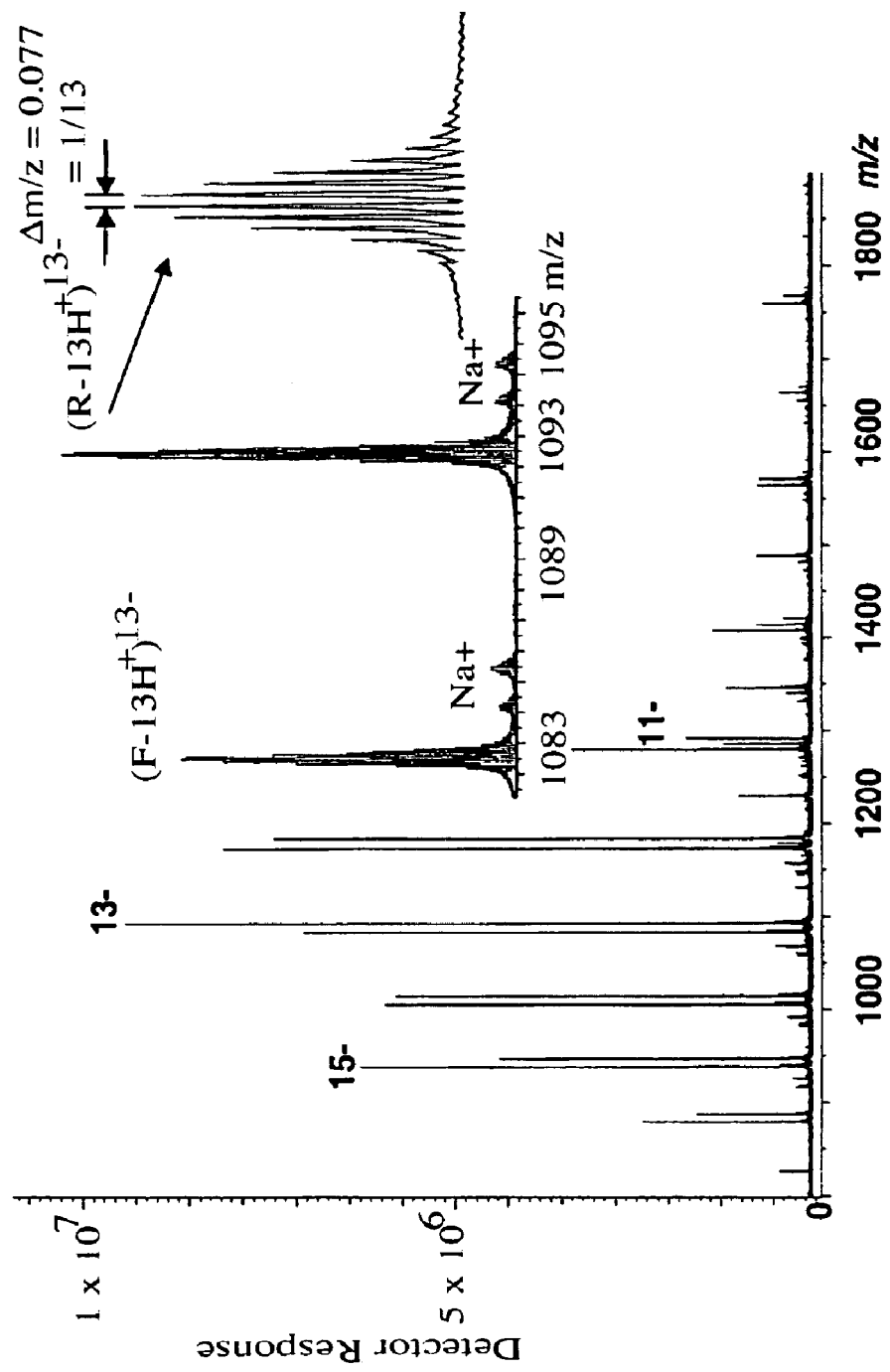
FIG. 10 is an ESI-FTICR-MS of a synthetic *B. anthracis* 16S_1337 46 base pair duplex.

An ESI-FTICR-MS spectrum was obtained from an aqueous solution containing 5 μM each of synthetic analogs of the expected forward and reverse PCR products from the nucleotide 1337 region of the *B. anthracis* 16S rRNA gene. The results (FIG. 10) show that the molecular weights of the strands can be distinguished by this method. The $[M-16H^+]^{16-}$ through $[M-10H^+]^{10-}$ charge states are shown. The insert highlights the resolution that can be realized on the FTICR-MS instrument, which allows the charge state of the ion to be determined from the mass difference between peaks differing by a single 13C substitution.

Example 9

Figure 11:
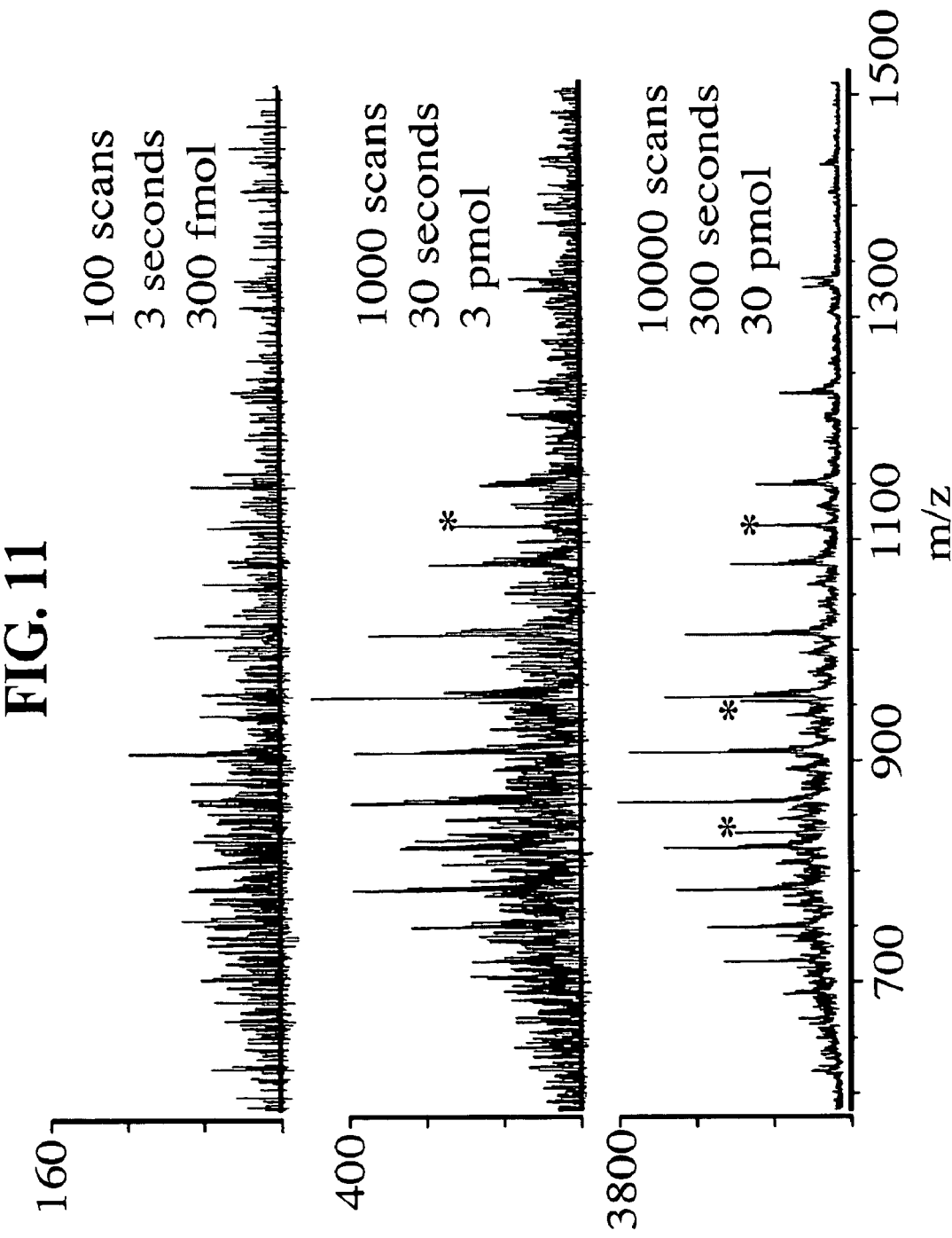
FIG. 11 is an ESI-TOF-MS of a 56 mer oligonucleotide (3 scans) from the *B. anthracis* saspB gene with an internal mass standard. The internal mass standards are designated by asterisks.

ESI-TOF MS of 56-mer Oligonucleotide from saspB Gene of *B. anthracis* with Internal Mass Standard ESI-TOF MS spectra were obtained on a synthetic 56-mer oligonucleotide (5 μM) from the saspB gene of *B. anthracis* containing an internal mass standard at an ESI of 1.7 μL/min as a function of sample consumption. The results (FIG. 11) show that the signal to noise is improved as more scans are summed, and that the standard and the product are visible after only 100 scans.

Example 10

Figure 12:
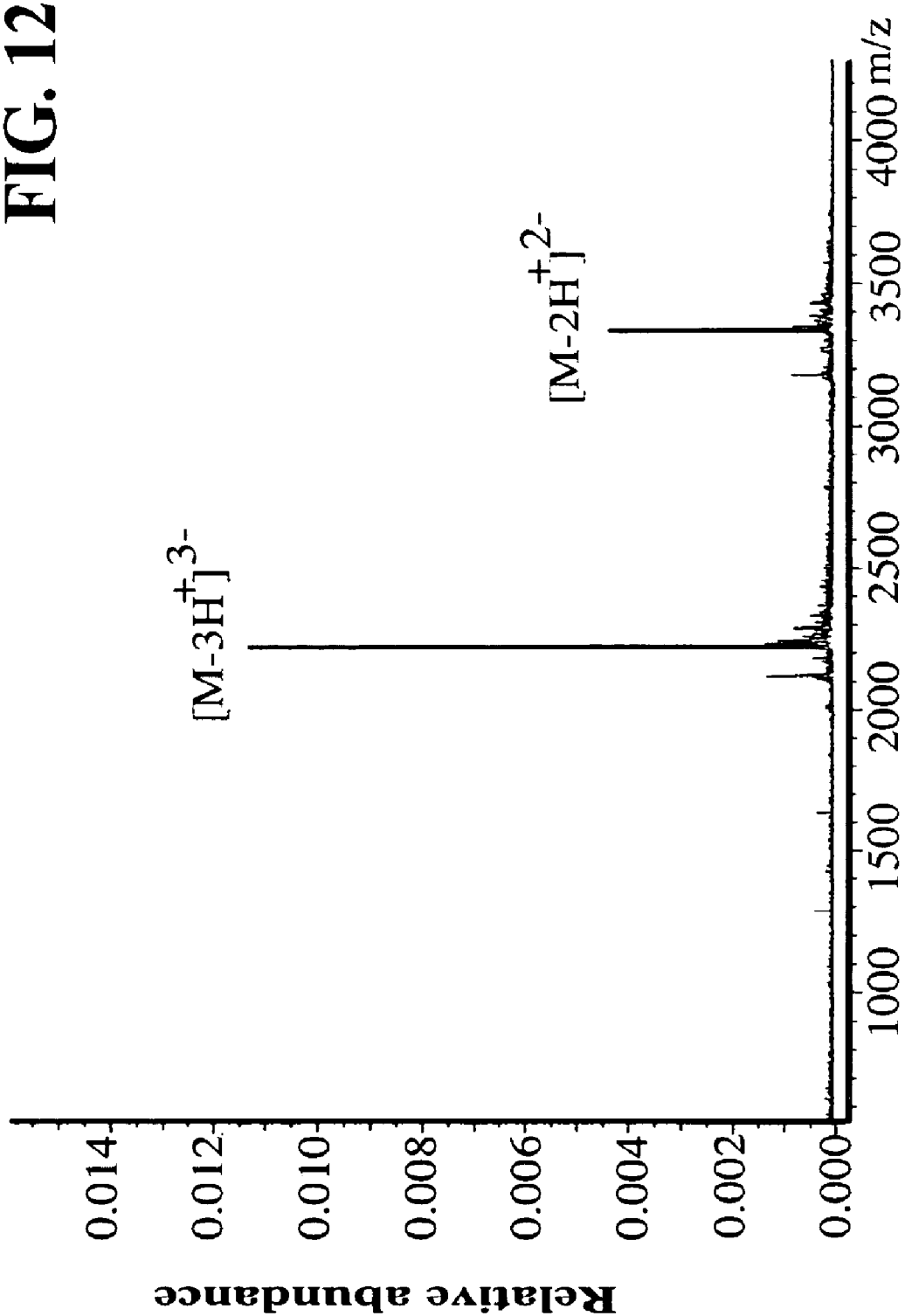
FIG. 12 is an ESI-TOF-MS of an internal standard with 5 mM TBA-TFA buffer showing that charge stripping with tributylammonium trifluoroacetate reduces the most abundant charge state from [M-8H+]8− to [M-3H+]3−.
Figure 13:
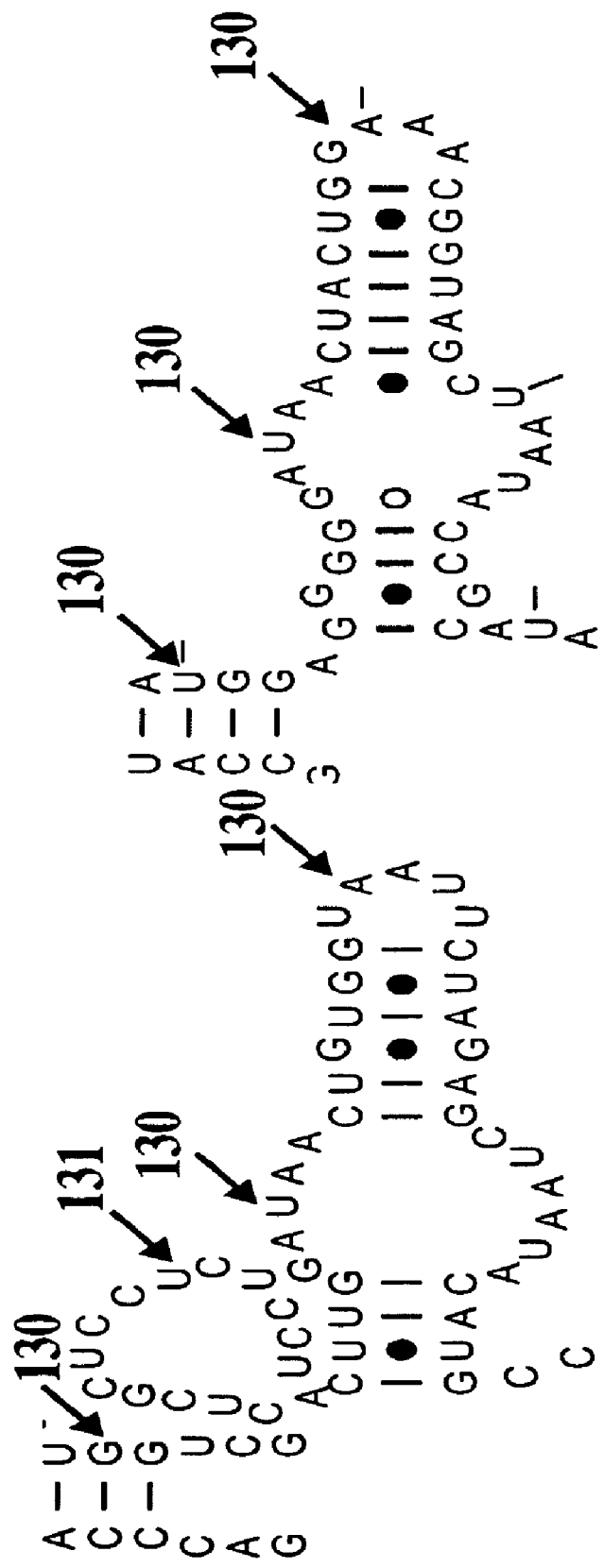
FIG. 13 is a portion of a secondary structure defining database according to one embodiment of the present invention, where two examples of selected sequences are displayed graphically thereunder.
Figure 14:
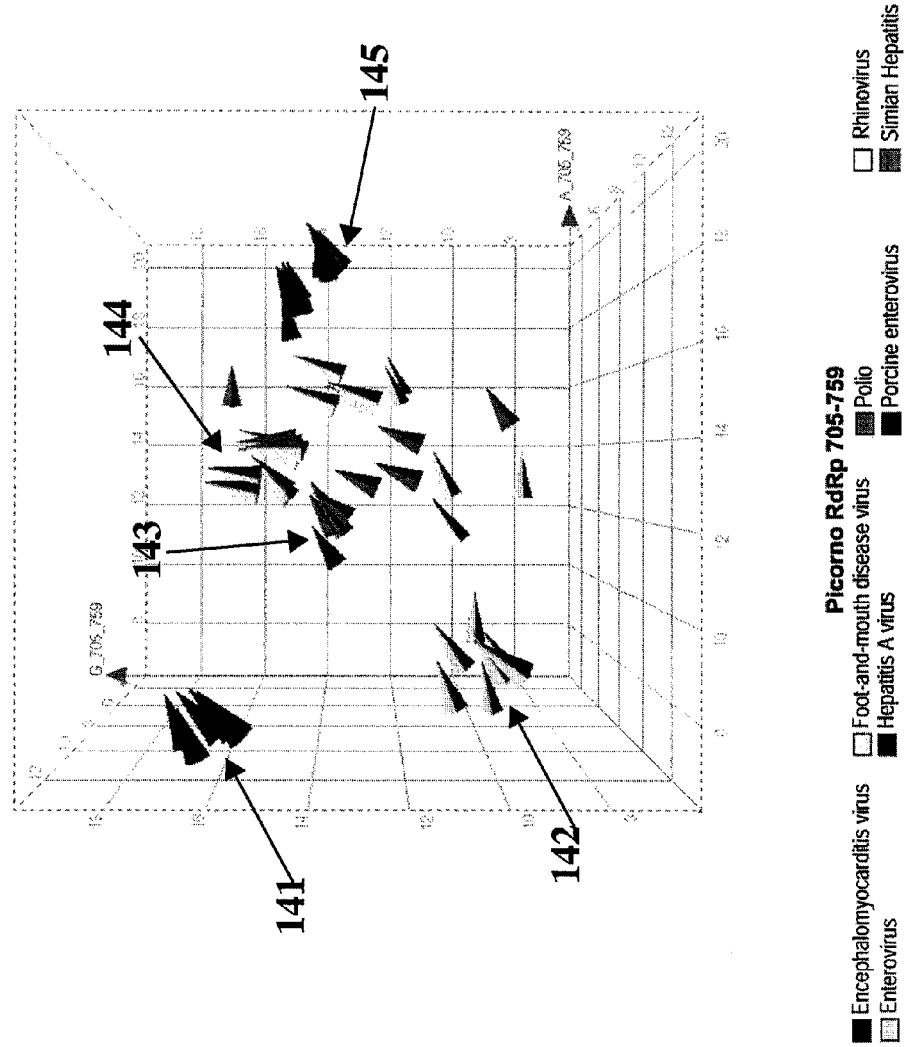
FIG. 14 is a three dimensional graph demonstrating the grouping of sample molecular weight according to species.
Figure 15:
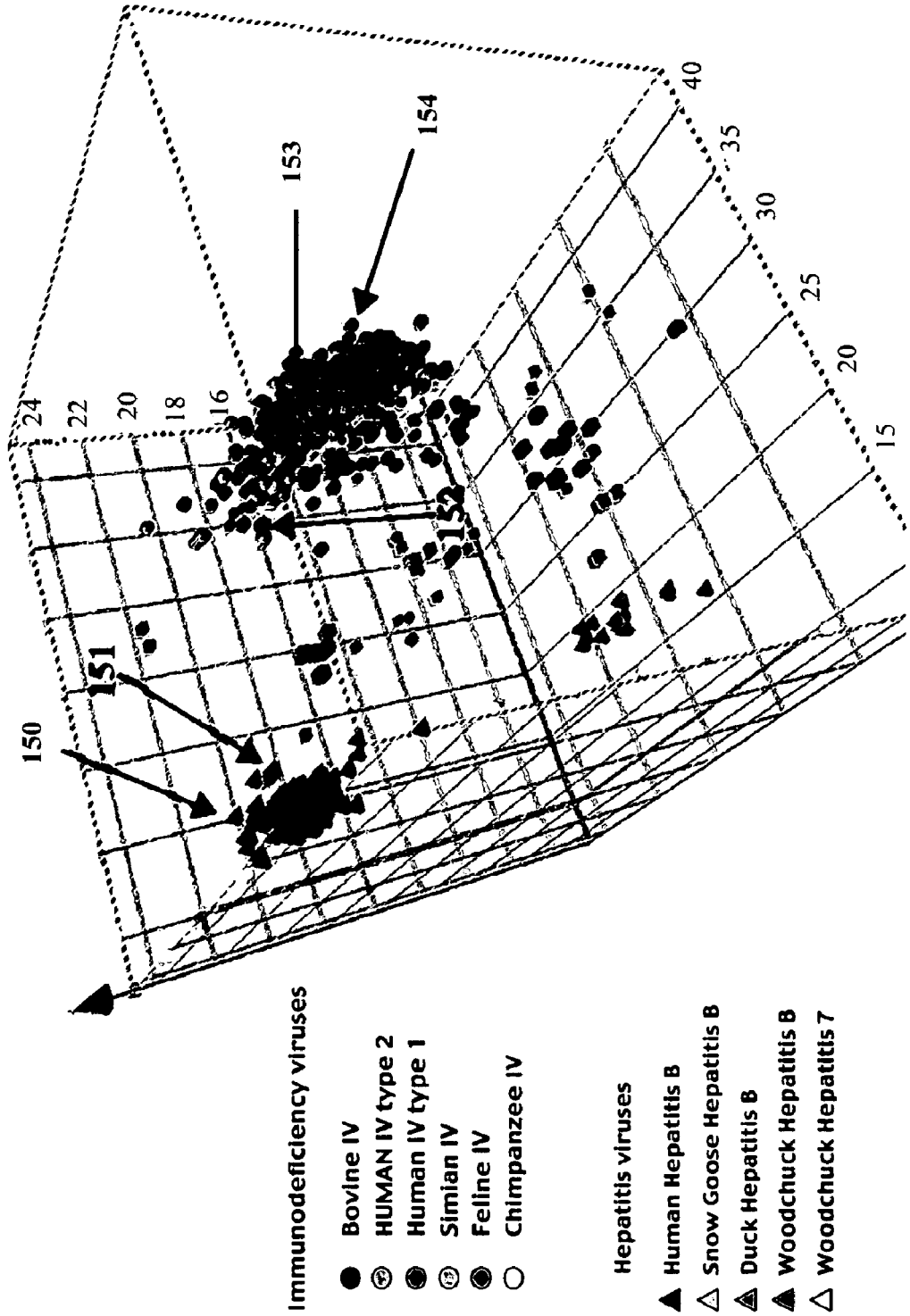
FIG. 15 is a three dimensional graph demonstrating the grouping of sample molecular weights according to species of virus and mammal infected.
Figure 16:
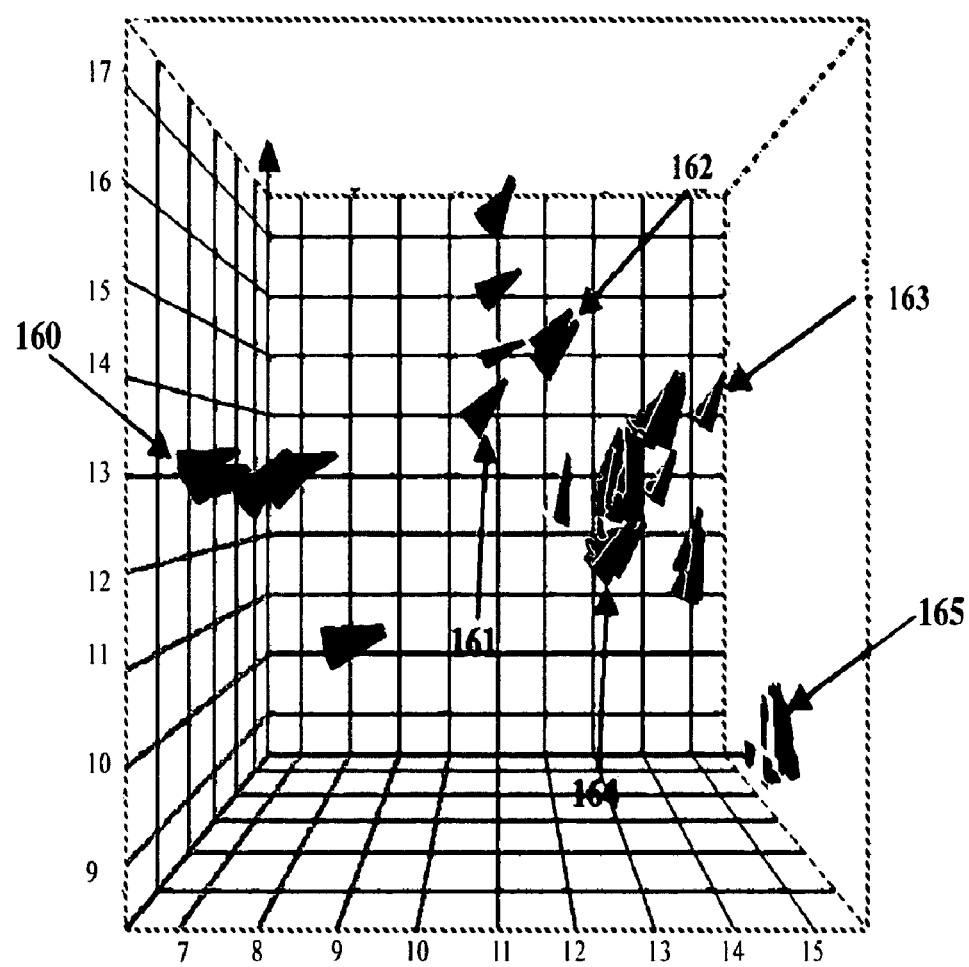
FIG. 16 is a three dimensional graph demonstrating the grouping of sample molecular weights according to species of virus, and animal-origin of infectious agent.
Figure 17:
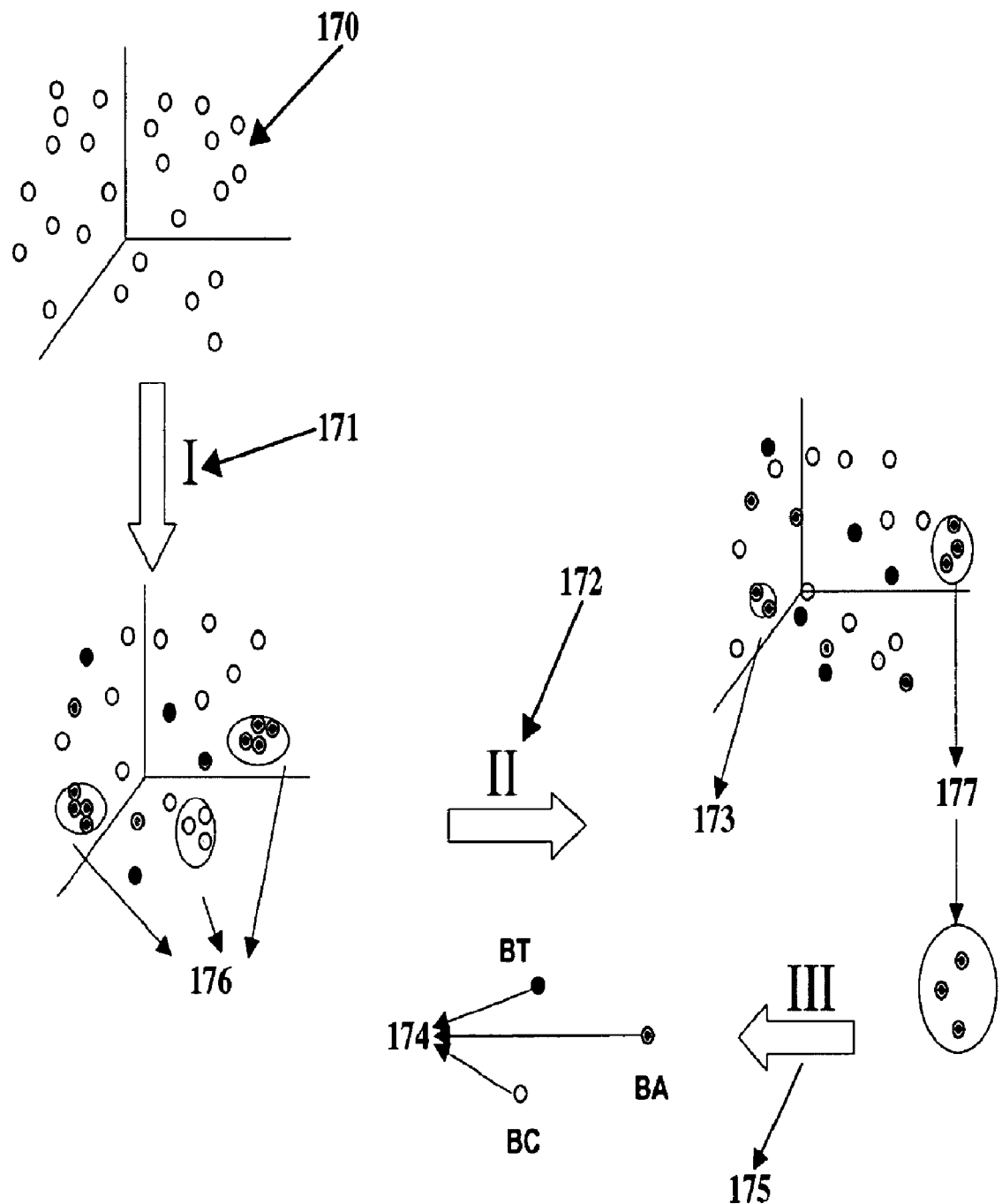
FIG. 17 is a figure depicting how a typical triangulation method of the present invention provides for the identification of an unknown bioagent without prior knowledge of the unknown agent. The use of different primer sets to distinguish and identify the unknown is also depicted as primer sets I, II and III within this figure. A three-dimensional graph depicts all of bioagent space (170), including the unknown bioagent, which after use of primer set I (171) according to a method according to the present invention further differentiates and classifies bioagents according to major classifications (176) which, upon further analysis using primer set II (172) differentiates the unknown agent (177) from other, known agents (173) and finally, the use of a third primer set (175) further specifies subgroups within the family of the unknown (174).

ESI-TOF MS of an Internal Standard with Tributylammonium (TBA)-Trifluoroacetate (TFA) Buffer An ESI-TOF-MS spectrum of a 20-mer phosphorothioate mass standard was obtained following addition of 5 mM TBA-TFA buffer to the solution. This buffer strips charge from the oligonucleotide and shifts the most abundant charge state from $[M-8H^+]^{8-}$ to $[M-3H^+]^{3-}$ (FIG. 12).

Example 11

Master Database Comparison

The molecular masses obtained through Examples 1-10 are compared to molecular masses of known bioagents stored in a master database to obtain a high probability matching molecular mass.

Example 12

Master Data Base Interrogation over the Internet

The same procedure as in Example 11 is followed except that the local computer did not store the Master database. The Master database is interrogated over an internet connection, searching for a molecular mass match.

Example 13

Master Database Updating

The same procedure as in example 11 is followed except the local computer is connected to the internet and has the ability to store a master database locally. The local computer system periodically, or at the user's discretion, interrogates the Master database, synchronizing the local master database with the global Master database. This provides the current molecular mass information to both the local database as well as to the global Master database. This further provides more of a globalized knowledge base.

Example 14

Global Database Updating

The same procedure as in example 13 is followed except there are numerous such local stations throughout the world. The synchronization of each database adds to the diversity of information and diversity of the molecular masses of known bioagents.

Example 15

Demonstration of Detection and Identification of Five Species of Bacteria in a Mixture Broad range intelligent primers were chosen following analysis of a large collection of curated bacterial 16S rRNA sequences representing greater than 4000 species of bacteria. Examples of primers capable of priming from greater than 90% of the organisms in the collection include, but are not limited to, those exhibited in Table 8 wherein Tp=5'propynylated uridine and Cp=5'propynylated cytidine.

TABLE 8

| Intelligent Primer Pairs for Identification of Bacteria | | | | |
|---|---|---|---|---|
| Primer Pair Name | Forward Primer Sequence | Forward SEQ ID NO: | Reverse Primer Sequence | Reverse SEQ ID NO: |
| 16S_EC_1077_1195 | GTGAGATGTTGGGTTAAGTCCC GTAACGAG | 8 | GACGTCATCCCCACCTTCCTC | 9 |

TABLE 8-continued

Intelligent Primer Pairs for Identification of Bacteria

| Primer Pair Name | Forward Primer Sequence | Forward SEQ ID NO: | Reverse Primer Sequence | Reverse SEQ ID NO: |
|---|---|---|---|---|
| 16S_EC_1082-1197 | ATGTTGGGTTAAGTCCCGCAACGAG | 10 | TTGACGTCATCCCCACCTTCCTC | 11 |
| 16S_EC_1090_1196 | TTAAGTCCCGCAACGATCGCAA | 12 | TGACGTCATCCCCACCTTCCTC | 13 |
| 16S_EC_1222_1323 | GCTACACACGTGCTACAATG | 14 | CGAGTTGCAGACTGCGATCCG | 15 |
| 16S_EC_1332_1407 | AAGTCGGAATCGCTAGTAATCG | 16 | GACGGGCGGTGTGTACAAG | 17 |
| 16S_EC_30_126 | TGAACGCTGGTGGCATGCTTAACAC | 18 | TACGCATTACTCACCCGTCCGC | 19 |
| 16S_EC_38_120 | GTGGCATGCCTAATACATGCAAGTCG | 20 | TTACTCACCCGTCCGCCGCT | 21 |
| 16S_EC_49_120 | TAACACATGCAAGTCGAACG | 22 | TTACTCACCCGTCCGCC | 23 |
| 16S_EC_683_795 | GTGTAGCGGTGAAATGCG | 24 | GTATCTAATCCTGTTTGCTCCC | 25 |
| 16S_EC_713_809 | AGAACACCGATGGCGAAGGC | 26 | CGTGGACTACCAGGGTATCTA | 27 |
| 16S_EC_785_897 | GGATTAGAGACCCTGGTAGTCC | 28 | GGCCGTACTCCCCAGGCG | 29 |
| 16S_EC_785_897_2 | GGATTAGATACCCTGGTAGTCCACGC | 30 | GGCCGTACTCCCCAGGCG | 31 |
| 16S_EC_789_894 | TAGATACCCTGGTAGTCCACGC | 32 | CGTACTCCCCAGGCG | 33 |
| 16S_EC_960_1073 | TTCGATGCAACGCGAAGAACCT | 34 | ACGAGCTGACGACAGCCATG | 35 |
| 16S_EC_969_1078 | ACGCGAAGAACCTTACC | 36 | ACGACACGAGCTGACGAC | 37 |
| 23S_EC_1826_1924 | CTGACACCTGCCCGGTGC | 38 | GACCGTTATAGTTACGGCC | 39 |
| 23S_EC_2645_2761 | TCTGTCCCTAGTACGAGAGGACCGG | 40 | TGCTTAGATGCTTTCAGC | 41 |
| 23S_EC_2645_2767 | CTGTCCCTAGTACGAGAGGACCGG | 42 | GTTTCATGCTTAGATGCTTTCAGC | 43 |
| 23S_EC_493_571 | GGGGAGTGAAAGAGATCCTGAAACCG | 44 | ACAAAAGGTACGCCGTCACCC | 45 |
| 23S_EC_493_571_2 | GGGGAGTGAAAGAGATCCTGAAACCG | 46 | ACAAAAGGCACGCCATCACCC | 47 |
| 23S_EC_971_1077 | CGAGAGGGAAACAACCCAGACC | 48 | TGGCTGCTTCTAAGCCAAC | 49 |
| INFB_EC_1365_1467 | TGCTCGTGGTGCACAAGTAACGGATATTA | 50 | TGCTGCTTTCGCATGGTTAATTGCTTCAA | 51 |
| RPOC_EC_1018_1124 | CAAAACTTATTAGGTAAGCGTGTTGACT | 52 | TCAAGCGCCATTTCTTTTGGTAAACCACAT | 53 |
| RPOC_EC_1018_1124_2 | CAAAACTTATTAGGTAAGCGTGTTGACT | 54 | TCAAGCGCCATCTCTTTCGGTAATCCACAT | 55 |
| RPOC_EC_114_232 | TAAGAAGCCGGAAACCATCAACTACCG | 56 | GGCGCTTGTACTTACCGCAC | 57 |

TABLE 8-continued

Intelligent Primer Pairs for Identification of Bacteria

| Primer Pair Name | Forward Primer Sequence | Forward SEQ ID NO: | Reverse Primer Sequence | Reverse SEQ ID NO: |
|---|---|---|---|---|
| RPOC_EC_2178_2246 | TGATTCTGGTGCCCGTGGT | 58 | TTGGCCATCAGGCCACGCATAC | 59 |
| RPOC_EC_2178_2246_2 | TGATTCCGGTGCCCGTGGT | 60 | TTGGCCATCAGACCACGCATAC | 61 |
| RPOC_EC_2218_2337 | CTGGCAGGTATGCGTGGTCTGATG | 62 | CGCACCGTGGGTTGAGATGAAGTAC | 63 |
| RPOC_EC_2218_2337_2 | CTTGCTGGTATGCGTGGTCTGATG | 64 | CGCACCATGCGTAGAGATGAAGTAC | 65 |
| RPOC_EC_808_889 | CGTCGGGTGATTAACCGTAACAACCG | 66 | GTTTTTCGTTGCGTACGATGATGTC | 67 |
| RPOC_EC_808_891 | CGTCGTGTAATTAACCGTAACAACCG | 68 | ACGTTTTTCGTTTTGAACGATAATGCT | 69 |
| RPOC_EC_993_1059 | CAAAGGTAAGCAAGGTCGTTTCCGTCA | 70 | CGAACGGCCTGAGTAGTCAACACG | 71 |
| RPOC_EC_993_1059_2 | CAAAGGTAAGCAAGGACGTTTCCGTCA | 72 | CGAACGGCCAGAGTAGTCAACACG | 73 |
| TUFB_EC_239_303 | TAGACTGCCCAGGACACGCTG | 74 | GCCGTCCATCTGAGCAGCACC | 75 |
| TUFB_EC_239_303_2 | TTGACTGCCCAGGTCACGCTG | 76 | GCCGTCCATTTGAGCAGCACC | 77 |
| TUFB_EC_976_1068 | AACTACCGTCCGCAGTTCTACTTCC | 78 | GTTGTCGCCAGGCATAACCATTTC | 79 |
| TUFB_EC_976_1068_2 | AACTACCGTCCTCAGTTCTACTTCC | 80 | GTTGTCACCAGGCATTACCATTTC | 81 |
| TUFB_EC_985_1062 | CCACAGTTCTACTTCCGTACTACTGACG | 82 | TCCAGGCATTACCATTTCTACTCCTTCTGG | 83 |
| RPLB_EC_650_762 | GACCTACAGTAAGAGGTTCTGTAATGAACC | 84 | TCCAAGTGCTGGTTTACCCCATGG | 85 |
| RPLB_EC_688_757 | CATCCACACGGTGGTGGTGAAGG | 86 | GTGCTGGTTTACCCCATGGAGT | 87 |
| RPOC_EC_1036_1126 | CGTGTTGACTATTCGGGGCGTTCAG | 88 | ATTCAAGAGCCATTTCTTTTGGTAAACCAC | 89 |
| RPOB_EC_3762_3865 | TCAACAACCTCTTGGAGGTAAAGCTCAGT | 90 | TTTCTTGAAGAGTATGAGCTGCTCCGTAAG | 91 |
| RPLB_EC_688_771 | CATCCACACGGTGGTGGTGAAGG | 92 | TGTTTTGTATCCAGTGCTGGTTTACCCC | 93 |
| VALS_EC_1105_1218 | CGTGGCGGCGTGGTTATCGA | 94 | CGGTACGAACTGGATGTCGCCGTT | 95 |
| RPOB_EC_1845_1929 | TATCGCTCAGGCGAACTCCAAC | 96 | GCTGGATTCGCCTTTGCTACG | 97 |
| RPLB_EC_669_761 | TGTAATGAACCCTAATGACCATCCACACGG | 98 | CCAAGTGCTGGTTTACCCCATGGAGTA | 99 |
| RPLB_EC_671_762 | TAATGAACCCTAATGACCATCCACACGGTG | 100 | TCCAAGTGCTGGTTTACCCCATGGAG | 101 |
| RPOB_EC_3775_3858 | CTTGGAGGTAAGTCTCATTTTGGTGGGCA | 102 | CGTATAAGCTGCACCATAAGCTTGTAATGC | 103 |
| VALS_EC_1833_1943 | CGACGCGCTGCGCTTCAC | 104 | GCGTTCCACAGCTTGTTGCAGAAG | 105 |

TABLE 8-continued

Intelligent Primer Pairs for Identification of Bacteria

| Primer Pair Name | Forward Primer Sequence | Forward SEQ ID NO: | Reverse Primer Sequence | Reverse SEQ ID NO: |
|---|---|---|---|---|
| RPOB_EC_1336_1455 | GACCACCTCGGCAACCGT | 106 | TTCGCTCTCGGCCTGGCC | 107 |
| TUFB_EC_225_309 | GCACTATGCACACGTAGATTGTCCTGG | 108 | TATAGCACCATCCATCTGAGCGGCAC | 109 |
| DNAK_EC_428_522 | CGGCGTACTTCAACGACAGCCA | 110 | CGCGGTCGGCTCGTTGATGA | 111 |
| VALS_EC_1920_1970 | CTTCTGCAACAAGCTGTGGAACGC | 112 | TCGCAGTTCATCAGCACGAAGCG | 113 |
| TUFB_EC_757_867 | AAGACGACCTGCACGGGC | 114 | GCGCTCCACGTCTTCACGC | 115 |
| 23S_EC_2646_2765 | CTGTTCTTAGTACGAGAGGACC | 116 | TTCGTGCTTAGATGCTTTCAG | 117 |
| 16S_EC_969_1078_3P | ACGCGAAGAACCTTACpC | 118 | ACGACACGAGCpTpGACGAC | 119 |
| 16S_EC_972_1075_4P | CGAAGAACpCpTTACC | 120 | ACACGAGCpTpGAC | 121 |
| 16S_EC_972_1075 | CGAAGAACCTTACC | 122 | ACACGAGCTGAC | 123 |
| 23S_EC_-347_59 | CCTGATAAGGGTGAGGTCG | 124 | ACGTCCTTCATCGCCTCTGA | 125 |
| 23S_EC_-7_450 | GTTGTGAGGTTAAGCGACTAAG | 126 | CTATCGGTCAGTCAGGAGTAT | 127 |
| 23S_EC_-7_910 | GTTGTGAGGTTAAGCGACTAAG | 128 | TTGCATCGGGTTGGTAAGTC | 129 |
| 23S_EC_430_1442 | ATACTCCTGACTGACCGATAG | 130 | AACATAGCCTTCTCCGTCC | 131 |
| 23S_EC_891_1931 | GACTTACCAACCCGATGCAA | 132 | TACCTTAGGACCGTTATAGTTACG | 133 |
| 23S_EC_1424_2494 | GGACGGAGAAGGCTATGTT | 134 | CCAAACACCGCCGTCGATAT | 135 |
| 23S_EC_1908_2852 | CGTAACTATAACGGTCCTAAGGTA | 136 | GCTTACACACCCGGCCTATC | 137 |
| 23S_EC_2475_3209 | ATATCGACGGCGGTGTTTGG | 138 | GCGTGACAGGCAGCTATTC | 139 |
| 16S_EC_-60_525 | AGTCTCAAGAGTGAACACGTAA | 140 | GCTGCTGGCACGGAGTTA | 141 |
| 16S_EC_326_1058 | GACACGGTCCAGACTCCTAC | 142 | CCATGCAGCACCTGTCTC | 143 |
| 16S_EC_705_1512 | GATCTGGAGGAATACCGGTG | 144 | ACGGTTACCTTGTTACGACT | 145 |
| 16S_EC_1268_1775 | GAGAGCAAGCGGACCTCATA | 146 | CCTCCTGCGTGCAAAGC | 147 |
| GROL_EC_941_1060 | TGGAAGATCTGGGTCAGGC | 148 | CAATCTGCTGACGGATCTGAGC | 149 |
| INFB_EC_1103_1191 | GTCGTGAAAACGAGCTGGAAGA | 150 | CATGATGGTCACAACCGG | 151 |
| HFLB_EC_1082_1168 | TGGCGAACCTGGTGAACGAAGC | 152 | CTTTCGCTTTCTCGAACTCAACCAT | 153 |

TABLE 8-continued

Intelligent Primer Pairs for Identification of Bacteria

| Primer Pair Name | Forward Primer Sequence | Forward SEQ ID NO: | Reverse Primer Sequence | Reverse SEQ ID NO: |
|---|---|---|---|---|
| INFB_EC_1969_2058 | CGTCAGGGTAAATTCCGTGAAGTTAA | 154 | AACTTCGCCTTCGGTCATGTT | 155 |
| GROL_EC_219_350 | GGTGAAAGAAGTTGCCTCTAAAGC | 156 | TTCAGGTCCATCGGGTTCATGC | 157 |
| VALS_EC_1105_1214 | CGTGGCGGCGTGGTTATCGA | 158 | ACGAACTGGATGTCGCCGTT | 159 |
| 16S_EC_556_700 | CGGAATTACTGGGCGTAAAG | 160 | CGCATTTCACCGCTACAC | 161 |
| RPOC_EC_1256_1315 | ACCCAGTGCTGCTGAACCGTGC | 162 | GTTCAAATGCCTGGATACCCA | 163 |
| 16S_EC_774_894 | GGGAGCAAACAGGATTAGATAC | 164 | CGTACTCCCCAGGCG | 165 |
| RPOC_EC_1584_1643 | TGGCCCGAAAGAAGCTGAGCG | 166 | ACGCGGGCATGCAGAGATGCC | 167 |
| 16S_EC_1082_1196 | ATGTTGGGTTAAGTCCCGC | 168 | TGACGTCATCCCCACCTTCC | 169 |
| 16S_EC_1389_1541 | CTTGTACACACCGCCCGTC | 170 | AAGGAGGTGATCCAGCC | 171 |
| 16S_EC_1303_1407 | CGGATTGGAGTCTGCAACTCG | 172 | GACGGGCGGTGTGTACAAG | 173 |
| 23S_EC_23_130 | GGTGGATGCCTTGGC | 174 | GGGTTTCCCCATTCGG | 175 |
| 23S_EC_187_256 | GGGAACTGAAACATCTAAGTA | 176 | TTCGCTCGCCGCTAC | 177 |
| 23S_EC_1602_1703 | TACCCCAAACCGACACAGG | 178 | CCTTCTCCCGAAGTTACG | 179 |
| 23S_EC_1685_1842 | CCGTAACTTCGGGAGAAGG | 180 | CACCGGGCAGGCGTC | 181 |
| 23S_EC_1827_1949 | GACGCCTGCCCGGTGC | 182 | CCGACAAGGAATTTCGCTACC | 183 |
| 23S_EC_2434_2511 | AAGGTACTCCGGGGATAACAGGC | 184 | AGCCGACATCGAGGTGCCAAAC | 185 |
| 23S_EC_2599_2669 | GACAGTTCGGTCCCTATC | 186 | CCGGTCCTCTCGTACTA | 187 |
| 23S_EC_2653_2758 | TAGTACCAGACGACCGG | 188 | TTAGATGCTTTCAGCACTTATC | 189 |
| 23S_BS-68_21 | AAACTAGATAACAGTAGACATCAC | 190 | GTGCGCCCTTTCTAACTT | 191 |
| 16S_EC_8_358 | AGAGTTTGATCATGGCTCAG | 192 | ACTGCTGCCTCCCGTAG | 193 |
| 16S_EC_314_575 | CACTGGAACTGAGACACGG | 194 | CTTTACGCCCAGTAATTCCG | 195 |
| 16S_EC_518_795 | CCAGCAGCCGCGGTAATAC | 196 | GTATCTAATCCTGTTTGCTCCC | 197 |
| 16S_EC_683_985 | GTGTAGCGGTGAAATGCG | 198 | GGTAAGGTTCTTCGCGTTG | 199 |
| 16S_EC_937_1240 | AAGCGGTGGAGCATGTGG | 200 | ATTGTAGCACGTGTGTAGCCC | 201 |
| 16S_EC_1195_1541 | CAAGTCATCATGGCCCTTA | 202 | AAGGAGGTGATCCAGCC | 203 |

TABLE 8-continued

Intelligent Primer Pairs for Identification of Bacteria

| Primer Pair Name | Forward Primer Sequence | Forward SEQ ID NO: | Reverse Primer Sequence | Reverse SEQ ID NO: |
|---|---|---|---|---|
| 16S_EC_8_1541 | AGACTTTGATCATGGCTCAG | 204 | AAGGAGGTGATCCAGCC | 205 |
| 23S_EC_1831_1936 | ACCTGCCCAGTGCTGGAAG | 206 | TCGCTACCTTAGGACCGT | 207 |
| 16S_EC_1387_1513 | GCCTTGTACACACCTCCCGTC | 208 | CACGGCTACCTTGTTACGAC | 209 |
| 16S_EC_1390_1505 | TTGTACACACCGCCCGTCATAC | 210 | CCTTGTTACGACTTCACCCC | 211 |
| 16S_EC_1367_1506 | TACGGTGAATACGTTCCCGGG | 212 | ACCTTGTTACGACTTCACCCCA | 213 |
| 16S_EC_804_929 | ACCACGCCGTAAACGATGA | 214 | CCCCCGTCAATTCCTTTGAGT | 215 |
| 16S_EC_791_904 | GATACCCTGGTAGTCCACACCG | 216 | GCCTTGCGACCGTACTCCC | 217 |
| 16S_EC_789_899 | TAGATACCCTGGTAGTCCACGC | 218 | GCGACCGTACTCCCCAGG | 219 |
| 16S_EC_1092_1195 | TAGTCCCGCAACGAGCGC | 220 | GACGTCATCCCCACCTTCCTCC | 221 |
| 23S_EC_2586_2677 | TAGAACGTCGCGAGACAGTTCG | 222 | AGTCCATCCCGGTCCTCTCG | 223 |
| HEXAMER_EC_61_362 | GAGGAAAGTCCGGGCTC | 224 | ATAAGCCGGGTTCTGTCG | 225 |
| RNASEP_BS_43_384 | GAGGAAAGTCCATGCTCGC | 226 | GTAAGCCATGTTTTGTTCCATC | 227 |
| RNASEP_EC_61_362 | GAGGAAAGTCCGGGCTC | 228 | ATAAGCCGGGTTCTGTCG | 229 |
| YAED_TRNA_ALA-RRNH_EC_513_49 | GCGGGATCCTCTAGAGGTGTTAAATAGCCTGGCAG | 230 | GCGGGATCCTCTAGAAGACCTCCTGCGTGCAAAGC | 231 |
| RNASEP_SA_31_379 | GAGGAAAGTCCATGCTCAC | 232 | ATAACCCATGTTCTGTTCCATC | 233 |
| 16S_EC_1082_1541 | ATGTTGGGTTAAGTCCCGC | 234 | AAGGAGGTGATCCAGCC | 235 |
| 16S_EC_556_795 | CGGAATTACTGGGCGTAAAG | 236 | GTATCTAATCCTGTTTGCTCCC | 237 |
| 16S_EC_1082_1196_10G | ATGTTGGGTTAAGTCCCGC | 238 | TGACGTCATGCCCACCTTCC | 239 |
| 16S_EC_1082_1196_10G_11G | ATGTTGGGTTAAGTCCCGC | 240 | TGACGTCATGGCCACCTTCC | 241 |
| TRNA_ILERRNH_ASPRRNH_EC_32_41 | GCGGGATCCTCTAGACCTGATAAGGGTGAGGTCG | 242 | GCGGGATCCTCTAGAGCGTGACAGGCAGGTATTC | 243 |
| 16S_EC_969_1407 | ACGCGAAGAACCTTACC | 244 | GACGGGCGGTGTGTACAAG | 245 |
| 16S_EC_683_1323 | GTGTAGCGGTGAAATGCG | 246 | CCAGTTGCAGACTGCGATCCG | 247 |
| 16S_EC_49_894 | TAACACATGCAAGTCGAACG | 248 | CGTACTCCCCAGGCG | 249 |
| 16S_EC_49_1078 | TAACACATGCAAGTCGAACG | 250 | ACGACACGAGCTGACGAC | 251 |

TABLE 8-continued

Intelligent Primer Pairs for Identification of Bacteria

| Primer Pair Name | Forward Primer Sequence | Forward SEQ ID NO: | Reverse Primer Sequence | Reverse SEQ ID NO: |
|---|---|---|---|---|
| CYA_BA_1349_1447 | ACAACGAAGTACAATACAAGAC | 252 | CTTCTACATTTTTAGCCATCAC | 253 |
| 16S_EC_1090_1196_2 | TTAAGTCCCGCAACGAGCGCAA | 254 | TGACGTCATCCCCACCTTCCTC | 255 |
| 16S_EC_405_527 | TGAGTGATGAAGGCCTTAGGGTTGTAAA | 256 | CGGCTGCTGGCACGAAGTTAG | 257 |
| GROL_EC_496_596 | ATGGACAAGGTTGGCAAGGAAGG | 258 | TAGCCGCGGTCGAATTGCAT | 259 |
| GROL_EC_511_593 | AAGGAAGGCGTGATCACCGTTGAAGA | 260 | CCGCGGTCGAATTGCATGCCTTC | 261 |
| VALS_EC_1835_1928 | ACGCGCTGCGCTTCAC | 262 | TTGCAGAAGTTGCGGTAGCC | 263 |
| RPOB_EC_1334_1478 | TCGACCACCTGGGCAACC | 264 | ATCAGGTCGTGCGGCATCA | 265 |
| DNAK_EC_420_521 | CACGGTGCCGGCGTACT | 266 | GCGGTCGGCTCGTTGATGAT | 267 |
| RPOB_EC_3776_3853 | TTGGAGGTAAGTCTCATTTTGGTGG | 268 | AAGCTGCACCATAAGCTTGTAATGC | 269 |
| RPOB_EC_3802_3885 | CAGCGTTTCGGCGAAATGGA | 270 | CGACTTGACGGTTAACATTTCCTG | 271 |
| RPOB_EC_3799_3888 | GGGCAGCGTTTCGGCGAAATGGA | 272 | GTCCGACTTGACGGTCAACATTTCCTG | 273 |
| RPOC_EC_2146_2245 | CAGGAGTCGTTCAACTCGATCTACATGAT | 274 | ACGCCATCAGGCCACGCAT | 275 |
| ASPS_EC_405_538 | GCACAACCTGCGGCTGCG | 276 | ACGGCACGAGGTAGTCGC | 277 |
| RPOC_EC_1374_1455 | CGCCGACTTCGACGGTGACC | 278 | GAGCATCAGCGTGCGTGCT | 279 |
| TUFB_EC_957_1058 | CCACACGCCGTTCTTCAACAACT | 280 | GGCATCACCATTTCCTTGTCCTTCG | 281 |
| 16S_EC_7_122 | GAGAGTTTGATCCTGGCTCAGAACGAA | 282 | TGTTACTCACCCGTCTGCCACT | 283 |
| VALS_EC_610_727 | ACCGAGCAAGGAGACCAGC | 284 | TATAACGCACATCGTCAGGGTGA | 285 |

For evaluation in the laboratory, five species of bacteria were selected including three γ-proteobacteria (*E. coli, K. pneumoniae* and *P. auergiosa*) and two low G+C gram positive bacteria (*B. subtilitis* and *S. aureus*). The identities of the organisms were not revealed to the laboratory technicians.

Bacteria were grown in culture, DNA was isolated and processed, and PCR performed using standard protocols. Following PCR, all samples were desalted, concentrated, and analyzed by Fourier Transform Ion Cyclotron Resonance (FTICR) mass spectrometry. Due to the extremely high precision of the FTICR, masses could be measured to within 1 Da and unambiguously deconvoluted to a single base composition. The measured base compositions were compared with the known base composition signatures in our database. As expected when using broad range survey 16S primers, several phylogenetic near-neighbor organisms were difficult to distinguish from our test organisms. Additional non-ribosomal primers were used to triangulate and further resolve these clusters.

Figure 19:
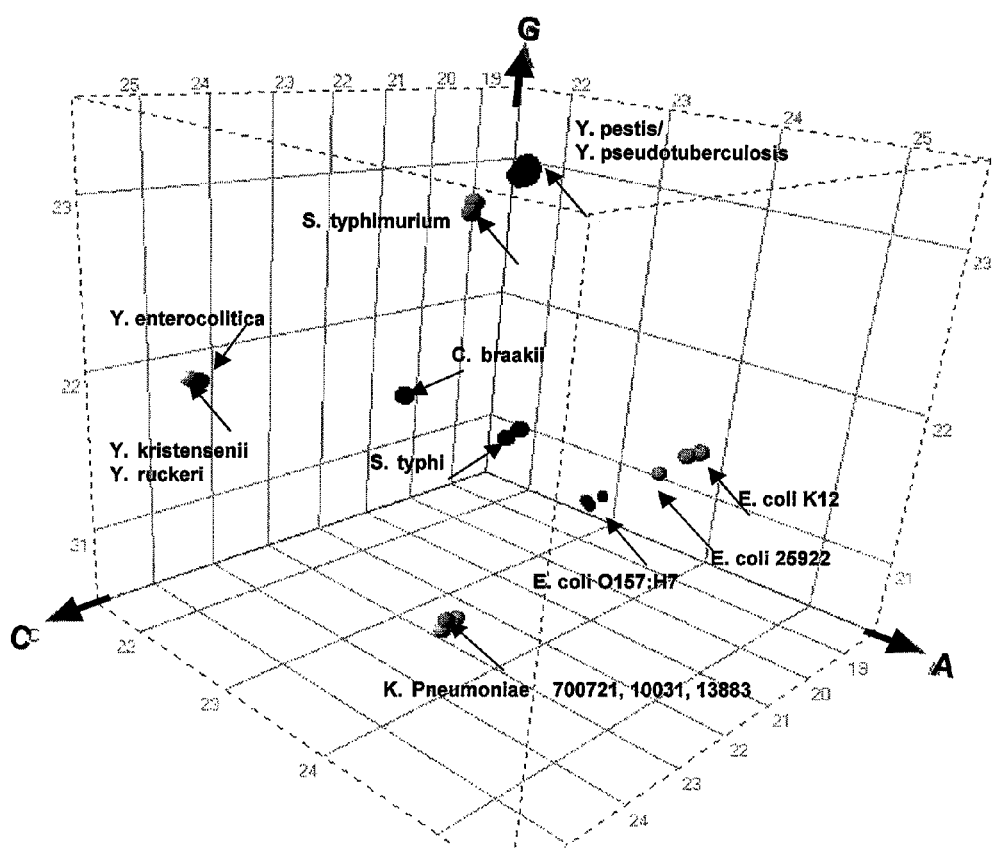
FIG. 19 shows resolution of enterobacteriae members with primers targeting RNA polymerase B (rpoB). A single pair of primers targeting a hyper-variable region within rpoB was sufficient to resolve most members of this group at the genus level (*Salmonella* from *Escherichia* from *Yersinia*) as well as the species/strain level (*E. coli* K12 from O157). All organisms with the exception of *Y. pestis* were tested in the lab and the measured base counts (shown with arrow) matched the predictions in every case.

An example of the use of primers directed to regions of RNA polymerase B (rpoB) is shown in FIG. 19. This gene has the potential to provide broad priming and resolving capabilities. A pair of primers directed against a conserved region of rpoB provided distinct base composition signatures that helped resolve the tight enterobacteriae cluster. Joint probability estimates of the signatures from each of the primers resulted in the identification of a single organism that matched the identity of the test sample. Therefore a combination of a small number of primers that amplify selected regions of the 16S ribosomal RNA gene and a few additional primers that amplify selected regions of protein encoding genes provide sufficient information to detect and identify all bacterial pathogens.

Example 16

Detection of *Staphylococcus aureus* in Blood Samples

Figure 20:
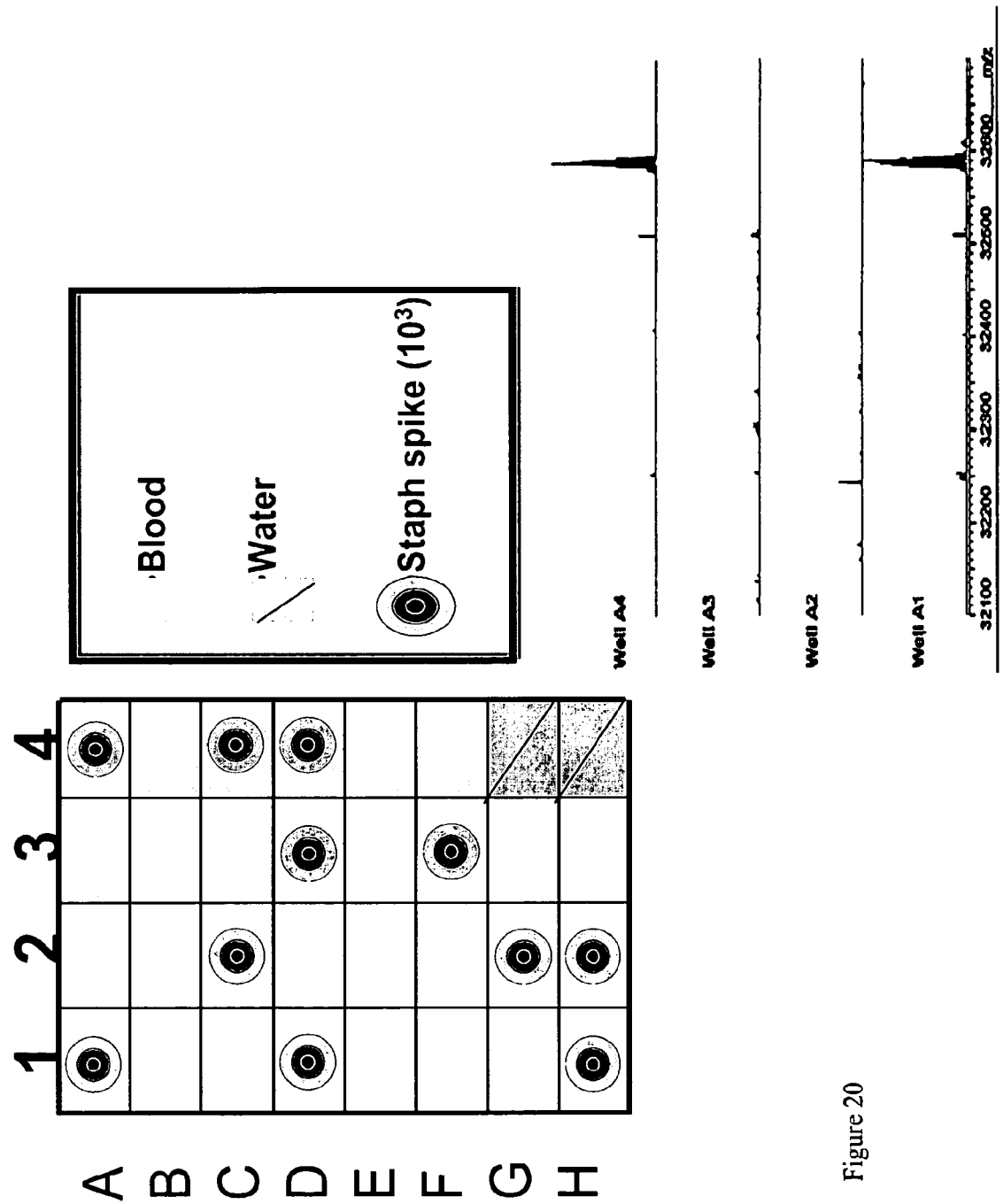
FIG. 20 shows detection of *S. aureus* in blood. Spectra on the right indicate signals corresponding to *S. aureus* detection in spiked wells A1 and A4 with no detection in control wells A2 and A3.

Blood samples in an analysis plate were spiked with genomic DNA equivalent of $10^3$ organisms/ml of *Staphylococcus aureus*. A single set of 16S rRNA primers was used for amplification. Following PCR, all samples were desalted, concentrated, and analyzed by Fourier Transform Ion Cyclotron Resonance (FTICR) mass spectrometry. In each of the spiked wells, strong signals were detected which are consistent with the expected BCS of the *S. aureus* amplicon (FIG. 20). Furthermore, there was no robotic carryover or contamination in any of the blood only or water blank wells. Methods similar to this one will be applied for other clinically relevant samples including, but not limited to: urine and throat or nasal swabs.

Example 17

Detection and Serotyping of Viruses

The virus detection capability of the present invention was demonstrated in collaboration with Naval health officers using adenoviruses as an example.

All available genomic sequences for human adenoviruses available in public databases were surveyed. The hexon gene was identified as a candidate likely to have broad specificity across all serotypes. Four primer pairs were selected from a group of primers designed to yield broad coverage across the majority of the adenoviral strain types (Table 9) wherein Tp=5'propynylated uridine and Cp=5'propynylated cytidine.

TABLE 9

Intelligent Primer Pairs for Serotyping of Adenoviruses

| Primer Pair Name | Forward Primer Sequence | Forward SEQ ID NO: | Reverse Primer Sequence | Reverse SEQ ID NO: |
|---|---|---|---|---|
| HEX_HAD7 + 4 + 21_934_995 | AGACCCAATTACATTGGCTT | 286 | CCAGTGCTGTTGTAGTACAT | 287 |
| HEX_HAD7 + 4 + 21_976_1050 | ATGTACTACAACAGTACTGG | 288 | CAAGTCAACCACAGCATTCA | 289 |
| HEX_HAD7 + 4 + 21_970_1059 | GGGCTTATGTACTACAACAG | 290 | TCTGTCTTGCAAGTCAACCAC | 291 |
| HEX_HAD7 + 3_771_827 | GGAATTTTTGATGGTAGAGA | 292 | TAAAGCACAATTTCAGGCG | 293 |
| HEX_HAD4 + 16_746_848 | TAGATCTGGCTTTCTTTGAC | 294 | ATATGAGTATCTGGAGTCTGC | 295 |
| HEX_HAD7_509_578 | GGAAAGACATTACTGCAGACA | 296 | CCAACTTGAGGCTCTGGCTG | 297 |
| HEX_HAD4_1216_1289 | ACAGACACTTACCAGGGTG | 298 | ACTGTGGTGTCATCTTTGTC | 299 |
| HEX_HAD21_515_567 | TCACTAAAGACAAAGGTCTTCC | 300 | GGCTTCGCCGTCTGTAATTTC | 301 |
| HEX_HAD_1342_1469 | CGGATCCAAGCTAATCTTTGG | 302 | GGTATGTACTCATAGGTGTTGGTG | 303 |
| HEX_HAD7 + 4 + 21_934_995P | AGACpCpCAATTpACpATpTGGCTT | 304 | CpCpAGTGCTGTpTpGTAGTACAT | 305 |
| HEX_HAD7 + 4 + 21_976_1050P | ATpGTpACTpACAACAGTACpTpGG | 306 | CAAGTpCpAACCACAGCATpTpCA | 307 |
| HEX_HAD7 + 4 + 21_970_1059P | GGGCpTpTATpGTpACTACAACpAG | 308 | TCTGTpCpTTGCAAGTpCpAACCAC | 309 |
| HEX_HAD7 + 3_771_827P | GGAATTpTpTpTpTGATGGTAGAGA | 310 | TAAAGCACAATpTpTpCpAGGCG | 311 |
| HEX_HAD4 + 16_746_848P | TAGATCTGGCTpTpTpCpTTTGAC | 312 | ATATGAGTATpCpTpGGAGTpCpTGC | 313 |
| HEX_HAD_1342_1469P | CGGATpCCAAGCpTAATCpTpTGG | 314 | GGTATGTACTCATAGGTGTpTpGGTG | 315 |
| HEX_HAD7 + 21 + 3_931_1645 | AACAGACCCAATTACATTGGCTT | 316 | GAGGCACTTGTATGTGGAAAGG | 317 |
| HEX_HAD4 + 2_925_1469 | ATGCCTAACAGACCCAATTACAT | 318 | TTCATGTAGTCGTAGGTGTTGG | 319 |

TABLE 9-continued

Intelligent Primer Pairs for Serotyping of Adenoviruses

| Primer Pair Name | Forward Primer Sequence | Forward SEQ ID NO: | Reverse Primer Sequence | Reverse SEQ ID NO: |
|---|---|---|---|---|
| HEX_HAD7 + 21 + 3_384_953 | CGCGCCTAATACATCTCACTGCAT | 320 | AAGCCAATGTAATTGGGTCTGTT | 321 |
| HEX_HAD4 + 2_345_947 | CTACTCTGGCACTGCCTACAAC | 322 | ATGTAATTGGGTCTGTTAGGCAT | 323 |
| HEX_HAD2_772_865 | CAATCCGTTCTGGTTCCGGATGAA | 324 | CTTGCCGGTCGTTCAAAGAGGTAG | 325 |
| HEX_HAD7 + 4 + 21_73_179 | AGTCCGGGTCTGGTGCAG | 326 | CGGTCGGTGGTCACATC | 327 |
| HEX_HAD7 + 4 + 21_1_54 | ATGGCCACCCCATCGATG | 328 | CTGTCCGGCGATGTGCATG | 329 |
| HEX_HAD7 + 4 + 21_1612_1718 | GGTCGTTATGTGCCTTTCCACAT | 330 | TCCTTTCTGAAGTTCCACTCATAGG | 331 |
| HEX_HAD7 + 4 + 21_2276_2368 | ACAACATTGGCTACCAGGGCTT | 332 | CCTGCCTGCTCATAGGCTGGAAGTT | 333 |

These primers also served to clearly distinguish those strains responsible for most disease (types 3, 4, 7 and 21) from all others. DNA isolated from field samples known to contain adenoviruses were tested using the hexon gene PCR primers, which provided unambiguous strain identification for all samples. A single sample was found to contain a mixture of two viral DNAs belonging to strains 7 and 21.

Figure 21:
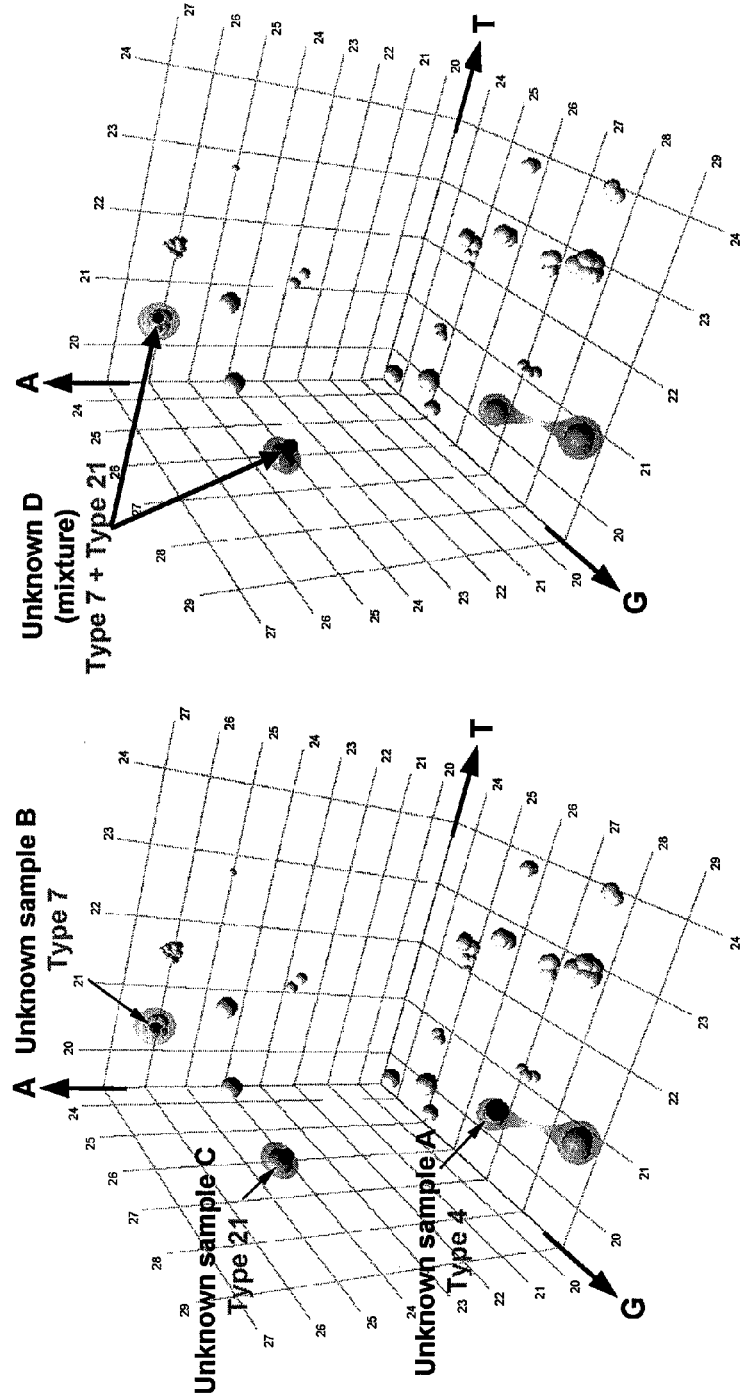
FIG. 21 shows a representative base composition distribution of human adenovirus strain types for a single primer pair region on the hexon gene. The circles represent different adenovirus sequences in our database that were used for primer design. Measurement of masses and base counts for each of the unknown samples A, B, C and D matched one or more of the known groups of adenoviruses.

Test results (FIG. 21) showed perfect concordance between predicted and observed base composition signatures for each of these samples. Classical serotyping results confirmed each of these observations. Processing of viral samples directly from collection material such as throat swabs rather than from isolated DNA, will result in a significant increase in throughput, eliminating the need for virus culture.

Example 18

Broad Rapid Detection and Strain Typing of Respiratory Pathogens for Epidemic Surveillance Genome preparation: Genomic materials from culture samples or swabs were prepared using a modified robotic protocol using DNeasy™ 96 Tissue Kit, Qiagen). Cultures of *Streptococcus pyogenes* were pelleted and transferred to a 1.5 mL tube containing 0.45 g of 0.7 mm Zirconia beads (Biospec Products, Inc.). Cells were lysed by shaking for 10 minutes at a speed of 19 l/s using a MM300 Vibration Mill (Retsch, Germany). The samples were centrifuged for 5 min and the supernatants transferred to deep well blocks and processed using the manufacture's protocol and a Qiagen 8000 BioRobot.

PCR: PCR reactions were assembled using a Packard MPII liquid handling platform and were performed in 50 µL volume using 1.8 units each of Platinum Taq (Invitrogen) and Hotstart PFU Turbo (Stratagene) polymerases. Cycling was performed on a DNA Engine Dyad (MJ Research) with cycling conditions consisting of an initial 2 min at 95° C. followed by 45 cycles of 20 s at 95° C., 15 s at 58° C., and 15 s at 72° C.

Broad-range primers: PCR primer design for base composition analysis from precise mass measurements is constrained by an upper limit where ionization and accurate deconvolution can be achieved. Currently, this limit is approximately 140 base pairs. Primers designed to broadly conserved regions of bacterial ribosomal RNAs (16 and 23S) and the gene encoding ribosomal protein L3 (rpoC) are shown in Table 10.

TABLE 10

| Target Gene | Direction | Primer | SEQ ID NO | Length of Amplicon |
|---|---|---|---|---|
| 16S_1 | F | GGATTAGAGACCCTGGTAGTCC | 334 | 116 |
| 16S_1 | R | GGCCGTACTCCCCAGGCG | 335 | 116 |
| 16S_2 | F | TTCGATGCAACGCGAAGAACCT | 336 | 115 |
| 16S_2 | R | ACGAGCTGACGACAGCCATG | 337 | 115 |
| 23S | F | TCTGTCCCTAGTACGAGAGGACCGG | 338 | 118 |
| 23S | R | TGCTTAGATGCTTTCAGC | 339 | 118 |
| rpoC | F | CTGGCAGGTATGCGTGGTCTGATG | 340 | 121 |
| rpoC | R | CGCACCGTGGGTTGAGATGAAGTAC | 341 | 121 |

Emm-typing primers: The allelic profile of a GAS strain by Multilocus Sequencing Technique (MLST) can be obtained by sequencing the internal fragments of seven housekeeping genes. The nucleotide sequences for each of these housekeeping genes, for 212 isolates of GAS (78 distinct emm types), are available (www.mlst.net). This corresponds to one hundred different allelic profiles or unique sequence types, referred to by Enright et al. as ST1-ST100 (Enright et al., Infection and Immunity, 2001, 69, 2416-2427). For each sequence type, we created a virtual transcript by concatenating sequences appropriate to their allelic profile from each of the seven genes. MLST primers were designed using these sequences and were constrained to be within each gene loci. Twenty-four primer pairs were initially designed and tested against the sequenced GAS strain 700294. A final subset of six primer pairs Table 11 was chosen based on a theoretical calculation of minimal number of primer pairs that maximized resolution of between emm types.

TABLE 11

Drill-Down Primer Pairs Used in Determining emm-type

| Target Gene | Direction | Primer | SEQ ID NO | Length of Amplicon |
|---|---|---|---|---|
| gki | F | GGGGATTCAGCCATCAAAGCAGCTATTGAC | 342 | 116 |
| gki | R | CCAACCTTTTCCACAACAGAATCAGC | 343 | 116 |
| gtr | F | CCTTACTTCGAACTATGAATCTTTTGGAAG | 344 | 115 |
| gtr | R | CCCATTTTTCACGCATGCTGAAAATATC | 345 | 115 |
| murI | F | CGCAAAAAAATCCAGCTATTAGC | 346 | 118 |
| murI | R | AAACTATTTTTTAGCTATACTCGAACAC | 347 | 118 |
| mutS | F | ATGATTACAATTCAAGAAGGTCGTCACGC | 348 | 121 |
| mutS | R | TTGGACCTGTAATCAGCTGAATACTGG | 349 | 121 |
| xpt | F | GATGACTTTTTAGCTAATGGTCAGGCAGC | 350 | 122 |
| xpt | R | AATCGACGACCATCTTGGAAAGATTTCTC | 351 | 122 |
| yqiL | F | GCTTCAGGAATCAATGATGGAGCAG | 352 | 119 |
| yqiL | R | GGGTCTACACCTGCACTTGCATAAC | 353 | 119 |

Microbiology: GAS isolates were identified from swabs on the basis of colony morphology and beta-hemolysis on blood agar plates, gram stain characteristics, susceptibility to bacitracin, and positive latex agglutination reactivity with group A-specific antiserum.

Sequencing: Bacterial genomic DNA samples of all isolates were extracted from freshly grown GAS strains by using QIAamp DNA Blood Mini Kit (Qiagen, Valencia, Calif.) according to the procedures described by the manufacture. Group A streptococcal cells were subjected to PCR and sequence analysis using emm-gene specific PCR as previously described (Beall et al., J. Clin. Micro., 1996, 34, 953-958; and Facklam et al., Emerg. Infect. Dis., 1999, 5, 247-253). Homology searches on DNA sequences were conducted against known emm sequences present in (www.cdc.gov/ncidod/biotech/infotech_hp.html). For MLST analysis, internal fragments of seven housekeeping genes, were amplified by PCR and analyzed as previously described (Enright et al., Infection and Immunity 2001, 69, 2416-2427). The emm-type was determined from comparison to the MLST database.

Broad Range Survey/Drill-Down Process (100): For *Streptococcus pyogenes*, the objective was the identification of a signature of the virulent epidemic strain and determination of its emm-type. Emm-type information is useful both for treatment considerations and epidemic surveillance. A total of 51 throat swabs were taken both from healthy recruits and from hospitalized patients in December 2002, during the peak of a GAS outbreak at a military training camp. Twenty-seven additional isolates from previous infections ascribed to GAS were also examined. Initially, isolated colonies were examined both from throat culture samples and throat swabs directly without the culture step. The latter path can be completed within 6-12 hours providing information on a significant number of samples rapidly enough to be useful in managing an ongoing epidemic.

Figure 22:
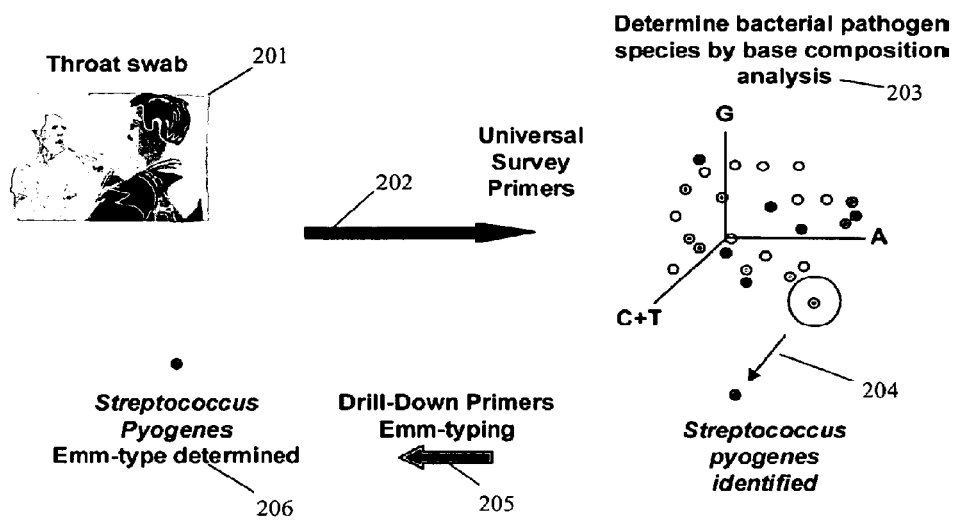
FIG. 22 shows a representative broad range survey/drill-down process as applied to emm-typing of *streptococcus pyogenes* (Group A *Streptococcus*: GAS). Genetic material is extracted (201) and amplified using broad range survey primers (202). The amplification products are analyzed (203) to determine the presence and identity of bioagents at the species level. If *Streptococcus pyogenes* is detected (204), the emm-typing "drill-down" primers are used to reexamine the extract to identify the emm-type of the sample (205). Different sets of drill down primers can be employed to determine a subspecies characteristic for various strains of various bioagents (206).

The process of broad range survey/drill-down (200) is shown in FIG. 22. A clinical sample such as a throat swab is first obtained from an individual (201). Broad range survey primers are used to obtain amplification products from the clinical sample (202) which are analyzed to determine a BCS (203) from which a species is identified (204). Drill-down primers are then employed to obtain PCR products (205) from which specific information is obtained about the species (such as Emm-type) (206).

Broad Range Survey Priming: Genomic regions targeted by the broad range survey primers were selected for their ability to allow amplification of virtually all known species of bacteria and for their capability to distinguish bacterial species from each other by base composition analysis. Initially, four broad-range PCR target sites were selected and the primers were synthesized and tested. The targets included universally conserved regions of 16S and 23S rRNA, and the gene encoding ribosomal protein L3 (rpoC).

Figure 23:
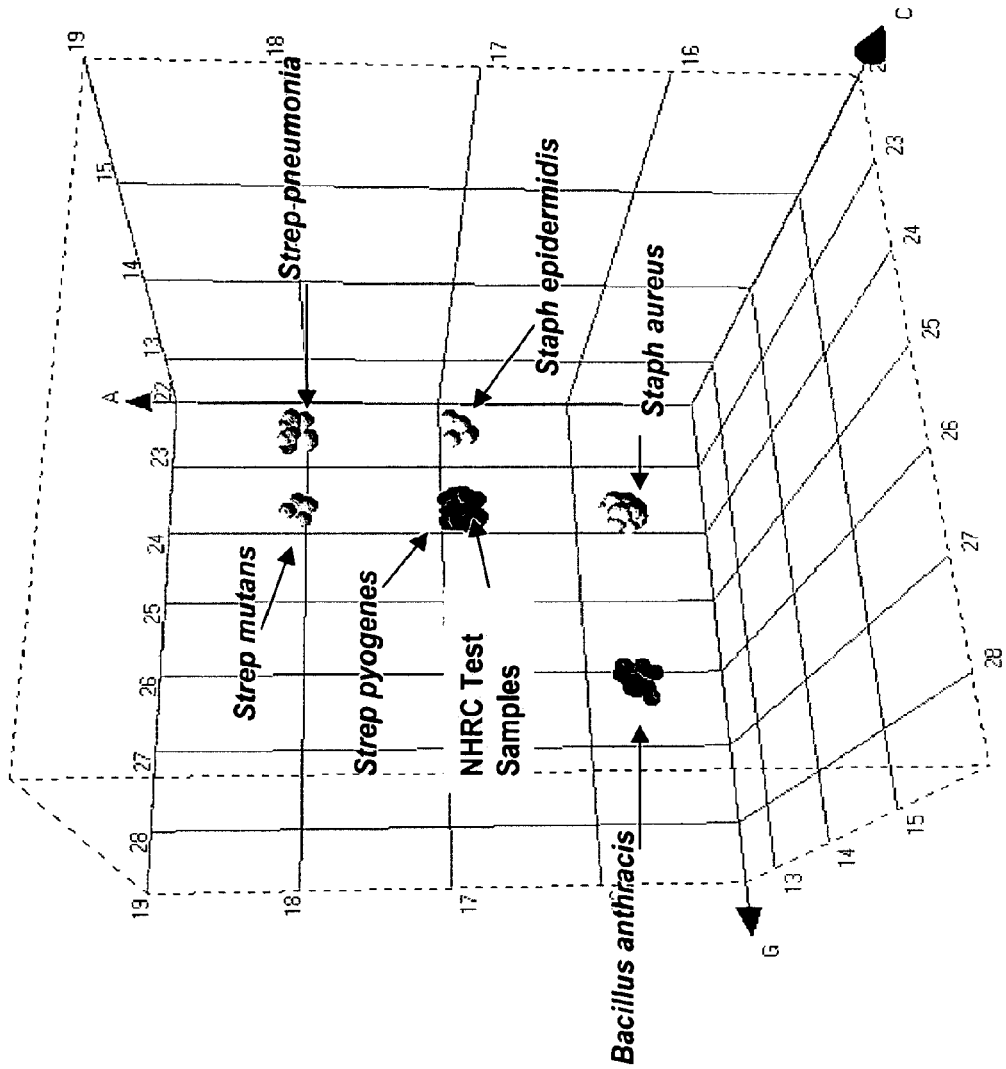
FIG. 23 shows a representative base composition distribution of bioagents detected in throat swabs from military personnel using a broad range primer pair directed to 16S rRNA.

While there was no special consideration of *Streptococcus pyogenes* in the selection of the broad range survey primers (which were optimized for distinguishing all important pathogens from each other), analysis of genomic sequences showed that the base compositions of these regions distinguished *Streptococcus pyogenes* from other respiratory pathogens and normal flora, including closely related species of streptococci, staphylococci, and bacilli (FIG. 23).

Drill Down Priming (Emm-Typing). In order to obtain strain-specific information about the epidemic, a strategy was designed to measure the base compositions of a set of fast clock target genes to generate strain-specific signatures and simultaneously correlate with emm-types. In classic MLST analysis, internal fragments of seven housekeeping genes (gki, gtr, murI, mutS, recP, xpt, yqiL) are amplified, sequenced and compared to a database of previously studied isolates whose emm-types have been determined (Horner et al. Fundamental and Applied Toxicology, 1997, 36, 147). Since the analysis enabled by the present embodiment of the present invention provides base composition data rather than sequence data, the challenge was to identify the target regions that provide the highest resolution of species and least ambiguous emm-classification. The data set from Table 2 of Enright et al. (Enright et al. Infection and Immunity, 2001, 69, 2416-2427) to bioinformatically construct an alignment of concatenated alleles of the seven housekeeping genes from each of 212 previously emm-typed strains, of which 101 were unique sequences that represented 75 distinct emm-types. This alignment was then analyzed to determine the number and location of the optimal primer pairs that would maximize strain discrimination strictly on base composition data.

Figure 24:
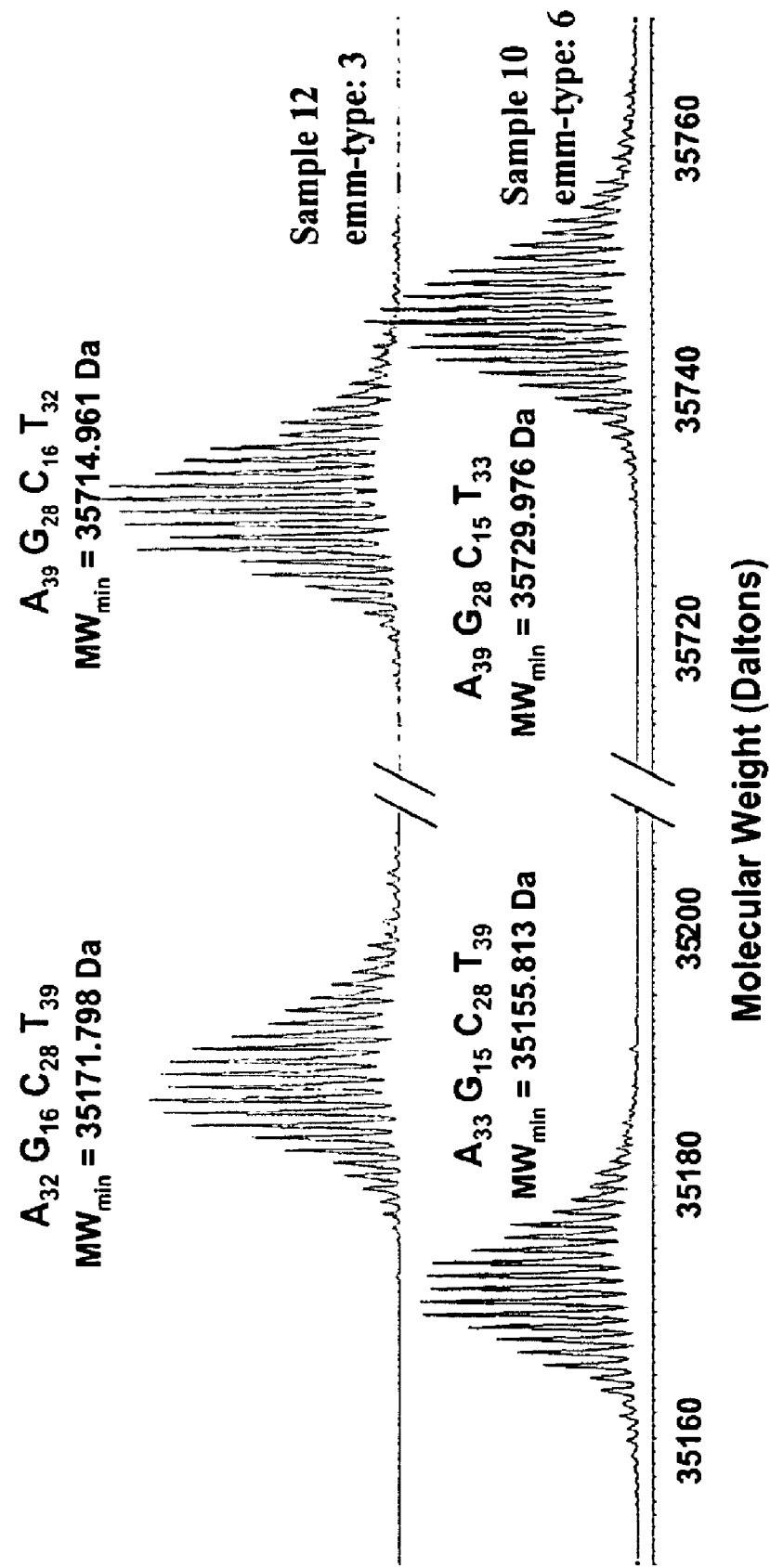
FIG. 24 shows a representative deconvoluted ESI-FTICR spectra of the PCR products produced by the gtr primer for samples 12 (top) and 10 (bottom) corresponding to emm types 3 and 6, respectively. Accurate mass measurements were obtained by using an internal mass standard and post-calibrating each spectrum; the experimental mass measurement uncertainty on each strand is +0.035 Daltons (1 ppm). Unambiguous base compositions of the amplicons were determined by calculating all putative base compositions of each stand within the measured mass (and measured mass uncertainty) and selecting complementary pairs within the mass measurement uncertainty. In all cases there was only one base composition within 25 ppm. The measured mass difference of 15.985 Da between the strands shown on the left is in excellent agreement with the theoretical mass difference of 15.994 Da expected for an A to G substitution.

An example of assignment of BCSs of PCR products is shown in FIG. 24 where PCR products obtained using the gtr primer (a drill-down emm-typing primer) from two different swab samples were analyzed (sample 12—top and sample 10—bottom). The deconvoluted ESI-FCTIR spectra provide accurate mass measurements of both strands of the PCR products, from which a series of candidate BCSs were calculated from the measured mass (and within the measured mass uncertainty). The identification of complementary candidate BCSs from each strand provides a means for unambiguous assignment of the BCS of the PCR product. BCSs and molecular masses for each strand of the PCR product from the two different samples are also shown in FIG. 24. In this case, the determination of BCSs for the two samples resulted in the identification of the emm-type of *Streptococcus pyogenes*—sample 12 was identified as emm-type 3 and sample 10 was identified as emm-type 6.

Figure 25:
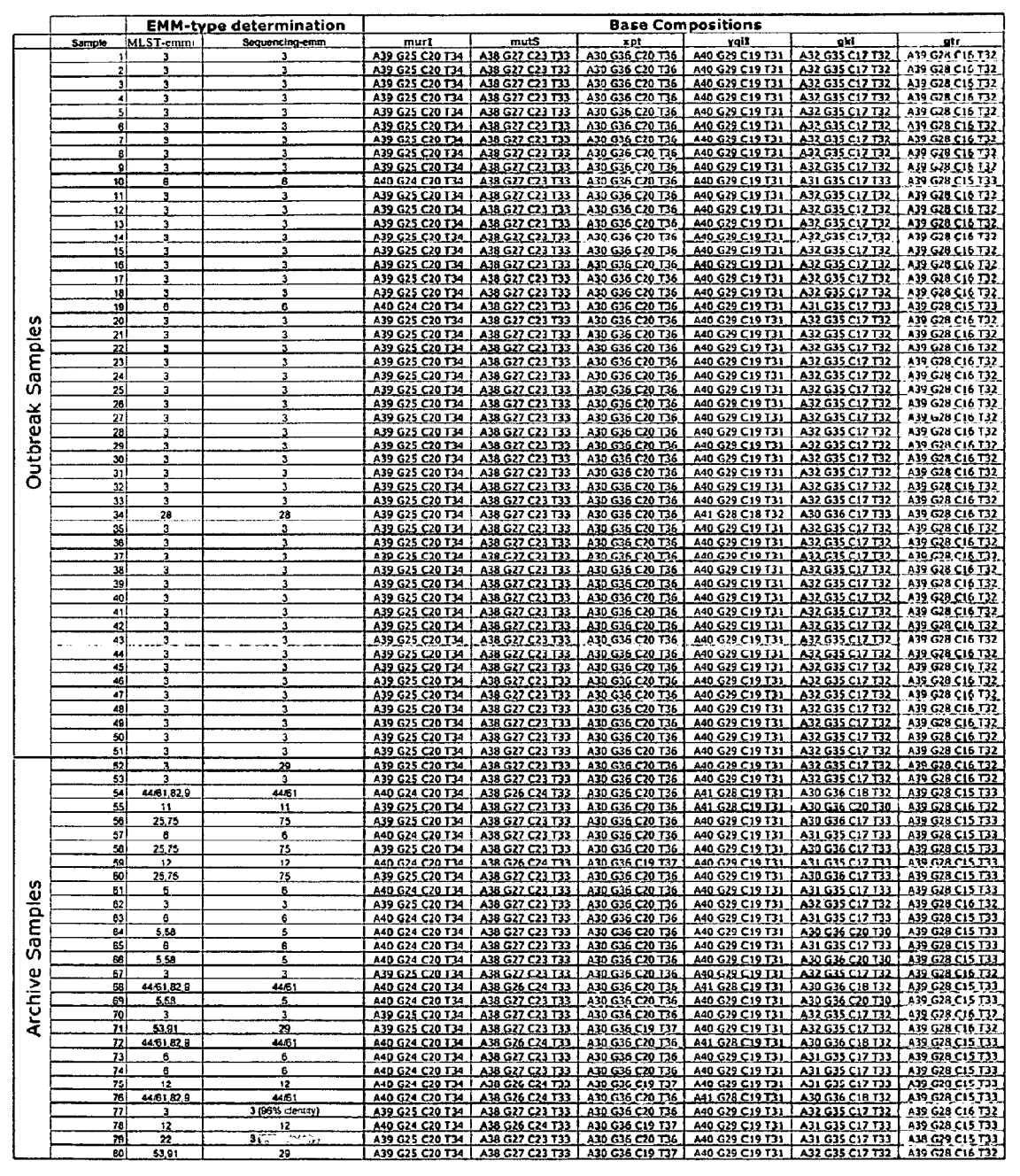

The results of the composition analysis using the six primer pairs, 5'-emm gene sequencing and MLST gene sequencing method for the GAS epidemic at a military training facility are compared in FIG. 25. The base composition results for the six primer pairs showed a perfect concordance with 5'-emm gene sequencing and MLST sequencing methods. Of the 51 samples taken during the peak of the epidemic, all but three had identical compositions and corresponded to emm-type 3. The three outliers, all from healthy individuals, probably represent non-epidemic strains harbored by asymptomatic carriers. Samples 52-80, which were archived from previous infections from Marines at other naval training facilities, showed a much greater heterogeneity of composition signatures and emm-types.

Example 19

Base Composition Probability Clouds

FIG. 18 illustrates the concept of base composition probability clouds via a pseudo-four dimensional plot of base compositions of enterobacteria including *Y. pestis, Y. psuedotuberculosis, S. typhimurium, S. typhi, Y. enterocolitica, E. coli* K12, and *E. coli* O157:H7. In the plot of FIG. 18, A, C and G compositions correspond to the x, y and z axes respectively whereas T compositions are represented by the size of the sphere at the junction of the x, y and z coordinates. There is no absolute requirement for having a particular nucleobase composition associated with a particular axis. For example, a plot could be designed wherein G, T and C compositions correspond to the x, y and z axes respectively whereas the A composition corresponds to the size of the sphere at the junction of the x, y and z coordinates. Furthermore, a different representation can be made of the "pseudo fourth" dimension i.e.: other than the size of the sphere at junction of the x, y and z coordinates. For example, a symbol having vector information such as an arrow or a cone can be rotated at an angle that varies proportionally with the composition of the nucleobase corresponding to the pseudo fourth dimension. The choice of axes and pseudo fourth dimensional representation is typically made with the aim of optimal visualization of the data being presented.

A similar base composition probability cloud analysis has been presented for a series of viruses in U.S. provisional patent application Ser. No. 60/431,319, which is commonly owned and incorporated herein by reference in its entirety. In this base composition probability cloud analysis, the closely related Dengue virus types 1-4 are clearly distinguishable from each other. This example is indicative of a challenging scenario for species identification based on BCS analysis because RNA viruses have a high mutation rate, it would be expected to be difficult to resolve closely related species. However, as this example illustrates, BCS analysis, aided by base composition probability cloud analysis is capable of resolution of closely related viral species.

A base composition probability cloud can also be represented as a three dimensional plot instead of a pseudo-four dimensional plot. An example of such a three dimensional plot is a plot of G, A and C compositions correspond to the x, y and z axes respectively, while the composition of T is left out of the plot. Another such example is a plot where the compositions of all four nucleobases is included: G, A and C+T compositions correspond to the x, y and z axes respectively. As for the pseudo-four dimensional plots, the choice of axes for a three dimensional plot is typically made with the aim of optimal visualization of the data being presented.

Example 20

Figure 26:
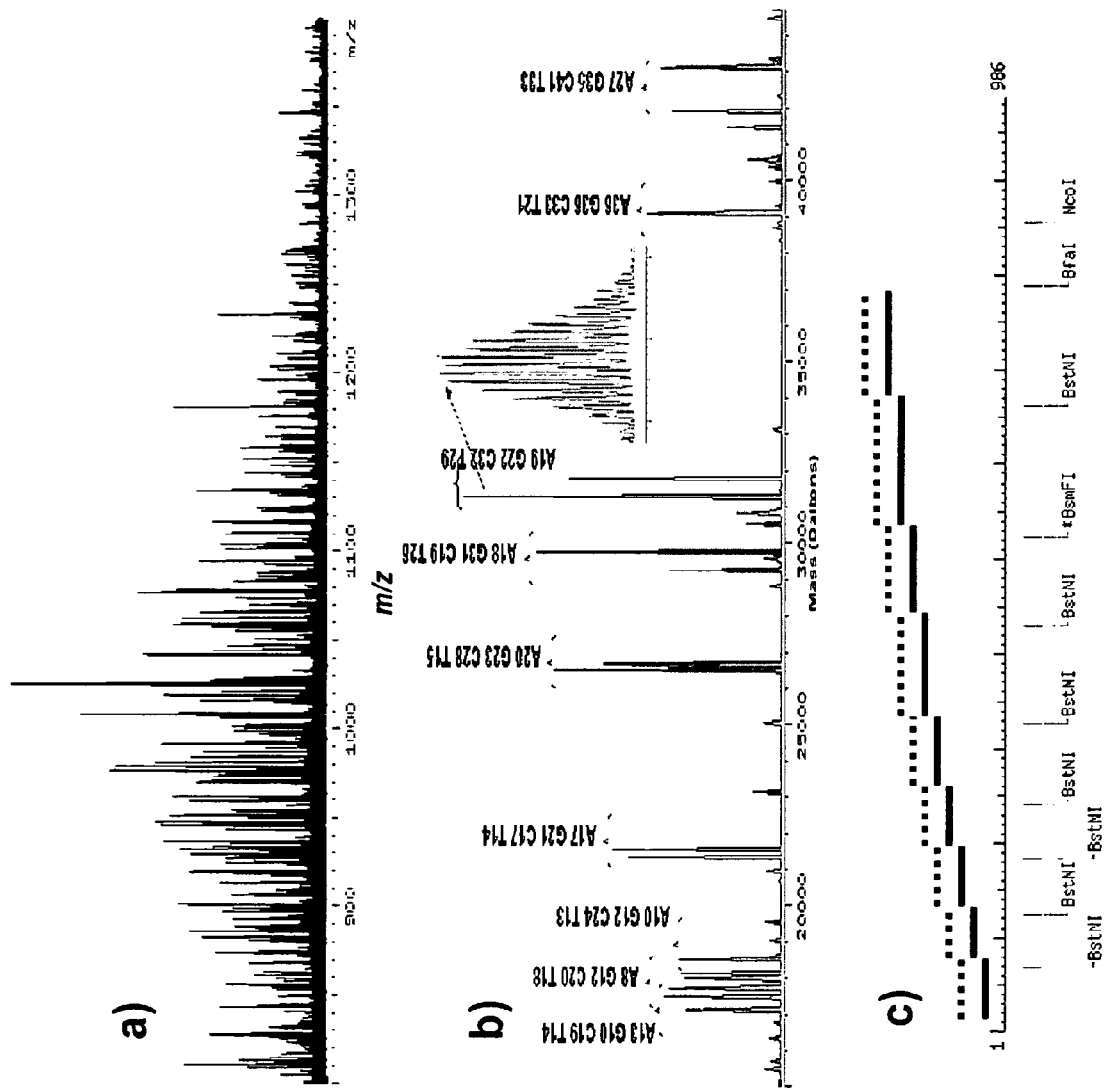
FIG. 26 shows: a) a representative ESI-FTICR mass spectrum of a restriction digest of a 986 bp region of the 16S ribosomal gene from *E. coli* K 12 digested with a mixture of BstNI, BsmFI, BfaI, and NcoI; b) a deconvoluted representation (neutral mass) of the above spectrum showing the base compositions derived from accurate mass measurements of each fragment; and c) a representative reconstructed restriction map showing complete base composition coverage for nucleotides 1-856. The Nco1 did not cut.

Biochemical Processing of Large Amplification Products for Analysis by Mass Spectrometry In the example illustrated in FIG. 26, a primer pair which amplifies a 986 bp region of the 16S ribosomal gene in *E. coli* (K12) was digested with a mixture of 4 restriction enzymes: BstN1, BsmF1, Bfa1, and Nco1. FIG. 26(*a*) illustrates the complexity of the resulting ESI-FTICR mass spectrum that contains multiple charge states of multiple restriction fragments. Upon mass deconvolution to neutral mass, the spectrum is significantly simplified and discrete oligonucleotide pairs are evident (FIG. 26*b*). When base compositions are derived from the masses of the restriction fragments, perfect agreement is observed for the known sequence of nucleotides 1-856 (FIG. 26*c*); the batch of Nco1 enzyme used in this experiment was inactive and resulted in a missed cleavage site and a 197-mer fragment went undetected as it is outside the mass range of the mass spectrometer under the conditions employed. Interestingly however, both a forward and reverse strand were detected for each fragment measured (solid and dotted lines in, respectively) within 2 ppm of the predicted molecular weights resulting in unambiguous determination of the base composition of 788 nucleotides of the 985 nucleotides in the amplicon. The coverage map offers redundant coverage as both 5' to 3' and 3' to 5' fragments are detected for fragments covering the first 856 nucleotides of the amplicon.

This approach is in many ways analogous to those widely used in MS-based proteomics studies in which large intact proteins are digested with trypsin, or other proteolytic enzyme(s), and the identity of the protein is derived by comparing the measured masses of the tryptic peptides with theoretical digests. A unique feature of this approach is that the precise mass measurements of the complementary strands of each digest product allow one to derive a de novo base composition for each fragment, which can in turn be "stitched together" to derive a complete base composition for the larger amplicon. An important distinction between this approach and a gel-based restriction mapping strategy is that, in addition to determination of the length of each fragment, an unambiguous base composition of each restriction fragment is derived. Thus, a single base substitution within a fragment (which would not be resolved on a gel) is readily observed using this approach. Because this study was performed on a 7 Tesla ESI-FTICR mass spectrometer, better than 2 ppm mass measurement accuracy was obtained for all fragments. Interestingly, calculation of the mass measurement accuracy required to derive unambiguous base compositions from the complementary fragments indicates that the highest mass measurement accuracy actually required is only 15 ppm for the 139 bp fragment (nucleotides 525-663). Most of the fragments were in the 50-70 bp size-range which would require mass accuracy of only ~50 ppm for unambiguous base composition determination. This level of performance is achievable on other more compact, less expensive MS platforms such as the ESI-TOF suggesting that the methods developed here could be widely deployed in a variety of diagnostic and human forensic arenas.

This example illustrates an alternative approach to derive base compositions from larger PCR products. Because the amplicons of interest cover many strain variants, for some of which complete sequences are not known, each amplicon can be digested under several different enzymatic conditions to ensure that a diagnostically informative region of the amplicon is not obscured by a "blind spot" which arises from a mutation in a restriction site. The extent of redundancy required to confidently map the base composition of amplicons from different markers, and determine which set of restriction enzymes should be employed and how they are most effectively used as mixtures can be determined. These parameters will be dictated by the extent to which the area of interest is conserved across the amplified region, the compatibility of the various restriction enzymes with respect to digestion protocol (buffer, temperature, time) and the degree of coverage required to discriminate one amplicon from another.

of DNA-dependent RNA polymerases A and B (DdRpA and DdRpB). These intelligent primers designed to identify members of the viral genus *Orthopoxvirus* are shown in Table 12 wherein Tp=5'propynylated uridine and Cp=5'propynylated cytidine.

TABLE 12

Intelligent Primer Pairs for Identification of members of the Viral Genus *Orthopoxvirus*

| Primer Pair Name | Forward Primer Sequence | Forward SEQ ID NO: | Reverse Primer Sequence | Reverse SEQ ID NO: |
|---|---|---|---|---|
| A25L_NC001611_28_127 | GTACTGAATCCGCCTAAG | 354 | GTGAATAAAGTATCGCCCTAATA | 355 |
| A18R_NC001611_100_207 | GAAGTTGAACCGGGATCA | 356 | ATTATCGGTCGTTGTTAATGT | 357 |
| A18R_NC001611_1348_1445 | CTGTCTGTAGATAAACTAGGATT | 358 | CGTTCTTCTCTGGAGGAT | 359 |
| E9L_N0001611_1119_1222 | CGATACTACGGACGC | 360 | CTTTATGAATTACTTTACATAT | 361 |
| K8R_NC001611_221_311 | CTCCTCCATCACTAGGAA | 362 | CTATAACATTCAAAGCTTATTG | 363 |
| A24R_NC001611_795_878 | CGCGATAATAGATAGTGCTAAAC | 364 | GCTTCCACCAGGTCATTAA | 365 |
| A25L_NC001611_28_127P | GTACpTpGAATpCpCpGCpCpTAAG | 366 | GTGAATAAAGTATpCpGCpCpCpTpAATA | 367 |
| A18R_NC001611_100_207P | GAAGTpTpGAACpCpGGGATCA | 368 | ATTATCGGTpCpGTpTpGTpTpAATGT | 369 |
| A18R_NC001611_1348_1445P | CTGTpCpTpGTAGATAAACpTpAGGATT | 370 | CGTTCpTpTpCpTpCpTpGGAGGAT | 371 |
| E9L_NC001611_1119_1222P | CGATACpTpACpGGACGC | 372 | CTTTATGAATpTpACpTpTpTpACATAT | 373 |
| K8R_NC001611_221_311P | CTpCpCpTpCpATCACpTpAGGAA | 374 | CTATAACATpTpCpAAAGCpTpTpATTG | 375 |
| A24R_NC001611_795_878P | CGCGATpAATpAGATAGTpGCpTpAAAC | 376 | GCTTCpCpACpCAGGTpCATpTAA | 377 |

Figure 27:
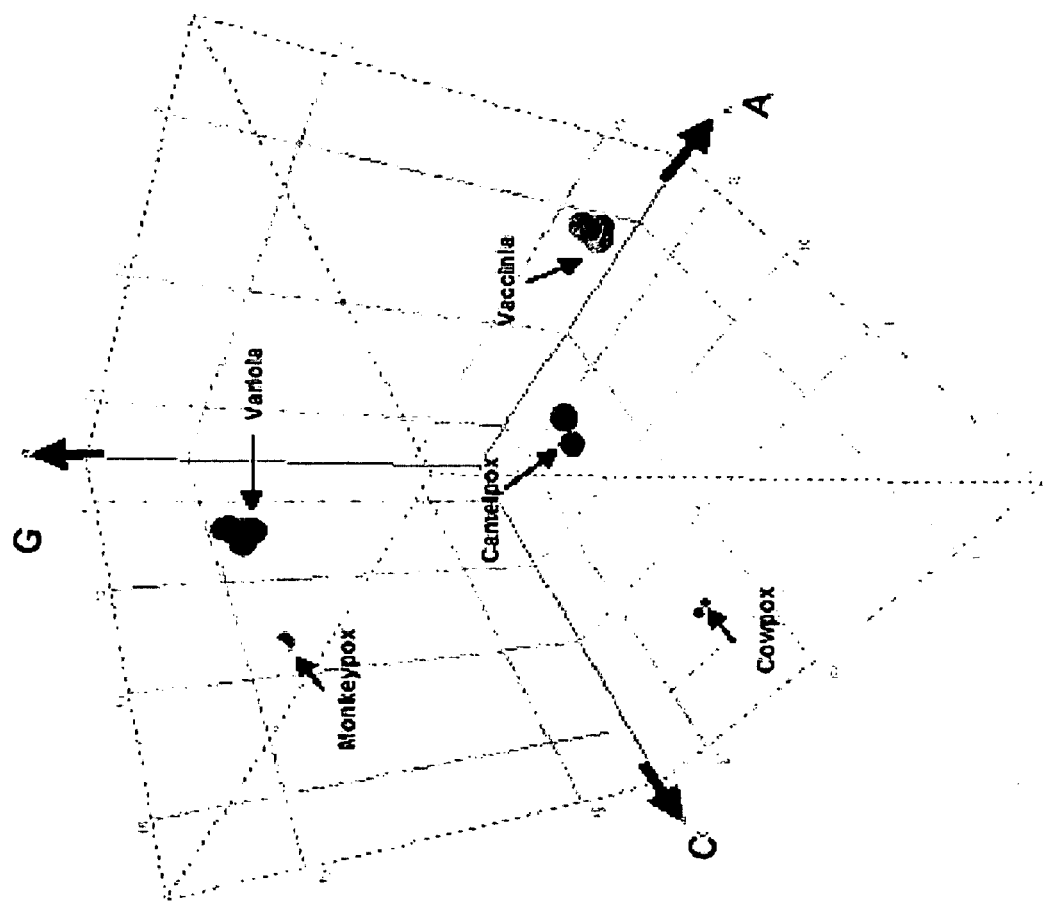
FIG. 27 shows a representative base composition distribution of poxviruses for a single primer pair region on the DNA-dependent polymerase B gene (DdDpB). The spheres represent different poxvirus sequences that were used for primer design.

As illustrated in FIG. 27, members of the *Orthopoxvirus* genus group can be identified, distinguished from one another, and distinguished from other members of the Poxvirus family using a single pair of primers designed against the DdRpB gene.

Since the primers were designed across regions of high conservation within this genus, the likelihood of missed detection due to sequence variations at these sites is minimized. Further, none of the primers is expected to amplify other viruses or any other DNA, based on the data available in GenBank. This method can be used for all families of viral threat agents and is not limited to members of the *Orthopoxvirus* genus.

Example 21

Identification of members of the Viral Genus *Orthopoxvirus*

Primer sites were identified on three essential viral genes—the DNA-dependent polymerase (DdDp), and two sub-units Example 22

Identification of Viruses that Cause Viral Hemorrhagic Fevers

In accordance with the present invention an approach of broad PCR priming across several different viral species is employed using conserved regions in the various viral genomes, amplifying a small, yet highly informative region in these organisms, and then analyzing the resultant amplicons with mass spectrometry and data analysis. These regions will be tested with live agents, or with genomic constructs thereof.

Detection of RNA viruses will necessitate a reverse transcription (RT) step prior to the PCR amplification of the TIGER reporter amplicon. To maximize throughput and yield while minimizing the handling of the samples, commercial one-step reverse transcription polymerase chain reaction (RT-PCR) kits will be evaluated for use. If necessary, a one-step RT-PCR mix using our selected DNA polymerase for the PCR portion of the reaction will be developed. To assure there is no variation in our reagent performance all new lots of enzymes, nucleotides and buffers will be individually tested prior to use.

Various modifications of the invention, in addition to those described herein, will be apparent to those skilled in the art from the foregoing description. Such modifications are also intended to fall within the scope of the appended claims. Each reference, web site, Genebank accession number, etc. cited in the present application is incorporated herein by reference in its entirety.

What is claimed is:

1. A method of differentiating two or more bioagents, comprising:

a) contacting nucleic acid from two or more bioagents with two or more oligonucleotide primers that hybridize to sequence regions of said nucleic acid from said two or more bioagents that are conserved among different bioagents, wherein said conserved sequence regions flank a variable sequence region to produce two or more amplification products;

b) determining base compositions of said two or more amplification products wherein said base compositions of said two or more amplification products comprise identification of the number, but not the nucleic acid sequence order, of A residues, C residues, T residues, G residues, U residues, analogs thereof and/or mass tag residues thereof in said two or more amplification products; and c) differentiating said two or more bioagents by comparing said determined base compositions to a database comprising a plurality of calculated or measured base compositions of amplification products from a plurality of different bioagents obtained by amplification of at least one nucleic acid gene sequence from said plurality of different bioagents using said two or more oligonucleotide primers.

2. The method of claim 1, wherein at least one of said two or more bioagents is selected from the group of bioagents consisting of a viral bioagent, a bacterial bioagent, a fungal bioagent, a protozoal bioagent, a parasitic bioagent, a mammalian bioagent, and a human bioagent.

3. The method of claim 1, wherein at least one of said two or more bioagents is selected from the group of bioagents consisting of an evolving bioagent, a mutating bioagent, a recombinant bioagent, and an engineered bioagent.

4. The method of claim 1, wherein at least one of said two or more bioagents is not previously known to exist.

5. The method of claim 1, wherein said two or more bioagents are differentiated in a sample.

6. The method of claim 5, wherein said sample is selected from the group consisting of a body fluid sample, an environmental sample, a culture media sample, a manufacturing sample, and a forensic sample.

7. The method of claim 5, wherein said sample comprises two or more bioagents of different genus, and wherein said nucleic acid from said sample is contacted with two or more oligonucleotide primers configured to differentiate two or more bioagents of different genus.

8. The method of claim 5, wherein said sample comprises two or more bioagents of different species, and wherein said nucleic acid from said sample is contacted with two or more oligonucleotide primers configured to differentiate two or more bioagents of different species.

9. The method of claim 1, further comprising purifying said nucleic acid prior to production of said amplification product.

10. The method of claim 1, further comprising modifying said nucleic acid prior to production of said two or more amplification products.

11. The method of claim 1, wherein said nucleic acid is selected from the group consisting of genomic DNA, RNA, DNA that is complementary to RNA, DNA that is synthesized from RNA, double-stranded DNA, single stranded DNA, DNA that is the product of amplification, DNA that is fragmented, nuclear DNA, mitochondrial DNA, cytoplasmic DNA and extracellular DNA.

12. The method of claim 1, wherein said two or more oligonucleotide primers are about 15-35 nucleobases in length, and wherein said two or more oligonucleotide primers comprise at least 70%, at least 80%, at least 90%, at least 95%, or at least 100% sequence identify with said conserved sequence regions.

13. The method of claim 1, wherein at least one of said two or more amplification products is 45 to 200 nucleobases in length.

14. The method of claim 1, wherein a non-templated T residue on the 5'-end of at least one of said two or more oligionucleotide primers is removed.

15. The method of claim 1, wherein at least one of said two or more oligonucleotide primers comprises a non-templated T residue on the 5'-end.

16. The method of claim 1, wherein at least one of said two or more oligonucleotide primers comprises at least one molecular mass modifying tag.

17. The method of claim 1, wherein at least one of said two or more oligonucleotide primers comprises at least one modified nucleobase.

18. The method of claim 17, wherein said modified nucleobase is 5-propynyluracil or 5-propynylcytosine.

19. The method of claim 17, wherein said modified nucleobase is a mass modified nucleobase.

20. The method of claim 19, wherein said mass modified nucleobase is 5-Iodo-C.

21. The method of claim 17, wherein said modified nucleobase is a universal nucleobase.

22. The method of claim 21, wherein said universal nucleobase is inosine.

23. The method of claim 1, wherein said two or more bioagents are differentiated at the genus, species, sub-species, strain, sub-type, or nucleotide polymorphism levels.

24. The method of claim 1, wherein said two or more oligonucleotide primers comprise multiple oligonucleotide primer sets configured for differentiation of diverse bioagents.

25. The method of claim 1, wherein said conserved sequence regions are within a gene.

26. The method of claim 1, wherein said conserved sequence regions are within a coding region of a gene.

27. The method of claim 1, wherein said conserved sequence regions are within a regulatory region of a gene.

28. The method of claim 1, wherein said variable sequence region is within a gene.

29. The method of claim 1, wherein said variable sequence region is within a coding region of a gene.

30. The method of claim 1, wherein said variable sequence region is within a regulatory region of a gene.

31. The method of claim 1, wherein said conserved sequence regions are about 10 to 100 nucleobases in length.

32. The method of claim 1, wherein said variable sequence region is about 10 to 200 nucleobases in length.

33. The method of claim 1, wherein said amplification product is produced by polymerase chain reaction.

34. The method of claim 1, further comprising purifying said amplification product.

35. The method of claim 1, wherein said base composition is determined by mass spectrometry.

36. The method of claim 35, wherein said mass spectrometry is ESI mass spectrometry.

37. The method of claim 1, wherein said comparing comprises identifying a match between said determined two or more base compositions and at least one entry within said database of base compositions from a plurality of different bioagents.

38. The method of claim 1, wherein said differentiating said two or more bioagents requires two or more oligonucleotide primer pairs.

39. The method of claim 1, wherein said database of base compositions from a plurality of different bioagents comprises base compositions of genus specific amplification products, family specific amplification products, species specific amplification products, strain specific amplification products, sub-type specific amplification products, or nucleotide polymorphism specific amplification products produced with said two or more oligonucleotide primers, wherein one or more matches between said determined base composition of said amplification product and one or more entries in said database identifies said two or more bioagents, classifies a major classification of said two or more bioagents, or differentiates between subgroups of known and unknown said two or more bioagents.

40. The method of claim 1, wherein said database of base compositions comprises base composition information for at least 3 different bioagents.

41. The method of claim 1, wherein said database of base compositions comprises base composition information for at least 4 different bioagents.

42. The method of claim 1, wherein said database of base compositions comprises base composition information for at least 8 different bioagents.

43. The method of claim 1, wherein said database of base compositions comprises base composition information for at least 19 different bioagents.

44. The method of claim 1, wherein said database of base compositions comprises base composition information for at least 30 different bioagents.

45. The method of claim 1, wherein said database of base compositions comprises at least 12 unique base compositions.

46. The method of claim 1, wherein said database of base compositions comprises at least 40 unique base compositions.

47. The method of claim 1, wherein said database of base compositions comprises base composition information for a bioagent from two or more genuses selected from the group consisting of *Acinetobacter, Aeromonas, Bacillus, Bacteroides, Bartonella, Bordetella, Borrelia, Brucella, Burkholderia, Campylobacter, Chlamydia, Chlamydophila, Clostridium, Coxiella, Enterococcus, Escherichia, Francisella, Fusobacterium, Haemophilus, Helicobacter, Klebsiella, Legionella, Leptospira, Listeria, Moraxella, Mycobacterium, Mycoplasma, Neisseria, Proteus, Pseudomonas,*

*Rhodobacter, Rickettsia, Salmonella, Shigella, Staphylococcus, Streptobacillus, Streptomyces, Treponema, Ureaplasma, Vibrio*, or *Yersinia*.

48. The method of claim 1, wherein said database of base compositions comprises base composition information for a bioagent from each of the genuses of *Acinetobacter, Aeromonas, Bacillus, Bacteroides, Bartonella, Bordetella, Borrelia, Brucella, Burkholderia, Campylobacter, Chlamydia, Chlamydophila, Clostridium, Coxiella, Enterococcus, Escherichia, Francisella, Fusobacterium, Haemophilus, Helicobacter, Klebsiella, Legionella, Leptospira, Listeria, Moraxella, Mycobacterium, Mycoplasma, Neisseria, Proteus, Pseudomonas, Rhodobacter, Rickettsia, Salmonella, Shigella, Staphylococcus, Streptobacillus, Streptomyces, Treponema, Ureaplasma, Vibrio*, or *Yersinia*.

49. The method of claim 1, wherein said database of base compositions comprises base composition information for a bioagent from two or more orders or families selected from the group consisting of Smallpox virus, Arenavirus, Bunyaviruses, Mononegavirales, Picornaviruses, Astroviruses, Calciviruses, Nidovirales, Flaviviruses, and Togaviruses.

50. The method of claim 1, wherein said database of base compositions comprises base composition information for a bioagent from each of the orders or families of Smallpox virus, Arenavirus, Bunyaviruses, Mononegavirales, Picornaviruses, Astroviruses, Calciviruses, Nidovirales, Flaviviruses, and Togaviruses.

51. The method of claim 1, wherein said base compositions in said database are associated with bioagent identity.

52. The method of claim 1, wherein said base compositions in said database are associated with bioagent geographic origin.

53. The method of claim 1, wherein said comparing step is performed by a computer.

54. The method of claim 53, wherein said computer identifies a match between said determined base composition of said amplification product and one or more entries in database of base compositions from a plurality of different bioagents with a probability algorithm.

55. The method of claim 1, wherein said database is stored on a computer.

56. The method of claim 55, wherein said computer is a local computer.

57. The method of claim 55, wherein said computer is a remote computer.

58. The method of claim 1, wherein said differentiating said two or more bioagents comprises interrogation of said database with two or more different base compositions associated with said two or more bioagents.

59. The method of claim 1, wherein said database of base compositions comprises at least 10 base compositions.

60. The method of claim 1, wherein said database of base compositions comprises at least 20 base compositions.

61. The method of claim 1, wherein said database of base compositions comprises at least 30 base compositions.

62. The method of claim 1, wherein said database of base compositions comprises at least 40 base compositions.

63. The method of claim 1, wherein said database of base compositions comprises at least 50 base compositions.

64. The method of claim 1, wherein said database of base compositions comprises at least 60 base compositions.

65. The method of claim 1, wherein said database of base compositions comprises at least 70 base compositions.

66. The method of claim 1, wherein said database of base compositions comprises at least 80 base compositions.

67. The method of claim 1, wherein said database of base compositions comprises at least 90 base compositions.

68. The method of claim 1, wherein said database of base compositions comprises at least 100 base compositions.

69. The method of claim 1, wherein said database of base compositions comprises at least 500 base compositions.

70. The method of claim 1, wherein said database of base compositions comprises at least 1000 base compositions.

71. The method of claim 1, wherein said two or more bioagents comprises at least 10, at least 20, at least 30, at least 40, at least 50, at least 60, at least 70, at least 80, at least 90, at least 100, at least 500 or at least 1000 bioagents.

72. The method of claim 1, wherein said two or more bioagents are differentiated by kingdom, phylum, class, order, family, genus, species, sub-species, strain, sub-type, or nucleotide polymorphism.

* * * * *

SEQUENCE LISTING

```
<160> NUMBER OF SEQ ID NOS: 377

<210> SEQ ID NO 1
<211> LENGTH: 1388
<212> TYPE: RNA
<213> ORGANISM: Artificial Sequence
<220> FEATURE:
<223> OTHER INFORMATION: 16S rRNA Sequence
<220> FEATURE:
<221> NAME/KEY: misc_feature
<222> LOCATION: 1-7, 15, 22-24, 36-38, 41, 42,44, 56, 59-90, 93, 97, 98,
      109, 110, 112-116, 118-120, 123-131, 134,136, 138-144, 149-155,
      161, 162, 164-177, 182-209, 212-220, 222-225, 227, 230, 231, 235,
      236, 241, 245, 246, 253, 255-257, 260, 261-263, 267, 269, 270,
      278, 279, 281, 282, 284, 291, 294, 301, 306, 310, 329, 330, 335,
      336-338, 344, 345, 347, 350, 351, 355, 356, 357, 361,363, 364,
      371, 372, 373, 376, 379, 382-386, 388, 389, 394-396, 398-405, 408,
      411-438, 442, 443, 445-451, 453, 454, 458-460, 465, 469, 491, 495,
      496, 499, 504-506, 511, 512, 514, 524, 526-528, 530, 534, 537-544,
      546-550, 552, 556-562, 565, 569-578, 580-586, 589-595, 597,
      601-606, 609, 612-617, 621-624, 629, 633, 636, 639, 643, 645, 646,
      648, 650, 654, 658-660, 669-674, 678-683, 689, 691, 693-696, 704,
      708, 712, 734, 737, 738, 744, 746-754, 756-758, 760-782, 784-786,
      791-793, 796-800, 815, 816, 823-825, 834, 845, 848, 857, 859, 864,
      869, 875, 877, 878, 884, 886, 894-898, 903-917, 920, 922-948, 955,
      961, 972, 973, 978, 990, 1005-1013, 1015, 1017, 1019, 1021-1029,
      1031, 1033, 1037-1043, 1049-1051, 1053, 1054, 1057-1059, 1069,
      1075, 1083, 1085, 1089, 1094, 1096-1099, 1104, 1110, 1111,
      1119-1123, 1127, 1128, 1130, 1132, 1133, 1136, 1138, 1139-1141,
      1143, 1144, 1146-1150, 1154, 1157, 1159-1162, 1166-1170, 1172,
      1173, 1176, 1181, 1183-1186, 1195-1198, 1200, 1205, 1206, 1210,
      1220-1222, 1227, 1229, 1231-1233, 1244, 1249, 1266-1268, 1271,
      1273, 1274, 1277-1285, 1288, 1289, 1293-1304, 1306-1311,
      1313-1322, 1324, 1326, 1329, 1330-1338, 1341, 1345-1347, 1361,
      1364, 1366-1368, 1372, 1373, 1375, 1378, 1388
<223> OTHER INFORMATION: n = A,U,C or G

<400> SEQUENCE: 1
nnnnnnnaga ggacnggcca gnnngaacgc ggcggnnngc nnanacagca agcgancgnn        60
nnnnnnnnnn nnnnnnnnnn nnnnnnnnnn agnggcnnac ggggagaann cnnnnnannn       120
ccnnnnnnnn nggnanannn nnnngaaann nnnnnaaacc nnannnnnnn nnnnnnnaaa       180
gnnnnnnnnn nnnnnnnnnn nnnnnnnnng annnnnnnnn gnnnnanagn ngggnnggaa       240
nggcnnacca agcnnngan  nnnagcngnn cgagagnng  nncngccaca nggnacgaga       300
nacggnccan acccacggga ggcagcagnn ggaannnnca aggnngnaan ncgannnagc       360 nanncgcgg  nnngangang gnnnnngnng aaannncnnn nnnnnganga nnnnnnnnnn       420
nnnnnnnnnn nnnnnnnnga cnnannnnnn nannaagnnn cggcnaacnc ggccagcagc       480
cgcggaaacg naggnngcna gcgnnncgga nnangggcga aagngnnngn aggnggnnnn       540
nnnngnnnnn gnaaannnnn nngcnaacnn nnnnnnnncn nnnnnnacnn nnnnncgag        600 nnnnnnagng gnnnnnngaa nnnnggagng ggnaancgna gananngnan gaanaccnnn       660
gcgaaggcnn nnnncggnnn nnnacgacnc nannnncgaa agcngggnag cnaacaggaa       720
```

-continued

```
gaacccggag ccangcnnaa acgngnnnnn nnnngnnngn nnnnnnnnnn nnnnnnnnnn    780
nnannnaacg nnnaannnnn ccgccgggga dacgnncgca agnnnaaacc aaangaagac    840
ggggnccngc acaagcngng gagnagggna acgangnnac gcgnanaacc accnnnnnga    900
cannnnnnnn nnnnnnngan annnnnnnnn nnnnnnnnnn nnnnnnnnac agggngcagg    960
ngcgcagccg gnnggagngg ggaagcccgn aacgagcgca acccnnnnnn nnngncnanc   1020
nnnnnnnnng ngnaccnnnn nnnacgccnn ngnnaannng gaggaaggng gggangacgc   1080
aancncagnc ccangnnnng ggcncacacn ncacaaggnn nnnacanngn gnngcnannn   1140
ngnnannnnn agcnaancnn nnaaannnnn cnnagncgga ngnnnncgca accgnnnncn   1200
gaagnnggan cgcagaacgn nnacagnang nnncgggaaa cgcncgggnc gacacaccgc   1260
ccgcannnca ngnnagnnnn nnnnnccnna agnnnnnnnn nnnncnnnnn ngnnnnnnnn   1320
nncnanggnn nnnnnnnnga ngggnnnaag cgaacaagga nccnannnga anngnggngg   1380 acaccccn                                                            1388

<210> SEQ ID NO 2
<211> LENGTH: 2654
<212> TYPE: RNA
<213> ORGANISM: Artificial Sequence
<220> FEATURE:
<223> OTHER INFORMATION: 16S rRNA Consensus Sequence
<220> FEATURE:
<221> NAME/KEY: misc_feature
<222> LOCATION: 1-4, 8-12, 16, 18-22, 31, 35-40, 43, 47, 54, 56-62, 64,
      65, 67-69, 71, 72, 74-76, 79, 80, 83, 84, 86-93, 95-99, 101,
      104-106, 108, 109, 119, 125-142, 144-171, 173-175, 178-182, 186,
      194, 198-202, 208, 214, 215, 218-221, 224, 226-229, 233, 244-246,
      248, 250, 251, 254, 256-280, 282-284, 288-292, 295, 299-307,
      309-311, 314, 316, 318, 319, 322, 325-328, 332-354, 358-360,
      362-365, 367, 370, 372, 373, 375-378, 380, 381, 385-387, 389-392,
      398-403, 407, 414-420, 425, 429, 431, 433, 434, 439, 443, 451,
      458, 463, 464, 465, 466, 467, 469, 479, 482, 483, 492-496, 498,
      500, 503-505, 507-509, 512-525, 528, 529, 533, 537, 539, 540,
      543-545, 547, 549, 552-561, 564, 567, 570-578, 580, 583, 586, 589,
      594, 599-601, 604, 605, 607, 611-613, 616-620, 622-625, 630, 635,
      637-639, 643, 646-648, 651, 652, 657, 662-666, 670, 672-676, 682,
      689-696, 703-708, 714, 715, 718-720, 722, 725, 730, 731, 733, 736,
      738, 742-744, 746, 747, 756, 757, 763-766, 770-773, 776-791, 794,
      805-814, 817-829, 832, 833, 835-842, 847, 852, 855-870, 872, 875,
      876, 878, 879, 881-883, 885, 887, 889, 892-894, 896-898, 900, 901,
      903, 908, 913, 920, 922, 923, 925-927, 932, 936, 939-946, 952,
      956, 959, 962-967, 969, 970, 972, 976-978, 983, 999, 1001, 1002,
      1008, 1009, 1015, 1022, 1023, 1025, 1028-1034, 1039, 1042, 1043,
      1045, 1047, 1052, 1056-1063, 1069-1074, 1076-1097, 1102, 1103,
      1109-1121, 1126-1132, 1134, 1135, 1137-1143, 1147-1155, 1159,
      1161, 1164, 1165, 1167, 1168, 1170, 1174, 1178-1185, 1189, 1191,
      1192, 1194-1198, 1200, 1204, 1206-1208, 1210, 1215, 1218-1223,
      1225, 1227-1229, 1231-1236, 1240, 1245-1247, 1253, 1254, 1257,
      1260, 1263,1265, 1267, 1268, 1271, 1272, 1277, 1278, 1280-1282,
      1285, 1286, 1291-1293, 1296-1316, 1321-1326, 1328-1345, 1348-1455,
      1457, 1458, 1464-1490, 1496, 1497, 1511, 1513-1516, 1518, 1519,
      1523, 1525, 1526, 1528, 1529, 1533, 1535-1537, 1539-1542,
      1545-1552, 1560, 1561, 1567-1571, 1576, 1583, 1588-1591,
      1593-1633, 1635-1638, 1640-1642, 1644-1646, 1648-1654, 1656, 1661,
      1662, 1673, 1674, 1676, 1677, 1680, 1683, 1684, 1687, 1691, 1692,
      1695, 1699, 1702, 1703, 1707, 1714, 1718, 1719, 1727, 1728,
      1730-1738, 1740-1744, 1746-1756, 1758-1760, 1767, 1768, 1770,
      1779, 1780, 1789, 1790, 1820, 1828, 1831, 1833, 1836, 1839-1846,
      1851-1859, 1861, 1863, 1865, 1869-1871, 1873-1877, 1879,
      1886-1890, 1892, 1896-1900, 1915, 1916, 1918, 1920, 1924, 1925,
      1927-1932, 1934, 1936-1950, 1952, 1953, 1956, 1961, 1966, 1968,
      1969, 1970, 1973-1980, 1983, 1984, 1987-1993, 1998, 2000-2004,
      2006, 2007, 2011, 2014, 2016-2029, 2034-2044, 2046, 2048-2056,
      2061, 2063-2065, 2067, 2068, 2072, 2075, 2085, 2086, 2091, 2095,
      2096, 2106, 2108, 2109, 2111, 2116-2118, 2120, 2122-2125, 2128,
      2129, 2132, 2133, 2136-2143, 2146, 2147, 2150, 2151, 2153, 2155,
      2159, 2160, 2161, 2164, 2165, 2169, 2170, 2173-2176, 2179-2182,
      2190-2192, 2199, 2200, 2203-2205, 2214, 2217-2222, 2228, 2232,
      2248, 2251, 2253, 2266, 2268-2271, 2280, 2283, 2291-2294, 2311,
      2313, 2324, 2327, 2328, 2339, 2340, 2349, 2350, 2355, 2358, 2362,
```

```
      2370, 2372, 2386, 2394, 2396, 2397, 2399, 2401, 2403, 2405-2407,
      2410-2412, 2415-2417, 2419-2421, 2423, 2424, 2426, 2442-2444,
      2446, 2449, 2450, 2452, 2454, 2459-2461, 2463, 2466-2468,
      2473-2475, 2479, 2480, 2483, 2485, 2486, 2491-2494, 2497-2500,
      2505, 2506, 2512, 2520-2522, 2526, 2528-2530, 2532-2535, 2539,
      2540, 2543-2545, 2547, 2549-2568, 2571-2573, 2575, 2576-2579,
      2583, 2584, 2586-2589, 2591, 2597-2599, 2601-2603, 2605,
      2609-2612, 2614, 2615, 2617, 2618-2622, 2625-2627, 2630-2632,
      2637-2640, 2642-2647, 2649-2654
<223> OTHER INFORMATION: n = A,U,C or G

<400> SEQUENCE: 2
nnnnaagnnn nnaagngnnn nngggggagcc nggcnnnnnn agncgangaa ggangnnnnn      60
nncnncnnna nncnnnggnn agnngnnnnn nnncnnnnna nccnnngnnc cgaaggggna     120
acccnnnnnn nnnnnnnnnn nnannnnnnn nnnnnnnnnn nnnnnnnnnn ngnnnacnnn     180
nngaangaaa cacnagannn nnaggaanag aaannaannn nganccnnnng agnggcgagc     240 gaannngnan nagncnnnnn nnnnnnnnnn nnnnnnnnnn annngaannn nnggnaagnn     300
nnnnnnnann nggnanannc cngannnnaa annnnnnnnn nnnnnnnnnn nnnnagannn     360
cnnnncncgn gnnannnngn ngaannngnn nngaccannn nnnaagncaa aacnnnnnnn     420
gaccnaagng nannagacng ganggaaagg ngaaaagnac ccnnnnnang ggaggaaana     480
gnnccgaaac cnnnnncnan aannngnnna gnnnnnnnnn nnnnnganng cgnccgnann     540
agnnncngng annnnnnnnn ngcnagnaan nnnnnnnngn agncgnagng aaancgagnn     600
naanngngcg nnnagnnnnn gnnnnagacn cgaancnnng gancannnag nncaggngaa     660
gnnnnngaan annnnnggag gnccgaacnn nnnnnnggaa aannnnnngg agannggnnn     720
gnggngaaan ncnaancnaa cnnngnnaag cggccnncga aannnnaggn nnngcnnnnn     780
nnnnnnnnnn nggnggagag cacgnnnnnn nnnnggnnnn nnnnnnnnna cnnannnnnn     840
nnaaacncga anccnnnnnn nnnnnnnnnn gnagnnannc nnngngngna annncnnngn     900
nanagggnaa cancccagan cnncnnnaag gncccnaann nnnnnnaagg gnaaangang     960
gnnnnnncnn anacannnag gangggcaga agcagccanc nnaaaganng cgaanagcca    1020
cnncnagnnn nnnngcgcng annanancgg gncaannnnn nnnccgaann nnnngnnnnn    1080
nnnnnnnnnn nnnnnnngga gnngagcgnn nnnnnnnnnn ngaagnnnnn nngnnannnn    1140
nnnggannnn nnnnnaggng nagnngnnan agancgannn nnnnnggana nncnnnnncn    1200
ccgnannncn aaggnccnnn nnnangnnnc nnnnnngggn agcgnnncca agnngagncn    1260
ganangnnag nngaggnnan nnggnnaacc nnnacnnnnn nnnnnnnnnn nnnnnngacg    1320
nnnnnngnnn nnnnnnnnnn nnnnnggnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnncnnga aaannnnnnn nnnnnnnnnn nnnnnnnnnn cgaccnnaaa    1500
ccgacacagg ngnnnngnng agnanncnna ggngnnngnn nnaannnnnn nnaaggaacn    1560
ngcaaannnn nccganccgg nanaaggnnn ncnnnnnnnn nnnnnnnnnn nnnnnnnnnn    1620
nnnnnnnnnn nnngnnnnan nnannngnnn nnnnncnacga nnaaaaacac agnncnngcn    1680
aanncgnaag nngangaang gnngacnccg cccnggcnng aaggaanngn nnnnnnnngn    1740
nnnngnnnnn nnnnnnannn aagcccnngn aacggcggnn gaacaaacnn ccaaggagcg    1800
aaaccgcggg aagccgaccn gcacgaangg ngnaangann nnnnnncgcc nnnnnnnnnc    1860
ncngngaann nannnnngna agagcnnnnn cncgcnnnnn gacggaaaga ccccnngnan    1920
cacnnannnn nnangnnnnn nnnnnnnnnn gnnagnaagg nggagncnnn gannnnnnnn    1980
cgnnagnnnn nnnggagncn nnnngnnaac nacncnnnnn nnnnnnnnnc aacnnnnnnn    2040
```

```
nnnnancnnn nnnnnngaca ngnnngnnng gnagnacggg gcggnnccc naaanngaac      2100 ggaggngnnc naaggnnncn annnnggnng gnnacnnnnn nnnagnnaan ngnanaagnn      2160
ngcnnacgnn agnnnnacnn nncgagcagn nncgaaagnn ggnnnaggac cggnggnnnn      2220
nnggaagngc cncgccaacg gaaaaagnac ncngggaaa caggcnannn nccccaagagn      2280 canacgacgg nnnngggcac ccgagcggcc ncncaccggg gcgnagnngg cccaaggggnn     2340 ggcgcgccnn aaagnggnac gngagcgggn anaacgcgga gacagnggcc cacngnngng     2400
ngngnnngan nngannngnn ngnncnagac gagaggaccg gnnngnacnn ancncgggnn     2460
ncnggnnngc cannngcann gcngnnagca nnnnggnnnn gaaanngcga angcacaagn     2520
nngaancnnn cnnnnagann agnnncncnn nnnnnnnnn nnnnnnnnag nnncnnnnna     2580
gannannnng ngaaggnnng nnngnaagnn ngnnannnn nnagnnnacn nnacaannnn     2640
cnnnnnncnn nnnn                                                       2654

<210> SEQ ID NO 3
<211> LENGTH: 13
<212> TYPE: DNA
<213> ORGANISM: Artificial Sequence
<220> FEATURE:
<223> OTHER INFORMATION: Primer

<400> SEQUENCE: 3
cgtggtgacc ctt                                                        13

<210> SEQ ID NO 4
<211> LENGTH: 14
<212> TYPE: DNA
<213> ORGANISM: Artificial Sequence
<220> FEATURE:
<223> OTHER INFORMATION: Primer

<400> SEQUENCE: 4
cgtcgtcacc gcta                                                       14

<210> SEQ ID NO 5
<211> LENGTH: 13
<212> TYPE: DNA
<213> ORGANISM: Artificial Sequence
<220> FEATURE:
<223> OTHER INFORMATION: Primer

<400> SEQUENCE: 5
cgtggtaccc ctt                                                        13

<210> SEQ ID NO 6
<211> LENGTH: 90
<212> TYPE: RNA
<213> ORGANISM: Bacillus anthracis
<220> FEATURE:
<223> OTHER INFORMATION: PCR Primer
<220> FEATURE:
<221> NAME/KEY: misc_feature
<222> LOCATION: 20
<223> OTHER INFORMATION: n = A, U, C or G

<400> SEQUENCE: 6
gcgaagaacc uuaccaggun uugacauccu cugacaaccc uagagauagg gcuucuccuu     60
cgggagcaga gugacaggug gugcaugguu                                      90

<210> SEQ ID NO 7
<211> LENGTH: 90
```

```
<212> TYPE: RNA
<213> ORGANISM: Bacillus cereus

<400> SEQUENCE: 7
gcgaagaacc uuaccagguc uugacauccu cugaaaaccc uagagauagg gcuucuccuu     60
cgggagcaga gugacaggug gugcaugguu                                     90

<210> SEQ ID NO 8
<211> LENGTH: 30
<212> TYPE: DNA
<213> ORGANISM: Artificial Sequence
<220> FEATURE:
<223> OTHER INFORMATION: PCR Primer

<400> SEQUENCE: 8
gtgagatgtt gggttaagtc ccgtaacgag                                     30

<210> SEQ ID NO 9
<211> LENGTH: 21
<212> TYPE: DNA
<213> ORGANISM: Artificial Sequence
<220> FEATURE:
<223> OTHER INFORMATION: PCR Primer

<400> SEQUENCE: 9
gacgtcatcc ccaccttcct c                                              21

<210> SEQ ID NO 10
<211> LENGTH: 25
<212> TYPE: DNA
<213> ORGANISM: Artificial Sequence
<220> FEATURE:
<223> OTHER INFORMATION: PCR Primer

<400> SEQUENCE: 10
atgttgggtt aagtcccgca acgag                                          25

<210> SEQ ID NO 11
<211> LENGTH: 23
<212> TYPE: DNA
<213> ORGANISM: Artificial Sequence
<220> FEATURE:
<223> OTHER INFORMATION: PCR Primer

<400> SEQUENCE: 11
ttgacgtcat ccccaccttc ctc                                            23

<210> SEQ ID NO 12
<211> LENGTH: 22
<212> TYPE: DNA
<213> ORGANISM: Artificial Sequence
<220> FEATURE:
<223> OTHER INFORMATION: PCR Primer

<400> SEQUENCE: 12
ttaagtcccg caacgatcgc aa                                             22

<210> SEQ ID NO 13
<211> LENGTH: 22
<212> TYPE: DNA
<213> ORGANISM: Artificial Sequence
<220> FEATURE:
<223> OTHER INFORMATION: PCR Primer

<400> SEQUENCE: 13
tgacgtcatc cccaccttcc tc                                             22
```

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
gctacacacg tgctacaatg                                          20

<210> SEQ ID NO 15
<211> LENGTH: 21
<212> TYPE: DNA
<213> ORGANISM: Artificial Sequence
<220> FEATURE:
<223> OTHER INFORMATION: PCR Primer

<400> SEQUENCE: 15
cgagttgcag actgcgatcc g                                        21

<210> SEQ ID NO 16
<211> LENGTH: 22
<212> TYPE: DNA
<213> ORGANISM: Artificial Sequence
<220> FEATURE:
<223> OTHER INFORMATION: PCR Primer

<400> SEQUENCE: 16
aagtcggaat cgctagtaat cg                                       22

<210> SEQ ID NO 17
<211> LENGTH: 19
<212> TYPE: DNA
<213> ORGANISM: Artificial Sequence
<220> FEATURE:
<223> OTHER INFORMATION: PCR Primer

<400> SEQUENCE: 17
gacgggcggt gtgtacaag                                           19

<210> SEQ ID NO 18
<211> LENGTH: 25
<212> TYPE: DNA
<213> ORGANISM: Artificial Sequence
<220> FEATURE:
<223> OTHER INFORMATION: PCR Primer

<400> SEQUENCE: 18
tgaacgctgg tggcatgctt aacac                                    25

<210> SEQ ID NO 19
<211> LENGTH: 22
<212> TYPE: DNA
<213> ORGANISM: Artificial Sequence
<220> FEATURE:
<223> OTHER INFORMATION: PCR Primer

<400> SEQUENCE: 19
tacgcattac tcacccgtcc gc                                       22

<210> SEQ ID NO 20
<211> LENGTH: 26
<212> TYPE: DNA
<213> ORGANISM: Artificial Sequence
<220> FEATURE:
<223> OTHER INFORMATION: PCR Primer

```
<400> SEQUENCE: 20
gtggcatgcc taatacatgc aagtcg                                    26

<210> SEQ ID NO 21
<211> LENGTH: 20
<212> TYPE: DNA
<213> ORGANISM: Artificial Sequence
<220> FEATURE:
<223> OTHER INFORMATION: PCR Primer

<400> SEQUENCE: 21
ttactcaccc gtccgccgct                                           20

<210> SEQ ID NO 22
<211> LENGTH: 20
<212> TYPE: DNA
<213> ORGANISM: Artificial Sequence
<220> FEATURE:
<223> OTHER INFORMATION: PCR Primer

<400> SEQUENCE: 22
taacacatgc aagtcgaacg                                           20

<210> SEQ ID NO 23
<211> LENGTH: 17
<212> TYPE: DNA
<213> ORGANISM: Artificial Sequence
<220> FEATURE:
<223> OTHER INFORMATION: PCR Primer

<400> SEQUENCE: 23
ttactcaccc gtccgcc                                              17

<210> SEQ ID NO 24
<211> LENGTH: 18
<212> TYPE: DNA
<213> ORGANISM: Artificial Sequence
<220> FEATURE:
<223> OTHER INFORMATION: PCR Primer

<400> SEQUENCE: 24
gtgtagcggt gaaatgcg                                             18

<210> SEQ ID NO 25
<211> LENGTH: 22
<212> TYPE: DNA
<213> ORGANISM: Artificial Sequence
<220> FEATURE:
<223> OTHER INFORMATION: PCR Primer

<400> SEQUENCE: 25
gtatctaatc ctgtttgctc cc                                        22

<210> SEQ ID NO 26
<211> LENGTH: 20
<212> TYPE: DNA
<213> ORGANISM: Artificial Sequence
<220> FEATURE:
<223> OTHER INFORMATION: PCR Primer

<400> SEQUENCE: 26
agaacaccga tggcgaaggc                                           20

<210> SEQ ID NO 27
<211> LENGTH: 21
```

```
<212> TYPE: DNA
<213> ORGANISM: Artificial Sequence
<220> FEATURE:
<223> OTHER INFORMATION: PCR Primer

<400> SEQUENCE: 27
cgtggactac cagggtatct a                                              21

<210> SEQ ID NO 28
<211> LENGTH: 22
<212> TYPE: DNA
<213> ORGANISM: Artificial Sequence
<220> FEATURE:
<223> OTHER INFORMATION: PCR Primer

<400> SEQUENCE: 28
ggattagaga ccctggtagt cc                                             22

<210> SEQ ID NO 29
<211> LENGTH: 18
<212> TYPE: DNA
<213> ORGANISM: Artificial Sequence
<220> FEATURE:
<223> OTHER INFORMATION: PCR Primer

<400> SEQUENCE: 29
ggccgtactc cccaggcg                                                  18

<210> SEQ ID NO 30
<211> LENGTH: 26
<212> TYPE: DNA
<213> ORGANISM: Artificial Sequence
<220> FEATURE:
<223> OTHER INFORMATION: PCR Primer

<400> SEQUENCE: 30
ggattagata ccctggtagt ccacgc                                         26

<210> SEQ ID NO 31
<211> LENGTH: 18
<212> TYPE: DNA
<213> ORGANISM: Artificial Sequence
<220> FEATURE:
<223> OTHER INFORMATION: PCR Primer

<400> SEQUENCE: 31
ggccgtactc cccaggcg                                                  18

<210> SEQ ID NO 32
<211> LENGTH: 22
<212> TYPE: DNA
<213> ORGANISM: Artificial Sequence
<220> FEATURE:
<223> OTHER INFORMATION: PCR Primer

<400> SEQUENCE: 32
tagataccct ggtagtccac gc                                             22

<210> SEQ ID NO 33
<211> LENGTH: 15
<212> TYPE: DNA
<213> ORGANISM: Artificial Sequence
<220> FEATURE:
<223> OTHER INFORMATION: PCR Primer

<400> SEQUENCE: 33
cgtactcccc aggcg                                                     15
```

<210> SEQ ID NO 34
<211> LENGTH: 22
<212> TYPE: DNA
<213> ORGANISM: Artificial Sequence
<220> FEATURE:
<223> OTHER INFORMATION: PCR Primer

<400> SEQUENCE: 34
ttcgatgcaa cgcgaagaac ct                                    22

<210> SEQ ID NO 35
<211> LENGTH: 20
<212> TYPE: DNA
<213> ORGANISM: Artificial Sequence
<220> FEATURE:
<223> OTHER INFORMATION: PCR Primer

<400> SEQUENCE: 35
acgagctgac gacagccatg                                       20

<210> SEQ ID NO 36
<211> LENGTH: 17
<212> TYPE: DNA
<213> ORGANISM: Artificial Sequence
<220> FEATURE:
<223> OTHER INFORMATION: PCR Primer

<400> SEQUENCE: 36
acgcgaagaa ccttacc                                          17

<210> SEQ ID NO 37
<211> LENGTH: 18
<212> TYPE: DNA
<213> ORGANISM: Artificial Sequence
<220> FEATURE:
<223> OTHER INFORMATION: PCR Primer

<400> SEQUENCE: 37
acgacacgag ctgacgac                                         18

<210> SEQ ID NO 38
<211> LENGTH: 18
<212> TYPE: DNA
<213> ORGANISM: Artificial Sequence
<220> FEATURE:
<223> OTHER INFORMATION: PCR Primer

<400> SEQUENCE: 38
ctgacacctg cccggtgc                                         18

<210> SEQ ID NO 39
<211> LENGTH: 19
<212> TYPE: DNA
<213> ORGANISM: Artificial Sequence
<220> FEATURE:
<223> OTHER INFORMATION: PCR Primer

<400> SEQUENCE: 39
gaccgttata gttacggcc                                        19

<210> SEQ ID NO 40
<211> LENGTH: 25
<212> TYPE: DNA
<213> ORGANISM: Artificial Sequence
<220> FEATURE:
<223> OTHER INFORMATION: PCR Primer

```
<400> SEQUENCE: 40
tctgtcccta gtacgagagg accgg                                         25

<210> SEQ ID NO 41
<211> LENGTH: 18
<212> TYPE: DNA
<213> ORGANISM: Artificial Sequence
<220> FEATURE:
<223> OTHER INFORMATION: PCR Primer

<400> SEQUENCE: 41
tgcttagatg ctttcagc                                                 18

<210> SEQ ID NO 42
<211> LENGTH: 24
<212> TYPE: DNA
<213> ORGANISM: Artificial Sequence
<220> FEATURE:
<223> OTHER INFORMATION: PCR Primer

<400> SEQUENCE: 42
ctgtccctag tacgagagga ccgg                                          24

<210> SEQ ID NO 43
<211> LENGTH: 24
<212> TYPE: DNA
<213> ORGANISM: Artificial Sequence
<220> FEATURE:
<223> OTHER INFORMATION: PCR Primer

<400> SEQUENCE: 43
gtttcatgct tagatgcttt cagc                                          24

<210> SEQ ID NO 44
<211> LENGTH: 26
<212> TYPE: DNA
<213> ORGANISM: Artificial Sequence
<220> FEATURE:
<223> OTHER INFORMATION: PCR Primer

<400> SEQUENCE: 44
ggggagtgaa agagatcctg aaaccg                                        26

<210> SEQ ID NO 45
<211> LENGTH: 21
<212> TYPE: DNA
<213> ORGANISM: Artificial Sequence
<220> FEATURE:
<223> OTHER INFORMATION: PCR Primer

<400> SEQUENCE: 45
acaaaaggta cgccgtcacc c                                             21

<210> SEQ ID NO 46
<211> LENGTH: 26
<212> TYPE: DNA
<213> ORGANISM: Artificial Sequence
<220> FEATURE:
<223> OTHER INFORMATION: PCR Primer

<400> SEQUENCE: 46
ggggagtgaa agagatcctg aaaccg                                        26

<210> SEQ ID NO 47
<211> LENGTH: 21
```

<212> TYPE: DNA
<213> ORGANISM: Artificial Sequence
<220> FEATURE:
<223> OTHER INFORMATION: PCR Primer

<400> SEQUENCE: 47
acaaaaggca cgccatcacc c                                              21

<210> SEQ ID NO 48
<211> LENGTH: 22
<212> TYPE: DNA
<213> ORGANISM: Artificial Sequence
<220> FEATURE:
<223> OTHER INFORMATION: PCR Primer

<400> SEQUENCE: 48
cgagagggaa acaacccaga cc                                             22

<210> SEQ ID NO 49
<211> LENGTH: 19
<212> TYPE: DNA
<213> ORGANISM: Artificial Sequence
<220> FEATURE:
<223> OTHER INFORMATION: PCR Primer

<400> SEQUENCE: 49
tggctgcttc taagccaac                                                 19

<210> SEQ ID NO 50
<211> LENGTH: 29
<212> TYPE: DNA
<213> ORGANISM: Artificial Sequence
<220> FEATURE:
<223> OTHER INFORMATION: PCR Primer

<400> SEQUENCE: 50
tgctcgtggt gcacaagtaa cggatatta                                      29

<210> SEQ ID NO 51
<211> LENGTH: 29
<212> TYPE: DNA
<213> ORGANISM: Artificial Sequence
<220> FEATURE:
<223> OTHER INFORMATION: PCR Primer

<400> SEQUENCE: 51
tgctgctttc gcatggttaa ttgcttcaa                                      29

<210> SEQ ID NO 52
<211> LENGTH: 28
<212> TYPE: DNA
<213> ORGANISM: Artificial Sequence
<220> FEATURE:
<223> OTHER INFORMATION: PCR Primer

<400> SEQUENCE: 52
caaaacttat taggtaagcg tgttgact                                       28

<210> SEQ ID NO 53
<211> LENGTH: 30
<212> TYPE: DNA
<213> ORGANISM: Artificial Sequence
<220> FEATURE:
<223> OTHER INFORMATION: PCR Primer

<400> SEQUENCE: 53
tcaagcgcca tttcttttgg taaaccacat                                     30

<210> SEQ ID NO 54
<211> LENGTH: 28
<212> TYPE: DNA
<213> ORGANISM: Artificial Sequence
<220> FEATURE:
<223> OTHER INFORMATION: PCR Primer

<400> SEQUENCE: 54
caaaacttat taggtaagcg tgttgact                                      28

<210> SEQ ID NO 55
<211> LENGTH: 30
<212> TYPE: DNA
<213> ORGANISM: Artificial Sequence
<220> FEATURE:
<223> OTHER INFORMATION: PCR Primer

<400> SEQUENCE: 55
tcaagcgcca tctctttcgg taatccacat                                    30

<210> SEQ ID NO 56
<211> LENGTH: 27
<212> TYPE: DNA
<213> ORGANISM: Artificial Sequence
<220> FEATURE:
<223> OTHER INFORMATION: PCR Primer

<400> SEQUENCE: 56
taagaagccg gaaccatca actaccg                                        27

<210> SEQ ID NO 57
<211> LENGTH: 20
<212> TYPE: DNA
<213> ORGANISM: Artificial Sequence
<220> FEATURE:
<223> OTHER INFORMATION: PCR Primer

<400> SEQUENCE: 57
ggcgcttgta cttaccgcac                                               20

<210> SEQ ID NO 58
<211> LENGTH: 19
<212> TYPE: DNA
<213> ORGANISM: Artificial Sequence
<220> FEATURE:
<223> OTHER INFORMATION: PCR Primer

<400> SEQUENCE: 58
tgattctggt gcccgtggt                                                19

<210> SEQ ID NO 59
<211> LENGTH: 22
<212> TYPE: DNA
<213> ORGANISM: Artificial Sequence
<220> FEATURE:
<223> OTHER INFORMATION: PCR Primer

<400> SEQUENCE: 59
ttggccatca ggccacgcat ac                                            22

<210> SEQ ID NO 60
<211> LENGTH: 19
<212> TYPE: DNA
<213> ORGANISM: Artificial Sequence
<220> FEATURE:
<223> OTHER INFORMATION: PCR Primer

<400> SEQUENCE: 60
tgattccggt gcccgtggt                                          19

<210> SEQ ID NO 61
<211> LENGTH: 22
<212> TYPE: DNA
<213> ORGANISM: Artificial Sequence
<220> FEATURE:
<223> OTHER INFORMATION: PCR Primer

<400> SEQUENCE: 61
ttggccatca gaccacgcat ac                                      22

<210> SEQ ID NO 62
<211> LENGTH: 24
<212> TYPE: DNA
<213> ORGANISM: Artificial Sequence
<220> FEATURE:
<223> OTHER INFORMATION: PCR Primer

<400> SEQUENCE: 62
ctggcaggta tgcgtggtct gatg                                    24

<210> SEQ ID NO 63
<211> LENGTH: 25
<212> TYPE: DNA
<213> ORGANISM: Artificial Sequence
<220> FEATURE:
<223> OTHER INFORMATION: PCR Primer

<400> SEQUENCE: 63
cgcaccgtgg gttgagatga agtac                                   25

<210> SEQ ID NO 64
<211> LENGTH: 24
<212> TYPE: DNA
<213> ORGANISM: Artificial Sequence
<220> FEATURE:
<223> OTHER INFORMATION: PCR Primer

<400> SEQUENCE: 64
cttgctggta tgcgtggtct gatg                                    24

<210> SEQ ID NO 65
<211> LENGTH: 25
<212> TYPE: DNA
<213> ORGANISM: Artificial Sequence
<220> FEATURE:
<223> OTHER INFORMATION: PCR Primer

<400> SEQUENCE: 65
cgcaccatgc gtagagatga agtac                                   25

<210> SEQ ID NO 66
<211> LENGTH: 26
<212> TYPE: DNA
<213> ORGANISM: Artificial Sequence
<220> FEATURE:
<223> OTHER INFORMATION: PCR Primer

<400> SEQUENCE: 66
cgtcgggtga ttaaccgtaa caaccg                                  26

<210> SEQ ID NO 67
<211> LENGTH: 25

```
<212> TYPE: DNA
<213> ORGANISM: Artificial Sequence
<220> FEATURE:
<223> OTHER INFORMATION: PCR Primer

<400> SEQUENCE: 67
gtttttcgtt gcgtacgatg atgtc                                         25

<210> SEQ ID NO 68
<211> LENGTH: 26
<212> TYPE: DNA
<213> ORGANISM: Artificial Sequence
<220> FEATURE:
<223> OTHER INFORMATION: PCR Primer

<400> SEQUENCE: 68
cgtcgtgtaa ttaaccgtaa caaccg                                        26

<210> SEQ ID NO 69
<211> LENGTH: 27
<212> TYPE: DNA
<213> ORGANISM: Artificial Sequence
<220> FEATURE:
<223> OTHER INFORMATION: PCR Primer

<400> SEQUENCE: 69
acgtttttcg ttttgaacga taatgct                                       27

<210> SEQ ID NO 70
<211> LENGTH: 27
<212> TYPE: DNA
<213> ORGANISM: Artificial Sequence
<220> FEATURE:
<223> OTHER INFORMATION: PCR Primer

<400> SEQUENCE: 70
caaaggtaag caaggtcgtt tccgtca                                       27

<210> SEQ ID NO 71
<211> LENGTH: 24
<212> TYPE: DNA
<213> ORGANISM: Artificial Sequence
<220> FEATURE:
<223> OTHER INFORMATION: PCR Primer

<400> SEQUENCE: 71
cgaacggcct gagtagtcaa cacg                                          24

<210> SEQ ID NO 72
<211> LENGTH: 27
<212> TYPE: DNA
<213> ORGANISM: Artificial Sequence
<220> FEATURE:
<223> OTHER INFORMATION: PCR Primer

<400> SEQUENCE: 72
caaaggtaag caaggacgtt tccgtca                                       27

<210> SEQ ID NO 73
<211> LENGTH: 24
<212> TYPE: DNA
<213> ORGANISM: Artificial Sequence
<220> FEATURE:
<223> OTHER INFORMATION: PCR Primer

<400> SEQUENCE: 73
cgaacggcca gagtagtcaa cacg                                          24
```

<210> SEQ ID NO 74
<211> LENGTH: 21
<212> TYPE: DNA
<213> ORGANISM: Artificial Sequence
<220> FEATURE:
<223> OTHER INFORMATION: PCR Primer

<400> SEQUENCE: 74
tagactgccc aggacacgct g                                              21

<210> SEQ ID NO 75
<211> LENGTH: 21
<212> TYPE: DNA
<213> ORGANISM: Artificial Sequence
<220> FEATURE:
<223> OTHER INFORMATION: PCR Primer

<400> SEQUENCE: 75
gccgtccatc tgagcagcac c                                              21

<210> SEQ ID NO 76
<211> LENGTH: 21
<212> TYPE: DNA
<213> ORGANISM: Artificial Sequence
<220> FEATURE:
<223> OTHER INFORMATION: PCR Primer

<400> SEQUENCE: 76
ttgactgccc aggtcacgct g                                              21

<210> SEQ ID NO 77
<211> LENGTH: 21
<212> TYPE: DNA
<213> ORGANISM: Artificial Sequence
<220> FEATURE:
<223> OTHER INFORMATION: PCR Primer

<400> SEQUENCE: 77
gccgtccatt tgagcagcac c                                              21

<210> SEQ ID NO 78
<211> LENGTH: 25
<212> TYPE: DNA
<213> ORGANISM: Artificial Sequence
<220> FEATURE:
<223> OTHER INFORMATION: PCR Primer

<400> SEQUENCE: 78
aactaccgtc cgcagttcta cttcc                                          25

<210> SEQ ID NO 79
<211> LENGTH: 24
<212> TYPE: DNA
<213> ORGANISM: Artificial Sequence
<220> FEATURE:
<223> OTHER INFORMATION: PCR Primer

<400> SEQUENCE: 79
gttgtcgcca ggcataacca tttc                                           24

<210> SEQ ID NO 80
<211> LENGTH: 25
<212> TYPE: DNA
<213> ORGANISM: Artificial Sequence
<220> FEATURE:
<223> OTHER INFORMATION: PCR Primer

```
<400> SEQUENCE: 80
aactaccgtc ctcagttcta cttcc                                         25

<210> SEQ ID NO 81
<211> LENGTH: 24
<212> TYPE: DNA
<213> ORGANISM: Artificial Sequence
<220> FEATURE:
<223> OTHER INFORMATION: PCR Primer

<400> SEQUENCE: 81
gttgtcacca ggcattacca tttc                                          24

<210> SEQ ID NO 82
<211> LENGTH: 28
<212> TYPE: DNA
<213> ORGANISM: Artificial Sequence
<220> FEATURE:
<223> OTHER INFORMATION: PCR Primer

<400> SEQUENCE: 82
ccacagttct acttccgtac tactgacg                                      28

<210> SEQ ID NO 83
<211> LENGTH: 30
<212> TYPE: DNA
<213> ORGANISM: Artificial Sequence
<220> FEATURE:
<223> OTHER INFORMATION: PCR Primer

<400> SEQUENCE: 83
tccaggcatt accatttcta ctccttctgg                                    30

<210> SEQ ID NO 84
<211> LENGTH: 30
<212> TYPE: DNA
<213> ORGANISM: Artificial Sequence
<220> FEATURE:
<223> OTHER INFORMATION: PCR Primer

<400> SEQUENCE: 84
gacctacagt aagaggttct gtaatgaacc                                    30

<210> SEQ ID NO 85
<211> LENGTH: 24
<212> TYPE: DNA
<213> ORGANISM: Artificial Sequence
<220> FEATURE:
<223> OTHER INFORMATION: PCR Primer

<400> SEQUENCE: 85
tccaagtgct ggtttacccc atgg                                          24

<210> SEQ ID NO 86
<211> LENGTH: 23
<212> TYPE: DNA
<213> ORGANISM: Artificial Sequence
<220> FEATURE:
<223> OTHER INFORMATION: PCR Primer

<400> SEQUENCE: 86
catccacacg gtggtggtga agg                                           23

<210> SEQ ID NO 87
<211> LENGTH: 22
```

```
<212> TYPE: DNA
<213> ORGANISM: Artificial Sequence
<220> FEATURE:
<223> OTHER INFORMATION: PCR Primer

<400> SEQUENCE: 87
gtgctggttt accccatgga gt                                              22

<210> SEQ ID NO 88
<211> LENGTH: 25
<212> TYPE: DNA
<213> ORGANISM: Artificial Sequence
<220> FEATURE:
<223> OTHER INFORMATION: PCR Primer

<400> SEQUENCE: 88
cgtgttgact attcggggcg ttcag                                           25

<210> SEQ ID NO 89
<211> LENGTH: 30
<212> TYPE: DNA
<213> ORGANISM: Artificial Sequence
<220> FEATURE:
<223> OTHER INFORMATION: PCR Primer

<400> SEQUENCE: 89
attcaagagc catttctttt ggtaaaccac                                      30

<210> SEQ ID NO 90
<211> LENGTH: 29
<212> TYPE: DNA
<213> ORGANISM: Artificial Sequence
<220> FEATURE:
<223> OTHER INFORMATION: PCR Primer

<400> SEQUENCE: 90
tcaacaacct cttggaggta aagctcagt                                       29

<210> SEQ ID NO 91
<211> LENGTH: 30
<212> TYPE: DNA
<213> ORGANISM: Artificial Sequence
<220> FEATURE:
<223> OTHER INFORMATION: PCR Primer

<400> SEQUENCE: 91
tttcttgaag agtatgagct gctccgtaag                                      30

<210> SEQ ID NO 92
<211> LENGTH: 23
<212> TYPE: DNA
<213> ORGANISM: Artificial Sequence
<220> FEATURE:
<223> OTHER INFORMATION: PCR Primer

<400> SEQUENCE: 92
catccacacg gtggtggtga agg                                             23

<210> SEQ ID NO 93
<211> LENGTH: 29
<212> TYPE: DNA
<213> ORGANISM: Artificial Sequence
<220> FEATURE:
<223> OTHER INFORMATION: PCR Primer

<400> SEQUENCE: 93
tgttttgtat ccaagtgctg gtttacccc                                       29
```

<210> SEQ ID NO 94
<211> LENGTH: 20
<212> TYPE: DNA
<213> ORGANISM: Artificial Sequence
<220> FEATURE:
<223> OTHER INFORMATION: PCR Primer

<400> SEQUENCE: 94
cgtggcggcg tggttatcga                                               20

<210> SEQ ID NO 95
<211> LENGTH: 24
<212> TYPE: DNA
<213> ORGANISM: Artificial Sequence
<220> FEATURE:
<223> OTHER INFORMATION: PCR Primer

<400> SEQUENCE: 95
cggtacgaac tggatgtcgc cgtt                                          24

<210> SEQ ID NO 96
<211> LENGTH: 22
<212> TYPE: DNA
<213> ORGANISM: Artificial Sequence
<220> FEATURE:
<223> OTHER INFORMATION: PCR Primer

<400> SEQUENCE: 96
tatcgctcag gcgaactcca ac                                            22

<210> SEQ ID NO 97
<211> LENGTH: 21
<212> TYPE: DNA
<213> ORGANISM: Artificial Sequence
<220> FEATURE:
<223> OTHER INFORMATION: PCR Primer

<400> SEQUENCE: 97
gctggattcg cctttgctac g                                             21

<210> SEQ ID NO 98
<211> LENGTH: 30
<212> TYPE: DNA
<213> ORGANISM: Artificial Sequence
<220> FEATURE:
<223> OTHER INFORMATION: PCR Primer

<400> SEQUENCE: 98
tgtaatgaac cctaatgacc atccacacgg                                    30

<210> SEQ ID NO 99
<211> LENGTH: 27
<212> TYPE: DNA
<213> ORGANISM: Artificial Sequence
<220> FEATURE:
<223> OTHER INFORMATION: PCR Primer

<400> SEQUENCE: 99
ccaagtgctg gtttacccca tggagta                                       27

<210> SEQ ID NO 100
<211> LENGTH: 30
<212> TYPE: DNA
<213> ORGANISM: Artificial Sequence
<220> FEATURE:
<223> OTHER INFORMATION: PCR Primer

```
<400> SEQUENCE: 100
taatgaaccc taatgaccat ccacacggtg                                    30

<210> SEQ ID NO 101
<211> LENGTH: 26
<212> TYPE: DNA
<213> ORGANISM: Artificial Sequence
<220> FEATURE:
<223> OTHER INFORMATION: PCR Primer

<400> SEQUENCE: 101
tccaagtgct ggtttacccc atggag                                        26

<210> SEQ ID NO 102
<211> LENGTH: 29
<212> TYPE: DNA
<213> ORGANISM: Artificial Sequence
<220> FEATURE:
<223> OTHER INFORMATION: PCR Primer

<400> SEQUENCE: 102
cttggaggta agtctcattt tggtgggca                                     29

<210> SEQ ID NO 103
<211> LENGTH: 30
<212> TYPE: DNA
<213> ORGANISM: Artificial Sequence
<220> FEATURE:
<223> OTHER INFORMATION: PCR Primer

<400> SEQUENCE: 103
cgtataagct gcaccataag cttgtaatgc                                    30

<210> SEQ ID NO 104
<211> LENGTH: 18
<212> TYPE: DNA
<213> ORGANISM: Artificial Sequence
<220> FEATURE:
<223> OTHER INFORMATION: PCR Primer

<400> SEQUENCE: 104
cgacgcgctg cgcttcac                                                 18

<210> SEQ ID NO 105
<211> LENGTH: 24
<212> TYPE: DNA
<213> ORGANISM: Artificial Sequence
<220> FEATURE:
<223> OTHER INFORMATION: PCR Primer

<400> SEQUENCE: 105
gcgttccaca gcttgttgca gaag                                          24

<210> SEQ ID NO 106
<211> LENGTH: 18
<212> TYPE: DNA
<213> ORGANISM: Artificial Sequence
<220> FEATURE:
<223> OTHER INFORMATION: PCR Primer

<400> SEQUENCE: 106
gaccacctcg gcaaccgt                                                 18

<210> SEQ ID NO 107
<211> LENGTH: 18
```

```
<212> TYPE: DNA
<213> ORGANISM: Artificial Sequence
<220> FEATURE:
<223> OTHER INFORMATION: PCR Primer

<400> SEQUENCE: 107
ttcgctctcg gcctggcc                                                 18

<210> SEQ ID NO 108
<211> LENGTH: 27
<212> TYPE: DNA
<213> ORGANISM: Artificial Sequence
<220> FEATURE:
<223> OTHER INFORMATION: PCR Primer

<400> SEQUENCE: 108
gcactatgca cacgtagatt gtcctgg                                       27

<210> SEQ ID NO 109
<211> LENGTH: 26
<212> TYPE: DNA
<213> ORGANISM: Artificial Sequence
<220> FEATURE:
<223> OTHER INFORMATION: PCR Primer

<400> SEQUENCE: 109
tatagcacca tccatctgag cggcac                                        26

<210> SEQ ID NO 110
<211> LENGTH: 22
<212> TYPE: DNA
<213> ORGANISM: Artificial Sequence
<220> FEATURE:
<223> OTHER INFORMATION: PCR Primer

<400> SEQUENCE: 110
cggcgtactt caacgacagc ca                                            22

<210> SEQ ID NO 111
<211> LENGTH: 20
<212> TYPE: DNA
<213> ORGANISM: Artificial Sequence
<220> FEATURE:
<223> OTHER INFORMATION: PCR Primer

<400> SEQUENCE: 111
cgcggtcggc tcgttgatga                                               20

<210> SEQ ID NO 112
<211> LENGTH: 24
<212> TYPE: DNA
<213> ORGANISM: Artificial Sequence
<220> FEATURE:
<223> OTHER INFORMATION: PCR Primer

<400> SEQUENCE: 112
cttctgcaac aagctgtgga acgc                                          24

<210> SEQ ID NO 113
<211> LENGTH: 23
<212> TYPE: DNA
<213> ORGANISM: Artificial Sequence
<220> FEATURE:
<223> OTHER INFORMATION: PCR Primer

<400> SEQUENCE: 113
tcgcagttca tcagcacgaa gcg                                           23
```

<210> SEQ ID NO 114
<211> LENGTH: 18
<212> TYPE: DNA
<213> ORGANISM: Artificial Sequence
<220> FEATURE:
<223> OTHER INFORMATION: PCR Primer

<400> SEQUENCE: 114
aagacgacct gcacgggc                                                 18

<210> SEQ ID NO 115
<211> LENGTH: 19
<212> TYPE: DNA
<213> ORGANISM: Artificial Sequence
<220> FEATURE:
<223> OTHER INFORMATION: PCR Primer

<400> SEQUENCE: 115
gcgctccacg tcttcacgc                                                19

<210> SEQ ID NO 116
<211> LENGTH: 22
<212> TYPE: DNA
<213> ORGANISM: Artificial Sequence
<220> FEATURE:
<223> OTHER INFORMATION: PCR Primer

<400> SEQUENCE: 116
ctgttcttag tacgagagga cc                                            22

<210> SEQ ID NO 117
<211> LENGTH: 21
<212> TYPE: DNA
<213> ORGANISM: Artificial Sequence
<220> FEATURE:
<223> OTHER INFORMATION: PCR Primer

<400> SEQUENCE: 117
ttcgtgctta gatgctttca g                                             21

<210> SEQ ID NO 118
<211> LENGTH: 17
<212> TYPE: DNA
<213> ORGANISM: Artificial Sequence
<220> FEATURE:
<223> OTHER INFORMATION: PCR Primer

<400> SEQUENCE: 118
acgcgaagaa ccttacc                                                  17

<210> SEQ ID NO 119
<211> LENGTH: 18
<212> TYPE: DNA
<213> ORGANISM: Artificial Sequence
<220> FEATURE:
<223> OTHER INFORMATION: PCR Primer

<400> SEQUENCE: 119
acgacacgag ctgacgac                                                 18

<210> SEQ ID NO 120
<211> LENGTH: 14
<212> TYPE: DNA
<213> ORGANISM: Artificial Sequence
<220> FEATURE:
<223> OTHER INFORMATION: PCR Primer

```
<400> SEQUENCE: 120
cgaagaacct tacc                                                     14

<210> SEQ ID NO 121
<211> LENGTH: 12
<212> TYPE: DNA
<213> ORGANISM: Artificial Sequence
<220> FEATURE:
<223> OTHER INFORMATION: PCR Primer

<400> SEQUENCE: 121
acacgagctg ac                                                       12

<210> SEQ ID NO 122
<211> LENGTH: 14
<212> TYPE: DNA
<213> ORGANISM: Artificial Sequence
<220> FEATURE:
<223> OTHER INFORMATION: PCR Primer

<400> SEQUENCE: 122
cgaagaacct tacc                                                     14

<210> SEQ ID NO 123
<211> LENGTH: 12
<212> TYPE: DNA
<213> ORGANISM: Artificial Sequence
<220> FEATURE:
<223> OTHER INFORMATION: PCR Primer

<400> SEQUENCE: 123
acacgagctg ac                                                       12

<210> SEQ ID NO 124
<211> LENGTH: 19
<212> TYPE: DNA
<213> ORGANISM: Artificial Sequence
<220> FEATURE:
<223> OTHER INFORMATION: PCR Primer

<400> SEQUENCE: 124
cctgataagg gtgaggtcg                                                19

<210> SEQ ID NO 125
<211> LENGTH: 20
<212> TYPE: DNA
<213> ORGANISM: Artificial Sequence
<220> FEATURE:
<223> OTHER INFORMATION: PCR Primer

<400> SEQUENCE: 125
acgtccttca tcgcctctga                                               20

<210> SEQ ID NO 126
<211> LENGTH: 22
<212> TYPE: DNA
<213> ORGANISM: Artificial Sequence
<220> FEATURE:
<223> OTHER INFORMATION: PCR Primer

<400> SEQUENCE: 126
gttgtgaggt taagcgacta ag                                            22

<210> SEQ ID NO 127
<211> LENGTH: 21
```

```
<212> TYPE: DNA
<213> ORGANISM: Artificial Sequence
<220> FEATURE:
<223> OTHER INFORMATION: PCR Primer

<400> SEQUENCE: 127
ctatcggtca gtcaggagta t                                              21

<210> SEQ ID NO 128
<211> LENGTH: 22
<212> TYPE: DNA
<213> ORGANISM: Artificial Sequence
<220> FEATURE:
<223> OTHER INFORMATION: PCR Primer

<400> SEQUENCE: 128
gttgtgaggt taagcgacta ag                                             22

<210> SEQ ID NO 129
<211> LENGTH: 20
<212> TYPE: DNA
<213> ORGANISM: Artificial Sequence
<220> FEATURE:
<223> OTHER INFORMATION: PCR Primer

<400> SEQUENCE: 129
ttgcatcggg ttggtaagtc                                                20

<210> SEQ ID NO 130
<211> LENGTH: 21
<212> TYPE: DNA
<213> ORGANISM: Artificial Sequence
<220> FEATURE:
<223> OTHER INFORMATION: PCR Primer

<400> SEQUENCE: 130
atactcctga ctgaccgata g                                              21

<210> SEQ ID NO 131
<211> LENGTH: 19
<212> TYPE: DNA
<213> ORGANISM: Artificial Sequence
<220> FEATURE:
<223> OTHER INFORMATION: PCR Primer

<400> SEQUENCE: 131
aacatagcct tctccgtcc                                                 19

<210> SEQ ID NO 132
<211> LENGTH: 20
<212> TYPE: DNA
<213> ORGANISM: Artificial Sequence
<220> FEATURE:
<223> OTHER INFORMATION: PCR Primer

<400> SEQUENCE: 132
gacttaccaa cccgatgcaa                                                20

<210> SEQ ID NO 133
<211> LENGTH: 24
<212> TYPE: DNA
<213> ORGANISM: Artificial Sequence
<220> FEATURE:
<223> OTHER INFORMATION: PCR Primer

<400> SEQUENCE: 133
taccttagga ccgttatagt tacg                                           24
```

<210> SEQ ID NO 134
<211> LENGTH: 19
<212> TYPE: DNA
<213> ORGANISM: Artificial Sequence
<220> FEATURE:
<223> OTHER INFORMATION: PCR Primer

<400> SEQUENCE: 134
ggacggagaa ggctatgtt                                              19

<210> SEQ ID NO 135
<211> LENGTH: 20
<212> TYPE: DNA
<213> ORGANISM: Artificial Sequence
<220> FEATURE:
<223> OTHER INFORMATION: PCR Primer

<400> SEQUENCE: 135
ccaaacaccg ccgtcgatat                                             20

<210> SEQ ID NO 136
<211> LENGTH: 24
<212> TYPE: DNA
<213> ORGANISM: Artificial Sequence
<220> FEATURE:
<223> OTHER INFORMATION: PCR Primer

<400> SEQUENCE: 136
cgtaactata acggtcctaa ggta                                        24

<210> SEQ ID NO 137
<211> LENGTH: 20
<212> TYPE: DNA
<213> ORGANISM: Artificial Sequence
<220> FEATURE:
<223> OTHER INFORMATION: PCR Primer

<400> SEQUENCE: 137
gcttacacac ccggcctatc                                             20

<210> SEQ ID NO 138
<211> LENGTH: 20
<212> TYPE: DNA
<213> ORGANISM: Artificial Sequence
<220> FEATURE:
<223> OTHER INFORMATION: PCR Primer

<400> SEQUENCE: 138
atatcgacgg cggtgtttgg                                             20

<210> SEQ ID NO 139
<211> LENGTH: 19
<212> TYPE: DNA
<213> ORGANISM: Artificial Sequence
<220> FEATURE:
<223> OTHER INFORMATION: PCR Primer

<400> SEQUENCE: 139
gcgtgacagg caggtattc                                              19

<210> SEQ ID NO 140
<211> LENGTH: 22
<212> TYPE: DNA
<213> ORGANISM: Artificial Sequence
<220> FEATURE:
<223> OTHER INFORMATION: PCR Primer

```
<400> SEQUENCE: 140
agtctcaaga gtgaacacgt aa                                              22

<210> SEQ ID NO 141
<211> LENGTH: 18
<212> TYPE: DNA
<213> ORGANISM: Artificial Sequence
<220> FEATURE:
<223> OTHER INFORMATION: PCR Primer

<400> SEQUENCE: 141
gctgctggca cggagtta                                                   18

<210> SEQ ID NO 142
<211> LENGTH: 20
<212> TYPE: DNA
<213> ORGANISM: Artificial Sequence
<220> FEATURE:
<223> OTHER INFORMATION: PCR Primer

<400> SEQUENCE: 142
gacacggtcc agactcctac                                                 20

<210> SEQ ID NO 143
<211> LENGTH: 18
<212> TYPE: DNA
<213> ORGANISM: Artificial Sequence
<220> FEATURE:
<223> OTHER INFORMATION: PCR Primer

<400> SEQUENCE: 143
ccatgcagca cctgtctc                                                   18

<210> SEQ ID NO 144
<211> LENGTH: 20
<212> TYPE: DNA
<213> ORGANISM: Artificial Sequence
<220> FEATURE:
<223> OTHER INFORMATION: PCR Primer

<400> SEQUENCE: 144
gatctggagg aataccggtg                                                 20

<210> SEQ ID NO 145
<211> LENGTH: 20
<212> TYPE: DNA
<213> ORGANISM: Artificial Sequence
<220> FEATURE:
<223> OTHER INFORMATION: PCR Primer

<400> SEQUENCE: 145
acggttacct tgttacgact                                                 20

<210> SEQ ID NO 146
<211> LENGTH: 20
<212> TYPE: DNA
<213> ORGANISM: Artificial Sequence
<220> FEATURE:
<223> OTHER INFORMATION: PCR Primer

<400> SEQUENCE: 146
gagagcaagc ggacctcata                                                 20

<210> SEQ ID NO 147
<211> LENGTH: 17
```

```
<212> TYPE: DNA
<213> ORGANISM: Artificial Sequence
<220> FEATURE:
<223> OTHER INFORMATION: PCR Primer

<400> SEQUENCE: 147
cctcctgcgt gcaaagc                                                    17

<210> SEQ ID NO 148
<211> LENGTH: 19
<212> TYPE: DNA
<213> ORGANISM: Artificial Sequence
<220> FEATURE:
<223> OTHER INFORMATION: PCR Primer

<400> SEQUENCE: 148
tggaagatct gggtcaggc                                                  19

<210> SEQ ID NO 149
<211> LENGTH: 22
<212> TYPE: DNA
<213> ORGANISM: Artificial Sequence
<220> FEATURE:
<223> OTHER INFORMATION: PCR Primer

<400> SEQUENCE: 149
caatctgctg acggatctga gc                                              22

<210> SEQ ID NO 150
<211> LENGTH: 22
<212> TYPE: DNA
<213> ORGANISM: Artificial Sequence
<220> FEATURE:
<223> OTHER INFORMATION: PCR Primer

<400> SEQUENCE: 150
gtcgtgaaaa cgagctggaa ga                                              22

<210> SEQ ID NO 151
<211> LENGTH: 18
<212> TYPE: DNA
<213> ORGANISM: Artificial Sequence
<220> FEATURE:
<223> OTHER INFORMATION: PCR Primer

<400> SEQUENCE: 151
catgatggtc acaaccgg                                                   18

<210> SEQ ID NO 152
<211> LENGTH: 22
<212> TYPE: DNA
<213> ORGANISM: Artificial Sequence
<220> FEATURE:
<223> OTHER INFORMATION: PCR Primer

<400> SEQUENCE: 152
tggcgaacct ggtgaacgaa gc                                              22

<210> SEQ ID NO 153
<211> LENGTH: 25
<212> TYPE: DNA
<213> ORGANISM: Artificial Sequence
<220> FEATURE:
<223> OTHER INFORMATION: PCR Primer

<400> SEQUENCE: 153
ctttcgcttt ctcgaactca accat                                           25
```

<210> SEQ ID NO 154
<211> LENGTH: 26
<212> TYPE: DNA
<213> ORGANISM: Artificial Sequence
<220> FEATURE:
<223> OTHER INFORMATION: PCR Primer

<400> SEQUENCE: 154
cgtcagggta aattccgtga agttaa					26

<210> SEQ ID NO 155
<211> LENGTH: 21
<212> TYPE: DNA
<213> ORGANISM: Artificial Sequence
<220> FEATURE:
<223> OTHER INFORMATION: PCR Primer

<400> SEQUENCE: 155
aacttcgcct tcggtcatgt t					21

<210> SEQ ID NO 156
<211> LENGTH: 24
<212> TYPE: DNA
<213> ORGANISM: Artificial Sequence
<220> FEATURE:
<223> OTHER INFORMATION: PCR Primer

<400> SEQUENCE: 156
ggtgaaagaa gttgcctcta aagc					24

<210> SEQ ID NO 157
<211> LENGTH: 23
<212> TYPE: DNA
<213> ORGANISM: Artificial Sequence
<220> FEATURE:
<223> OTHER INFORMATION: PCR Primer

<400> SEQUENCE: 157
ttcaggtcca tcgggttcat gcc					23

<210> SEQ ID NO 158
<211> LENGTH: 20
<212> TYPE: DNA
<213> ORGANISM: Artificial Sequence
<220> FEATURE:
<223> OTHER INFORMATION: PCR Primer

<400> SEQUENCE: 158
cgtggcggcg tggttatcga					20

<210> SEQ ID NO 159
<211> LENGTH: 20
<212> TYPE: DNA
<213> ORGANISM: Artificial Sequence
<220> FEATURE:
<223> OTHER INFORMATION: PCR Primer

<400> SEQUENCE: 159
acgaactgga tgtcgccgtt					20

<210> SEQ ID NO 160
<211> LENGTH: 20
<212> TYPE: DNA
<213> ORGANISM: Artificial Sequence
<220> FEATURE:
<223> OTHER INFORMATION: PCR Primer

<400> SEQUENCE: 160
cggaattact gggcgtaaag                                               20

<210> SEQ ID NO 161
<211> LENGTH: 18
<212> TYPE: DNA
<213> ORGANISM: Artificial Sequence
<220> FEATURE:
<223> OTHER INFORMATION: PCR Primer

<400> SEQUENCE: 161
cgcatttcac cgctacac                                                 18

<210> SEQ ID NO 162
<211> LENGTH: 22
<212> TYPE: DNA
<213> ORGANISM: Artificial Sequence
<220> FEATURE:
<223> OTHER INFORMATION: PCR Primer

<400> SEQUENCE: 162
acccagtgct gctgaaccgt gc                                            22

<210> SEQ ID NO 163
<211> LENGTH: 21
<212> TYPE: DNA
<213> ORGANISM: Artificial Sequence
<220> FEATURE:
<223> OTHER INFORMATION: PCR Primer

<400> SEQUENCE: 163
gttcaaatgc ctggataccc a                                             21

<210> SEQ ID NO 164
<211> LENGTH: 22
<212> TYPE: DNA
<213> ORGANISM: Artificial Sequence
<220> FEATURE:
<223> OTHER INFORMATION: PCR Primer

<400> SEQUENCE: 164
gggagcaaac aggattagat ac                                            22

<210> SEQ ID NO 165
<211> LENGTH: 15
<212> TYPE: DNA
<213> ORGANISM: Artificial Sequence
<220> FEATURE:
<223> OTHER INFORMATION: PCR Primer

<400> SEQUENCE: 165
cgtactcccc aggcg                                                    15

<210> SEQ ID NO 166
<211> LENGTH: 21
<212> TYPE: DNA
<213> ORGANISM: Artificial Sequence
<220> FEATURE:
<223> OTHER INFORMATION: PCR Primer

<400> SEQUENCE: 166
tggcccgaaa gaagctgagc g                                             21

<210> SEQ ID NO 167
<211> LENGTH: 21

```
<212> TYPE: DNA
<213> ORGANISM: Artificial Sequence
<220> FEATURE:
<223> OTHER INFORMATION: PCR Primer

<400> SEQUENCE: 167
acgcgggcat gcagagatgc c                                              21

<210> SEQ ID NO 168
<211> LENGTH: 19
<212> TYPE: DNA
<213> ORGANISM: Artificial Sequence
<220> FEATURE:
<223> OTHER INFORMATION: PCR Primer

<400> SEQUENCE: 168
atgttgggtt aagtcccgc                                                 19

<210> SEQ ID NO 169
<211> LENGTH: 20
<212> TYPE: DNA
<213> ORGANISM: Artificial Sequence
<220> FEATURE:
<223> OTHER INFORMATION: PCR Primer

<400> SEQUENCE: 169
tgacgtcatc cccaccttcc                                                20

<210> SEQ ID NO 170
<211> LENGTH: 19
<212> TYPE: DNA
<213> ORGANISM: Artificial Sequence
<220> FEATURE:
<223> OTHER INFORMATION: PCR Primer

<400> SEQUENCE: 170
cttgtacaca ccgcccgtc                                                 19

<210> SEQ ID NO 171
<211> LENGTH: 17
<212> TYPE: DNA
<213> ORGANISM: Artificial Sequence
<220> FEATURE:
<223> OTHER INFORMATION: PCR Primer

<400> SEQUENCE: 171
aaggaggtga tccagcc                                                   17

<210> SEQ ID NO 172
<211> LENGTH: 21
<212> TYPE: DNA
<213> ORGANISM: Artificial Sequence
<220> FEATURE:
<223> OTHER INFORMATION: PCR Primer

<400> SEQUENCE: 172
cggattggag tctgcaactc g                                              21

<210> SEQ ID NO 173
<211> LENGTH: 19
<212> TYPE: DNA
<213> ORGANISM: Artificial Sequence
<220> FEATURE:
<223> OTHER INFORMATION: PCR Primer

<400> SEQUENCE: 173
gacgggcggt gtgtacaag                                                 19
```

<210> SEQ ID NO 174
<211> LENGTH: 15
<212> TYPE: DNA
<213> ORGANISM: Artificial Sequence
<220> FEATURE:
<223> OTHER INFORMATION: PCR Primer

<400> SEQUENCE: 174
ggtggatgcc ttggc                                                     15

<210> SEQ ID NO 175
<211> LENGTH: 16
<212> TYPE: DNA
<213> ORGANISM: Artificial Sequence
<220> FEATURE:
<223> OTHER INFORMATION: PCR Primer

<400> SEQUENCE: 175
gggtttcccc attcgg                                                    16

<210> SEQ ID NO 176
<211> LENGTH: 21
<212> TYPE: DNA
<213> ORGANISM: Artificial Sequence
<220> FEATURE:
<223> OTHER INFORMATION: PCR Primer

<400> SEQUENCE: 176
gggaactgaa acatctaagt a                                              21

<210> SEQ ID NO 177
<211> LENGTH: 15
<212> TYPE: DNA
<213> ORGANISM: Artificial Sequence
<220> FEATURE:
<223> OTHER INFORMATION: PCR Primer

<400> SEQUENCE: 177
ttcgctcgcc gctac                                                     15

<210> SEQ ID NO 178
<211> LENGTH: 19
<212> TYPE: DNA
<213> ORGANISM: Artificial Sequence
<220> FEATURE:
<223> OTHER INFORMATION: PCR Primer

<400> SEQUENCE: 178
taccccaaac cgacacagg                                                 19

<210> SEQ ID NO 179
<211> LENGTH: 18
<212> TYPE: DNA
<213> ORGANISM: Artificial Sequence
<220> FEATURE:
<223> OTHER INFORMATION: PCR Primer

<400> SEQUENCE: 179
ccttctcccg aagttacg                                                  18

<210> SEQ ID NO 180
<211> LENGTH: 19
<212> TYPE: DNA
<213> ORGANISM: Artificial Sequence
<220> FEATURE:
<223> OTHER INFORMATION: PCR Primer

```
<400> SEQUENCE: 180
ccgtaacttc gggagaagg                                                19

<210> SEQ ID NO 181
<211> LENGTH: 15
<212> TYPE: DNA
<213> ORGANISM: Artificial Sequence
<220> FEATURE:
<223> OTHER INFORMATION: PCR Primer

<400> SEQUENCE: 181
caccgggcag gcgtc                                                    15

<210> SEQ ID NO 182
<211> LENGTH: 16
<212> TYPE: DNA
<213> ORGANISM: Artificial Sequence
<220> FEATURE:
<223> OTHER INFORMATION: PCR Primer

<400> SEQUENCE: 182
gacgcctgcc cggtgc                                                   16

<210> SEQ ID NO 183
<211> LENGTH: 21
<212> TYPE: DNA
<213> ORGANISM: Artificial Sequence
<220> FEATURE:
<223> OTHER INFORMATION: PCR Primer

<400> SEQUENCE: 183
ccgacaagga atttcgctac c                                             21

<210> SEQ ID NO 184
<211> LENGTH: 23
<212> TYPE: DNA
<213> ORGANISM: Artificial Sequence
<220> FEATURE:
<223> OTHER INFORMATION: PCR Primer

<400> SEQUENCE: 184
aaggtactcc ggggataaca ggc                                           23

<210> SEQ ID NO 185
<211> LENGTH: 22
<212> TYPE: DNA
<213> ORGANISM: Artificial Sequence
<220> FEATURE:
<223> OTHER INFORMATION: PCR Primer

<400> SEQUENCE: 185
agccgacatc gaggtgccaa ac                                            22

<210> SEQ ID NO 186
<211> LENGTH: 18
<212> TYPE: DNA
<213> ORGANISM: Artificial Sequence
<220> FEATURE:
<223> OTHER INFORMATION: PCR Primer

<400> SEQUENCE: 186
gacagttcgg tccctatc                                                 18

<210> SEQ ID NO 187
<211> LENGTH: 17
```

```
<212> TYPE: DNA
<213> ORGANISM: Artificial Sequence
<220> FEATURE:
<223> OTHER INFORMATION: PCR Primer

<400> SEQUENCE: 187
ccggtcctct cgtacta                                                  17

<210> SEQ ID NO 188
<211> LENGTH: 17
<212> TYPE: DNA
<213> ORGANISM: Artificial Sequence
<220> FEATURE:
<223> OTHER INFORMATION: PCR Primer

<400> SEQUENCE: 188
tagtacgaga ggaccgg                                                  17

<210> SEQ ID NO 189
<211> LENGTH: 22
<212> TYPE: DNA
<213> ORGANISM: Artificial Sequence
<220> FEATURE:
<223> OTHER INFORMATION: PCR Primer

<400> SEQUENCE: 189
ttagatgctt tcagcactta tc                                            22

<210> SEQ ID NO 190
<211> LENGTH: 24
<212> TYPE: DNA
<213> ORGANISM: Artificial Sequence
<220> FEATURE:
<223> OTHER INFORMATION: PCR Primer

<400> SEQUENCE: 190
aaactagata acagtagaca tcac                                          24

<210> SEQ ID NO 191
<211> LENGTH: 18
<212> TYPE: DNA
<213> ORGANISM: Artificial Sequence
<220> FEATURE:
<223> OTHER INFORMATION: PCR Primer

<400> SEQUENCE: 191
gtgcgccctt tctaactt                                                 18

<210> SEQ ID NO 192
<211> LENGTH: 20
<212> TYPE: DNA
<213> ORGANISM: Artificial Sequence
<220> FEATURE:
<223> OTHER INFORMATION: PCR Primer

<400> SEQUENCE: 192
agagtttgat catggctcag                                               20

<210> SEQ ID NO 193
<211> LENGTH: 17
<212> TYPE: DNA
<213> ORGANISM: Artificial Sequence
<220> FEATURE:
<223> OTHER INFORMATION: PCR Primer

<400> SEQUENCE: 193
actgctgcct cccgtag                                                  17
```

<210> SEQ ID NO 194
<211> LENGTH: 19
<212> TYPE: DNA
<213> ORGANISM: Artificial Sequence
<220> FEATURE:
<223> OTHER INFORMATION: PCR Primer

<400> SEQUENCE: 194
cactggaact gagacacgg                                                19

<210> SEQ ID NO 195
<211> LENGTH: 20
<212> TYPE: DNA
<213> ORGANISM: Artificial Sequence
<220> FEATURE:
<223> OTHER INFORMATION: PCR Primer

<400> SEQUENCE: 195
ctttacgccc agtaattccg                                               20

<210> SEQ ID NO 196
<211> LENGTH: 19
<212> TYPE: DNA
<213> ORGANISM: Artificial Sequence
<220> FEATURE:
<223> OTHER INFORMATION: PCR Primer

<400> SEQUENCE: 196
ccagcagccg cggtaatac                                                19

<210> SEQ ID NO 197
<211> LENGTH: 22
<212> TYPE: DNA
<213> ORGANISM: Artificial Sequence
<220> FEATURE:
<223> OTHER INFORMATION: PCR Primer

<400> SEQUENCE: 197
gtatctaatc ctgtttgctc cc                                            22

<210> SEQ ID NO 198
<211> LENGTH: 18
<212> TYPE: DNA
<213> ORGANISM: Artificial Sequence
<220> FEATURE:
<223> OTHER INFORMATION: PCR Primer

<400> SEQUENCE: 198
gtgtagcggt gaaatgcg                                                 18

<210> SEQ ID NO 199
<211> LENGTH: 19
<212> TYPE: DNA
<213> ORGANISM: Artificial Sequence
<220> FEATURE:
<223> OTHER INFORMATION: PCR Primer

<400> SEQUENCE: 199
ggtaaggttc ttcgcgttg                                                19

<210> SEQ ID NO 200
<211> LENGTH: 18
<212> TYPE: DNA
<213> ORGANISM: Artificial Sequence
<220> FEATURE:
<223> OTHER INFORMATION: PCR Primer

```
<400> SEQUENCE: 200
aagcggtgga gcatgtgg                                               18

<210> SEQ ID NO 201
<211> LENGTH: 21
<212> TYPE: DNA
<213> ORGANISM: Artificial Sequence
<220> FEATURE:
<223> OTHER INFORMATION: PCR Primer

<400> SEQUENCE: 201
attgtagcac gtgtgtagcc c                                           21

<210> SEQ ID NO 202
<211> LENGTH: 19
<212> TYPE: DNA
<213> ORGANISM: Artificial Sequence
<220> FEATURE:
<223> OTHER INFORMATION: PCR Primer

<400> SEQUENCE: 202
caagtcatca tggccctta                                              19

<210> SEQ ID NO 203
<211> LENGTH: 17
<212> TYPE: DNA
<213> ORGANISM: Artificial Sequence
<220> FEATURE:
<223> OTHER INFORMATION: PCR Primer

<400> SEQUENCE: 203
aaggaggtga tccagcc                                                17

<210> SEQ ID NO 204
<211> LENGTH: 20
<212> TYPE: DNA
<213> ORGANISM: Artificial Sequence
<220> FEATURE:
<223> OTHER INFORMATION: PCR Primer

<400> SEQUENCE: 204
agagtttgat catggctcag                                             20

<210> SEQ ID NO 205
<211> LENGTH: 17
<212> TYPE: DNA
<213> ORGANISM: Artificial Sequence
<220> FEATURE:
<223> OTHER INFORMATION: PCR Primer

<400> SEQUENCE: 205
aaggaggtga tccagcc                                                17

<210> SEQ ID NO 206
<211> LENGTH: 19
<212> TYPE: DNA
<213> ORGANISM: Artificial Sequence
<220> FEATURE:
<223> OTHER INFORMATION: PCR Primer

<400> SEQUENCE: 206
acctgcccag tgctggaag                                              19

<210> SEQ ID NO 207
<211> LENGTH: 18
```

```
<212> TYPE: DNA
<213> ORGANISM: Artificial Sequence
<220> FEATURE:
<223> OTHER INFORMATION: PCR Primer

<400> SEQUENCE: 207
tcgctacctt aggaccgt                                                    18

<210> SEQ ID NO 208
<211> LENGTH: 21
<212> TYPE: DNA
<213> ORGANISM: Artificial Sequence
<220> FEATURE:
<223> OTHER INFORMATION: PCR Primer

<400> SEQUENCE: 208
gccttgtaca cacctcccgt c                                                21

<210> SEQ ID NO 209
<211> LENGTH: 20
<212> TYPE: DNA
<213> ORGANISM: Artificial Sequence
<220> FEATURE:
<223> OTHER INFORMATION: PCR Primer

<400> SEQUENCE: 209
cacggctacc ttgttacgac                                                  20

<210> SEQ ID NO 210
<211> LENGTH: 22
<212> TYPE: DNA
<213> ORGANISM: Artificial Sequence
<220> FEATURE:
<223> OTHER INFORMATION: PCR Primer

<400> SEQUENCE: 210
ttgtacacac cgcccgtcat ac                                               22

<210> SEQ ID NO 211
<211> LENGTH: 20
<212> TYPE: DNA
<213> ORGANISM: Artificial Sequence
<220> FEATURE:
<223> OTHER INFORMATION: PCR Primer

<400> SEQUENCE: 211
ccttgttacg acttcacccc                                                  20

<210> SEQ ID NO 212
<211> LENGTH: 21
<212> TYPE: DNA
<213> ORGANISM: Artificial Sequence
<220> FEATURE:
<223> OTHER INFORMATION: PCR Primer

<400> SEQUENCE: 212
tacggtgaat acgttcccgg g                                                21

<210> SEQ ID NO 213
<211> LENGTH: 22
<212> TYPE: DNA
<213> ORGANISM: Artificial Sequence
<220> FEATURE:
<223> OTHER INFORMATION: PCR Primer

<400> SEQUENCE: 213
accttgttac gacttcaccc ca                                               22
```

<210> SEQ ID NO 214
<211> LENGTH: 19
<212> TYPE: DNA
<213> ORGANISM: Artificial Sequence
<220> FEATURE:
<223> OTHER INFORMATION: PCR Primer

<400> SEQUENCE: 214
accacgccgt aaacgatga                                           19

<210> SEQ ID NO 215
<211> LENGTH: 21
<212> TYPE: DNA
<213> ORGANISM: Artificial Sequence
<220> FEATURE:
<223> OTHER INFORMATION: PCR Primer

<400> SEQUENCE: 215
cccccgtcaa ttcctttgag t                                        21

<210> SEQ ID NO 216
<211> LENGTH: 22
<212> TYPE: DNA
<213> ORGANISM: Artificial Sequence
<220> FEATURE:
<223> OTHER INFORMATION: PCR Primer

<400> SEQUENCE: 216 gatacccctgg tagtccacac cg                                      22

<210> SEQ ID NO 217
<211> LENGTH: 19
<212> TYPE: DNA
<213> ORGANISM: Artificial Sequence
<220> FEATURE:
<223> OTHER INFORMATION: PCR Primer

<400> SEQUENCE: 217
gccttgcgac cgtactccc                                           19

<210> SEQ ID NO 218
<211> LENGTH: 22
<212> TYPE: DNA
<213> ORGANISM: Artificial Sequence
<220> FEATURE:
<223> OTHER INFORMATION: PCR Primer

<400> SEQUENCE: 218
tagataccct ggtagtccac gc                                       22

<210> SEQ ID NO 219
<211> LENGTH: 18
<212> TYPE: DNA
<213> ORGANISM: Artificial Sequence
<220> FEATURE:
<223> OTHER INFORMATION: PCR Primer

<400> SEQUENCE: 219
gcgaccgtac tccccagg                                            18

<210> SEQ ID NO 220
<211> LENGTH: 18
<212> TYPE: DNA
<213> ORGANISM: Artificial Sequence
<220> FEATURE:
<223> OTHER INFORMATION: PCR Primer

```
<400> SEQUENCE: 220
tagtcccgca acgagcgc                                                 18

<210> SEQ ID NO 221
<211> LENGTH: 22
<212> TYPE: DNA
<213> ORGANISM: Artificial Sequence
<220> FEATURE:
<223> OTHER INFORMATION: PCR Primer

<400> SEQUENCE: 221
gacgtcatcc ccaccttcct cc                                            22

<210> SEQ ID NO 222
<211> LENGTH: 22
<212> TYPE: DNA
<213> ORGANISM: Artificial Sequence
<220> FEATURE:
<223> OTHER INFORMATION: PCR Primer

<400> SEQUENCE: 222
tagaacgtcg cgagacagtt cg                                            22

<210> SEQ ID NO 223
<211> LENGTH: 20
<212> TYPE: DNA
<213> ORGANISM: Artificial Sequence
<220> FEATURE:
<223> OTHER INFORMATION: PCR Primer

<400> SEQUENCE: 223
agtccatccc ggtcctctcg                                               20

<210> SEQ ID NO 224
<211> LENGTH: 17
<212> TYPE: DNA
<213> ORGANISM: Artificial Sequence
<220> FEATURE:
<223> OTHER INFORMATION: PCR Primer

<400> SEQUENCE: 224
gaggaaagtc cgggctc                                                  17

<210> SEQ ID NO 225
<211> LENGTH: 18
<212> TYPE: DNA
<213> ORGANISM: Artificial Sequence
<220> FEATURE:
<223> OTHER INFORMATION: PCR Primer

<400> SEQUENCE: 225
ataagccggg ttctgtcg                                                 18

<210> SEQ ID NO 226
<211> LENGTH: 19
<212> TYPE: DNA
<213> ORGANISM: Artificial Sequence
<220> FEATURE:
<223> OTHER INFORMATION: PCR Primer

<400> SEQUENCE: 226
gaggaaagtc catgctcgc                                                19

<210> SEQ ID NO 227
<211> LENGTH: 22
```

```
<212> TYPE: DNA
<213> ORGANISM: Artificial Sequence
<220> FEATURE:
<223> OTHER INFORMATION: PCR Primer

<400> SEQUENCE: 227
gtaagccatg ttttgttcca tc                                              22

<210> SEQ ID NO 228
<211> LENGTH: 17
<212> TYPE: DNA
<213> ORGANISM: Artificial Sequence
<220> FEATURE:
<223> OTHER INFORMATION: PCR Primer

<400> SEQUENCE: 228
gaggaaagtc cgggctc                                                    17

<210> SEQ ID NO 229
<211> LENGTH: 18
<212> TYPE: DNA
<213> ORGANISM: Artificial Sequence
<220> FEATURE:
<223> OTHER INFORMATION: PCR Primer

<400> SEQUENCE: 229
ataagccggg ttctgtcg                                                   18

<210> SEQ ID NO 230
<211> LENGTH: 35
<212> TYPE: DNA
<213> ORGANISM: Artificial Sequence
<220> FEATURE:
<223> OTHER INFORMATION: PCR Primer

<400> SEQUENCE: 230
gcgggatcct ctagaggtgt taaatagcct ggcag                                35

<210> SEQ ID NO 231
<211> LENGTH: 35
<212> TYPE: DNA
<213> ORGANISM: Artificial Sequence
<220> FEATURE:
<223> OTHER INFORMATION: PCR Primer

<400> SEQUENCE: 231
gcgggatcct ctagaagacc tcctgcgtgc aaagc                                35

<210> SEQ ID NO 232
<211> LENGTH: 19
<212> TYPE: DNA
<213> ORGANISM: Artificial Sequence
<220> FEATURE:
<223> OTHER INFORMATION: PCR Primer

<400> SEQUENCE: 232
gaggaaagtc catgctcac                                                  19

<210> SEQ ID NO 233
<211> LENGTH: 22
<212> TYPE: DNA
<213> ORGANISM: Artificial Sequence
<220> FEATURE:
<223> OTHER INFORMATION: PCR Primer

<400> SEQUENCE: 233
ataagccatg ttctgttcca tc                                              22
```

<210> SEQ ID NO 234
<211> LENGTH: 19
<212> TYPE: DNA
<213> ORGANISM: Artificial Sequence
<220> FEATURE:
<223> OTHER INFORMATION: PCR Primer

<400> SEQUENCE: 234
atgttgggtt aagtcccgc                                            19

<210> SEQ ID NO 235
<211> LENGTH: 17
<212> TYPE: DNA
<213> ORGANISM: Artificial Sequence
<220> FEATURE:
<223> OTHER INFORMATION: PCR Primer

<400> SEQUENCE: 235
aaggaggtga tccagcc                                              17

<210> SEQ ID NO 236
<211> LENGTH: 20
<212> TYPE: DNA
<213> ORGANISM: Artificial Sequence
<220> FEATURE:
<223> OTHER INFORMATION: PCR Primer

<400> SEQUENCE: 236
cggaattact gggcgtaaag                                           20

<210> SEQ ID NO 237
<211> LENGTH: 22
<212> TYPE: DNA
<213> ORGANISM: Artificial Sequence
<220> FEATURE:
<223> OTHER INFORMATION: PCR Primer

<400> SEQUENCE: 237
gtatctaatc ctgtttgctc cc                                        22

<210> SEQ ID NO 238
<211> LENGTH: 19
<212> TYPE: DNA
<213> ORGANISM: Artificial Sequence
<220> FEATURE:
<223> OTHER INFORMATION: PCR Primer

<400> SEQUENCE: 238
atgttgggtt aagtcccgc                                            19

<210> SEQ ID NO 239
<211> LENGTH: 20
<212> TYPE: DNA
<213> ORGANISM: Artificial Sequence
<220> FEATURE:
<223> OTHER INFORMATION: PCR Primer

<400> SEQUENCE: 239
tgacgtcatg cccaccttcc                                           20

<210> SEQ ID NO 240
<211> LENGTH: 19
<212> TYPE: DNA
<213> ORGANISM: Artificial Sequence
<220> FEATURE:
<223> OTHER INFORMATION: PCR Primer

```
<400> SEQUENCE: 240
atgttgggtt aagtcccgc                                                19

<210> SEQ ID NO 241
<211> LENGTH: 20
<212> TYPE: DNA
<213> ORGANISM: Artificial Sequence
<220> FEATURE:
<223> OTHER INFORMATION: PCR Primer

<400> SEQUENCE: 241
tgacgtcatg gccaccttcc                                               20

<210> SEQ ID NO 242
<211> LENGTH: 34
<212> TYPE: DNA
<213> ORGANISM: Artificial Sequence
<220> FEATURE:
<223> OTHER INFORMATION: PCR Primer

<400> SEQUENCE: 242
gcgggatcct ctagacctga taagggtgag gtcg                               34

<210> SEQ ID NO 243
<211> LENGTH: 34
<212> TYPE: DNA
<213> ORGANISM: Artificial Sequence
<220> FEATURE:
<223> OTHER INFORMATION: PCR Primer

<400> SEQUENCE: 243
gcgggatcct ctagagcgtg acaggcaggt attc                               34

<210> SEQ ID NO 244
<211> LENGTH: 17
<212> TYPE: DNA
<213> ORGANISM: Artificial Sequence
<220> FEATURE:
<223> OTHER INFORMATION: PCR Primer

<400> SEQUENCE: 244
acgcgaagaa ccttacc                                                  17

<210> SEQ ID NO 245
<211> LENGTH: 19
<212> TYPE: DNA
<213> ORGANISM: Artificial Sequence
<220> FEATURE:
<223> OTHER INFORMATION: PCR Primer

<400> SEQUENCE: 245
gacgggcggt gtgtacaag                                                19

<210> SEQ ID NO 246
<211> LENGTH: 18
<212> TYPE: DNA
<213> ORGANISM: Artificial Sequence
<220> FEATURE:
<223> OTHER INFORMATION: PCR Primer

<400> SEQUENCE: 246
gtgtagcggt gaaatgcg                                                 18

<210> SEQ ID NO 247
<211> LENGTH: 21
```

```
<212> TYPE: DNA
<213> ORGANISM: Artificial Sequence
<220> FEATURE:
<223> OTHER INFORMATION: PCR Primer

<400> SEQUENCE: 247
cgagttgcag actgcgatcc g                                              21

<210> SEQ ID NO 248
<211> LENGTH: 20
<212> TYPE: DNA
<213> ORGANISM: Artificial Sequence
<220> FEATURE:
<223> OTHER INFORMATION: PCR Primer

<400> SEQUENCE: 248
taacacatgc aagtcgaacg                                                20

<210> SEQ ID NO 249
<211> LENGTH: 15
<212> TYPE: DNA
<213> ORGANISM: Artificial Sequence
<220> FEATURE:
<223> OTHER INFORMATION: PCR Primer

<400> SEQUENCE: 249
cgtactcccc aggcg                                                     15

<210> SEQ ID NO 250
<211> LENGTH: 20
<212> TYPE: DNA
<213> ORGANISM: Artificial Sequence
<220> FEATURE:
<223> OTHER INFORMATION: PCR Primer

<400> SEQUENCE: 250
taacacatgc aagtcgaacg                                                20

<210> SEQ ID NO 251
<211> LENGTH: 18
<212> TYPE: DNA
<213> ORGANISM: Artificial Sequence
<220> FEATURE:
<223> OTHER INFORMATION: PCR Primer

<400> SEQUENCE: 251
acgacacgag ctgacgac                                                  18

<210> SEQ ID NO 252
<211> LENGTH: 22
<212> TYPE: DNA
<213> ORGANISM: Artificial Sequence
<220> FEATURE:
<223> OTHER INFORMATION: PCR Primer

<400> SEQUENCE: 252
acaacgaagt acaatacaag ac                                             22

<210> SEQ ID NO 253
<211> LENGTH: 22
<212> TYPE: DNA
<213> ORGANISM: Artificial Sequence
<220> FEATURE:
<223> OTHER INFORMATION: PCR Primer

<400> SEQUENCE: 253
cttctacatt tttagccatc ac                                             22
```

<210> SEQ ID NO 254
<211> LENGTH: 22
<212> TYPE: DNA
<213> ORGANISM: Artificial Sequence
<220> FEATURE:
<223> OTHER INFORMATION: PCR Primer

<400> SEQUENCE: 254
ttaagtcccg caacgagcgc aa                                    22

<210> SEQ ID NO 255
<211> LENGTH: 22
<212> TYPE: DNA
<213> ORGANISM: Artificial Sequence
<220> FEATURE:
<223> OTHER INFORMATION: PCR Primer

<400> SEQUENCE: 255
tgacgtcatc cccaccttcc tc                                    22

<210> SEQ ID NO 256
<211> LENGTH: 28
<212> TYPE: DNA
<213> ORGANISM: Artificial Sequence
<220> FEATURE:
<223> OTHER INFORMATION: PCR Primer

<400> SEQUENCE: 256
tgagtgatga aggccttagg gttgtaaa                              28

<210> SEQ ID NO 257
<211> LENGTH: 21
<212> TYPE: DNA
<213> ORGANISM: Artificial Sequence
<220> FEATURE:
<223> OTHER INFORMATION: PCR Primer

<400> SEQUENCE: 257
cggctgctgg cacgaagtta g                                     21

<210> SEQ ID NO 258
<211> LENGTH: 23
<212> TYPE: DNA
<213> ORGANISM: Artificial Sequence
<220> FEATURE:
<223> OTHER INFORMATION: PCR Primer

<400> SEQUENCE: 258
atggacaagg ttggcaagga agg                                   23

<210> SEQ ID NO 259
<211> LENGTH: 20
<212> TYPE: DNA
<213> ORGANISM: Artificial Sequence
<220> FEATURE:
<223> OTHER INFORMATION: PCR Primer

<400> SEQUENCE: 259
tagccgcggt cgaattgcat                                       20

<210> SEQ ID NO 260
<211> LENGTH: 26
<212> TYPE: DNA
<213> ORGANISM: Artificial Sequence
<220> FEATURE:
<223> OTHER INFORMATION: PCR Primer

<400> SEQUENCE: 260
aaggaaggcg tgatcaccgt tgaaga                26

<210> SEQ ID NO 261
<211> LENGTH: 23
<212> TYPE: DNA
<213> ORGANISM: Artificial Sequence
<220> FEATURE:
<223> OTHER INFORMATION: PCR Primer

<400> SEQUENCE: 261
ccgcggtcga attgcatgcc ttc                   23

<210> SEQ ID NO 262
<211> LENGTH: 16
<212> TYPE: DNA
<213> ORGANISM: Artificial Sequence
<220> FEATURE:
<223> OTHER INFORMATION: PCR Primer

<400> SEQUENCE: 262
acgcgctgcg cttcac                           16

<210> SEQ ID NO 263
<211> LENGTH: 20
<212> TYPE: DNA
<213> ORGANISM: Artificial Sequence
<220> FEATURE:
<223> OTHER INFORMATION: PCR Primer

<400> SEQUENCE: 263
ttgcagaagt tgcggtagcc                       20

<210> SEQ ID NO 264
<211> LENGTH: 18
<212> TYPE: DNA
<213> ORGANISM: Artificial Sequence
<220> FEATURE:
<223> OTHER INFORMATION: PCR Primer

<400> SEQUENCE: 264
tcgaccacct gggcaacc                         18

<210> SEQ ID NO 265
<211> LENGTH: 19
<212> TYPE: DNA
<213> ORGANISM: Artificial Sequence
<220> FEATURE:
<223> OTHER INFORMATION: PCR Primer

<400> SEQUENCE: 265
atcaggtcgt gcggcatca                        19

<210> SEQ ID NO 266
<211> LENGTH: 17
<212> TYPE: DNA
<213> ORGANISM: Artificial Sequence
<220> FEATURE:
<223> OTHER INFORMATION: PCR Primer

<400> SEQUENCE: 266
cacggtgccg gcgtact                          17

<210> SEQ ID NO 267
<211> LENGTH: 20

```
<212> TYPE: DNA
<213> ORGANISM: Artificial Sequence
<220> FEATURE:
<223> OTHER INFORMATION: PCR Primer

<400> SEQUENCE: 267
gcggtcggct cgttgatgat                                              20

<210> SEQ ID NO 268
<211> LENGTH: 25
<212> TYPE: DNA
<213> ORGANISM: Artificial Sequence
<220> FEATURE:
<223> OTHER INFORMATION: PCR Primer

<400> SEQUENCE: 268
ttggaggtaa gtctcatttt ggtgg                                        25

<210> SEQ ID NO 269
<211> LENGTH: 25
<212> TYPE: DNA
<213> ORGANISM: Artificial Sequence
<220> FEATURE:
<223> OTHER INFORMATION: PCR Primer

<400> SEQUENCE: 269
aagctgcacc ataagcttgt aatgc                                        25

<210> SEQ ID NO 270
<211> LENGTH: 20
<212> TYPE: DNA
<213> ORGANISM: Artificial Sequence
<220> FEATURE:
<223> OTHER INFORMATION: PCR Primer

<400> SEQUENCE: 270
cagcgtttcg gcgaaatgga                                              20

<210> SEQ ID NO 271
<211> LENGTH: 24
<212> TYPE: DNA
<213> ORGANISM: Artificial Sequence
<220> FEATURE:
<223> OTHER INFORMATION: PCR Primer

<400> SEQUENCE: 271
cgacttgacg gttaacattt cctg                                         24

<210> SEQ ID NO 272
<211> LENGTH: 23
<212> TYPE: DNA
<213> ORGANISM: Artificial Sequence
<220> FEATURE:
<223> OTHER INFORMATION: PCR Primer

<400> SEQUENCE: 272
gggcagcgtt tcggcgaaat gga                                          23

<210> SEQ ID NO 273
<211> LENGTH: 27
<212> TYPE: DNA
<213> ORGANISM: Artificial Sequence
<220> FEATURE:
<223> OTHER INFORMATION: PCR Primer

<400> SEQUENCE: 273
gtccgacttg acggtcaaca tttcctg                                      27
```

<210> SEQ ID NO 274
<211> LENGTH: 29
<212> TYPE: DNA
<213> ORGANISM: Artificial Sequence
<220> FEATURE:
<223> OTHER INFORMATION: PCR Primer

<400> SEQUENCE: 274
caggagtcgt tcaactcgat ctacatgat                              29

<210> SEQ ID NO 275
<211> LENGTH: 19
<212> TYPE: DNA
<213> ORGANISM: Artificial Sequence
<220> FEATURE:
<223> OTHER INFORMATION: PCR Primer

<400> SEQUENCE: 275
acgccatcag gccacgcat                                         19

<210> SEQ ID NO 276
<211> LENGTH: 18
<212> TYPE: DNA
<213> ORGANISM: Artificial Sequence
<220> FEATURE:
<223> OTHER INFORMATION: PCR Primer

<400> SEQUENCE: 276
gcacaacctg cggctgcg                                          18

<210> SEQ ID NO 277
<211> LENGTH: 18
<212> TYPE: DNA
<213> ORGANISM: Artificial Sequence
<220> FEATURE:
<223> OTHER INFORMATION: PCR Primer

<400> SEQUENCE: 277
acggcacgag gtagtcgc                                          18

<210> SEQ ID NO 278
<211> LENGTH: 20
<212> TYPE: DNA
<213> ORGANISM: Artificial Sequence
<220> FEATURE:
<223> OTHER INFORMATION: PCR Primer

<400> SEQUENCE: 278
cgccgacttc gacggtgacc                                        20

<210> SEQ ID NO 279
<211> LENGTH: 19
<212> TYPE: DNA
<213> ORGANISM: Artificial Sequence
<220> FEATURE:
<223> OTHER INFORMATION: PCR Primer

<400> SEQUENCE: 279
gagcatcagc gtgcgtgct                                         19

<210> SEQ ID NO 280
<211> LENGTH: 23
<212> TYPE: DNA
<213> ORGANISM: Artificial Sequence
<220> FEATURE:
<223> OTHER INFORMATION: PCR Primer

```
<400> SEQUENCE: 280
ccacacgccg ttcttcaaca act                                    23

<210> SEQ ID NO 281
<211> LENGTH: 25
<212> TYPE: DNA
<213> ORGANISM: Artificial Sequence
<220> FEATURE:
<223> OTHER INFORMATION: PCR Primer

<400> SEQUENCE: 281
ggcatcacca tttccttgtc cttcg                                  25

<210> SEQ ID NO 282
<211> LENGTH: 27
<212> TYPE: DNA
<213> ORGANISM: Artificial Sequence
<220> FEATURE:
<223> OTHER INFORMATION: PCR Primer

<400> SEQUENCE: 282
gagagtttga tcctggctca gaacgaa                                27

<210> SEQ ID NO 283
<211> LENGTH: 22
<212> TYPE: DNA
<213> ORGANISM: Artificial Sequence
<220> FEATURE:
<223> OTHER INFORMATION: PCR Primer

<400> SEQUENCE: 283
tgttactcac ccgtctgcca ct                                     22

<210> SEQ ID NO 284
<211> LENGTH: 19
<212> TYPE: DNA
<213> ORGANISM: Artificial Sequence
<220> FEATURE:
<223> OTHER INFORMATION: PCR Primer

<400> SEQUENCE: 284
accgagcaag gagaccagc                                         19

<210> SEQ ID NO 285
<211> LENGTH: 23
<212> TYPE: DNA
<213> ORGANISM: Artificial Sequence
<220> FEATURE:
<223> OTHER INFORMATION: PCR Primer

<400> SEQUENCE: 285
tataacgcac atcgtcaggg tga                                    23

<210> SEQ ID NO 286
<211> LENGTH: 20
<212> TYPE: DNA
<213> ORGANISM: Artificial Sequence
<220> FEATURE:
<223> OTHER INFORMATION: PCR Primer

<400> SEQUENCE: 286
agacccaatt acattggctt                                        20

<210> SEQ ID NO 287
<211> LENGTH: 20
```

```
<212> TYPE: DNA
<213> ORGANISM: Artificial Sequence
<220> FEATURE:
<223> OTHER INFORMATION: PCR Primer

<400> SEQUENCE: 287
ccagtgctgt tgtagtacat                                               20

<210> SEQ ID NO 288
<211> LENGTH: 20
<212> TYPE: DNA
<213> ORGANISM: Artificial Sequence
<220> FEATURE:
<223> OTHER INFORMATION: PCR Primer

<400> SEQUENCE: 288
atgtactaca acagtactgg                                               20

<210> SEQ ID NO 289
<211> LENGTH: 20
<212> TYPE: DNA
<213> ORGANISM: Artificial Sequence
<220> FEATURE:
<223> OTHER INFORMATION: PCR Primer

<400> SEQUENCE: 289
caagtcaacc acagcattca                                               20

<210> SEQ ID NO 290
<211> LENGTH: 20
<212> TYPE: DNA
<213> ORGANISM: Artificial Sequence
<220> FEATURE:
<223> OTHER INFORMATION: PCR Primer

<400> SEQUENCE: 290
gggcttatgt actacaacag                                               20

<210> SEQ ID NO 291
<211> LENGTH: 21
<212> TYPE: DNA
<213> ORGANISM: Artificial Sequence
<220> FEATURE:
<223> OTHER INFORMATION: PCR Primer

<400> SEQUENCE: 291
tctgtcttgc aagtcaacca c                                             21

<210> SEQ ID NO 292
<211> LENGTH: 21
<212> TYPE: DNA
<213> ORGANISM: Artificial Sequence
<220> FEATURE:
<223> OTHER INFORMATION: PCR Primer

<400> SEQUENCE: 292
ggaatttttt gatggtagag a                                             21

<210> SEQ ID NO 293
<211> LENGTH: 19
<212> TYPE: DNA
<213> ORGANISM: Artificial Sequence
<220> FEATURE:
<223> OTHER INFORMATION: PCR Primer

<400> SEQUENCE: 293
taaagcacaa tttcaggcg                                                19
```

<210> SEQ ID NO 294
<211> LENGTH: 20
<212> TYPE: DNA
<213> ORGANISM: Artificial Sequence
<220> FEATURE:
<223> OTHER INFORMATION: PCR Primer

<400> SEQUENCE: 294
tagatctggc tttctttgac                                              20

<210> SEQ ID NO 295
<211> LENGTH: 21
<212> TYPE: DNA
<213> ORGANISM: Artificial Sequence
<220> FEATURE:
<223> OTHER INFORMATION: PCR Primer

<400> SEQUENCE: 295
atatgagtat ctggagtctg c                                            21

<210> SEQ ID NO 296
<211> LENGTH: 21
<212> TYPE: DNA
<213> ORGANISM: Artificial Sequence
<220> FEATURE:
<223> OTHER INFORMATION: PCR Primer

<400> SEQUENCE: 296
ggaaagacat tactgcagac a                                            21

<210> SEQ ID NO 297
<211> LENGTH: 20
<212> TYPE: DNA
<213> ORGANISM: Artificial Sequence
<220> FEATURE:
<223> OTHER INFORMATION: PCR Primer

<400> SEQUENCE: 297
ccaacttgag gctctggctg                                              20

<210> SEQ ID NO 298
<211> LENGTH: 19
<212> TYPE: DNA
<213> ORGANISM: Artificial Sequence
<220> FEATURE:
<223> OTHER INFORMATION: PCR Primer

<400> SEQUENCE: 298
acagacactt accagggtg                                               19

<210> SEQ ID NO 299
<211> LENGTH: 20
<212> TYPE: DNA
<213> ORGANISM: Artificial Sequence
<220> FEATURE:
<223> OTHER INFORMATION: PCR Primer

<400> SEQUENCE: 299
actgtggtgt catctttgtc                                              20

<210> SEQ ID NO 300
<211> LENGTH: 22
<212> TYPE: DNA
<213> ORGANISM: Artificial Sequence
<220> FEATURE:
<223> OTHER INFORMATION: PCR Primer

```
<400> SEQUENCE: 300
tcactaaaga caaaggtctt cc                                          22

<210> SEQ ID NO 301
<211> LENGTH: 21
<212> TYPE: DNA
<213> ORGANISM: Artificial Sequence
<220> FEATURE:
<223> OTHER INFORMATION: PCR Primer

<400> SEQUENCE: 301
ggcttcgccg tctgtaattt c                                           21

<210> SEQ ID NO 302
<211> LENGTH: 21
<212> TYPE: DNA
<213> ORGANISM: Artificial Sequence
<220> FEATURE:
<223> OTHER INFORMATION: PCR Primer

<400> SEQUENCE: 302
cggatccaag ctaatctttg g                                           21

<210> SEQ ID NO 303
<211> LENGTH: 24
<212> TYPE: DNA
<213> ORGANISM: Artificial Sequence
<220> FEATURE:
<223> OTHER INFORMATION: PCR Primer

<400> SEQUENCE: 303
ggtatgtact cataggtgtt ggtg                                        24

<210> SEQ ID NO 304
<211> LENGTH: 20
<212> TYPE: DNA
<213> ORGANISM: Artificial Sequence
<220> FEATURE:
<223> OTHER INFORMATION: PCR Primer

<400> SEQUENCE: 304
agacccaatt acattggctt                                             20

<210> SEQ ID NO 305
<211> LENGTH: 20
<212> TYPE: DNA
<213> ORGANISM: Artificial Sequence
<220> FEATURE:
<223> OTHER INFORMATION: PCR Primer

<400> SEQUENCE: 305
ccagtgctgt tgtagtacat                                             20

<210> SEQ ID NO 306
<211> LENGTH: 20
<212> TYPE: DNA
<213> ORGANISM: Artificial Sequence
<220> FEATURE:
<223> OTHER INFORMATION: PCR Primer

<400> SEQUENCE: 306
atgtactaca acagtactgg                                             20

<210> SEQ ID NO 307
<211> LENGTH: 20
```

```
<212> TYPE: DNA
<213> ORGANISM: Artificial Sequence
<220> FEATURE:
<223> OTHER INFORMATION: PCR Primer

<400> SEQUENCE: 307
caagtcaacc acagcattca                                                    20

<210> SEQ ID NO 308
<211> LENGTH: 20
<212> TYPE: DNA
<213> ORGANISM: Artificial Sequence
<220> FEATURE:
<223> OTHER INFORMATION: PCR Primer

<400> SEQUENCE: 308
gggcttatgt actacaacag                                                    20

<210> SEQ ID NO 309
<211> LENGTH: 21
<212> TYPE: DNA
<213> ORGANISM: Artificial Sequence
<220> FEATURE:
<223> OTHER INFORMATION: PCR Primer

<400> SEQUENCE: 309
tctgtcttgc aagtcaacca c                                                  21

<210> SEQ ID NO 310
<211> LENGTH: 21
<212> TYPE: DNA
<213> ORGANISM: Artificial Sequence
<220> FEATURE:
<223> OTHER INFORMATION: PCR Primer

<400> SEQUENCE: 310 ggaattttt gatggtagag a                                                   21

<210> SEQ ID NO 311
<211> LENGTH: 19
<212> TYPE: DNA
<213> ORGANISM: Artificial Sequence
<220> FEATURE:
<223> OTHER INFORMATION: PCR Primer

<400> SEQUENCE: 311
taaagcacaa tttcaggcg                                                     19

<210> SEQ ID NO 312
<211> LENGTH: 20
<212> TYPE: DNA
<213> ORGANISM: Artificial Sequence
<220> FEATURE:
<223> OTHER INFORMATION: PCR Primer

<400> SEQUENCE: 312
tagatctggc tttctttgac                                                    20

<210> SEQ ID NO 313
<211> LENGTH: 21
<212> TYPE: DNA
<213> ORGANISM: Artificial Sequence
<220> FEATURE:
<223> OTHER INFORMATION: PCR Primer

<400> SEQUENCE: 313
atatgagtat ctggagtctg c                                                  21
```

<210> SEQ ID NO 314
<211> LENGTH: 21
<212> TYPE: DNA
<213> ORGANISM: Artificial Sequence
<220> FEATURE:
<223> OTHER INFORMATION: PCR Primer

<400> SEQUENCE: 314
cggatccaag ctaatctttg g                                            21

<210> SEQ ID NO 315
<211> LENGTH: 24
<212> TYPE: DNA
<213> ORGANISM: Artificial Sequence
<220> FEATURE:
<223> OTHER INFORMATION: PCR Primer

<400> SEQUENCE: 315
ggtatgtact cataggtgtt ggtg                                         24

<210> SEQ ID NO 316
<211> LENGTH: 23
<212> TYPE: DNA
<213> ORGANISM: Artificial Sequence
<220> FEATURE:
<223> OTHER INFORMATION: PCR Primer

<400> SEQUENCE: 316
aacagaccca attacattgg ctt                                          23

<210> SEQ ID NO 317
<211> LENGTH: 22
<212> TYPE: DNA
<213> ORGANISM: Artificial Sequence
<220> FEATURE:
<223> OTHER INFORMATION: PCR Primer

<400> SEQUENCE: 317
gaggcacttg tatgtggaaa gg                                           22

<210> SEQ ID NO 318
<211> LENGTH: 23
<212> TYPE: DNA
<213> ORGANISM: Artificial Sequence
<220> FEATURE:
<223> OTHER INFORMATION: PCR Primer

<400> SEQUENCE: 318
atgcctaaca gacccaatta cat                                          23

<210> SEQ ID NO 319
<211> LENGTH: 22
<212> TYPE: DNA
<213> ORGANISM: Artificial Sequence
<220> FEATURE:
<223> OTHER INFORMATION: PCR Primer

<400> SEQUENCE: 319
ttcatgtagt cgtaggtgtt gg                                           22

<210> SEQ ID NO 320
<211> LENGTH: 24
<212> TYPE: DNA
<213> ORGANISM: Artificial Sequence
<220> FEATURE:
<223> OTHER INFORMATION: PCR Primer

```
<400> SEQUENCE: 320
cgcgcctaat acatctcagt ggat                                          24

<210> SEQ ID NO 321
<211> LENGTH: 23
<212> TYPE: DNA
<213> ORGANISM: Artificial Sequence
<220> FEATURE:
<223> OTHER INFORMATION: PCR Primer

<400> SEQUENCE: 321
aagccaatgt aattgggtct gtt                                           23

<210> SEQ ID NO 322
<211> LENGTH: 22
<212> TYPE: DNA
<213> ORGANISM: Artificial Sequence
<220> FEATURE:
<223> OTHER INFORMATION: PCR Primer

<400> SEQUENCE: 322
ctactctggc actgcctaca ac                                            22

<210> SEQ ID NO 323
<211> LENGTH: 23
<212> TYPE: DNA
<213> ORGANISM: Artificial Sequence
<220> FEATURE:
<223> OTHER INFORMATION: PCR Primer

<400> SEQUENCE: 323
atgtaattgg gtctgttagg cat                                           23

<210> SEQ ID NO 324
<211> LENGTH: 24
<212> TYPE: DNA
<213> ORGANISM: Artificial Sequence
<220> FEATURE:
<223> OTHER INFORMATION: PCR Primer

<400> SEQUENCE: 324
caatccgttc tggttccgga tgaa                                          24

<210> SEQ ID NO 325
<211> LENGTH: 24
<212> TYPE: DNA
<213> ORGANISM: Artificial Sequence
<220> FEATURE:
<223> OTHER INFORMATION: PCR Primer

<400> SEQUENCE: 325
cttgccggtc gttcaaagag gtag                                          24

<210> SEQ ID NO 326
<211> LENGTH: 18
<212> TYPE: DNA
<213> ORGANISM: Artificial Sequence
<220> FEATURE:
<223> OTHER INFORMATION: PCR Primer

<400> SEQUENCE: 326
agtccgggtc tggtgcag                                                 18

<210> SEQ ID NO 327
<211> LENGTH: 17
```

```
<212> TYPE: DNA
<213> ORGANISM: Artificial Sequence
<220> FEATURE:
<223> OTHER INFORMATION: PCR Primer

<400> SEQUENCE: 327
cggtcggtgg tcacatc                                              17

<210> SEQ ID NO 328
<211> LENGTH: 18
<212> TYPE: DNA
<213> ORGANISM: Artificial Sequence
<220> FEATURE:
<223> OTHER INFORMATION: PCR Primer

<400> SEQUENCE: 328
atggccaccc catcgatg                                             18

<210> SEQ ID NO 329
<211> LENGTH: 19
<212> TYPE: DNA
<213> ORGANISM: Artificial Sequence
<220> FEATURE:
<223> OTHER INFORMATION: PCR Primer

<400> SEQUENCE: 329
ctgtccggcg atgtgcatg                                            19

<210> SEQ ID NO 330
<211> LENGTH: 23
<212> TYPE: DNA
<213> ORGANISM: Artificial Sequence
<220> FEATURE:
<223> OTHER INFORMATION: PCR Primer

<400> SEQUENCE: 330
ggtcgttatg tgcctttcca cat                                       23

<210> SEQ ID NO 331
<211> LENGTH: 25
<212> TYPE: DNA
<213> ORGANISM: Artificial Sequence
<220> FEATURE:
<223> OTHER INFORMATION: PCR Primer

<400> SEQUENCE: 331
tcctttctga agttccactc atagg                                     25

<210> SEQ ID NO 332
<211> LENGTH: 22
<212> TYPE: DNA
<213> ORGANISM: Artificial Sequence
<220> FEATURE:
<223> OTHER INFORMATION: PCR Primer

<400> SEQUENCE: 332
acaacattgg ctaccagggc tt                                        22

<210> SEQ ID NO 333
<211> LENGTH: 25
<212> TYPE: DNA
<213> ORGANISM: Artificial Sequence
<220> FEATURE:
<223> OTHER INFORMATION: PCR Primer

<400> SEQUENCE: 333
cctgcctgct cataggctgg aagtt                                     25
```

<210> SEQ ID NO 334
<211> LENGTH: 22
<212> TYPE: DNA
<213> ORGANISM: Artificial Sequence
<220> FEATURE:
<223> OTHER INFORMATION: PCR Primer

<400> SEQUENCE: 334
ggattagaga ccctggtagt cc                                              22

<210> SEQ ID NO 335
<211> LENGTH: 18
<212> TYPE: DNA
<213> ORGANISM: Artificial Sequence
<220> FEATURE:
<223> OTHER INFORMATION: PCR Primer

<400> SEQUENCE: 335
ggccgtactc cccaggcg                                                   18

<210> SEQ ID NO 336
<211> LENGTH: 22
<212> TYPE: DNA
<213> ORGANISM: Artificial Sequence
<220> FEATURE:
<223> OTHER INFORMATION: PCR Primer

<400> SEQUENCE: 336
ttcgatgcaa cgcgaagaac ct                                              22

<210> SEQ ID NO 337
<211> LENGTH: 20
<212> TYPE: DNA
<213> ORGANISM: Artificial Sequence
<220> FEATURE:
<223> OTHER INFORMATION: PCR Primer

<400> SEQUENCE: 337
acgagctgac gacagccatg                                                 20

<210> SEQ ID NO 338
<211> LENGTH: 25
<212> TYPE: DNA
<213> ORGANISM: Artificial Sequence
<220> FEATURE:
<223> OTHER INFORMATION: PCR Primer

<400> SEQUENCE: 338
tctgtcccta gtacgagagg accgg                                           25

<210> SEQ ID NO 339
<211> LENGTH: 18
<212> TYPE: DNA
<213> ORGANISM: Artificial Sequence
<220> FEATURE:
<223> OTHER INFORMATION: PCR Primer

<400> SEQUENCE: 339
tgcttagatg ctttcagc                                                   18

<210> SEQ ID NO 340
<211> LENGTH: 24
<212> TYPE: DNA
<213> ORGANISM: Artificial Sequence
<220> FEATURE:
<223> OTHER INFORMATION: PCR Primer

```
<400> SEQUENCE: 340
ctggcaggta tgcgtggtct gatg                                          24

<210> SEQ ID NO 341
<211> LENGTH: 25
<212> TYPE: DNA
<213> ORGANISM: Artificial Sequence
<220> FEATURE:
<223> OTHER INFORMATION: PCR Primer

<400> SEQUENCE: 341
cgcaccgtgg gttgagatga agtac                                         25

<210> SEQ ID NO 342
<211> LENGTH: 30
<212> TYPE: DNA
<213> ORGANISM: Artificial Sequence
<220> FEATURE:
<223> OTHER INFORMATION: PCR Primer

<400> SEQUENCE: 342
ggggattcag ccatcaaagc agctattgac                                    30

<210> SEQ ID NO 343
<211> LENGTH: 26
<212> TYPE: DNA
<213> ORGANISM: Artificial Sequence
<220> FEATURE:
<223> OTHER INFORMATION: PCR Primer

<400> SEQUENCE: 343 ccaaccttttt ccacaacaga atcagc                                       26

<210> SEQ ID NO 344
<211> LENGTH: 30
<212> TYPE: DNA
<213> ORGANISM: Artificial Sequence
<220> FEATURE:
<223> OTHER INFORMATION: PCR Primer

<400> SEQUENCE: 344
ccttacttcg aactatgaat cttttggaag                                    30

<210> SEQ ID NO 345
<211> LENGTH: 29
<212> TYPE: DNA
<213> ORGANISM: Artificial Sequence
<220> FEATURE:
<223> OTHER INFORMATION: PCR Primer

<400> SEQUENCE: 345
cccatttttt cacgcatgct gaaaatatc                                     29

<210> SEQ ID NO 346
<211> LENGTH: 23
<212> TYPE: DNA
<213> ORGANISM: Artificial Sequence
<220> FEATURE:
<223> OTHER INFORMATION: PCR Primer

<400> SEQUENCE: 346
cgcaaaaaaa tccagctatt agc                                           23

<210> SEQ ID NO 347
<211> LENGTH: 29
```

```
<212> TYPE: DNA
<213> ORGANISM: Artificial Sequence
<220> FEATURE:
<223> OTHER INFORMATION: PCR Primer

<400> SEQUENCE: 347
aaactatttt tttagctata ctcgaacac                                29

<210> SEQ ID NO 348
<211> LENGTH: 29
<212> TYPE: DNA
<213> ORGANISM: Artificial Sequence
<220> FEATURE:
<223> OTHER INFORMATION: PCR Primer

<400> SEQUENCE: 348
atgattacaa ttcaagaagg tcgtcacgc                                29

<210> SEQ ID NO 349
<211> LENGTH: 27
<212> TYPE: DNA
<213> ORGANISM: Artificial Sequence
<220> FEATURE:
<223> OTHER INFORMATION: PCR Primer

<400> SEQUENCE: 349
ttggacctgt aatcagctga atactgg                                  27

<210> SEQ ID NO 350
<211> LENGTH: 29
<212> TYPE: DNA
<213> ORGANISM: Artificial Sequence
<220> FEATURE:
<223> OTHER INFORMATION: PCR Primer

<400> SEQUENCE: 350
gatgactttt tagctaatgg tcaggcagc                                29

<210> SEQ ID NO 351
<211> LENGTH: 29
<212> TYPE: DNA
<213> ORGANISM: Artificial Sequence
<220> FEATURE:
<223> OTHER INFORMATION: PCR Primer

<400> SEQUENCE: 351
aatcgacgac catcttggaa agatttctc                                29

<210> SEQ ID NO 352
<211> LENGTH: 25
<212> TYPE: DNA
<213> ORGANISM: Artificial Sequence
<220> FEATURE:
<223> OTHER INFORMATION: PCR Primer

<400> SEQUENCE: 352
gcttcaggaa tcaatgatgg agcag                                    25

<210> SEQ ID NO 353
<211> LENGTH: 25
<212> TYPE: DNA
<213> ORGANISM: Artificial Sequence
<220> FEATURE:
<223> OTHER INFORMATION: PCR Primer

<400> SEQUENCE: 353
gggtctacac ctgcacttgc ataac                                    25
```

<210> SEQ ID NO 354
<211> LENGTH: 18
<212> TYPE: DNA
<213> ORGANISM: Artificial Sequence
<220> FEATURE:
<223> OTHER INFORMATION: PCR Primer

<400> SEQUENCE: 354
gtactgaatc cgcctaag                                                    18

<210> SEQ ID NO 355
<211> LENGTH: 23
<212> TYPE: DNA
<213> ORGANISM: Artificial Sequence
<220> FEATURE:
<223> OTHER INFORMATION: PCR Primer

<400> SEQUENCE: 355
gtgaataaag tatcgcccta ata                                              23

<210> SEQ ID NO 356
<211> LENGTH: 18
<212> TYPE: DNA
<213> ORGANISM: Artificial Sequence
<220> FEATURE:
<223> OTHER INFORMATION: PCR Primer

<400> SEQUENCE: 356
gaagttgaac cgggatca                                                    18

<210> SEQ ID NO 357
<211> LENGTH: 21
<212> TYPE: DNA
<213> ORGANISM: Artificial Sequence
<220> FEATURE:
<223> OTHER INFORMATION: PCR Primer

<400> SEQUENCE: 357
attatcggtc gttgttaatg t                                                21

<210> SEQ ID NO 358
<211> LENGTH: 23
<212> TYPE: DNA
<213> ORGANISM: Artificial Sequence
<220> FEATURE:
<223> OTHER INFORMATION: PCR Primer

<400> SEQUENCE: 358
ctgtctgtag ataaactagg att                                              23

<210> SEQ ID NO 359
<211> LENGTH: 18
<212> TYPE: DNA
<213> ORGANISM: Artificial Sequence
<220> FEATURE:
<223> OTHER INFORMATION: PCR Primer

<400> SEQUENCE: 359
cgttcttctc tggaggat                                                    18

<210> SEQ ID NO 360
<211> LENGTH: 15
<212> TYPE: DNA
<213> ORGANISM: Artificial Sequence
<220> FEATURE:
<223> OTHER INFORMATION: PCR Primer

```
<400> SEQUENCE: 360
cgatactacg gacgc                                                     15

<210> SEQ ID NO 361
<211> LENGTH: 22
<212> TYPE: DNA
<213> ORGANISM: Artificial Sequence
<220> FEATURE:
<223> OTHER INFORMATION: PCR Primer

<400> SEQUENCE: 361
ctttatgaat tactttacat at                                             22

<210> SEQ ID NO 362
<211> LENGTH: 18
<212> TYPE: DNA
<213> ORGANISM: Artificial Sequence
<220> FEATURE:
<223> OTHER INFORMATION: PCR Primer

<400> SEQUENCE: 362
ctcctccatc actaggaa                                                  18

<210> SEQ ID NO 363
<211> LENGTH: 22
<212> TYPE: DNA
<213> ORGANISM: Artificial Sequence
<220> FEATURE:
<223> OTHER INFORMATION: PCR Primer

<400> SEQUENCE: 363
ctataacatt caaagcttat tg                                             22

<210> SEQ ID NO 364
<211> LENGTH: 23
<212> TYPE: DNA
<213> ORGANISM: Artificial Sequence
<220> FEATURE:
<223> OTHER INFORMATION: PCR Primer

<400> SEQUENCE: 364
cgcgataata gatagtgcta aac                                            23

<210> SEQ ID NO 365
<211> LENGTH: 19
<212> TYPE: DNA
<213> ORGANISM: Artificial Sequence
<220> FEATURE:
<223> OTHER INFORMATION: PCR Primer

<400> SEQUENCE: 365
gcttccacca ggtcattaa                                                 19

<210> SEQ ID NO 366
<211> LENGTH: 18
<212> TYPE: DNA
<213> ORGANISM: Artificial Sequence
<220> FEATURE:
<223> OTHER INFORMATION: PCR Primer

<400> SEQUENCE: 366
gtactgaatc cgcctaag                                                  18

<210> SEQ ID NO 367
<211> LENGTH: 23
```

```
<212> TYPE: DNA
<213> ORGANISM: Artificial Sequence
<220> FEATURE:
<223> OTHER INFORMATION: PCR Primer

<400> SEQUENCE: 367
gtgaataaag tatcgcccta ata                                            23

<210> SEQ ID NO 368
<211> LENGTH: 18
<212> TYPE: DNA
<213> ORGANISM: Artificial Sequence
<220> FEATURE:
<223> OTHER INFORMATION: PCR Primer

<400> SEQUENCE: 368
gaagttgaac cgggatca                                                  18

<210> SEQ ID NO 369
<211> LENGTH: 21
<212> TYPE: DNA
<213> ORGANISM: Artificial Sequence
<220> FEATURE:
<223> OTHER INFORMATION: PCR Primer

<400> SEQUENCE: 369
attatcggtc gttgttaatg t                                              21

<210> SEQ ID NO 370
<211> LENGTH: 23
<212> TYPE: DNA
<213> ORGANISM: Artificial Sequence
<220> FEATURE:
<223> OTHER INFORMATION: PCR Primer

<400> SEQUENCE: 370
ctgtctgtag ataaactagg att                                            23

<210> SEQ ID NO 371
<211> LENGTH: 18
<212> TYPE: DNA
<213> ORGANISM: Artificial Sequence
<220> FEATURE:
<223> OTHER INFORMATION: PCR Primer

<400> SEQUENCE: 371
cgttcttctc tggaggat                                                  18

<210> SEQ ID NO 372
<211> LENGTH: 15
<212> TYPE: DNA
<213> ORGANISM: Artificial Sequence
<220> FEATURE:
<223> OTHER INFORMATION: PCR Primer

<400> SEQUENCE: 372
cgatactacg gacgc                                                     15

<210> SEQ ID NO 373
<211> LENGTH: 22
<212> TYPE: DNA
<213> ORGANISM: Artificial Sequence
<220> FEATURE:
<223> OTHER INFORMATION: PCR Primer

<400> SEQUENCE: 373
ctttatgaat tactttacat at                                             22
```

```
<210> SEQ ID NO 374
<211> LENGTH: 18
<212> TYPE: DNA
<213> ORGANISM: Artificial Sequence
<220> FEATURE:
<223> OTHER INFORMATION: PCR Primer

<400> SEQUENCE: 374
ctcctccatc actaggaa                                                 18

<210> SEQ ID NO 375
<211> LENGTH: 22
<212> TYPE: DNA
<213> ORGANISM: Artificial Sequence
<220> FEATURE:
<223> OTHER INFORMATION: PCR Primer

<400> SEQUENCE: 375
ctataacatt caaagcttat tg                                            22

<210> SEQ ID NO 376
<211> LENGTH: 23
<212> TYPE: DNA
<213> ORGANISM: Artificial Sequence
<220> FEATURE:
<223> OTHER INFORMATION: PCR Primer

<400> SEQUENCE: 376
cgcgataata gatagtgcta aac                                           23

<210> SEQ ID NO 377
<211> LENGTH: 19
<212> TYPE: DNA
<213> ORGANISM: Artificial Sequence
<220> FEATURE:
<223> OTHER INFORMATION: PCR Primer

<400> SEQUENCE: 377
gcttccacca ggtcattaa                                                19
```